(12) United States Patent
Ray et al.

(10) Patent No.: US 9,307,763 B2
(45) Date of Patent: Apr. 12, 2016

(54) LIGANDS FOR ODOR RECEPTORS AND OLFACTORY NEURONS

(71) Applicant: The Regents of the University of California, Oakland, CA (US)

(72) Inventors: Anandasankar Ray, Riverside, CA (US); Sean Michael Boyle, Lakewood Ranch, FL (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/540,908

(22) Filed: Nov. 13, 2014

(65) Prior Publication Data

US 2015/0223458 A1    Aug. 13, 2015

Related U.S. Application Data

(63) Continuation of application No. 13/641,065, filed as application No. PCT/US2011/032804 on Apr. 16, 2011, now abandoned.

(60) Provisional application No. 61/325,236, filed on Apr. 16, 2010.

(51) Int. Cl.

| | |
|---|---|
| *A01M 1/10* | (2006.01) |
| *A01N 33/00* | (2006.01) |
| *A01N 43/60* | (2006.01) |
| *A01N 61/00* | (2006.01) |
| *A23L 1/221* | (2006.01) |
| *G06F 19/00* | (2011.01) |
| *A01M 1/02* | (2006.01) |
| *A01M 1/14* | (2006.01) |
| *A01M 1/20* | (2006.01) |
| *A01M 1/22* | (2006.01) |

(52) U.S. Cl.
CPC ............. *A01N 43/60* (2013.01); *A01M 1/02* (2013.01); *A01M 1/10* (2013.01); *A01M 1/106* (2013.01); *A01M 1/145* (2013.01); *A01M 1/2011* (2013.01); *A01M 1/223* (2013.01); *A01N 33/00* (2013.01); *A01N 61/00* (2013.01); *A23L 1/221* (2013.01); *G06F 19/704* (2013.01); *G06F 19/707* (2013.01)

(58) Field of Classification Search
CPC . A61K 45/06; A61K 2300/00; A61K 31/506; A61K 31/5383; A61K 31/4985; A61K 31/519; A61K 31/5377; A61K 31/437; A61K 31/439; A61K 31/4439; A61K 31/444; A61K 31/497; A61K 31/137; A61K 31/197
See application file for complete search history.

(56) References Cited

U.S. PATENT DOCUMENTS

| | | | |
|---|---|---|---|
| 5,089,469 A | * | 2/1992 | Zampino ................ A01N 49/00 131/276 |
| 6,372,804 B1 | | 4/2002 | Ikemoto et al. |
| 2007/0142795 A1 | | 6/2007 | Cohen et al. |

OTHER PUBLICATIONS

Non-Final Office Action received for U.S. Appl. No. 13/641,065 mailed on Aug. 15, 2014, 9 pages.
International Preliminary Report on Patentability received for PCT Patent Application No. PCT/US2011/032804, mailed on Oct. 26, 2012, 9 pages.
International Search Report received for PCT Patent Application No. PCT/US2011/032804, mailed on Dec. 26, 2011, 5 pages.
International Written Opinion received for PCT Patent Application No. PCT/US2011/032804, mailed on Dec. 26, 2011, 7 pages.
Carey et al., "Odorant Reception in the Malaria Mosquito Anopheles Gambiae", Nature, 2010, pp. 1-7.
Gutierrez-Osuna Ricardo, "Pattern Analysis for Machine Olfaction: A Review", IEEE Sensors Journal vol. 2, No. 3, Jun. 2002, pp. 189-202.
Jones et al., "Two Chemosensory Receptors Together Mediate Carbon Dioxide Detection in Drosophila", Nature, vol. 445, Jan. 4, 2007, pp. 86-90.
Praag et al., "Steam Volatile Aroma Constituents of Roasted Cocoa Beans", Journal of Agricultural Food Chemestry, vol. 16, No. 6, Nov.-Dec. 1968, pp. 1005-1008.
Saito et al., "Odor Coding by a Mammalian Receptor Repertoire", Science Signaling, vol. 2, No. 60, Mar. 3, 2009, 28 pages.

* cited by examiner

*Primary Examiner* — Audrea Buckley
(74) *Attorney, Agent, or Firm* — Morrison & Foerster LLP

(57) ABSTRACT

The disclosure provides compounds useful as insect repellents and compositions comprising such repellents. The disclosure further provides insect traps and method for identifying ligands and cognates for biological molecules.

35 Claims, 60 Drawing Sheets

| | Distance Metrics | Descriptor Sets | Activity Thresholds |
|---|---|---|---|
| 1 | Euclidean | Cerius2 | Cluster Based |
| 2 | Euclidean | Cerius2 | 200,150,100,50 |
| 3 | Euclidean | Dragon | Cluster Based |
| 4 | Euclidean | Dragon | 200,150,100,50 |
| 5 | Euclidean | Dragon+Cerius2 | Cluster Based |
| 6 | Euclidean | Dragon+Cerius2 | 200,150,100,50 |
| 7 | Spearman | Cerius2 | Cluster Based |
| 8 | Spearman | Cerius2 | 200,150,100,50 |
| 9 | Spearman | Dragon | Cluster Based |
| 10 | Spearman | Dragon | 200,150,100,50 |
| 11 | Spearman | Dragon+Cerius2 | Cluster Based |
| 12 | Spearman | Dragon+Cerius2 | 200,150,100,50 |
| 13 | Pearson | Cerius2 | Cluster Based |
| 14 | Pearson | Cerius2 | 200,150,100,50 |
| 15 | Pearson | Dragon | Cluster Based |
| 16 | Pearson | Dragon | 200,150,100,50 |
| 17 | Pearson | Dragon+Cerius2 | Cluster Based |
| 18 | Pearson | Dragon+Cerius2 | 200,150,100,50 |

FIG. 2

Receptors with strong activators

Or7a (>150 s/sec)

Or9a (>151 s/sec)

Or22a (>188 s/sec)

Or35a (>162 s/sec)

Or49b (>101 s/sec)

Or59b (>130 s/sec)

Activity scale
-52  288

Receptors with strong activators

Or10a (>123 s/sec)

Or19a (>123 s/sec)

Or43b (>132 s/sec)

Or47a (>183 s/sec)

Or67a (>160 s/sec)

Or67c (>109 s/sec)

Activity scale  −52  288

Receptors with strong activators

Or82a (>55 s/sec)

Or85a (>125 s/sec)

Or85b (>163 s/sec)

Or98a (>188 s/sec)

Activity scale
-52  288

Receptors without Weak activators
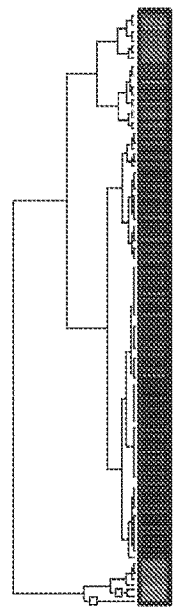
FIG. 3Q  Or2a (>51 s/sec)
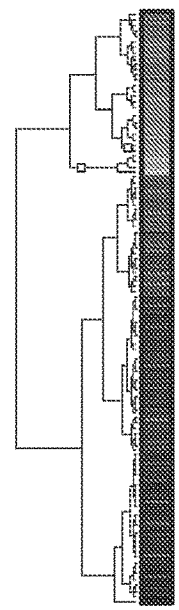
FIG. 3R  Or23a (>51 s/sec)
FIG. 3S  Or43a (>96 s/sec)
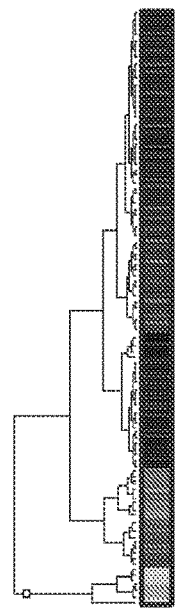
FIG. 3T  Or85f (>63 s/sec)
Activity scale  -31   133

Legend for FIGS. 6A-6D

Strong Predictions

Legend for FIGS. 6E-6H

*Strong Predictions*
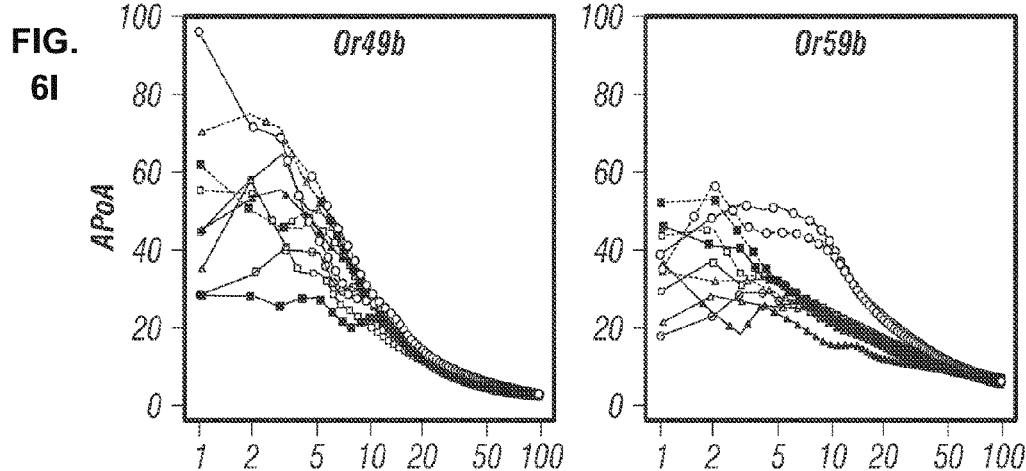
FIG. 6I / FIG. 6J
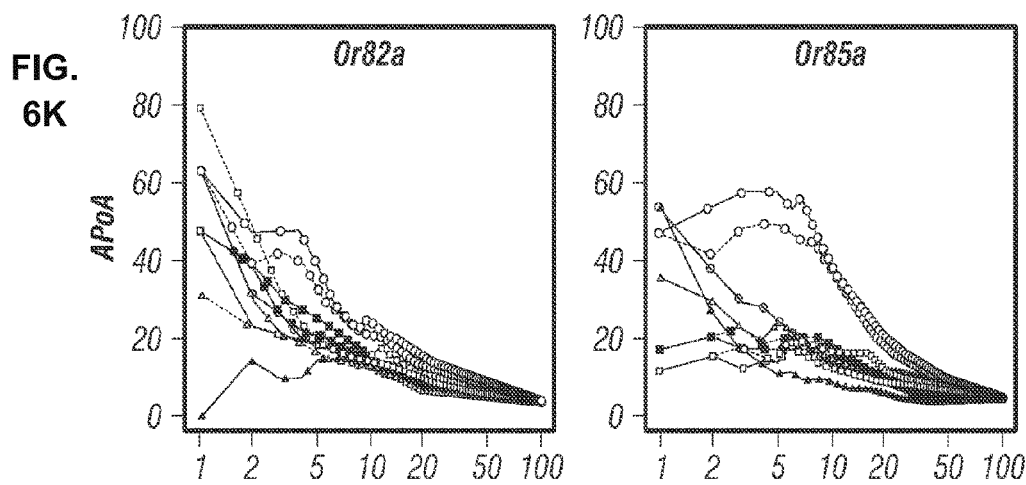
FIG. 6K / FIG. 6L
Legend for FIGS. 6I-6L
- Optimized Method 5
- Optimized Method 11
- MCS
- Atom Pair
- Cerius (Euclid)
- Cerius (Spearman)
- Previous (Euclid)
- Previous (Spearman)
- Dragon (Euclid)
- Dragon (Spearman)

*Strong Predictions*

*Number of Compounds Considered*   *Number of Compounds Considered*

- ○ *Optimized Method 5*
- ○ *Optimized Method 11*
- ▲ *MCS*
- ○ *Atom Pair*
- □ *Cerius (Euclid)*
- □ *Cerius (Spearman)*
- ■ *Previous (Euclid)*
- ■ *Previous (Spearman)*
- △ *Dragon (Euclid)*
- △ *Dragon (Spearman)*

Legend for FIGS. 6M-6P

*Fishing Predictions*

*Number of Compounds Considered    Number of Compounds Considered*

—○— Optimized Method 5   —□— Cerius (Euclid)    —▲— Dragon (Euclid)
--○-- Optimized Method 11  --□-- Cerius (Spearman)  --▲-- Dragon (Spearman)
—▲— MCS                    —✳— Previous (Euclid)
—◇— Atom Pair              --✳-- Previous (Spearman)

Legend for FIGS. 6Q-6T

FIG. 7

| | 2a | 7a | 9a | 10a | 19a | 22a | 23a | 35a | 43a | 43b | 47a | 49b | 59b | 67a | 67c | 82a | 85a | 85b | 85f | 98a | Percent Optimal |
|---|---|---|---|---|---|---|---|---|---|---|---|---|---|---|---|---|---|---|---|---|---|
| Cerius2 | | | | | | | | | | | | | | | | n.d. | | | | | 0% |
| Dragon | | | | | | | | | | | | | | | | n.d. | | | | | 0% |
| MCS | | | | | | | | | | | | | | | | n.d. | | | | | 0% |
| AP | | | | | | | | | | | | | | | | n.d. | | | | | 0% |
| Previous | | | | | | | | | | | | | | | | n.d. | | | | | 0% |
| Optimized | 5 | 5 | 5 | 11 | 5 | 5 | 5 | 5 | 11 | 5 | 5 | 11 | 5 | 5 | 5 | n.d. | 5 | 5 | 5 | 11 | 100% |

Ors with Previously Known Strong Ligands

Or7a (Euclidean)

Or9a (Euclidean)

Or22a (Euclidean)

Or35a (Euclidean)

Or49b (Spearman)

Or59b (Euclidean)

Activity scale  -52  288

Ors with Previously Known Strong Ligands

Or10a (Spearman)

Or19a (Euclidean)

Or43b (Euclidean)

Or47a (Spearman)

Or67a (Euclidean)

Or67c (Euclidean)

Activity scale −52 288

Ors with Previously Known Strong Ligands
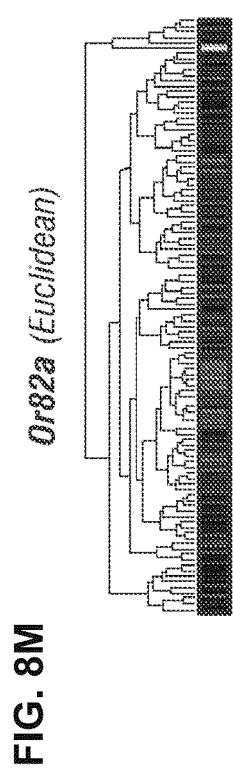
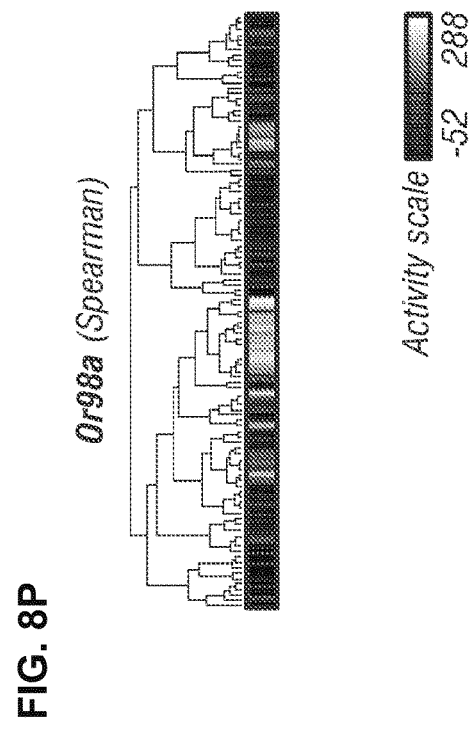
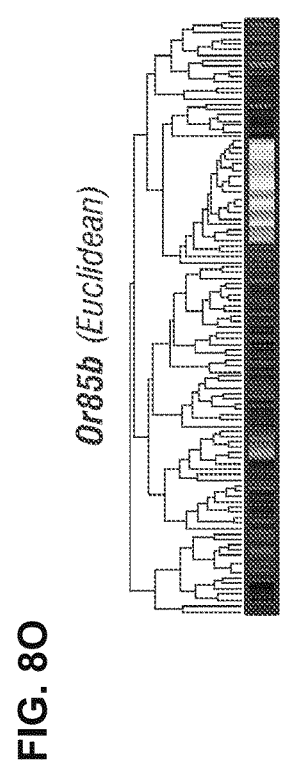
FIG. 8M — Or82a (Euclidean)
FIG. 8N — Or85a (Euclidean)
FIG. 8O — Or85b (Euclidean)
FIG. 8P — Or98a (Spearman)
Activity scale -52 — 288

Ors with Previously Known Weak Ligands
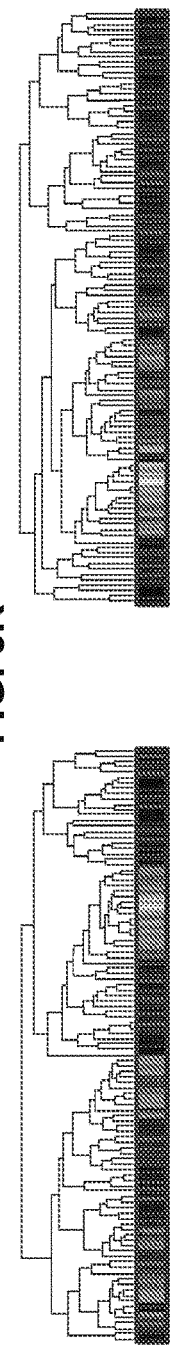
FIG. 8Q Or2a (Euclidean)
FIG. 8R Or23a (Euclidean)
FIG. 8S Or43a (Spearman)
FIG. 8T Or85f (Euclidean)
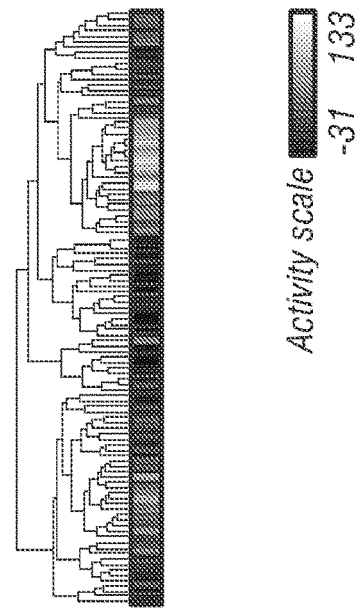
Activity scale −31 133

FIG. 12D

| Classific. | Or7a | Or10a | Or22a | Or47a | Or49b | Or59b | Or85a | Or85b | Or98a | Ab1A | Total |
|---|---|---|---|---|---|---|---|---|---|---|---|
| Ligands | 87.5 | 31.25 | 89.47 | 38.89 | 27.27 | 90.61 | 92.31 | 85.72 | 100.0 | 100.0 | 100.00 |
| Agonists (>50 spike /sec) | 62.5 | 31.25 | 84.21 | 33.33 | 18.18 | 63.64 | 69.23 | 66.67 | 91.67 | 94.12 | 61.48 |
| Agonists (>100 spike/sec) | 31.25 | 12.50 | 5.89 | 11.11 | 9.09 | 36.26 | 53.85 | 47.62 | 66.67 | 82.35 | 40.87 |
| Inhib. | 25.0 | 0.00 | 5.26 | 5.56 | 9.09 | 27.27 | 23.08 | 19.05 | 8.22 | 5.88 | 12.85 |

All values are percent.

*FIG. 14*

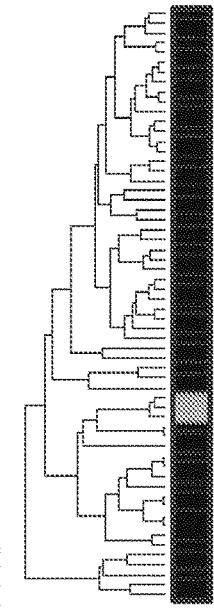
FIG. 17M
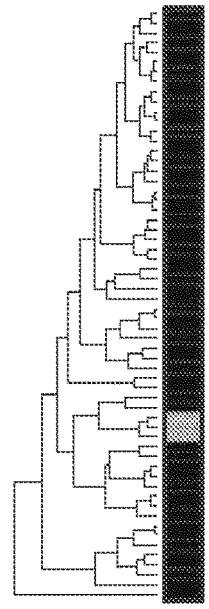
FIG. 17O
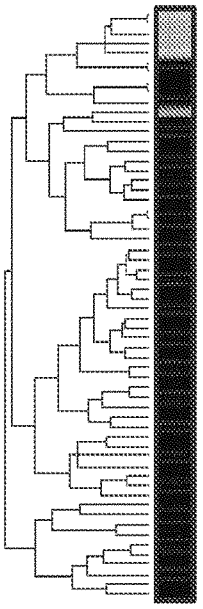
FIG. 17Q
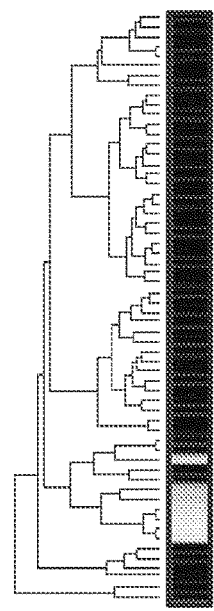
FIG. 17N
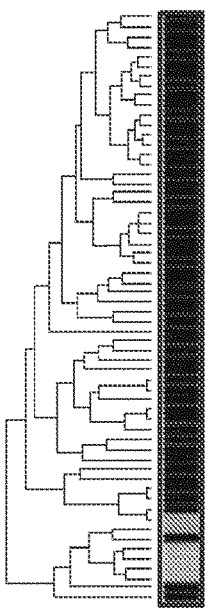
FIG. 17P
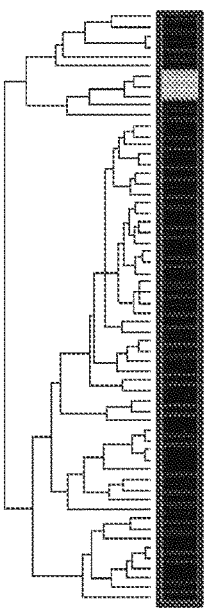
FIG. 17R
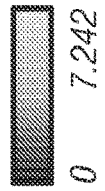

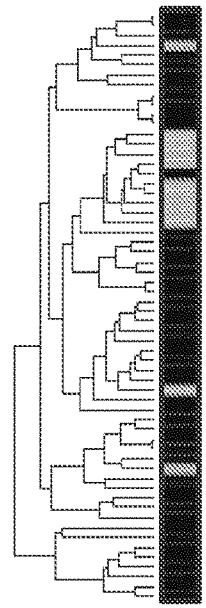
FIG. 17S MOR250-1
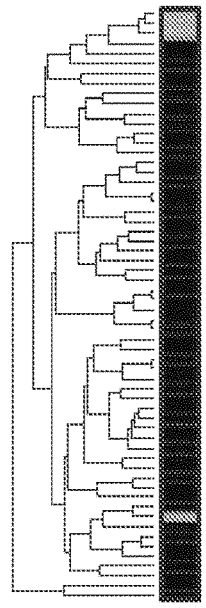
FIG. 17U MOR261-1
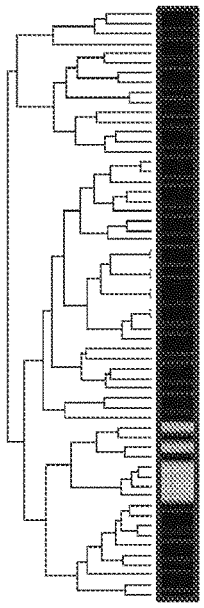
FIG. 17W MOR277-1
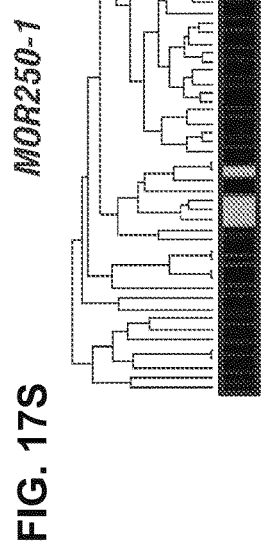
FIG. 17T MOR256-17
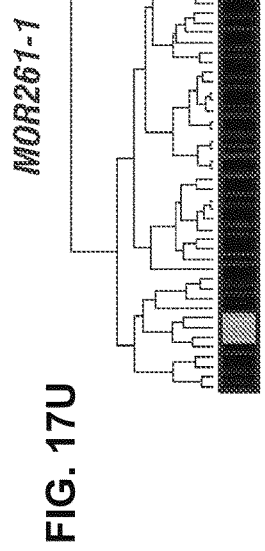
FIG. 17V MOR268-1
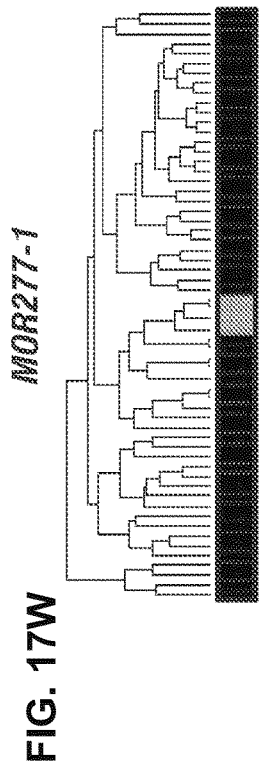
FIG. 17X MOR30-1

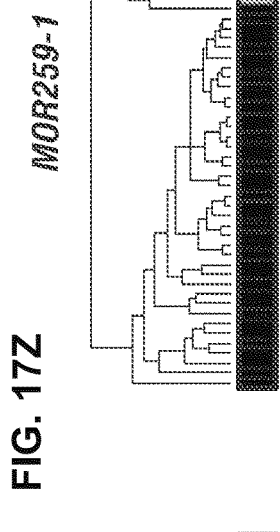
FIG. 17Y
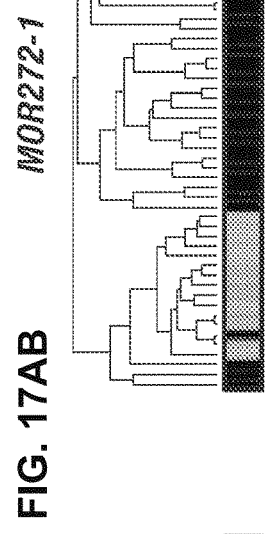
FIG. 17AA
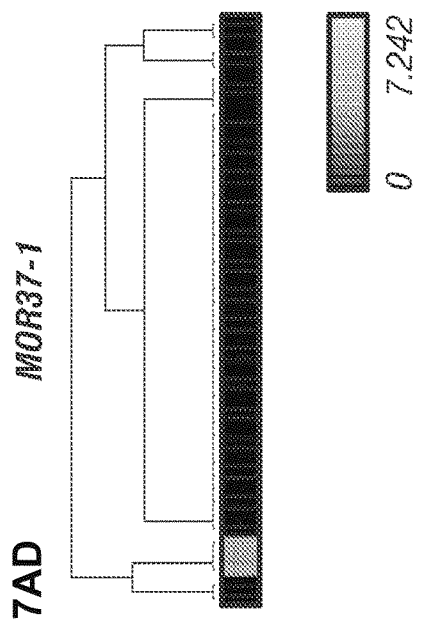
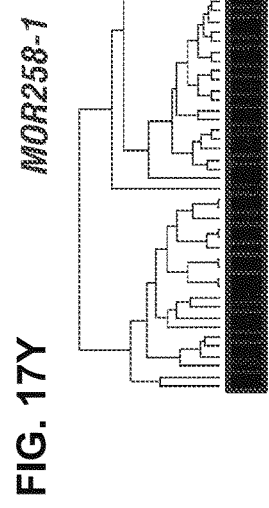
FIG. 17Z
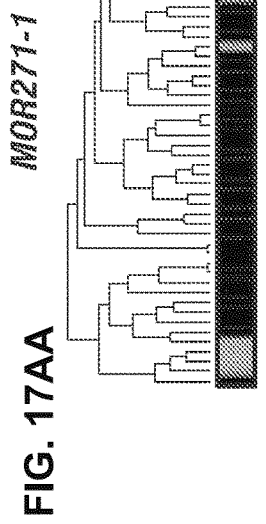
FIG. 17AB
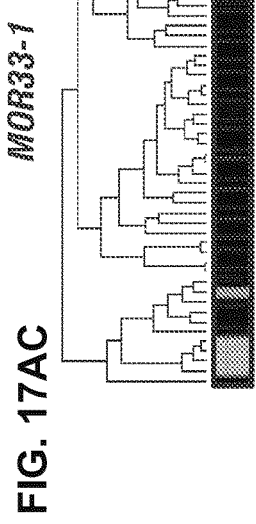
FIG. 17AD

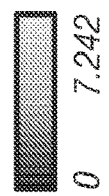
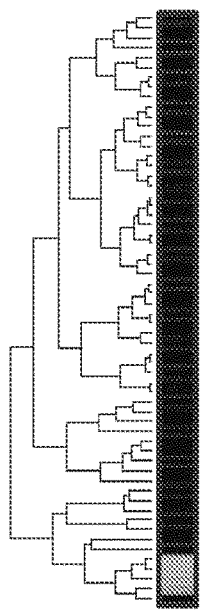
FIG. 17AE
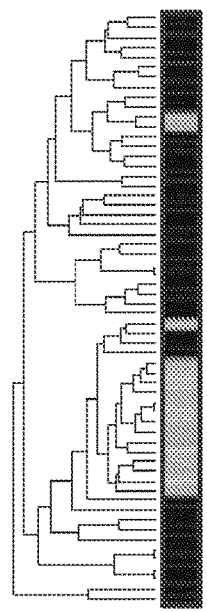
FIG. 17AF
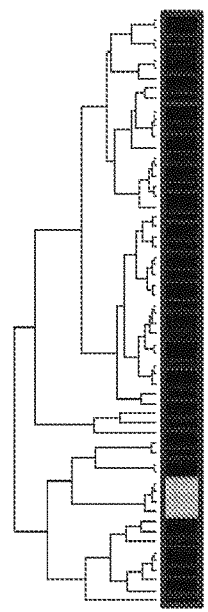
FIG. 17AG

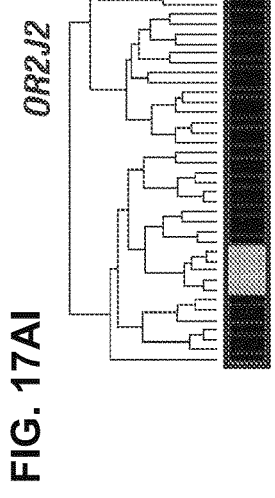
FIG. 17AH
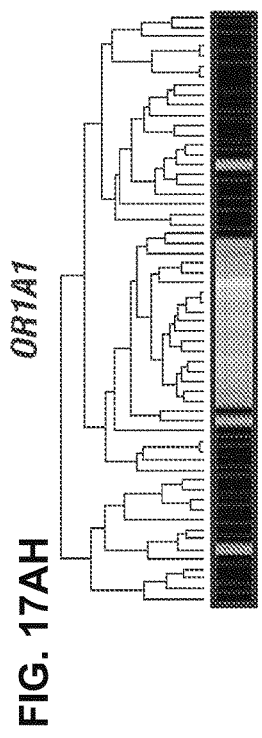
FIG. 17AJ
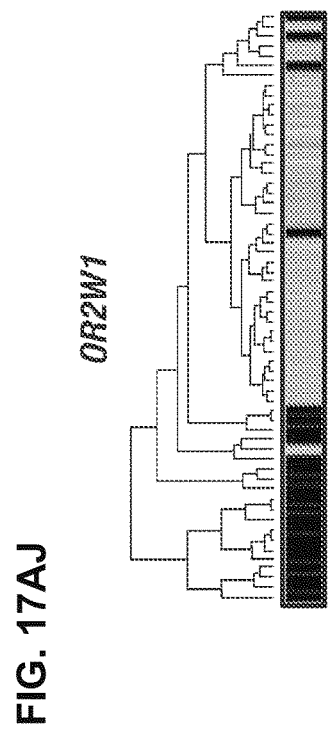
FIG. 17AI
FIG. 17AK
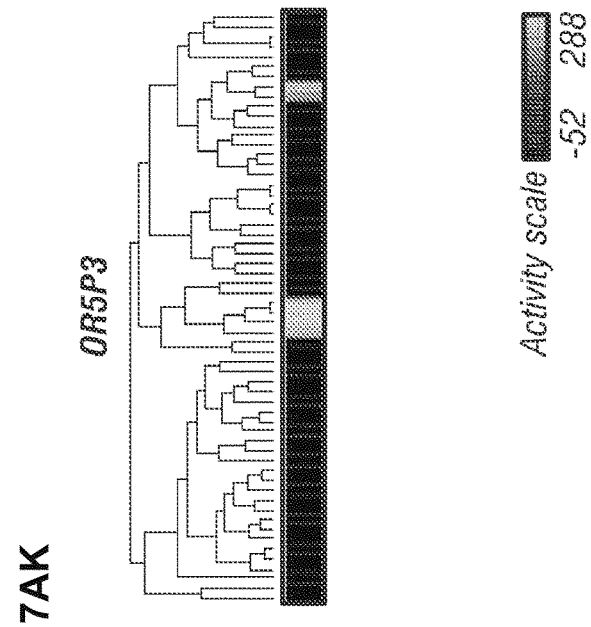

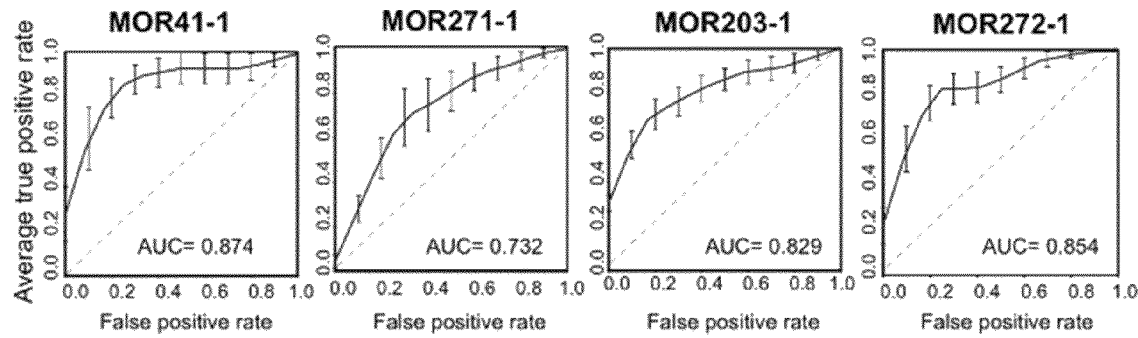
*FIG. 18A*   *FIG. 18B*   *FIG. 18C*   *FIG. 18D*
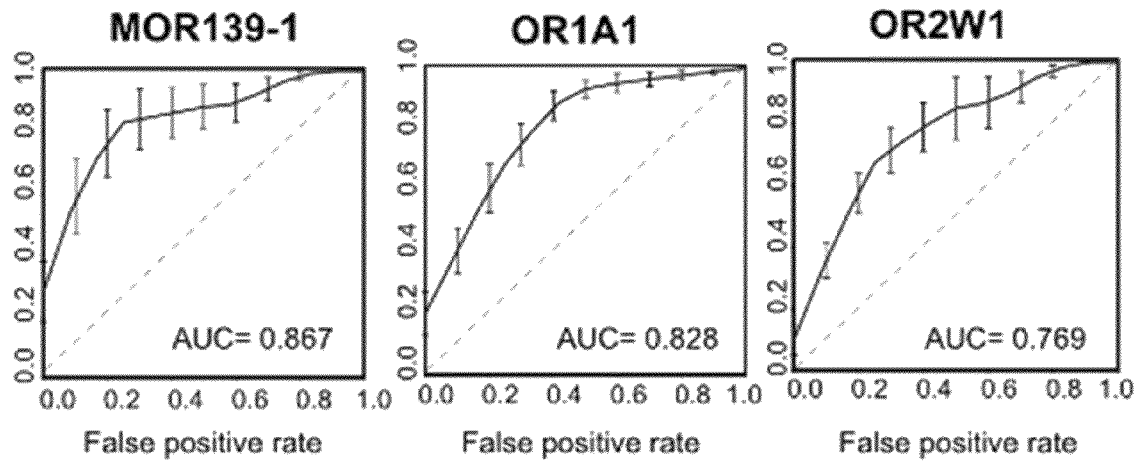
*FIG. 18E*   *FIG. 18F*   *FIG. 18G*

Calculating accumulated percentage of actives (APoA)

| Compounds clustered by descriptor distances | Calculate APoAs for all Actives | | | | Average APoAs from all actives | | |
|---|---|---|---|---|---|---|---|
| | Sort by active A | Calculate APoA | Sort by active F | Calculate APoA | Individual APoAs from each active | | Mean APoA |
| | | | | | A  B  C  F | | |
| A | A Reference Active | | F Main Active | | | | |
| B | B | 1/1 ··· | E | 0/1 | 1/1 1/1 1/1 0/1 | | 3/4 |
| C | C | 2/2 ··· | D | 0/2 | 2/2 2/2 2/2 0/2 | | 6/8 |
| D | D | 3/3 ··· | C | 1/3 | 2/3 2/3 2/3 1/3 | | 7/12 |
| E | E | 2/4  Repeat | B | 2/4 | 2/4 2/4 2/4 2/4 | Calculate Mean | 8/16 |
| F | F | 3/5  for each | A | 3/5 | 3/5 3/5 3/5 3/5 | | 12/20 |
| G | G | 3/6   active | G | 3/6 | 3/6 3/6 3/6 3/6 | | 12/24 |
| H | H | 3/7 ··· | H | 3/7 | 3/7 3/7 3/7 3/7 | | 12/28 |
| I | I | 3/8 ··· | I | 3/8 | 3/8 3/8 3/8 3/8 | | 12/32 |
| J | J | 3/9 ··· | J | 3/9 | 3/9 3/9 3/9 3/9 | | 12/36 |

*FIG. 21A*

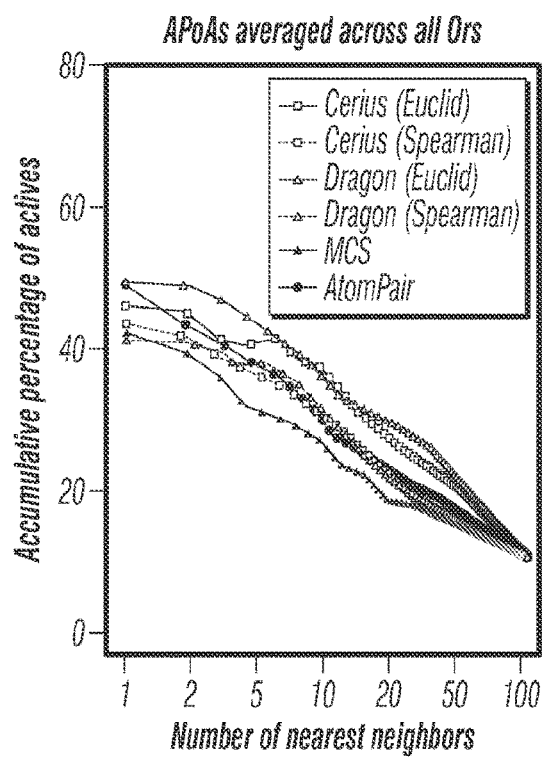

*FIG. 21B*

Comparison of molecular descriptor method with highest APoA for each Or

| | 2a | 7a | 9a | 10a | 19a | 22a | 23a | 35a | 42a | 43b | 47a | 49b | 56b | 67a | 67c | 82a | 85a | 86b | 86f | 88a | Percent Optional |
|---|---|---|---|---|---|---|---|---|---|---|---|---|---|---|---|---|---|---|---|---|---|
| Cerius2 | | E | | | | | E | | E | | | | S | | E | | | | | | 26% |
| Dragon | S | | E | E | E | E | | E | | E | | S | | E | | E | E | E | E | E | 70% |
| MCS | | | | | | | | | | | | | | | | | | | | | 0% |
| AP | | | | | | | | | | | T | | | | | | | | | | 5% |

FIG. 21C

Compound activity classification through activity clustering
Receptors with strong activators Or7a (>150 s/sec)

Or9a (>151 s/sec)

Or22a (>188 s/sec)

Or35a (>162 s/sec)

Or49b (>101 s/sec)

Or59b (>130 s/sec)

Activity scale
-52   288

Compound activity classification through activity clustering
Receptors with strong activators
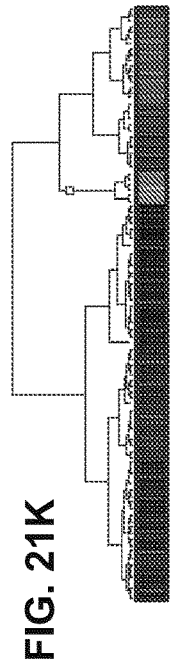
FIG. 21J
Or10a (>123 s/sec)
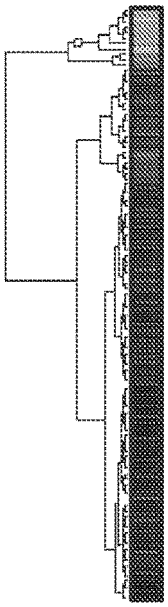
FIG. 21K
Or19a (>123 s/sec)
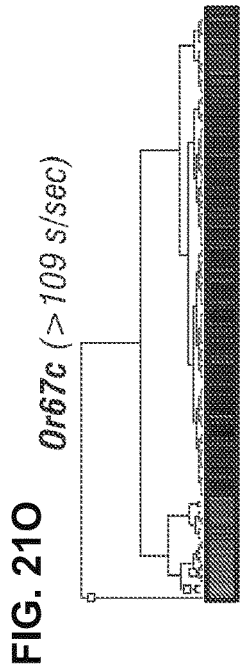
FIG. 21M
Or47a (>183 s/sec)
Activity scale
−52    288
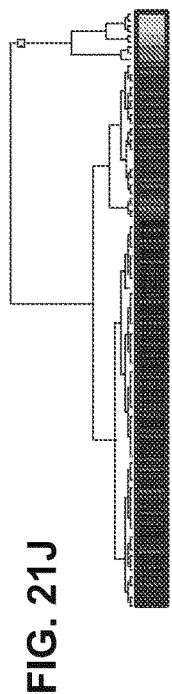
FIG. 21L
Or43b (>132 s/sec)
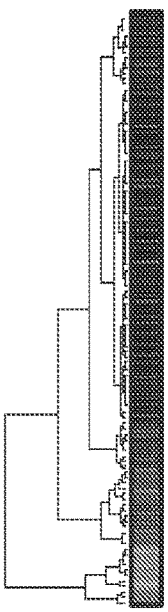
FIG. 21N
Or67a (>160 s/sec)
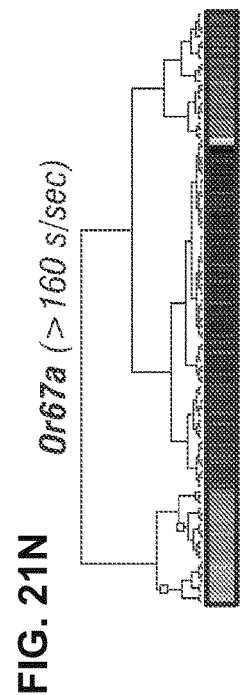
FIG. 21O
Or67c (>109 s/sec)

Compound activity classification through activity clustering
Receptors with strong activators
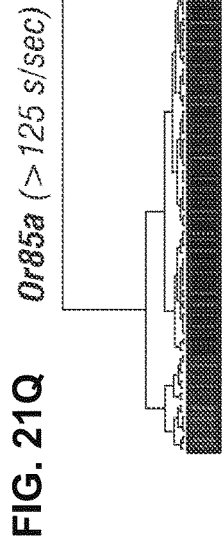
FIG. 21P  Or82a (>55 s/sec)
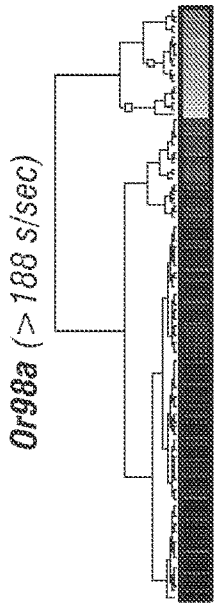
FIG. 21Q  Or85a (>125 s/sec)
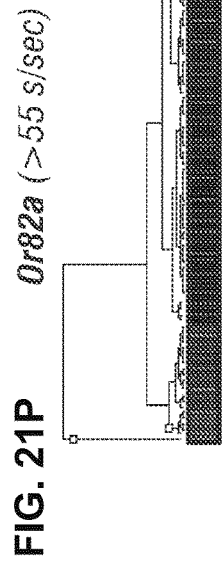
FIG. 21R  Or85b (>163 s/sec)
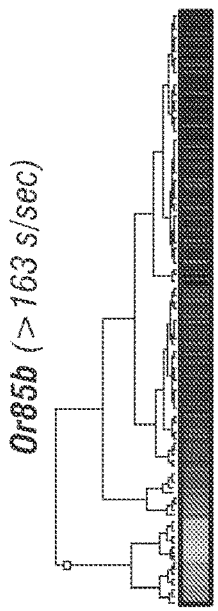
FIG. 21S  Or98a (>188 s/sec)
Activity scale
−52  288

Receptors without Weak activators
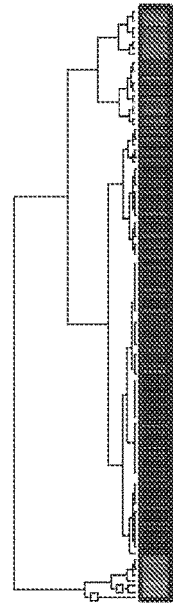
FIG. 21T Or2a (>51 s/sec)
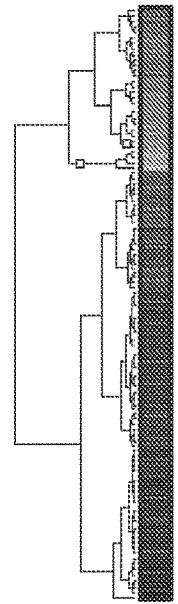
FIG. 21U Or23a (>51 s/sec)
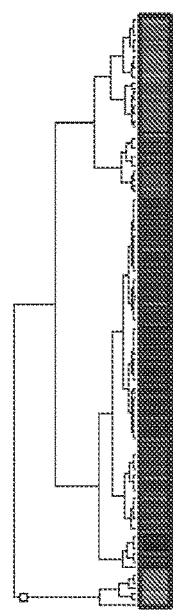
FIG. 21V Or43a (>96 s/sec)
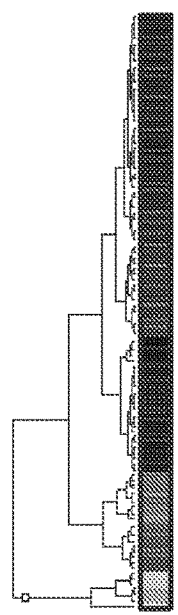
FIG. 21W Or85f (>63 s/sec)
Activity scale
−31  133

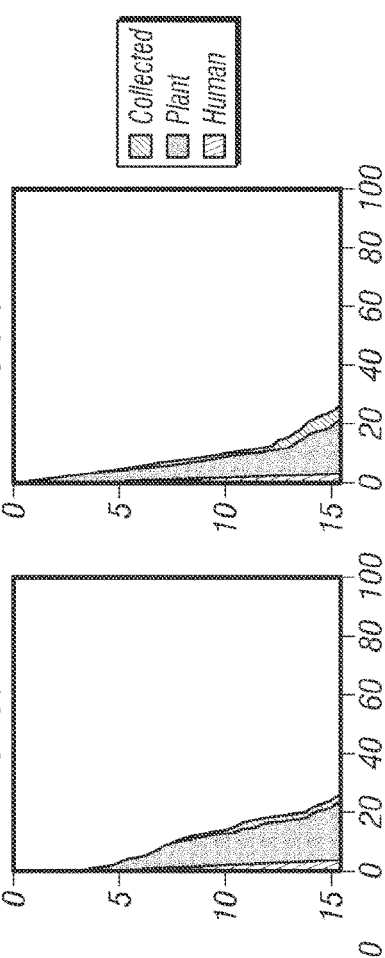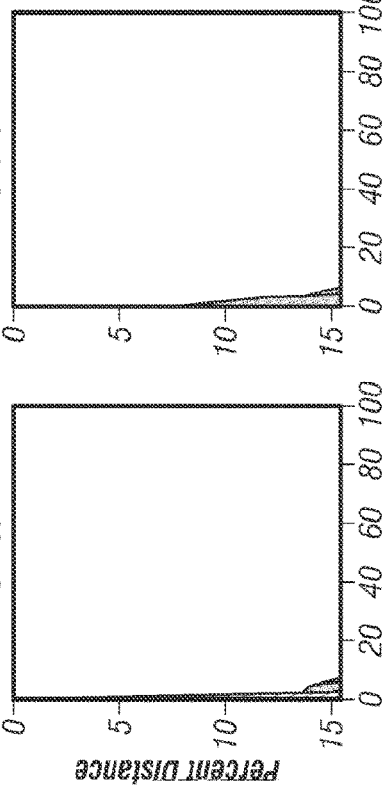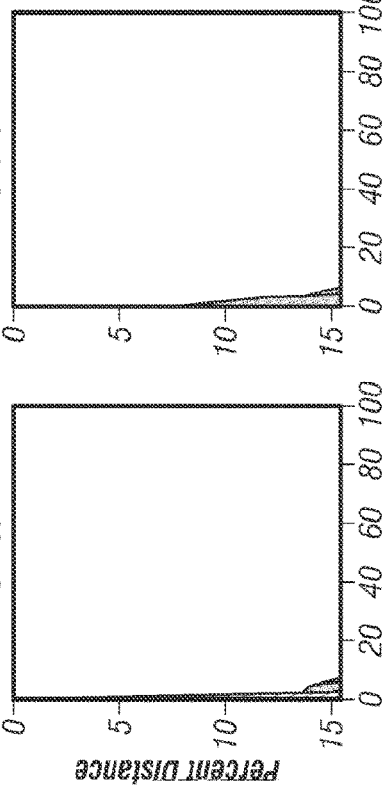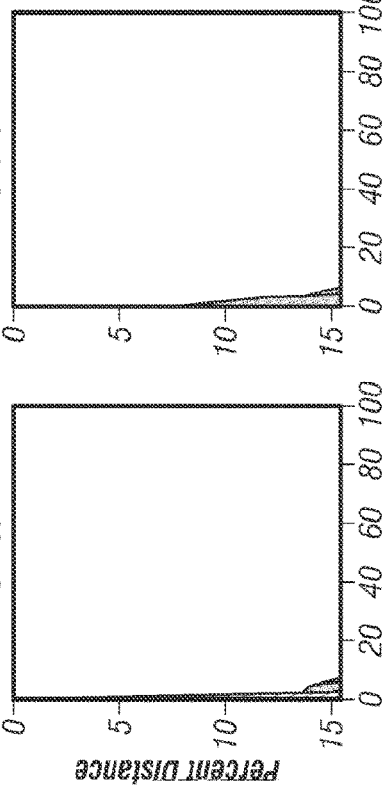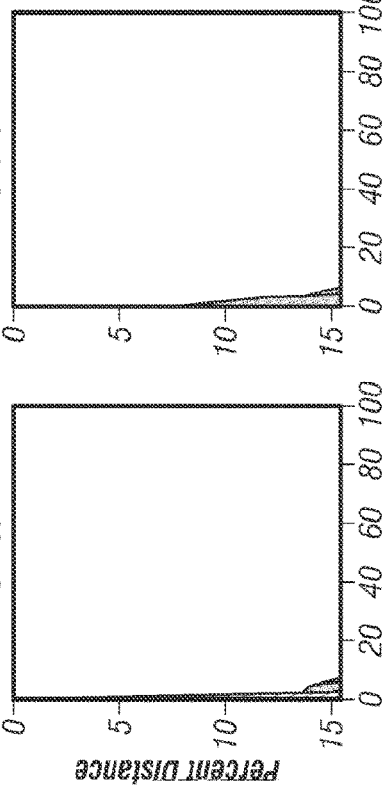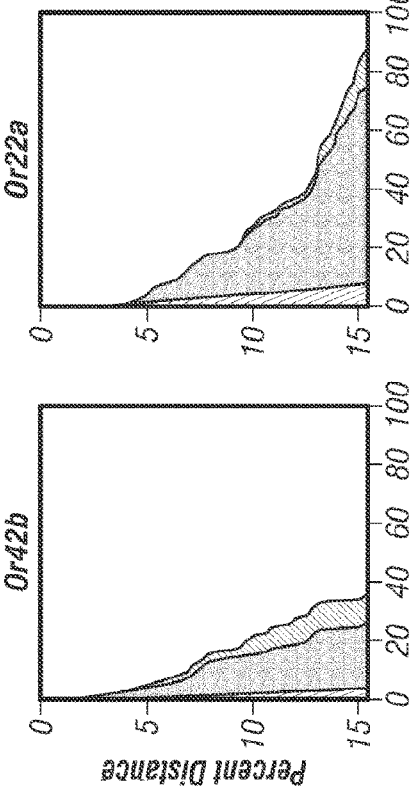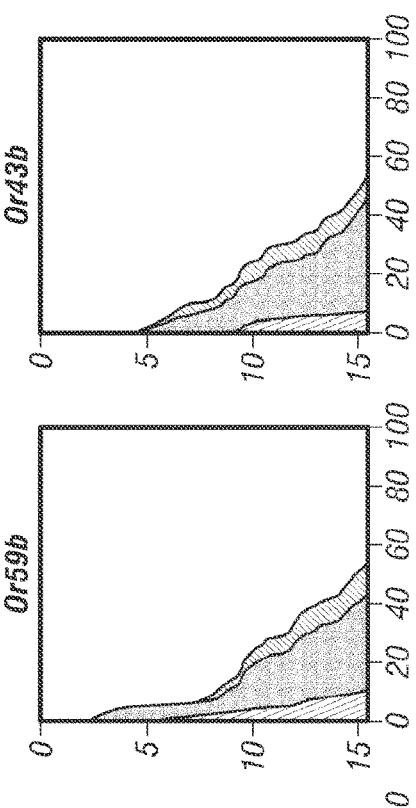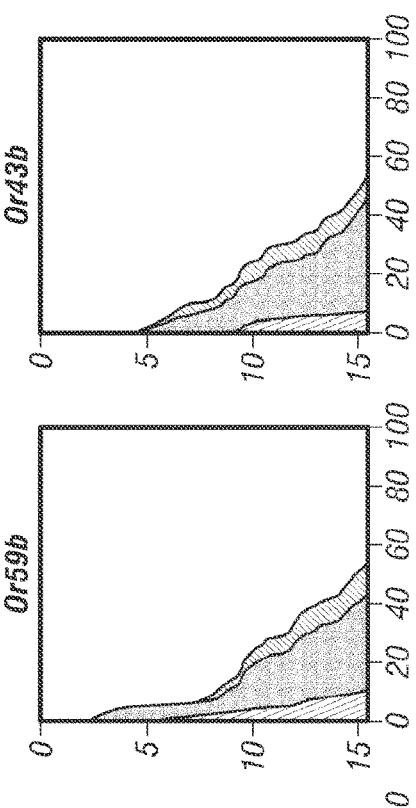

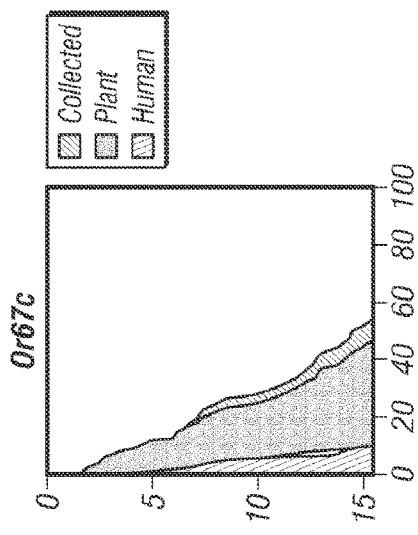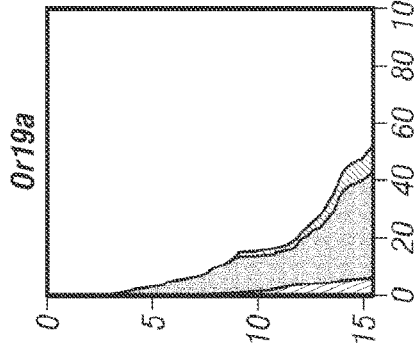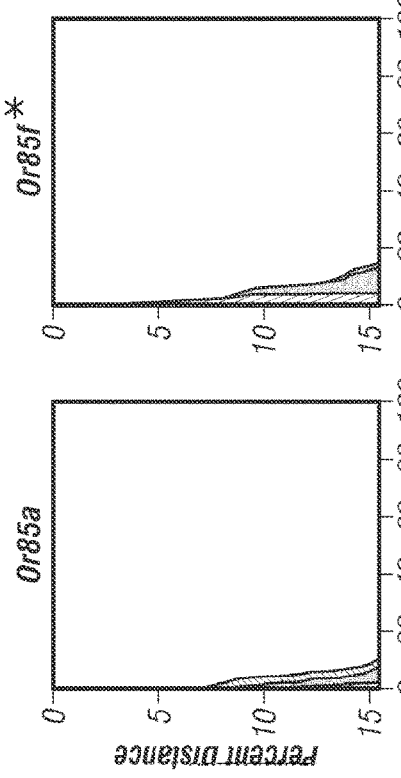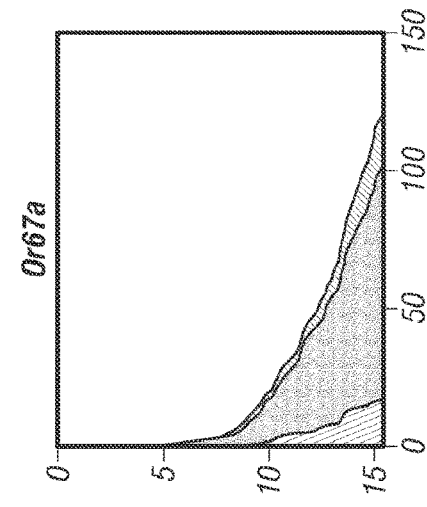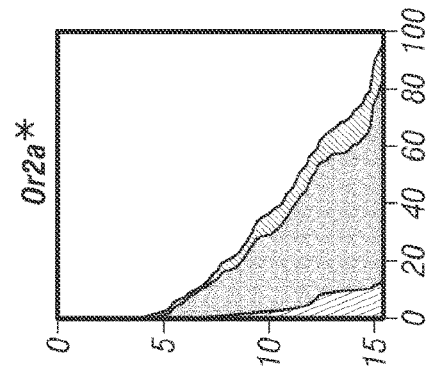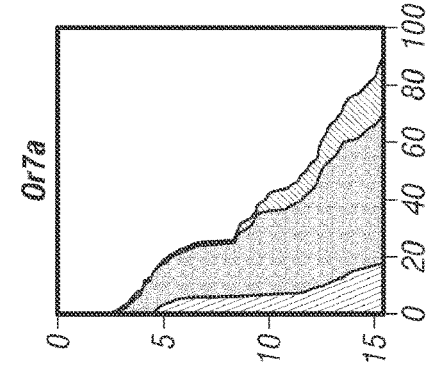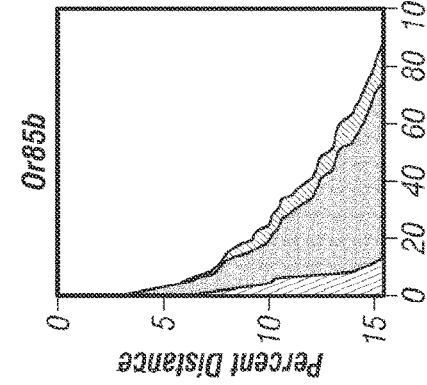
FIG. 23I  FIG. 23J  FIG. 23K  FIG. 23L
FIG. 23M  FIG. 23N  FIG. 23O  FIG. 23P

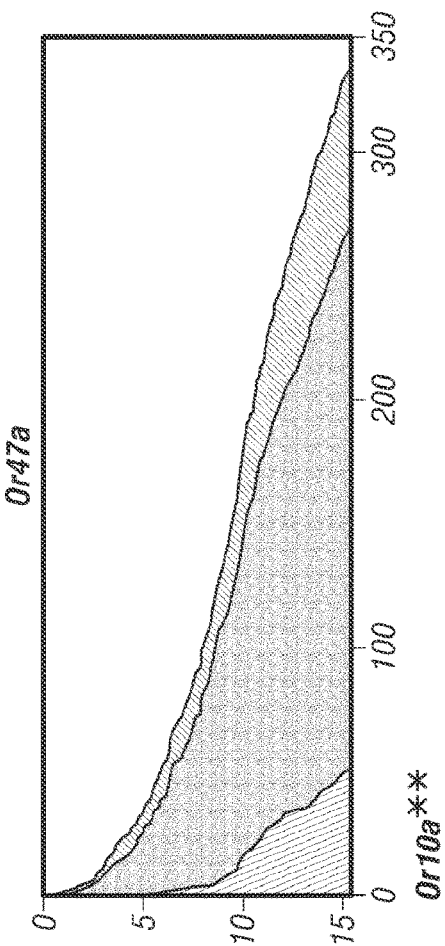
FIG. 23T
FIG. 23U
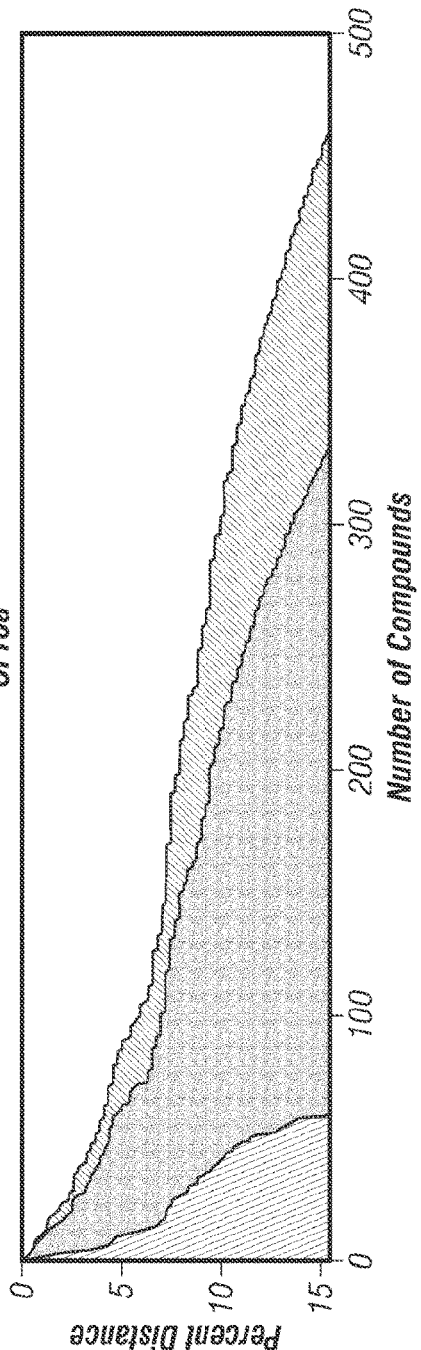
FIG. 23V

LIGANDS FOR ODOR RECEPTORS AND OLFACTORY NEURONS

CROSS REFERENCE TO RELATED APPLICATIONS

This application is a continuation application of U.S. application Ser. No. 13/641,065, which is a national phase patent application of PCT/US2011/032804, filed Apr. 16, 2011, which claims priority to and benefit of U.S. Patent Application No. 61/325,236, filed Apr. 16, 2010, the disclosures of which are hereby incorporated by reference in their entireties.

TECHNICAL FIELD

The disclosure provides compounds useful as insect repellents and compositions comprising such repellents. The disclosure further provides compounds useful as insect attractants and compositions comprising such attractants. The disclosure further provides compounds useful as insect traps.

BACKGROUND

Numerous insects are vectors for disease. Mosquitoes in the genus *Anopheles* are the principle vectors of malaria, a disease caused by protozoa in the genus *Trypanosoma*. *Aedes aegypti* is the main vector of the viruses that cause Yellow fever and Dengue. Other viruses, the causal agents of various types of encephalitis, are also carried by *Aedes* spp. mosquitoes. *Wuchereria bancrofti* and *Brugia malayi*, parasitic roundworms that cause filariasis, are usually spread by mosquitoes in the genera *Culex, Mansonia*, and *Anopheles*.

Horse flies and deer flies may transmit the bacterial pathogens of tularemia (*Pasteurella tularensis*) and anthrax (*Bacillus anthracia*), as well as a parasitic roundworm (*Loa loa*) that causes loiasis in tropical Africa.

Eye gnats in the genus *Hippelates* can carry the spirochaete pathogen that causes yaws (*Treponema pertenue*), and may also spread conjunctivitis (pinkeye). Tsetse flies in the genus *Glossina* transmit the protozoan pathogens that cause African sleeping sickness (*Trypanosoma gambiense* and *T. rhodesiense*). Sand flies in the genus *Phlebotomus* are vectors of a bacterium (*Bartonella bacilliformis*) that causes Carrion's disease (oroyo fever) in South America. In parts of Asia and North Africa, they spread a viral agent that causes sand fly fever (pappataci fever) as well as protozoan pathogens (*Leishmania* spp.) that cause Leishmaniasis.

SUMMARY

The methods of the disclosure provide an odor receptor optimized descriptor-based in silico screen of chemical space. The methods of the disclosure are useful for identifying ligands for odor receptors (Ors), greatly reducing the number of compounds needing to be physically tested through methods such as single-unit electrophysiology or cell imaging. In addition a very large number of odorants can be computationally predicted in a single run of a chemical informatics pipeline, thus enabling one to select the appropriate chemicals to use as ligand for target odor receptor based on other important considerations that can be easily determined such as volatility, solubility, toxicity, costs, environmental safety or other physico-chemical properties. As most approaches to ligand identification require physically testing odorants using expensive assays and purchasing large collections of test chemicals is very expensive, the in silico approaches described herein provides the ability to predict ligands with high accuracy greatly reduces the cost of identifying novel ligands.

The disclosure provides a method of identifying a ligand for a biological molecule comprising: (a) identifying a known ligand or set of known ligands for a biological molecule, or identifying a compound which causes a specific biological activity, (b) identifying a plurality of descriptors for the known ligand or compound, (c) using a Sequential Forward Selection (SFS) descriptor selection algorithm to incrementally create a unique optimized descriptor subsets from the plurality of descriptors for the known ligand or compound, (d) identifying a putative ligand or compound that best-fits the unique optimized descriptor subset, and (e) testing the putative ligand or compound in a biological assay comprising the biological molecule wherein a change in activity of the biological molecule compared to the molecule without the putative ligand is indicative of a ligand the interacts with the biological molecule. The method above can be applied to any number of biological molecules that have a binding cognate. For example, the biological molecule can be a receptor, a ligand gated ion channel or G-protein coupled receptor. In a specific embodiment, the receptor is an odor receptor. In another embodiment, the receptor is expressed in a cell. In any of the foregoing embodiments, the plurality of descriptors are selected from the group consisting of distance metrics, descriptor sets, and activity thresholds. Further, in any of the foregoing embodiments, the distance metrics are selected from the group consisting of Euclidean, Spearman, and Pearson coefficients. In any of the foregoing embodiment, the descriptor sets are selected from Dragon, Cerius2, and a combined Dragon/Cerius2 set. In yet another embodiment, which can be implemented and used with any of the foregoing embodiments, two activity threshold methods are compared. In a further embodiment, the activity threshold comprises spike activity cutoffs and a cluster-based cutoff. In yet another embodiment of any of the foregoing the identifying further comprises selecting a putative ligand or compound with in a desired Euclidian distance of the known ligand or biological compound. For example, the Euclidian distance is about 0.001 to about 6.60 from a known ligand or cluster of ligands in chemical space. In another embodiment, the ligand binds to a $CO_2$ receptor and wherein the ligand has a Euclidian distance of about 0.001 to 6.60 from a known ligand for a $CO_2$ receptor. In yet another embodiment, the putative ligand is selected from a compound in Table 9 and 10. In another embodiment of any of the foregoing the descriptors are selected from the descriptors in Table 7 and 8. The methods described above can utilize a known ligand or set of known ligands identified through electrophysiology, imaging assays, or binding assays. The methods above can be used to screen a library of compounds. The method may be fully automated or may output the putative ligand or compound to a user who may then perform a biological assay. The biological assay can use various indicators for determining a ligand (e.g., an agonist or antagonist ligand) including a biological assay measuring a change in spike frequency, florescence intensity, or binding affinity. The odor receptor may be a vertebrate or invertebrate odor receptor. In yet another embodiment of any of the foregoing, the putative ligands or compounds are soluble ligands or compounds and the receptor is a gustatory receptor expressed by an invertebrate species or a gustatory receptor neurons present in an invertebrate. In yet another embodiment of any of the foregoing, the putative ligands or compounds the receptor is a gustatory receptor expressed by an invertebrate species or a gustatory receptor neurons present in an invertebrate. In yet another embodiment of any of the foregoing, the putative ligands or compounds the receptor is a gustatory receptor expressed by an invertebrate species or a gustatory receptor neurons present in an invertebrate. In yet another embodiment of any of the foregoing, the putative ligands or compounds the receptor is a gustatory receptor expressed by an mammal species or a gustatory receptor neurons present in an mammal. In yet another embodiment of any of the foregoing, the putative ligands or compounds the receptor is a gustatory receptor expressed by an mammal species or a gustatory receptor neurons present in an mammal. In yet another embodiment of any of the foregoing, the putative ligands or compounds the receptor is a gustatory receptor expressed by an mammal species or a gustatory receptor neurons present in an mammal.

The disclosure also provides a ligand or compound identified by the method of any of the foregoing claims. In one embodiment, the compound/ligand is set forth in Table 4, 6, 9 and 10. The ligand or compound can be an odor receptor ligand having a desired Euclidian distance from a cluster of known ligands defined by structural-data information wherein the compound reversibly or irreversibly binds an odor receptor.

The disclosure also provides use of a ligand or compound identified by the methods of the disclosure or a ligand or compound in Table 4, 6, 9 or 10 to lure insect species into traps by virtue of activating odor receptors or odor receptor neurons. In an embodiment, the trap is suction based, light based, electric current based. In another embodiment, the ligand or compound is used the preparation of a topical cream, spray or dust present within or near a trap entrance. The ligand or compound can be used in a vapor emitted from vaporizers, treated mats, treated pods, absorbed material, cylinders, oils, candles, wicked apparatus, fans, within or near trap entrances. The ligand or compound can be used a repellant or attractant. The repellant or attractant can be used in a cream, lotion, spray, dust, vapor emitter, candle, oil, wicked apparatus, fan, or vaporizer. The ligand or compound can be used to affect mating behavior.

The disclosure also provides a composition comprising a ligand or compound of as described above in a cream, oil, lotion, spray, perfume, cologne, fragrance, deodorant, masking agent, candle, vaporizer, and the like.

The methods of the disclosure can also be used to identify food additives of flavorants.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIG. 1 shows a schematic of a method of the disclosure used to identify an optimized descriptor subsets for each Or.

FIG. 2 shows a variety of selection method combinations.

FIG. 7 shows a comparison of highest molecular descriptor APoA for each Or.

Figure 12D:
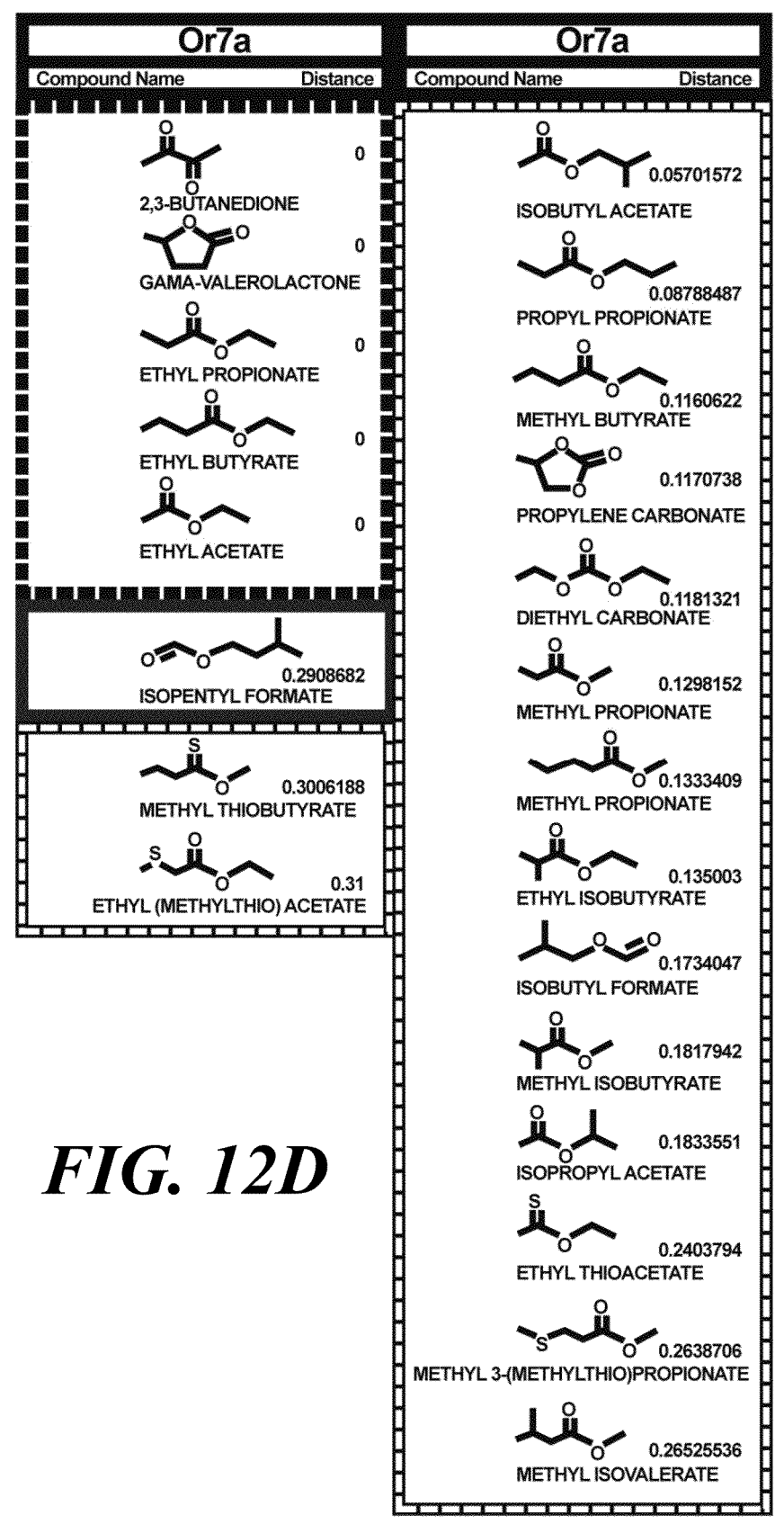

FIGS. 12A-12F show table 2, *drosophila* compounds tested for activity: Or2a-Or49b. Compounds tested for activity: *Drosophila* Or2a-Or49b. Chemical name, a 2-D structural image, and distance measure are listed for each tested compound. All distances are Euclidean and represent the distance between each compound and their closest known active by optimized descriptor values. Known active compounds from the training set are the top 12, 7, 13, 5, 9 and 3 compounds respectively in each column, predicted compounds that were validated as actives are appropriately boxed, inhibitors are appropriately boxed, and inactive compounds are boxed.

FIG. 14 shows validation accuracy for predicted *drosophila* ligands.

FIG. 15A shows an optimized descriptor based cluster for Or42b. FIG. 15B shows an electrophysiology validation for various compounds. FIG. 15C is a 3-D structural image of a compound from the electrophysiology validation.

FIG. 16A shows flow diagrams for (i) predicting initial screening compounds from single strong ligand, (ii) identifying additional activators through electrophysiology validation, and (iii) predicting additional activating compounds from single strong ligand and validated activators. FIG. 16B shows an example for Or82a of (i) an all descriptor cluster, (ii) electrophysiology validation, and (iii) an optimized descriptor based cluster.

FIGS. 18A-18G show computational validation of mammalian OR compound clustering for MOR41-1 (FIG. 18A); MOR271-1 (FIG. 18B); MOR203-1 (FIG. 18C); MOR272-1 (FIG. 18D); MOR139-1 (FIG. 18E); OR1A1 (FIG. 18F); and OR2W1 (FIG. 18G).

FIGS. 21A-21W show accumulated percentage of actives and activity based cluster analysis. FIG. 21A shows a representative example for an Accumulated Percentage of Actives (APoA) calculation. Green box=active, grey box=inactive. To calculate APoA each active compound was iteratively used as a reference active. Compounds are sorted based upon their increasing descriptor based distance from reference active, and the APoA calculated for each of the other compounds as a ratio of the number of actives over the total number of compounds considered from the reference compound. This process was repeated using each active odorant as a reference active. Reference compound APoAs were averaged to a single mean APoA value. The higher the APoA value while considering a fixed number of nearest neighboring compounds, the greater the proportion of active compounds clustered together. FIG. 21B shows a plot of the mean APoA calculated values calculated using each molecular descriptor method, averaged across all 20 Ors for Dragon, Cerius2, MCS and Atom Pair. FIG. 21C shows coloured cells mark the method that clusters active ligands best as determined by the highest Area-Under-Curve (AUC) values. E=Euclidean, S=Spearmans coefficient, and T=Tanimoto coefficient. FIG. 21D-21S show compounds clustered based on activity of Or, such as Or7a (FIG. 21D); Or9a (FIG. 21E); Or22a (FIG. 21F); Or35a (FIG. 21G); Or49b (FIG. 21H); Or59b (FIG. 21I); Or10a (FIG. 21J); Or19a (FIG. 21K); Or43b (FIG. 21L); Or47a (FIG. 21M); Or67a (FIG. 21N); Or67c (FIG. 21O); Or82a (FIG. 21P); Or85a (FIG. 21Q); Or85b (FIG. 21R); and Or98a (FIG. 21S). Activity color scale is indicated. Branches marked with small green squares (either 1 or 2) were considered as actives. FIGS. 21T-21W show dependent cluster analysis for Ors that have only weak ligands as done in FIGS. 21D-21S, including Or2a (FIG. 21T); Or23a (FIG. 21U); Or43a (FIG. 21V); and Or85f (FIG. 21W).

DETAILED DESCRIPTION

Figure 1:
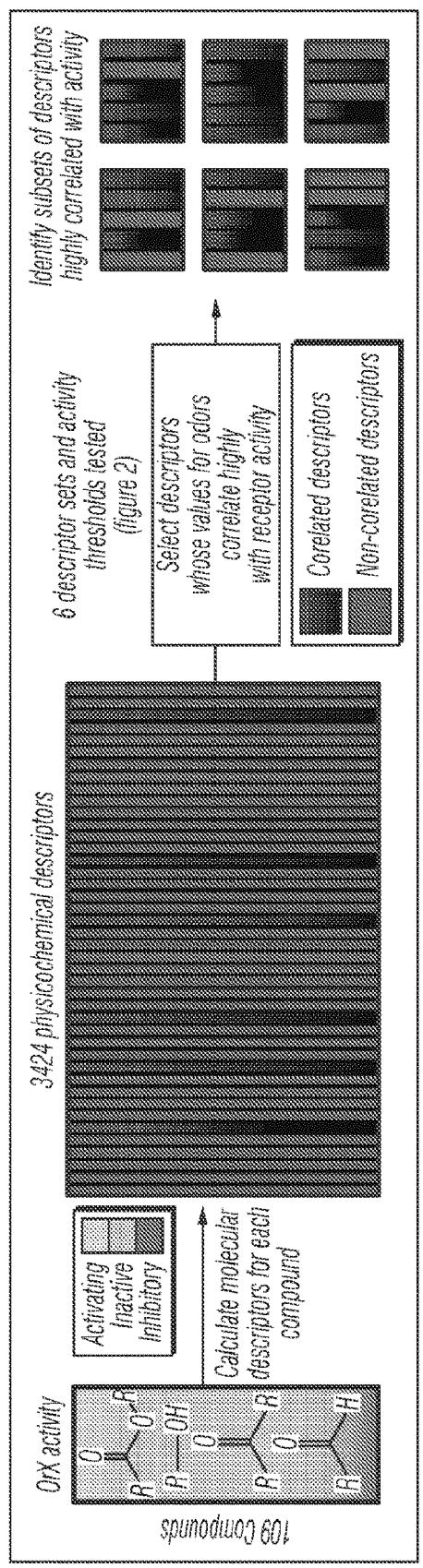

As used herein and in the appended claims, the singular forms "a," "and," and "the" include plural referents unless the context clearly dictates otherwise. Thus, for example, reference to "an insect" includes a plurality of such insects and reference to "the compound" includes reference to one or more compounds, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

The methods of the disclosure allows intelligent and rapid screening of untested volatile chemical space by computationally identifying important characteristics shared between known active compounds. Also provided are compounds identified by the methods of the disclosure for use as insect repellents and attractants.

The olfactory system can detect and discriminate amongst an extremely large number of volatile compounds in the environment, and this is critical for important behaviors like finding food, finding mates, and avoiding predators. To detect this wide variety of volatiles, most organisms have evolved extremely large families of receptor genes that typically encode 7-transmembrane proteins that are expressed in the olfactory neurons. Little is known, however, about how small volatile molecules are detected and represented with high levels of specificity and sensitivity by the activities of odor receptor repertoires. The disclosure is able to greatly increase this understanding, and improve the ability to manipulate the olfactory based behavior of an organism. Additionally the computational method can be used to identify novel fragrances for individual odor receptors, which can have use in the fragrance, food, beverage, cleaning and other volatile chemical related industries.

Most blood feeding insects, including mosquitoes, sandflies, Testse flies, use olfactory cues to identify human hosts. This group of hematophagous insects can transmit a wide assortment of deadly human diseases that together cause more suffering and deaths globally than any other disease condition. Diseases transmitted by such insects include malaria, dengue fever, yellow fever, West Nile virus, filariasis, river blindness, epidemic polyarthritis, Leshmaniasis, trypanosomiasis, Japanese encephalitis, St. Louis Encephalitis amongst others.

Traditional vector control methods often involve the heavy use of chemical insecticides that are harmful to the environment and often to human health. Moreover, insects can develop resistance to these chemicals, suggesting that there is a need to identify novel ways of insect control that are effective, cheap, and environmentally friendly. Integrating methods that inhibit vector-human contact, such as vector control and the use of insect repellents, bednets, or traps, may play a complementary and critical role in controlling the spread of these deadly diseases.

In insects host-odor cues, among others, are detected by olfactory receptor neurons (ORNs) that are present on the surface of at least two types of olfactory organs, the antennae and the maxillary palps. The antenna is the main olfactory organ and its surface is covered by hundreds of sensilla, each of which is innervated by the dendrites of 1-5 ORNs. Odor molecules pass through pores on the surface of sensilla and activate odor receptor proteins present on the dendritic membranes of the ORNs.

The odor receptor (Or) gene family in insects was first identified in *D. melanogaster*. It comprises a highly divergent family of 60 Odor receptor (Or) genes that encode proteins predicted to contain seven trans-membrane regions.

One of the most important host-seeking cues for hematophagous insects is $CO_2$. The $CO_2$ receptor was first identified in *D. melanogaster*. This receptor comprises two proteins, Gr21a and Gr63a, which are encoded by two members of a large Gustatory receptor (Gr) gene family that is distantly related in sequence to the Or genes. Both Gr21a and Gr63a are extremely well conserved in sequence across several insect species. Orthologs for both Gr21a and Gr63a have been identified in *An. gambiae* and *Ae. aegypti*. Moreover, both mosquitoes possess a third gene that is closely related to Gr21a. The three *An. gambiae* homologs AgGr22, AgGr23 and AgGr24 are co-expressed in ORNs of the maxillary palp. Functional expression studies in *Drosophila* have demonstrated that they are $CO_2$ receptors as well.

Odor responses of ORNs on the surface of the antennae and maxillary palps have been studied using two separate techniques. Whole organ recordings called electroantennograms (EAGs) and electropalpograms (EPGs) have been used to detect the aggregate electrical activities from a large number of neurons in response to odors. A more sensitive and exact method has also been used to examine the functional properties of olfactory neurons within a single sensillum, and neurons that respond to behaviourally important ligands such as $CO_2$, ammonia, phenols, 1-octen-3-ol, lactic acid, and carboxylic acids have been identified.

Because mosquitoes rely on their sense of smell to identify human odors, olfactory system function is a prime target to modify host-seeking behaviour. The kairomone $CO_2$ is used as bait by several mosquito traps that are currently sold on the market. In some instances an additional odor, usually 1-octen-3-ol, is also included to increase the efficiency of mosquito catches. Identification of more potent attractant odors, or more efficacious odor blends are required to further improve the efficiency of these $CO_2$ traps. Development of cheap $CO_2$-free traps may be of particular importance since generating $CO_2$ in a trap is problematic.

In a complementary fashion, blocking of insect odor receptors may be effective in masking human hosts, or may even work as repellents. There has been a great interest to identify novel classes of volatile compounds that can block mosquito receptors that detect kairomones like $CO_2$.

Volatile chemical space is immense. Odors in the environment that have been catalogued in some plant sources alone number more than two thousand. A very small proportion of chemical space has been systematically tested for the ability to activate or inhibit individual odor receptors, and a very small fraction of odor receptors, whose sequences are known, have been tested for activity. The complete 3-D structures of odor receptor proteins have not yet been determined, thus modeling of odor-protein interactions is not yet possible except in rare instances. Furthermore, were a 3-D receptor structure to become available, application of one odor-receptor interaction to study others may be confounded by the possibility of multiple ligand binding sites in a single receptor, as well as the sequence divergence amongst different odor receptors.

Odor receptor responses to odorants have been tested in vivo in the organism of interest predominately through two separate techniques. One approach involves whole organ recordings called electroantennograms (EAGs), eletropalpograms (EPGs), and electroolfactograms (EOGs) which have been used to detect the aggregate electrical activities from a large number of olfactory neurons in response to odors. This technique does not allow for differentiation between odor receptor neuron responses and thus does not allow for identification of individual odor receptor responses to an odorant. A more sensitive and precise technique called single unit electrophysiology allows for individual odor receptor neuron responses to odors to be quantitatively measured. This technique either requires the odor receptor map to have been previously established by molecular tools or use of an "empty-neuron" system that utilizes a transgenic approach.

In *Drosophila melanogaster* a mutant antennal neuron called the "empty neuron" has been identified. The system uses a mutant strain of *D. melanogaster* in which a chromosomal deletion has resulted in the loss of the Or22a gene. The Or22a gene product is usually expressed in an easily identifiable and accessible neuron type in the antenna called ab3A, which now does not express an odor receptor and therefore does not respond to any odors. An exogenous Or gene can then be functionally expressed in this mutant "empty neuron" genetic background using the promoter of Or22a. Responses to a diverse set of odorants can be recorded using single-sensillum electrophysiology. Through iteratively inserting and testing Or genes, electrophysiological responses of 24 Ors to a preliminary set of 110 diverse compounds was determined, as well as 21 additional Or genes to a set of 27 compounds. The compound sets consisted of volatile compounds with varying functional groups and hydrocarbon chain lengths. It has also been demonstrated that expression of functional odor receptors from other organisms is possible in the *Drosophila* "empty neuron" system. The level of throughput of this system is ~100s to 1000s of odors in one year.

Additionally, other in vivo techniques have been used involving testing individual odor receptors of interest through transgenic expression in other organisms. Heterologous expression of Odor receptor genes from many species has been performed in *Xenopus* oocytes and Human Embryonic Kidney (HEK) 293 cells. Exposure of these cells to volatile compounds allows for a quantitative measure of response.

While these systems do provide a means to specifically express an odor receptor and obtain a quantitative measure of activation to a panel of odorants, their use is a very time consuming, expensive, and difficult process. Use of the "empty neuron" system and other heterologous expression approaches require transgenic fly lines to be produced or cDNA expression constructs made for each odor receptor to be tested. It has also been debated whether these expression systems produce wild type responses in all cases, as some cell specific components such as odorant binding proteins (OBPs) may be absent. Additionally all systems require the requirement of purchasing odors, diluting them, and performing the technically challenging testing of odorants.

In previous studies, individual odor receptors have sometimes been found to recognize compounds of similar functional groups containing similar hydrocarbon chain lengths. In addition it has also been shown that many Ors can be responsive to multiple distinct groups of structurally similar compounds. This property of odor receptors recognizing structurally similar compounds provides a framework for using cheminformatic similarity measures to predict novel active odorants.

Molecular descriptors are able to describe the structure of molecules through computationally derived values, which represent zero, one, two, or three-dimensional information of a compound. These descriptor type dimensionalities confer molecular information through classes such as constitutional, structural fragment, topographic, or spatial information, respectively.

Comparison of molecular descriptors to identify commonalities between highly active odorant structures has recently proven to be highly beneficial. In species where a specific behaviour, such as avoidance, has been tested against a panel of odors it is possible to use molecular descriptors to identify novel potential ligands using the known actives as a training set. For instance, the structure of N,N-diethyl-m-toluamide (DEET) was recently used to create a focused structural library, which was computationally ranked using Artificial Neural Networks (ANNs), and used to identify a more potent mosquito repellent. In another study a group analyzed *Drosophila* ORN responses to odors to identify activation metrics that were used to predict and test ligands from a small set of 21 compounds (Schmuker et al., 2007). The success rate of this strategy, as established by applying a neuronal firing rate cut-off of 50 spikes/sec to categorize activators, was <25%. Most recently a multi species approach was used to identify molecular descriptors that were important in compounds involved in olfaction however predictions were not possible. In another study by the same lab, an electronic nose was trained such that when presented with a novel odor it could predict whether or not the odor would activate an individual Or.

The methods of the disclosure allows intelligent and rapid screening of untested volatile chemical space and chemical libraries by computationally identifying important characteristics shared between known active compounds, circumventing many of the previously described obstacles.

The disclosure provides a chemical informatics method that identifies important structural features shared by ligands such as activating odors for individual odor receptors or olfactory neurons and utilizes these important features to screen large libraries of compounds in silico for novel ligands. These important structural features can also be used to increase understanding of breadth of tuning for each cognate of a ligand such as an odor receptor in chemical space and perform reverse chemical ecology in silico.

Although the methods of the disclosure have been exemplified using odor receptor and volatile chemical species. The method is also predicatable to taste receptors, g-protein coupled receptors, ion gated channels, ligand gated channels and the like.

The disclosure provides methods for identifying and the identified compositions comprising volatile odorants that can modulate the electrophysiological response of neuron in various insect disease vectors including *Drosophila melanogaster, Culex quinquefasciatus, An. gambiae* and *Aedes aegypti* mosquitoes. In some embodiment, the odorants can completely inhibit the electrophysiological response of the neuron at very low concentrations.

The odorants of the disclosure provide new and useful compositions for insect repellents, masking agents and traps. The compounds of the disclosure are useful in small quantities, can be delivered in multiple forms like vapors and lotions, are economical, environmentally friendly, and are present in natural sources.

Based upon the data and chemical odorants identified herein, additional odorants can be identified using the structural information of the odorants, in silico modeling and screening and biological assays.

The disclosure provides a group of volatile chemicals that can be used to modify host-seeking behaviour by stimulating or inhibiting odor and taste receptors.

The compounds and compositions of the disclosure can be used as antagonist to mask the chemo attractant activity for a particular odor receptor. Alternatively, the certain compounds may at as agonist in which they activate the receptor and stimulate the neuron. In such instances the compounds and compositions can be used as attractants alone or in combination with other materials depending upon the subject and purpose (e.g. an insecticide, trap, or other mechanical, electrical or chemical that kills the insect or prevents its escape).

An antagonist refers to a compound the can reversibly or irreversibly inhibit that activity of a sensing neuron upon exposure to the compound such that the neuron ORN cannot properly signal upon a change in odor levels.

Structure-based clustering can be used to identify compounds useful in compositions of the disclosure. The algorithm can include linkage clustering to join compounds into similarity groups, where every member in a cluster shares with at least one other member a similarity value above a user-specified threshold.

The identified compounds can then be assayed to identify their biological activity using the electrophysiology measurements described below. For example, a compound can be contacted with a CO2 receptor neuron and changes in the electrical signal measured. Alternatively, the compounds may be screened in a *Drosophila* $CO_2$ avoidance chamber.

The disclosure provides chemicals that can be used as insect repellents and/or masking agents by virtue of their property to block a critical component of the host odor cue.

The compounds are effective if they are capable of inhibiting the electrophysiological response of the neuron.

The volatile compounds of the disclosure have masking and repellant effects by impairing the ability to find a host via long-range cues emitted from a typical target or subject (e.g., human breath).

The disclosure provides a method of controlling insect attraction to a subject, the method comprising the step of inhibiting receptor activation (e.g., $CO_2$ sensing gustatory receptors) in the insect or over stimulating the receptor with an antagonist (or a combination of antagonists).

In another embodiment, this disclosure provides a method of inhibiting, preventing or reducing the incidence of insect-borne disease in a subject, the method comprising the step of over stimulating or antagonizing a receptor in an insect with a compounds or combination of compounds, wherein the receptor response is modified and attraction to the subject inhibited, thereby inhibiting, preventing or reducing the incidence of insect-borne disease in a subject.

In one embodiment, the disease is malaria, dengue, yellow fever, river blindness, lymphatic filariasis, sleeping sickness, leishmaniasis, epidemic polyarthritis, West Nile virus disease or Australian encephalitis.

The compounds may be used alone or in combination with other agents. The compounds of the disclosure may be combined with additional active agent, insecticides and the like in traps to reduce the presence of amount of an insect in the environment. For example, compounds of the disclosure may be used in combination with insect traps (e.g., tape, combustibles, electric traps).

In yet a further embodiment, the compounds may be formulated for application to the skin, clothing or other material. The compounds of the disclosure can "mask" the location of a subject by antagonizing the receptor neurons of an insect etc. thereby inhibiting the ability to locate a prey.

For example, the compounds of the disclosure may be used as repellents or in compositions comprising said repellent compounds and the use of such repellent compounds and compositions in controlling pests.

Liquid formulations may be aqueous-based or non-aqueous (e.g., organic solvents), or combinations thereof, and may be employed as lotions, foams, gels, suspensions, emulsions, microemulsions or emulsifiable concentrates or the like. The formulations may be designed to be slowly release from a patch or canister.

The compositions may comprise various combinations of compounds as well as varying concentrations of the compound depending upon the insect to be repelled or masked, the type of surface that the composition will be applied to, or the type of trap to be used. Typically the active ingredient compound of the disclosure will be present in the composition in a concentration of at least about 0.0001% by weight and may be 10, 50, 99 or 100% by weight of the total composition. The repellent carrier may be from 0.1% to 99.9999% by weight of the total composition. The dry formulations will have from about 0.0001-95% by weight of the pesticide while the liquid formulations will generally have from about 0.0001-60% by weight of the solids in the liquid phase.

As mentioned above, the compositions may be formulated for administration to a subject. Such formulations are typically administered to a subject's skin. The composition may also be formulated for administration to garments, belts, collars, or other articles worn or used by the subject from whom insects are to be repelled. The formulation may be applied to bedding, netting, screens, camping gear and the like. It will be recognized that the application of the compositions and compounds of the disclosure do not only include human subjects, but include canines, equines, bovines and other animals subject to biting insects. For topical application, the formulation may take the form of a spray formulation or a lotion formulation.

The compounds according to the disclosure may be employed alone or in mixtures with one another and/or with such solid and/or liquid dispersible carrier vehicles as described herein or as otherwise known in the art, and/or with other known compatible active agents, including, for example, insecticides, acaricides, rodenticides, fungicides, bactericides, nematocides, herbicides, fertilizers, growth-regulating agents, and the like, if desired, in the form of particular dosage preparations for specific application made therefrom, such as solutions, emulsions, suspensions, powders, pastes, and granules as described herein or as otherwise known in the art which are thus ready for use.

The repellent compounds may be administered with other insect control chemicals, for example, the compositions of the invention may employ various chemicals that affect insect behaviour, such as insecticides, attractants and/or repellents, or as otherwise known in the art. The repellent compounds may also be administered with chemosterilants.

In yet another aspect, the volatile compounds of the disclosure may be emitted from vaporizers, treated mats, cylinders, oils, candles, wicked apparatus, fans and the like. Liquid source that can evaporate to form vapors may be used in barns, houses, or patios.

The disclosure also provides chemicals that can be used as bait to lure insects to traps by virtue of activating neurons. An advantage of these odorants will be their ability to be delivered in an economical and convenient form for use with traps. This function can be achieved by applying or locating the chemotractant compound of the disclosure near a suction based, or light based, or electric current based or other forms of trapping apparatus.

The disclosure provides a structural basis of odorant molecule interaction with odor receptors through a novel chemical informatics platform. The disclosure provides a method to identify molecular structural properties that are shared between the activating odorants (actives) for an individual odor receptor. By identifying the molecular features shared by actives, the disclosure provides a system to perform in silico screens of large chemical space (100s of thousands to millions) to predict novel ligands for odor receptors or odor receptor neurons. This method can be applied in virtually any species where a training set of odorant responses is known for individual receptor or cellular level. The disclosure demonstrates this using a single unit electrophysiology to test a subset of the predictions in vivo. The data demonstrate that the method is very successful in predicting novel ligands.

The disclosure demonstrates the method can be modified to be able to predict ligands for narrowly-tuned receptors and neurons that are thought to be highly specialized, like pheromone receptors. In addition olfactory neurons whose response profiles are known, but whose odor receptors have not yet been decoded are provided. The method is also able to predict odorant ligands for two distinctly different classes of odor receptors. Insect odor receptors are proposed to be 7 transmembrane GPCR like proteins with inverse orientation in the membrane that function as either heteromeric ligand gated ion channels or cyclic-nucleotide activated cation channels. Mammalian odor receptors on the other hand are true GPCRs. The method is able to predict ligands for both insect and mammalian odor receptor classes. In addition to predicting ligands the disclosure also allows investigation of the coding of each tested receptor or receptor neuron in chemical space consisting of plant volatiles, fragrances and human volatiles.

The $CO_2$ receptor is believed to be very important in host seeking behaviour in mosquitoes. There are several commercially available approaches that use $CO_2$ as a lure to trap insects. However, these current approaches have several drawbacks. Many traps require the use of a $CO_2$ tank or dry ice to produce the $CO_2$ lure plume. These $CO_2$ tanks are large and heavy, making the trap itself cumbersome. Dry ice melts quickly and must be replaced often. A much smaller and longer lasting trapping approach would be advantageous. Identification of odors that could specifically activate this receptor could provide a very effective means of luring mosquitoes into traps. The approach can be used to identify odors that activate individual receptors, such as the $CO_2$ receptor.

Since different odor receptors can respond to vastly differing compound shapes and sizes it is unlikely that the full collection of molecular descriptors would be optimal for all receptors. Depending upon the unique structural features of active odors certain molecular descriptors may be better suited at describing characteristics of activating compounds for an individual receptor, and such descriptors can be identified from much larger sets by dimensionality reduction. Thus it is possible to greatly improve Or-specific descriptor space by identifying specific molecular descriptors from amongst the large collection that were best suited for each Or.

The disclosure provides a method of computationally screening a vast number of compounds to predict ligands (activators or inhibitors) for individual receptors or receptor expressing cells, wherein a known ligand or set of known ligands for a receptor or receptor expressing cell, either identified through electrophysiology, imaging assays, or binding assays, are used as a training set for selecting optimized molecular descriptors, which can subsequently be used to screen a large collection of untested compounds computationally to identify compounds that are structurally related to the known ligands, outputting the identified putative ligands to a user and exposing a receptor or receptor expressing cell to the putative ligand and determining either a change in spike frequency, florescence intensity, or binding affinity in the receptor or receptor expressing cell, wherein a change compared to baseline is indicative of a ligand for the receptor or receptor expressing cell.

The disclosure also provides a method of computationally screening a vast number of compounds to predict ligands (activators or inhibitors) for individual receptors or receptor expressing cells that have only one known strong activator or inhibitor, either identified through electrophysiology, imaging assays or binding assays, wherein a single known ligand from a receptor or receptor expressing cell is used to identify the structurally closest compounds in a chemical space made using several or all available structural descriptors, outputting the identified putative ligands to a user and exposing a receptor or receptor expressing cell to the putative ligand and determining either a change in spike frequency, florescence intensity, or binding affinity in the receptor or receptor expressing cell, wherein a change compared to baseline is indicative of a ligand for the receptor or receptor expressing neuron. In one embodiment, positives having a desired functional activity are used to further define the structural descriptors along with previously known activating odorants.

The disclosure also provides a method of computationally screening a vast number of compounds to predict compounds which cause a specific behavior (attraction, repellency, mating, aggression, or oviposition), wherein an compound or set of known compounds causing a specific behavior are used as a training set for selecting optimized molecular descriptors, which can subsequently be used to screen a large collection of untested odorants computationally to identify compounds that are structurally related to the known behavior modifying compounds, outputting the identified putative behavior modifying compounds to a user and testing the compounds for behavior modification, wherein a change compared to baseline behavior is indicative of a behavior modifying compound. In various embodiments, compounds are volatile odors and either the receptor is an odor receptor expressed by a specific neuron or cell type in a specific invertebrate species or receptor-expressing cells are odor receptor neurons present in a specific species of invertebrate.

In other embodiment, compounds are soluble ligands and either the receptor is a gustatory receptor expressed by a specific neuron or cell type in a specific invertebrate species or receptor-expressing cells are gustatory receptor neurons present in a specific species of invertebrate. In yet other embodiments, the compounds are volatile ligands and either the receptor is a gustatory receptor expressed by a specific neuron or cell type in a specific invertebrate species or receptor-expressing cells are gustatory receptor neurons present in a specific species of invertebrate. In further embodiments, the compounds are volatile odors and either the receptor is an odor receptor expressed by a specific neuron or cell type in a specific vertebrate species or receptor-expressing cells are odor receptor neurons present in a specific species of mammals. In some embodiments, the compounds are soluble ligands of volatile ligands and either the receptor is a gustatory receptor expressed by a specific neuron or cell type in a specific vertebrate species or receptor-expressing cells are gustatory receptor neurons present in a specific species of mammals.

As mentioned above, the methods of the disclosure can be used to screen ligands for a number of different biological molecules including GPCR. Accordingly, in one embodiment, the compounds are soluble or volatile ligands and either the receptor is a GPCR expressed by a specific neuron or cell type in a specific invertebrate or vertebrate species or receptor-expressing cells are GPCR expressing cells present in a specific species of invertebrate or vertebrate.

In yet other embodiment, the compounds are identified by the method of the disclosure and are identified as compounds for ligand gated ion channels. For example, the compounds can be soluble or volatile ligand and either the receptor is a ligand gated ion channel expressed by a specific neuron or cell type in a specific invertebrate or vertebrate species or receptor-expressing cells are ligand gated ion channel expressing cells present in a specific species of invertebrate or vertebrate.

The disclosure provides a method of identifying a ligand for a biological molecule comprising (a) identifying a known ligand or set of known ligands for a biological molecule, or identifying a compound which causes a specific biological activity, (b) identifying a plurality of descriptors for the known ligand or compound, (c) using a Sequential Forward Selection (SFS) descriptor selection algorithm to incrementally create a unique optimized descriptor subsets from the plurality of descriptors for the known ligand or compound, (d) identifying a putative ligand or compound that best-fits the unique optimized descriptor subset, and (e) testing the putative ligand or compound in a biological assay comprising the biological molecule wherein a change in activity of the biological molecule compared to the molecule without the putative ligand is indicative of a ligand the interacts with the biological molecule.

The disclosure utilizes in one embodiment a Sequential Forward Selection (SFS) descriptor selection method to incrementally create unique optimized descriptor subsets for each odor receptor. For example, starting with the combined group of 3424 descriptors from the full sets of Dragon and Cerius2 descriptors, an initial descriptor was selected whose values for the 109 odors showed the greatest correlation with activity for a specific Or. Additional descriptors were incrementally added to the growing optimized descriptor set based on their ability to further increase the Pearson correlation with activity for a specific Or. Each iteration increased the size of the optimized descriptor set for that Or by one. When a round of descriptor selection failed to increase the correlation between compound distance based upon the descriptor sets and those based upon known compound activity, the selection process was halted. As a result, optimized descriptor sets and their sizes are expected to vary across Ors. Additionally, 6 selection method combinations were used to identify the best statistical method for determining descriptor inclusion in the optimized set (FIG. 2).

Figure 3A:
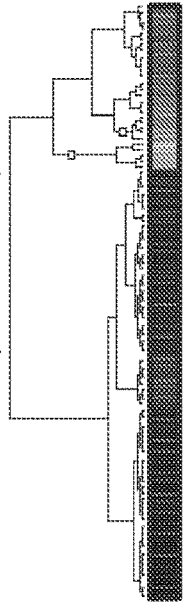
FIGS. 3A-3T show diagrams of compound activity classification through activity clustering. Compounds were clustered based on difference in activity. Compounds below certain squares, indicate cut points. Diagrams are provided for receptors: Or7a (FIG. 3A); Or9a (FIG. 3B); Or22a (FIG. 3C); Or35a (FIG. 3D); Or49b (FIG. 3E); Or59b (FIG. 3F); Or10a (FIG. 3G); Or19a (FIG. 3H); Or43b (FIG. 3I); Or47a (FIG. 3J); Or67a (FIG. 3K); Or67c (FIG. 3L); Or82a (FIG. 3M); Or85a (FIG. 3N); Or85b (FIG. 3O); Or98a (FIG. 3P); Or2a (FIG. 3Q); Or23a (FIG. 3R); Or43a (FIG. 3S); and Or85f (FIG. 3T).
Figure 3B:
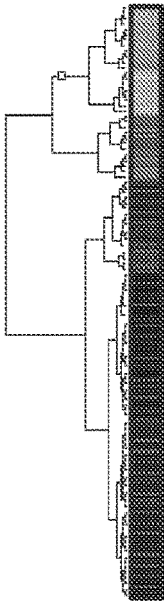
Figure 3C:
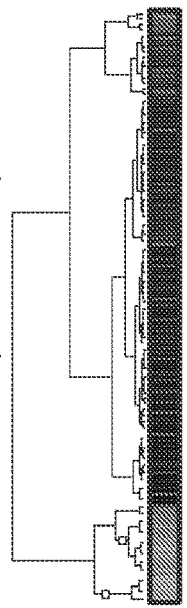
Figure 3D:
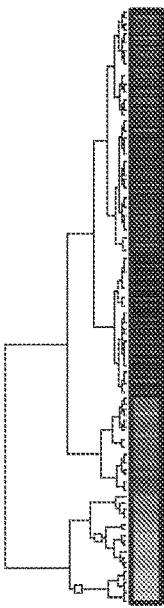
Figure 3E:
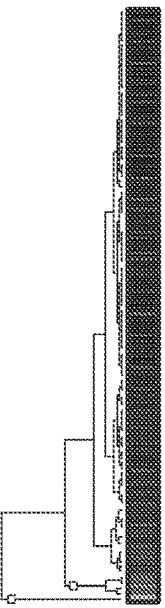
Figure 3F:
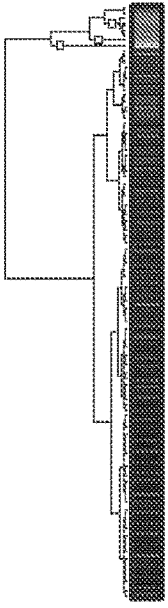
Figure 3G:
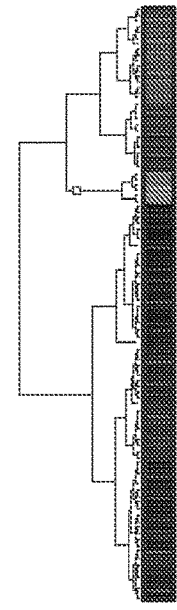
Figure 3H:
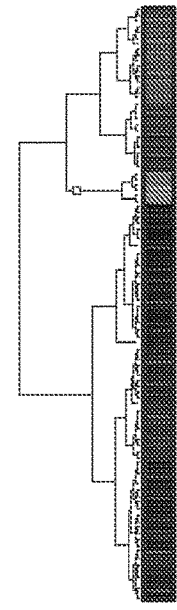
Figure 3I:
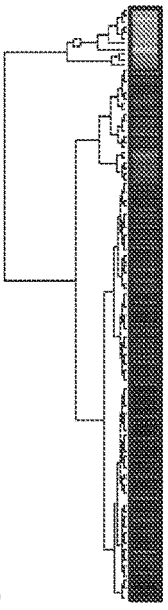
Figure 3J:
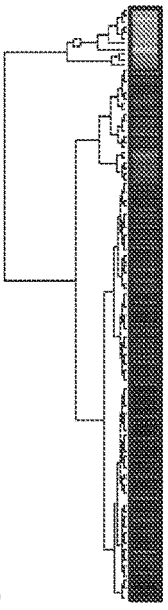
Figure 3K:
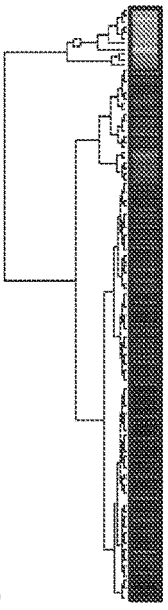
Figure 3L:
Figure 3M:
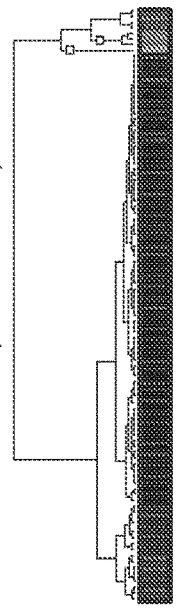
Figure 3N:
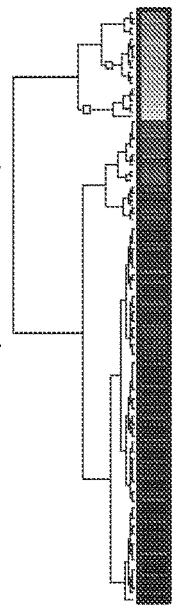
Figure 3O:
Figure 3P:
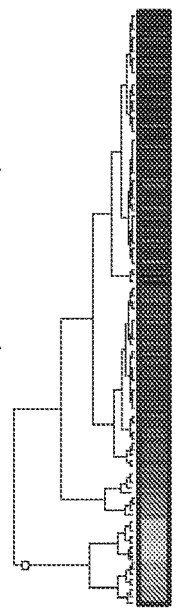
Figure 4:
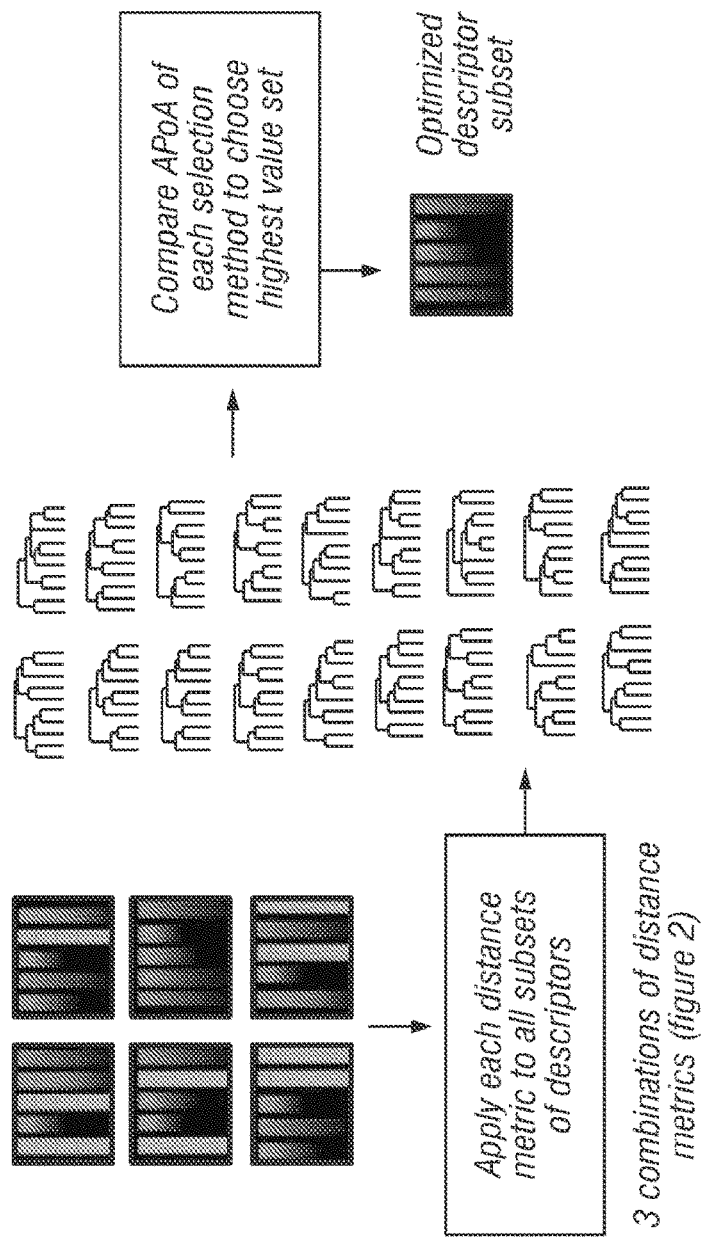
FIG. 4 shows a schematic of selecting highest scoring optimization methods.

In order to identify a method to select optimized descriptors for each Or the method was applied to 18 combinations of distance metrics, descriptor sets, and activity thresholds. Distance metrics included Euclidean, Spearman, and Pearson coefficients. Descriptor sets included Dragon, Cerius2, and a combined Dragon/Cerius2 set from which optimized descriptors would be chosen. Two activity threshold methods were compared for each combination. First, the four (>200, >150, >100, and >50 spikes/second) activity cut-offs were used. Second, a cluster based cut-off method was used to determine actives. For this approach a cluster analysis of the 109 odors for each individual Or was used using compound activity to calculate distances between Ors. The resulting activity trees for each Or were inspected, and active compounds were classified by selecting either one or two branches containing the active clusters (FIGS. 3A-3T).

Compounds are then clustered based on differences in activity. Compounds falling below a cut point are classified as active. Cut point locations can be determined manually. For example, each of the 3 distance metrics (FIG. 2) were applied to the 6 descriptor subsets (FIG. 1) to produce 18 unique descriptor based odor relationship sets. Accumulative Percentage of Actives (APoAs) values were calculated from distances between compounds based on each of the 18 methods and compared by AUC values as has been described previously. The highest-scoring selection method and the resulting optimized molecular descriptor set were identified for each Or.

If the optimized descriptor sets are better than the large collections of non-optimized descriptors, then one would find that they are able to cluster known active ligands closer together in chemical space. In order to determine whether the optimized descriptor sets are better at bringing the active compounds closer together in chemical space 4 non-optimized descriptor methods including Dragon, Cerius2, Maximum Common Substructure (MCS), Atom Pair (AP), were compared to a "selected" descriptor set from a published study that was selected for activation of the olfactory system by all 20 *Drosophila* Ors and across multiple species. The averaged APoA values for each of the 6 descriptor sets (Or-optimized, all Dragon, all Cerius2, Atom-pair, MCS, previous study) were compared for each of the 20 Ors and the Or-optimized descriptor sets provided APoA values far greater than all other methods, across all numbers of nearest neighbours.

Figure 6A:
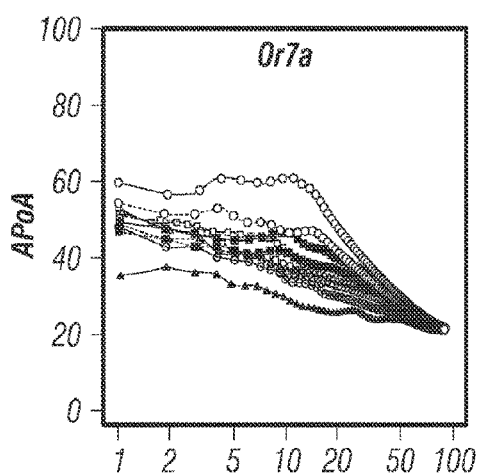
FIGS. 6A-6T show analyses of APoA for individual Odor receptors. Analyses are provided for receptors: Or7a (FIG. 6A); Or9a (FIG. 6B); Or22a (FIG. 6C); Or35a (FIG. 6D); Or10a (FIG. 6E); Or19a (FIG. 6F); Or43b (FIG. 6G); Or47a (FIG. 6H); Or49b (FIG. 6I); Or59b (FIG. 6J); Or82a (FIG. 6K); Or85a (FIG. 6L); Or67a (FIG. 6M); Or67c (FIG. 6N); Or85b (FIG. 6O); Or98a (FIG. 6P); Or2a (FIG. 6Q); Or23a (FIG. 6R); Or43a (FIG. 6S); and Or85f (FIG. 6T).
Figure 6B:
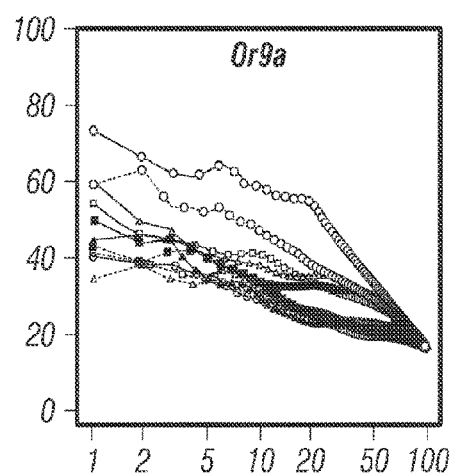
Figure 6C:
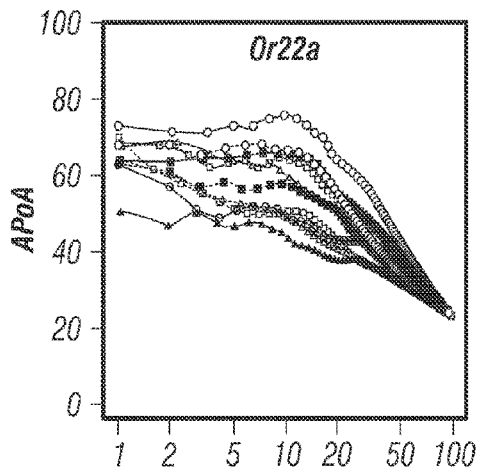
Figure 6D:
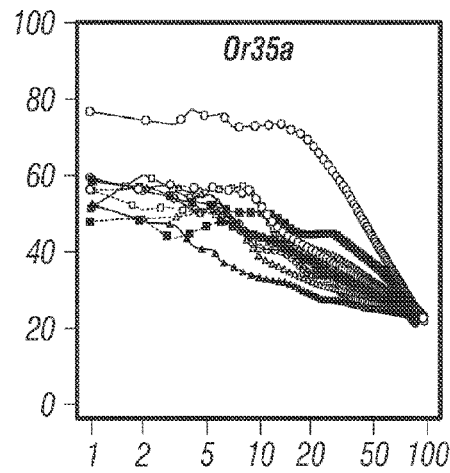
Figure 6E:
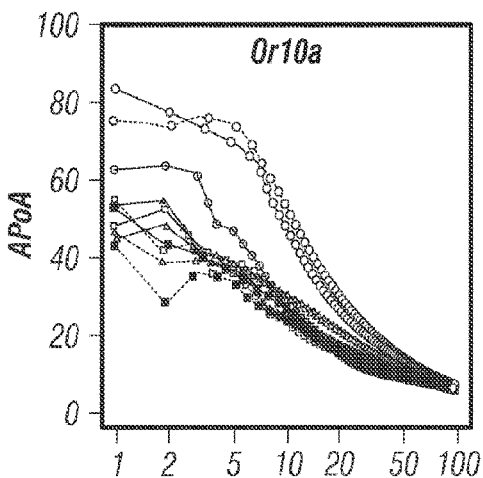
Figure 6F:
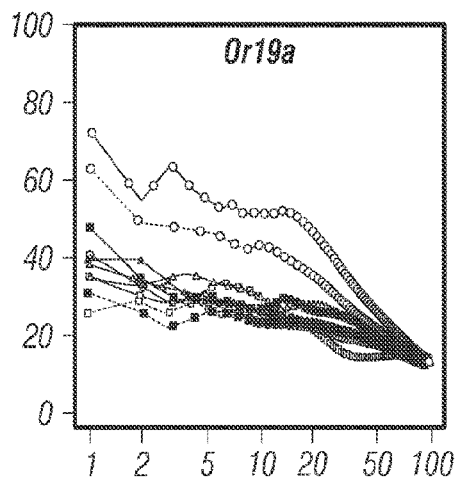
Figure 6G:
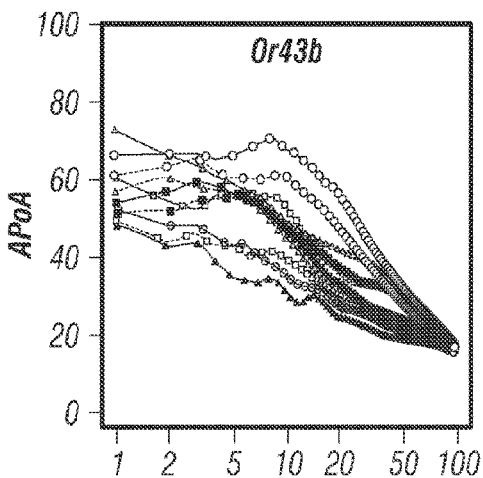
Figure 6H:
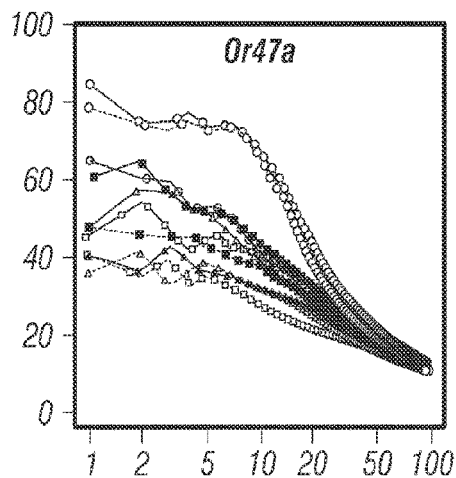
Figure 6M:
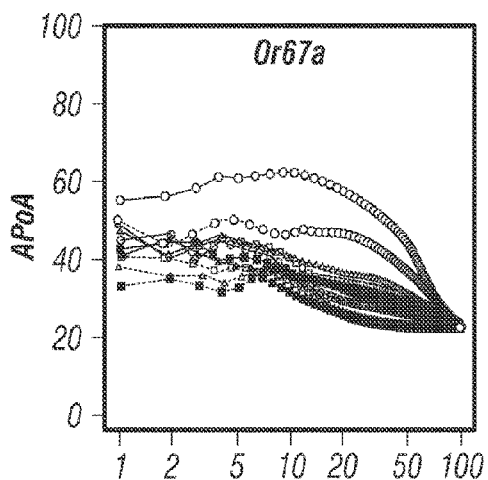
Figure 6N:
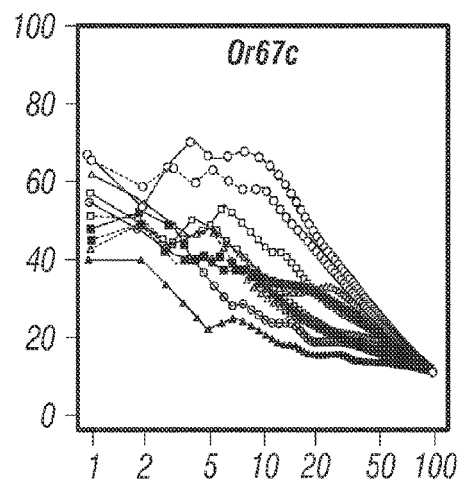
Figure 6O:
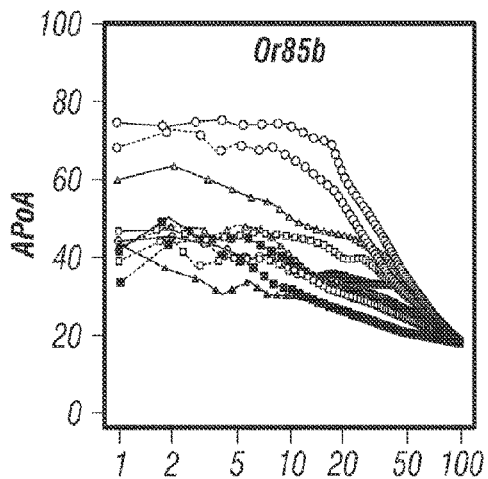
Figure 6P:
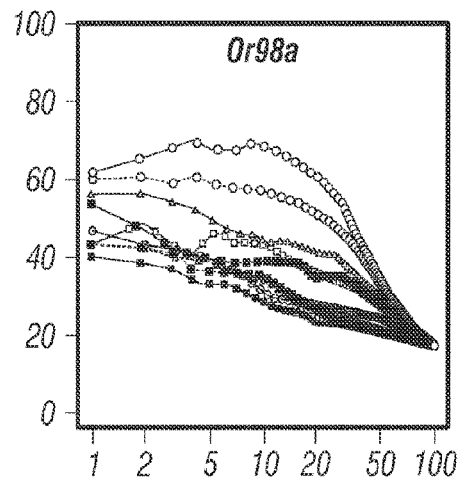
Figure 6Q:
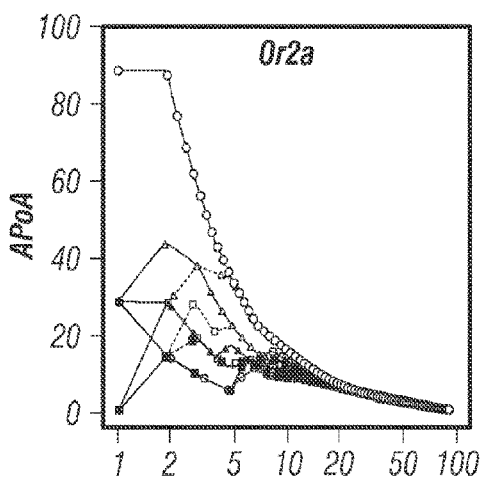
Figure 6R:
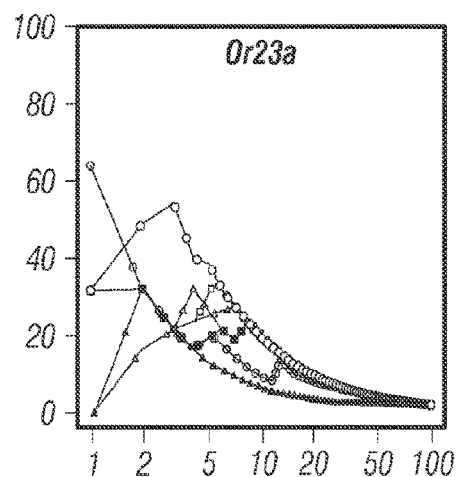
Figure 6S:
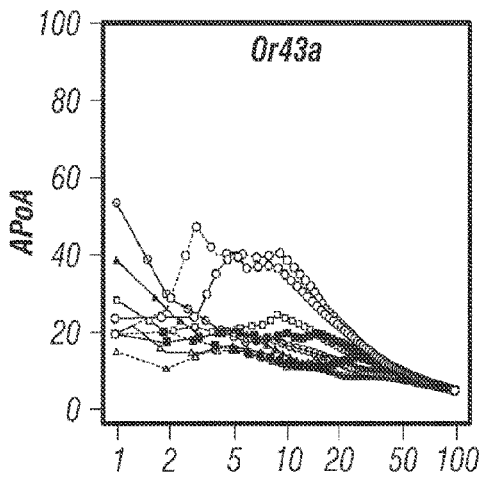
Figure 6T:
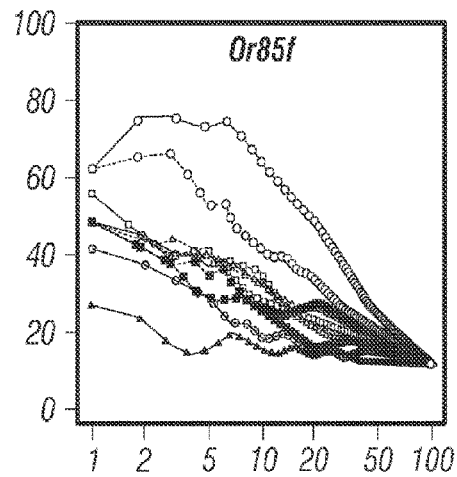
Figure 8A:
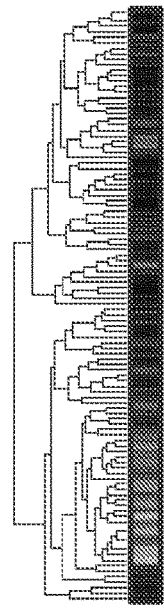
FIGS. 8A-8T show clustering of *drosophila* odorants by optimized descriptor subsets. Clustering diagrams are provided for receptors: Or7a (FIG. 8A); Or9a (FIG. 8B); Or22a (FIG. 8C); Or35a (FIG. 8D); Or49b (FIG. 8E); Or59b (FIG. 8F); Or10a (FIG. 8G); Or19a (FIG. 8H); Or43b (FIG. 8I); Or47a (FIG. 8J); Or67a (FIG. 8K); Or67c (FIG. 8L); Or82a (FIG. 8M); Or85a (FIG. 8N); Or85b (FIG. 8O); Or98a (FIG. 8P); Or2a (FIG. 8Q); Or23a (FIG. 8R); Or43a (FIG. 8S); and Or85f (FIG. 8T).
Figure 8B:
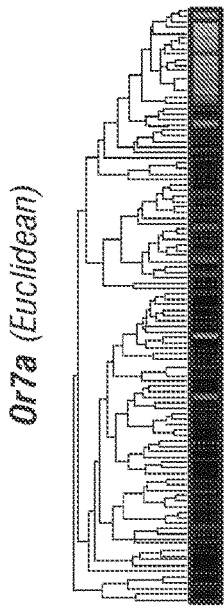
Figure 8C:
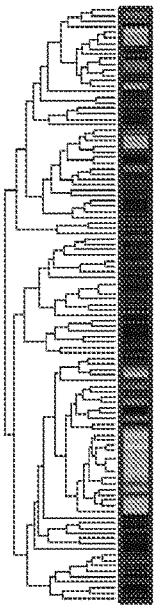
Figure 8D:
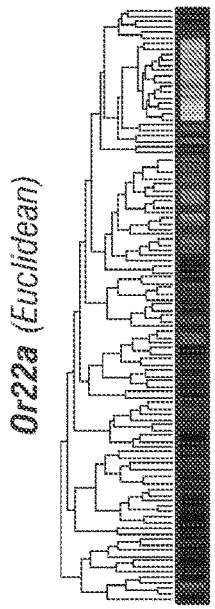
Figure 8E:
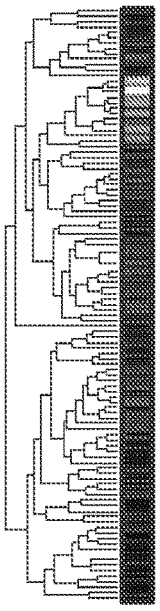
Figure 8F:
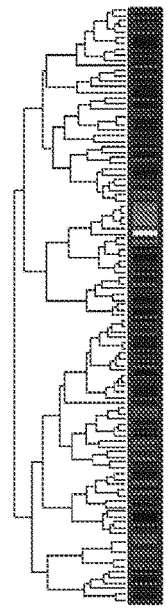
Figure 8G:
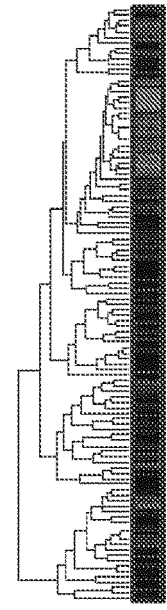
Figure 8H:
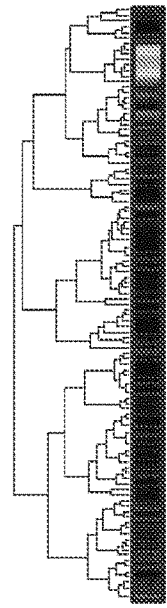
Figure 8I:
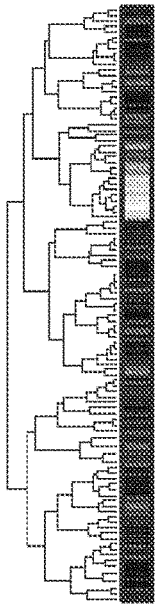
Figure 8J:
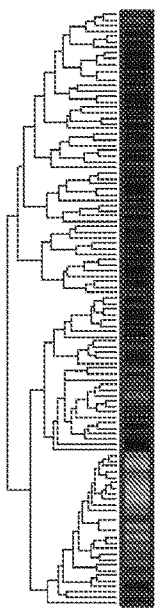
Figure 8K:
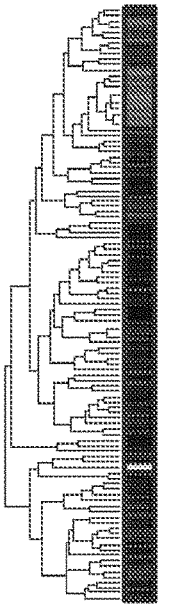
Figure 8L:
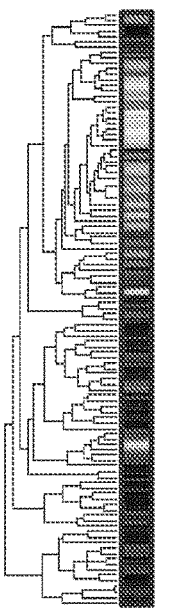

FIGS. 6A-6T show analyses of APoA for individual Odor receptors. Plots of the mean APoA values obtained from various Molecular Descriptor methods demonstrates that optimized descriptor subsets generate highest values. Molecular descriptor methods were compared using 109 compounds.

The highest-scoring selection method and the resulting optimized molecular descriptor set were identified for each Or. Selection method 5 followed by 11, which proved to work the best by virtue of having the highest AUC scores when considered at an individual Or level, used the combined Dragon+Cerius2 descriptor set, activity-cluster threshold method, and either Euclidean distance Or Spearman correlation as a similarity metric. Euclidean distance provided the highest AUC values for 18 of the Ors and Spearman for 2.

To better visualize how well each Or-optimized descriptor set grouped active ligands, the compounds can be clustered by distances calculated using the optimized descriptor sets for each Or. For example, the 109 compounds were clustered by distances calculated using the optimized descriptor sets for each Or. As expected from the APoA values, highly active ligands are seen tightly clustered for each Or. There were some differences in the ability to cluster actives with Or7a, Or9a, Or10a, Or22a, Or35a, Or43b, Or47a, Or59b, Or67a, Or85a, Or85b and Or98a providing the best clusters, while Or2a, Or23a, Or43a and Or85f did not provide as tight a clustering as predicted. A correlation can be observed between APoA values and the number of highly active compounds grouped tightly together by descriptors. The simplest interpretation of these results is that the Or-descriptor selection method and resulting optimized descriptor sets are considerably better at clustering activating odors than previously tested sets.

The poorer performance of Or2a, Or23a, Or43a and Or85f was expected since of the 109 odorants that were tested, very few showed any activity. The simplest interpretation is that "true" ligands for these 4 receptors have not been discovered from within the tested panel. However, the few odors that poorly activate each of these 4 receptors do cluster together in chemical space after identification of Or-optimized sets, albeit not as well as the ones with known strong ligands. This indicates that the Or-descriptor selection method was able to identify common features amongst the weakly activating odors and hence cluster them together, suggesting the possibility that stronger ligands may be identified from a larger chemical space using this information. From this point onwards these 4 Ors are referred to as "Semi-orphan" Ors.

Using the principles above, an in silico method of compound identification and clustering was used to characterize potential receptor ligands. Since the Or-optimized descriptors can group highly active compounds tightly together in chemical space for each Or, this method can be used to rank untested compounds according to their distance from known actives. This allowed us to computationally screen a vast area of chemical space of potential volatiles in a very efficient and accurate manner. In total close to 5,000,000 interactions were systematically tested between 20 Ors and >240,000 different putative volatile compounds. This would be entirely unfeasible using current assay technology. With electrophysiology the largest screen so far has tested <3000 different interactions, which is ~0.06% the size of the in silico screen. Moreover traditional high-throughput plate-based assays, as used for GPCRs that detect ligands in solution, are not appropriate for odor receptors since volatile ligands are largely (if not completely) absent from soluble plate-based combinatorial chemical libraries available.

A large collection of potential volatile compounds were identified by using criteria from known odors, such as molecular weight>200 and atom types limited to C, O, N, S, and H. Using these criteria over 240,000 compounds were selected from Pubchem and their structures were obtained. The distances in chemical space was then calculated for each of the >240,000 compounds based on the Or-optimized descriptor sets for each of the 20 Ors. In this fashion the unknown compounds were sorted by distances from each of the compounds considered as active from the 109 tested compounds. Euclidean distance or Spearman correlation, depending on which had previously been determined to be optimal for the corresponding Or, was used as similarity measures. Using this system the untested compounds in the 240,000 compound library were ranked according to their closeness to the known active ligands. The top 500 (0.2%) of hits in this large chemical space for each Or is listed below. Since each Or-optimized descriptor set was unique, unknowns were ranked independently for each receptor. Compounds were ranked systematically as actives for each of the 20 Ors using the Or-optimized descriptor sets and similarity measures to computationally rank all 240,000 compounds. These predictions could prove to be extremely valuable, not only do they provide an incredibly rich array of information regarding the coding of information by the peripheral olfactory system, it also provides an extremely large number of putative novel ligands for each of these 20 Or genes in *Drosophila*.

The results of the in silico screen are provocative. However in order to verify whether these predictions were meaningful, functional evidence was obtained. In order to validate the success of the in silico predictions the responses of 9 Odor receptors using single-sensillum electrophysiology directly on the *Drosophila melanogaster* antenna were analyzed. For each Odor receptor several odorants were tested from the top 500 predicted hits. A sampling of ~192 novel odorants were tested with ~11-21 novel odorants tested for each receptor, which were scattered somewhat randomly within the top 500 predictions for each receptor, providing a relatively unbiased set of chemical structures.

To test identified compounds any number of biological assays can be used to measure ORN activity in the presence of a putative ligand/compounds. For example, to demonstrate the activity of the compounds identified above, a single-unit electrophysiology test was performed on *D. melanogaster* antenna for each predicted compound, resulting in a quantitative value of activation. For the purpose of testing each of these volatile compounds the compounds were diluted to $~10^{-2}$ in paraffin oil or distilled water. The 9 Ors tested are expressed in well-defined olfactory receptor neurons (ORNs) housed within the large and small basiconic sensilla (ab1-ab7) on the antenna. A previously identified diagnostic panel of odorants was used to distinguish individual classes of sensilla (ab1-ab7) and therefore identified the sensilla that contained the target Or expressing ORN.

FIGS. 10A-10I show the firing rates of odorants that were not predicted to be actives were tested using single unit electrophysiology. This demonstrates the specificity of the invention. Bars indicate the strength of response (spikes/s). All values have been corrected for spontaneous firing rate. Spontaneous activity of neuron was subtracted. All odorants were tested at a concentration of $10^{-2}$. N=3. Error bars=s.e.m.

FIGS. 11 and 12A-12F provide a list of exemplary compounds. Chemical name, a 2-D structural image, and distance measure are listed for each tested compound. All distances are Euclidean and represent the distance between each compound and their closest known active by optimized descriptor values. Known active compounds from the training set are in yellow boxes, predicted compounds that were validated as actives are green, inhibitors are red, and inactive compounds are white.

As can be seen a majority of the predicted actives evoked responses from the target ORNs; ~71% evoked either activation (>50 spikes/sec above the spontaneous activity) or inhibition (>50% reduction in spontaneous activity). The success rates for different Ors varied from 100% for Or98a, to 27% for Or49b. Extrapolation of these values to the entire in silico screen suggests that between 500 and 135 novel ligands were identified for each of the 19 Ors.

The data demonstrate that >61% of the predicted compounds elicited >50 spikes per second, and >40% evoked strong responses of >100 spikes per second. In a few instances volatiles were identified that could activate the odor receptors extremely strongly (>250 spikes/sec); e.g. isopropyl acetate (Or59b, ab2A) and prenyl acetate (Or98a, ab7A). (see, e.g., FIG. 14).

The top 500 out of 240,000 compounds are an arbitrarily selected criteria and it is possible that compounds beyond the top 500 may also activate the receptors. Further examples were tested using two receptors Or22a and Or85b to extend the analysis to the top 1000 compounds. An additional 4 compounds were selected that are ranked between 500-1000 in the predictions and tested them using electrophysiology. Approximately 100% of these compounds were ligands, suggesting that the total number of new ligands identified by using the top 500 cut-off is underestimated.

Taken together these results demonstrate that the Or-optimized descriptor set based in silico screening of chemical space is extremely efficient at identifying volatile ligands for odor receptors.

The disclosure provides a chemical informatics method that identifies important structural features shared by activating odors for individual odor receptors or olfactory neurons and utilizes these important features to screen large libraries of compounds in silico for novel ligands. These important structural features can also be used to increase understanding of breadth of tuning for each Or in chemical space and perform reverse chemical ecology in silico.

The examples are illustrative. It will be recognized the use of specific odor receptors in the examples below can be substituted with any biological molecule that is capable or binds to a cognate/ligand. Such ligands can be small or large molecule organic molecules. The tables below are also illustrative. Each molecule in the table can be used independently in formulations, compositions or devices or may be used in combination. To described each and every combination would be redundant to the general descriptions herein and one of skill in the art will recognize that the various individual compositions, the various receptors can be utilized by the methods and compositions of the disclosure.

The following examples are intended to illustrate but not limit the disclosure. While they are typical of those that might be used, other procedures known to those skilled in the art may alternatively be used.

EXAMPLES

Chemical informatics. Maximum Common Substructures, Atom Pairs, Cerius2 (Accelerys), Dragon (Talete) were used to compute distances. Energy minimized 3-D structures for Dragon were generated using Omega2 software (OpenEye). Optimized descriptor subsets were identified based on the correlation between descriptor distances with the distances between compounds based upon activity. The process is iteratively used to search for additional descriptors leading to further increases in correlation and stopped when increase stops.

Actives were classified either by thresholds of (>200, >150, >100, and >50 spikes/second), or using cluster analysis of receptor activity to compounds to select branch with strongest actives. The Accumulative Percentage of Actives (APoA) calculated for each descriptor set individually using a method used previously. The Area Under the Curve (AUC) scores from APoA values for each of the combinations were calculated by approximation of the integral under each plotted APoA line.

For each Odor receptor, the "optimized descriptor set" was used to calculate a distance metric that could be used for rank 240,000 compounds according to their closest distance to each known active compound. Compound distances were converted into a relative percentage distances based on the maximum possible compound distance for each Or individually.

Cluster analysis of Ors. Euclidean distance matrixes were used to create clusters using hierarchical clustering and complete linkage for three cases. The first 20 descriptors selected for each Or were used to create an identity matrix. The top 500 predicted compounds were used to create an identity matrix for all Ors. The responses of each of the Ors to a panel of 109 compounds[6] were converted into an Or-by-Or Euclidean distance matrix.

Calculation of descriptors. Commercially available software packages Cerius2 (200 individual descriptors) and Dragon (3224 individual descriptors) from Accelerys and Talete were used to calculate molecular descriptors. Prior to inputting compounds into Dragon, 3-Dimensional structures were predicted for compounds through use of the Omega2 software. Descriptor values were normalized across compounds to standard scores by subtracting the mean value for each descriptor type and dividing by the standard deviation. Molecular descriptors that did not show variation across all compounds were removed. Maximum Common Substructures were determined using an existing algorithm. Atom Pairs were computed from the version implemented in Chemmine®.

Classification of active compounds. In *Drosophila* actives were classified using two methods. In method one four different thresholds were based on the activation of action potentials by the compounds on the odour receptor (>200, >150, >100, and >50 spikes/second) as done in the electrophysiology study. For each odour receptor, APoA values were calculated using odorants falling within each of the four thresholds. The average APoA values for each threshold were then averaged, providing a relatively unbiased representation for which method best brought active odours closer together. In the second method cluster analysis was performed for the 109 compounds for each receptor based on activity in spikes/sec. Active compounds present in a single branch, or two branches, were selected manually as actives.

In mammals actives were classified through cluster analysis. $EC_{50}$ values obtained were converted to positive values by subtraction from 0 and used directly as measures of compound activity. Converted values ranged from 0 (inactive) to 7.242 (Strongest Activator). Activating compounds for each receptor were clustered by distances in activity. Active compounds present in a single branch, or two branches, were selected manually as actives.

Determination of optimized *Drosophila* descriptor subsets. A compound-by-compound activity distance matrix was calculated from activity data available for each of the Ors that have been tested for activity to 109 odours. Separate 3424 compound-by-compound descriptor distance matrices were calculated using values from Dragon and Cerius2. Active compounds for each Or were identified individually through activity thresholds. The correlation between the compound-by-compound activity and compound-by-compound descriptor distance matrices were compared for each actively classified compound, considering their distances to all other compounds. The goal was to identify the descriptor that calculates distance between compounds that most closely correlates with the distances between compounds based upon activity. The descriptor that correlates best is retained and the process iteratively used to search for additional descriptors leading to further increases in correlation. In this manner the size of the optimized descriptor set increases by one in each iteration as the best descriptor set from the previous step is combined with all possible descriptors to find the next best descriptor. This process is halted when all possible descriptor additions in iteration fail to improve the correlation value from the previous step. This whole process is repeated once for each Or resulting in unique descriptor sets that are optimized for each Or.

Determination of optimized mammalian descriptor subsets. Mammalian descriptor set optimization was performed the same as for *drosophila*. The only difference for mammalian is that actives were classified only by cluster analysis.

Calculation of Accumulative Percentage of Actives (APoA). The accumulative percentage of actives is calculated for each descriptor set individually using a method used previously. The "optimized descriptor set" for a given odour receptor is used to calculate distances (Euclidean or Spearman) between the 109 compounds of known activity and the compounds are ranked according to their distance from each known active, resulting in one set of ranked compound distances for each active. Moving down the list for each of these rankings, ratios are calculated for the number of active compounds observed divided by the total number of compounds inspected, or the APoA. APoA values are averaged across all active compound rankings, creating a single set of mean values representing the APoA for a single Or and descriptor set. Using this approach ApoA mean values are calculated for each of the 24 Odour receptors, separately for each of the descriptor sets used, optimized set, all Dragon, all Cerius2, Atom Pair, Maximum Common Substructure. The Area Under the Curve (AUC) scores from APoA values for each of the combinations were calculated by approximation of the integral under each plotted APoA line.

Ranking untested putative volatile compounds. A large collection of >240,000 untested compound structures were obtained from Pubchem using the following criteria. Compounds had molecular weights between 32 and 200 and were limited to H, C, N, O, or S atom types. Compound structures were converted into 3-Dimensional models using Omega2. Cerius2 and Dragon descriptors were calculated for each compound followed by the standard normalization of values through subtraction of the mean and division by standard deviation. For each Odour receptor, the previously determined "optimized descriptor set" was used to calculate a distance metric that could be used for ranking. The known active compounds for each Or were used individually to rank the set of greater than 240,000 compounds according to their closest distance to each known active compound, resulting in a matrix of dimensions 240,000 by the number of actives for the particular Or. Using this matrix each of the 240,000 compound structures were ranked according to their closest distance to any known active compound.

Clustering Ors by Most Common Descriptors. The first 20 descriptors selected by the optimized descriptor selection algorithm for each Or were used to create an identity matrix. Each row representing an Or and column a specific descriptor. Ors that share common descriptors contain is in the same column. This matrix was then converted into an Or by Or Euclidean distance matrix and clustered using hierarchical clustering and complete linkage.

Clustering compounds by activity of Or. The responses of each of the Ors that had previously been tested against a panel of compounds were converted into an Or-by-Or Euclidean distance matrix. Ors were clustered using hierarchical clustering and complete linkage. Specifically, this was achieved by creating a compound-by-compound distance matrix using the differences in activity between compounds tested on a single Or. Hierarchical clustering using each Or distance matrix and then manually identifying the sub cluster which contained the most compact group of highly active compounds resulted in each Or's actively classified compounds.

Calculation of Pharmacophores. Pharmacophore calculation was performed by Ligand Scout. Tightly clustering validated compounds for each *Drosophila* Or were aligned by shared pharmacophore features.

Clustering Ors by predicted ligand space. Percentages of overlapping predictions within the top 500 predicted compounds were calculated pair-wise for all Ors. Euclidean distances were calculated from the similarity between Ors Calculation of Or Tuning Using Pubchem and Collected Datasets. Initially all extreme outliers were manually removed from the dataset for each Or. On average 5.82 compounds were manually removed for each Or resulting in a mean dataset reduction of 0.0024%. Next all compounds whose distance was greater than 3 standard deviations from the strongest activating compound were removed to reduce outliers. Distance-densities were produced for each Or. The large majority of these densities follow a Gaussian distribution with the exception of Or10, which appears bimodal. All remaining compound distances were converted into a relative percentage distances based on the maximum possible compound distance for each Or individually. The numbers of compounds within the top 15 percent of relative distance were plotted on a logarithmic scale for each Or to generate computationally derived tuning curves. The same maximum distance value for each Or was also used to calculate and plot the top 15 percent of collected compound relative distance.

Collected Volatile Compound Library. A subset of 3197 volatile compounds were assembled from acknowledged origins including plants, humans, and a fragrance collection (Sigma flavours & fragrances, 2003 and 2007) that may have additional fruit and floral volatiles.

Calculation of Breadth of Or Tuning Across Datasets. From each of the three datasets (Hallem, Collected, Collected+Pubchem) an Or by Compound binary identity matrix was created. For the Hallem plot all compounds known to activate at least one Or at greater than 50 spikes/sec and any Or for which at least one activating compound was known were considered. Using these criteria the identity matrix was created and filled for each case of Or activation. For both the Collected and Pubchem+Collected datasets the top 500 predicted compounds for each Or for which predictions were made were used to fill binary identity matrices. All matrices were sorted in decreasing order of the percent of either known or predicted cross activation and plotted.

Figure 9A:
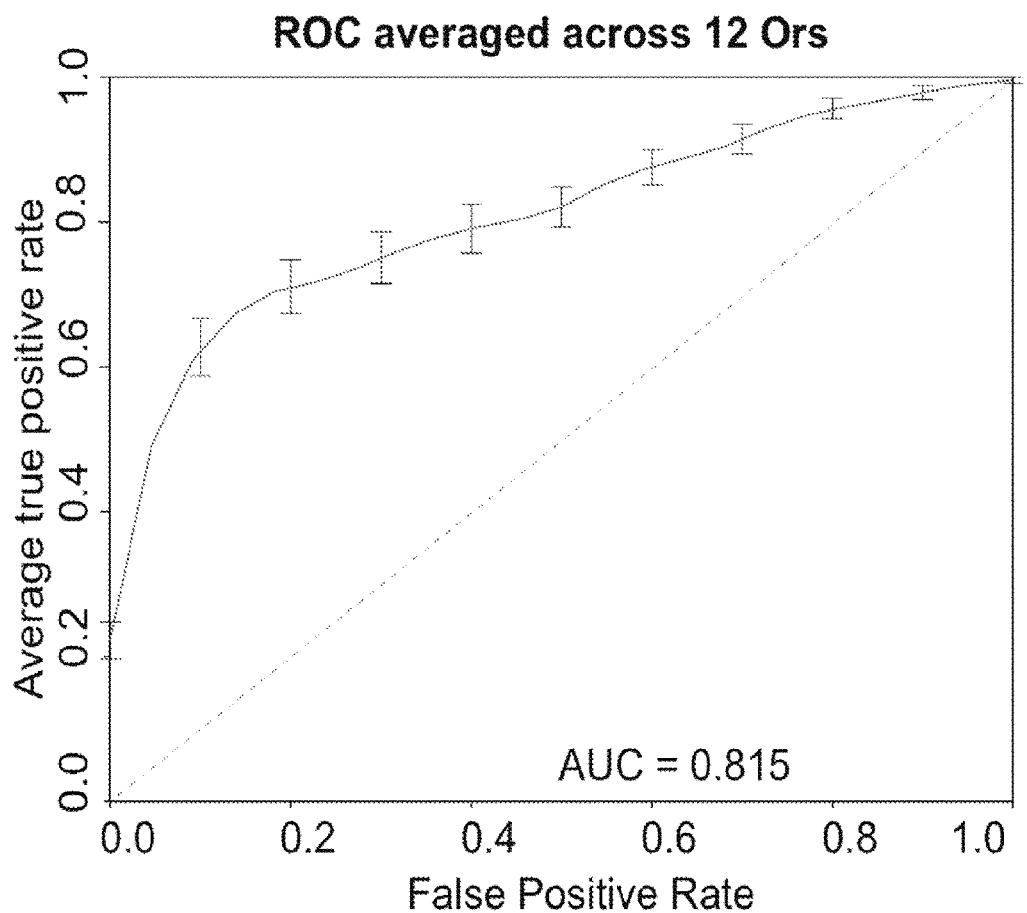
FIG. 9A shows a computational validation of *Drosophila* optimized descriptor sets.
Figure 9B:
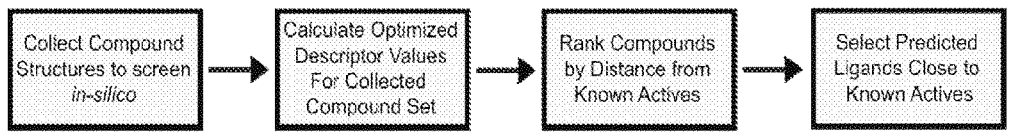
FIG. 9B shows high-throughput flowchart for in silico screen of each Or with >240,000 compounds.
Figures 10A, 10B, 10C:
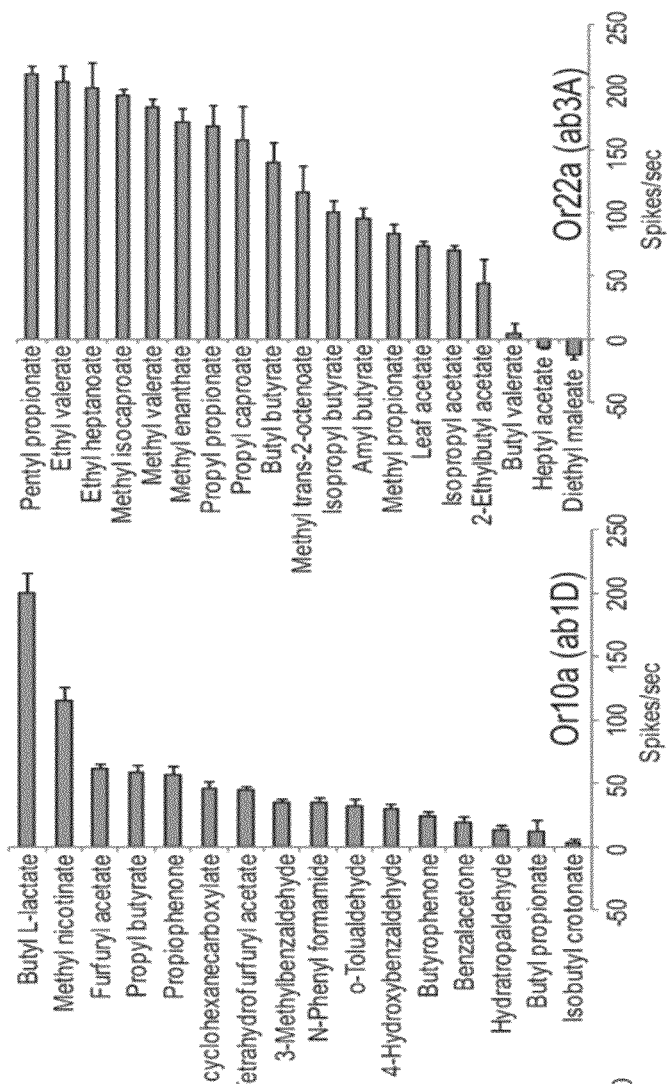
FIGS. 10A-10I show electrophysiology validations of *drosophila* in silico screen for the following receptors: Or7a (FIG. 10A); Or10a (FIG. 10B); Or22a (FIG. 10C); Or47a (FIG. 10D); Or49b (FIG. 10E); Or59b (FIG. 10F); Or85a (FIG. 10G); Or85b (FIG. 10H); and Or98a (FIG. 10I).
Figures 10D, 10E, 10F:
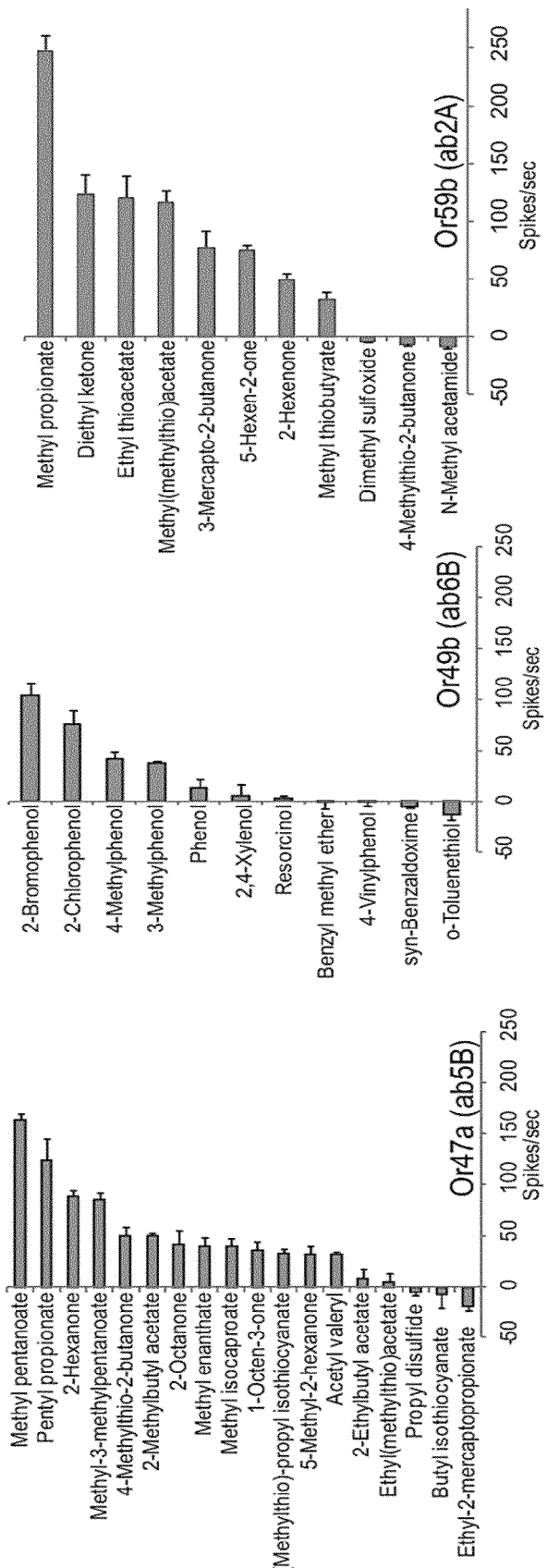
Figures 10G, 10H, 10I:
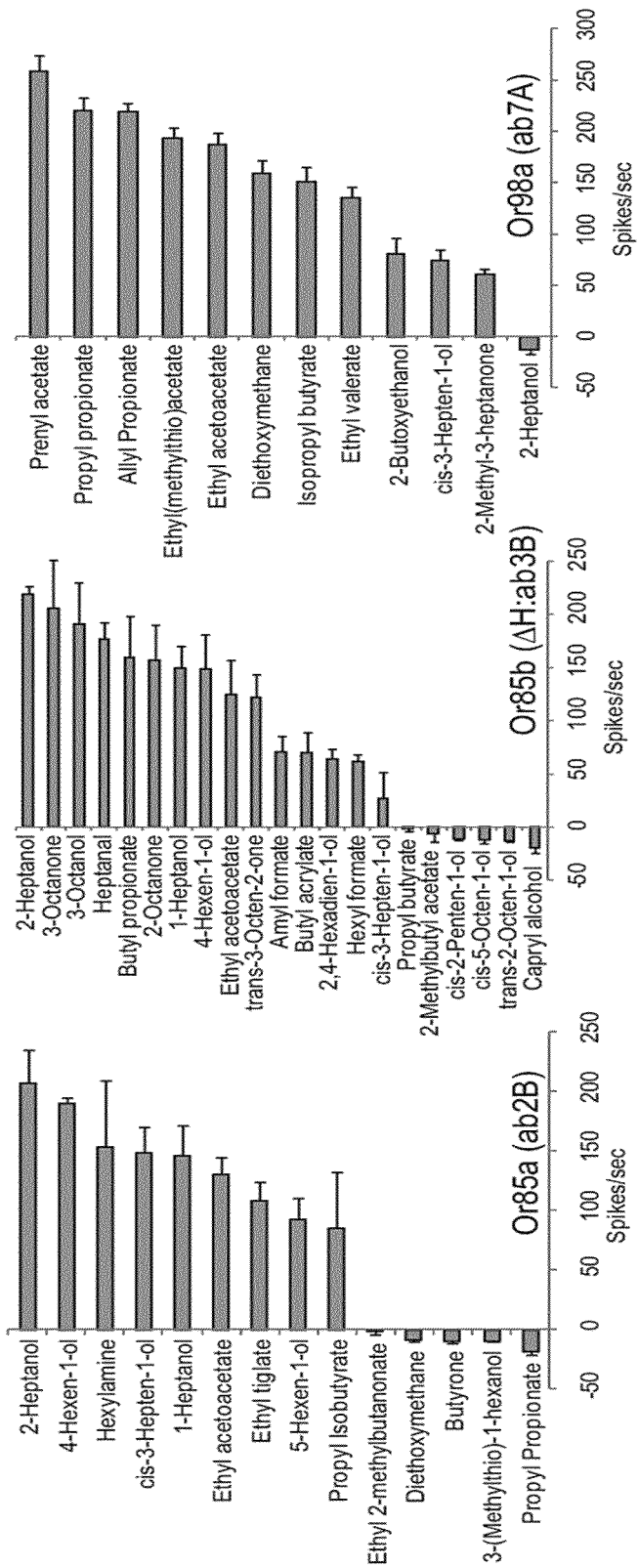
Figure 11:
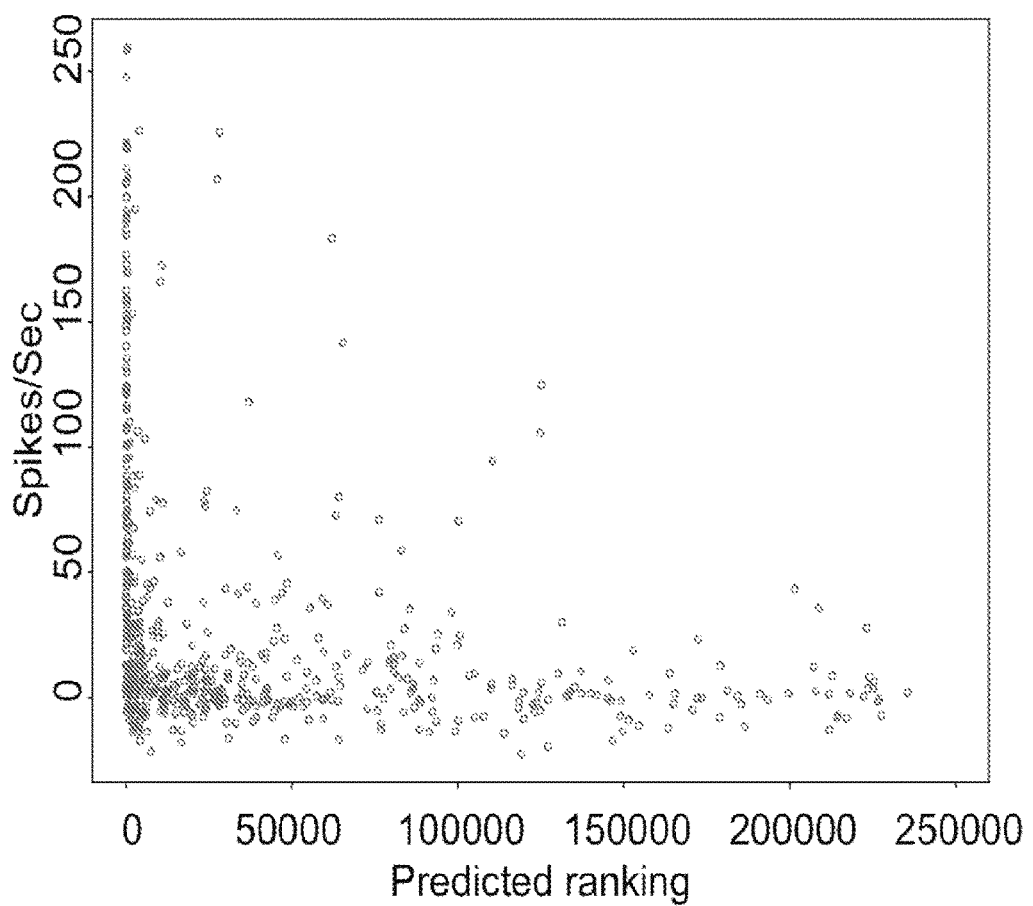
FIG. 11 shows an electrophysiology testing for *drosophila* "false negative" rates of prediction.
Figure 12A:
Figure 12B:
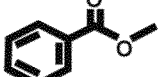
Figure 12C:
Figure 12E:
Figure 12F:
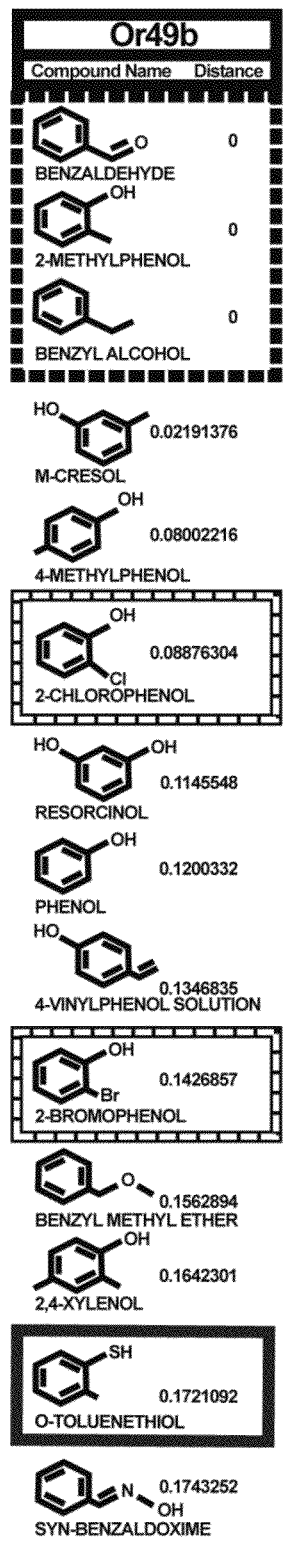
Figure 13A:
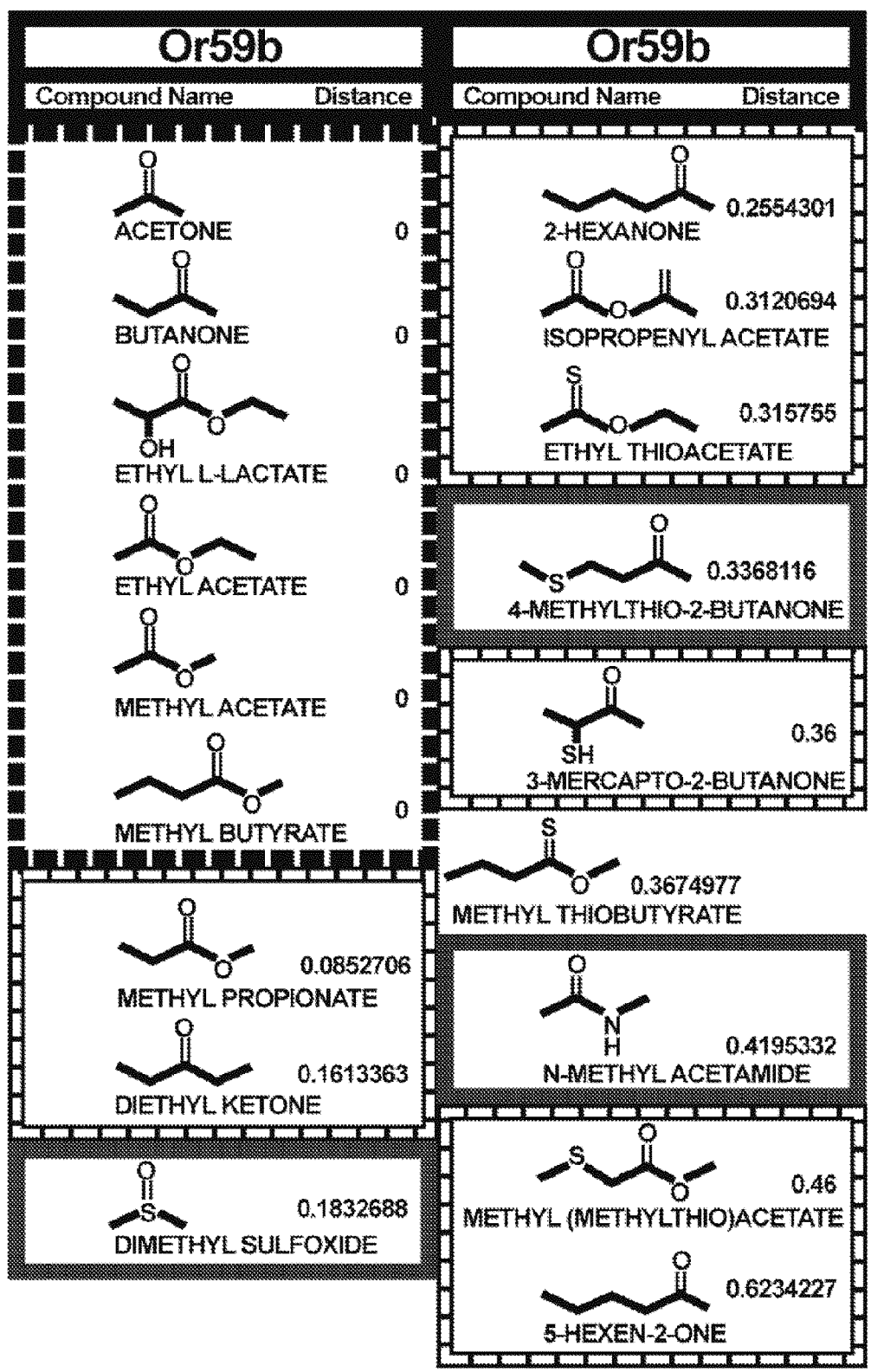
FIGS. 13A-13F show table 3 *drosophila* compounds tested for activity: Or59b-Or98a. Compounds tested for activity: *Drosophila* Or59b-Or98a. List of compounds that were tested using electrophysiology for each Or. Chemical name, a 2-D structural image, and distance measure are listed for each tested compound. All distances are Euclidean and represent the distance between each compound and their closest known active by optimized descriptor values. Known active compounds from the training set are the top 12, 7, 13, 5, 9 and 3 compounds respectively in each column, predicted compounds that were validated as actives are appropriately boxed, inhibitors are appropriately boxed, and inactive compounds are boxed.
Figure 13B:
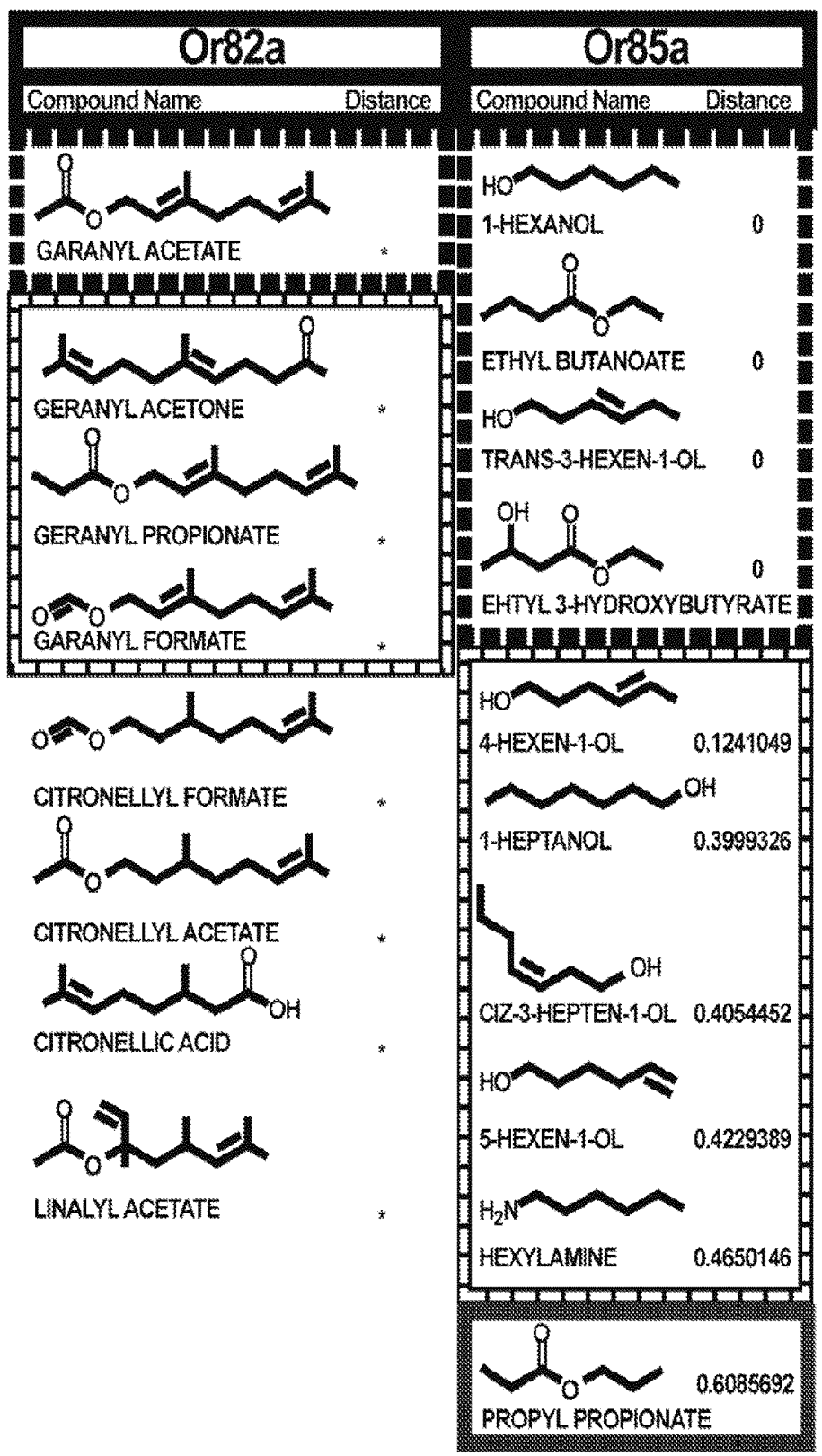
Figure 13C:
Figure 13D:
Figure 13E:
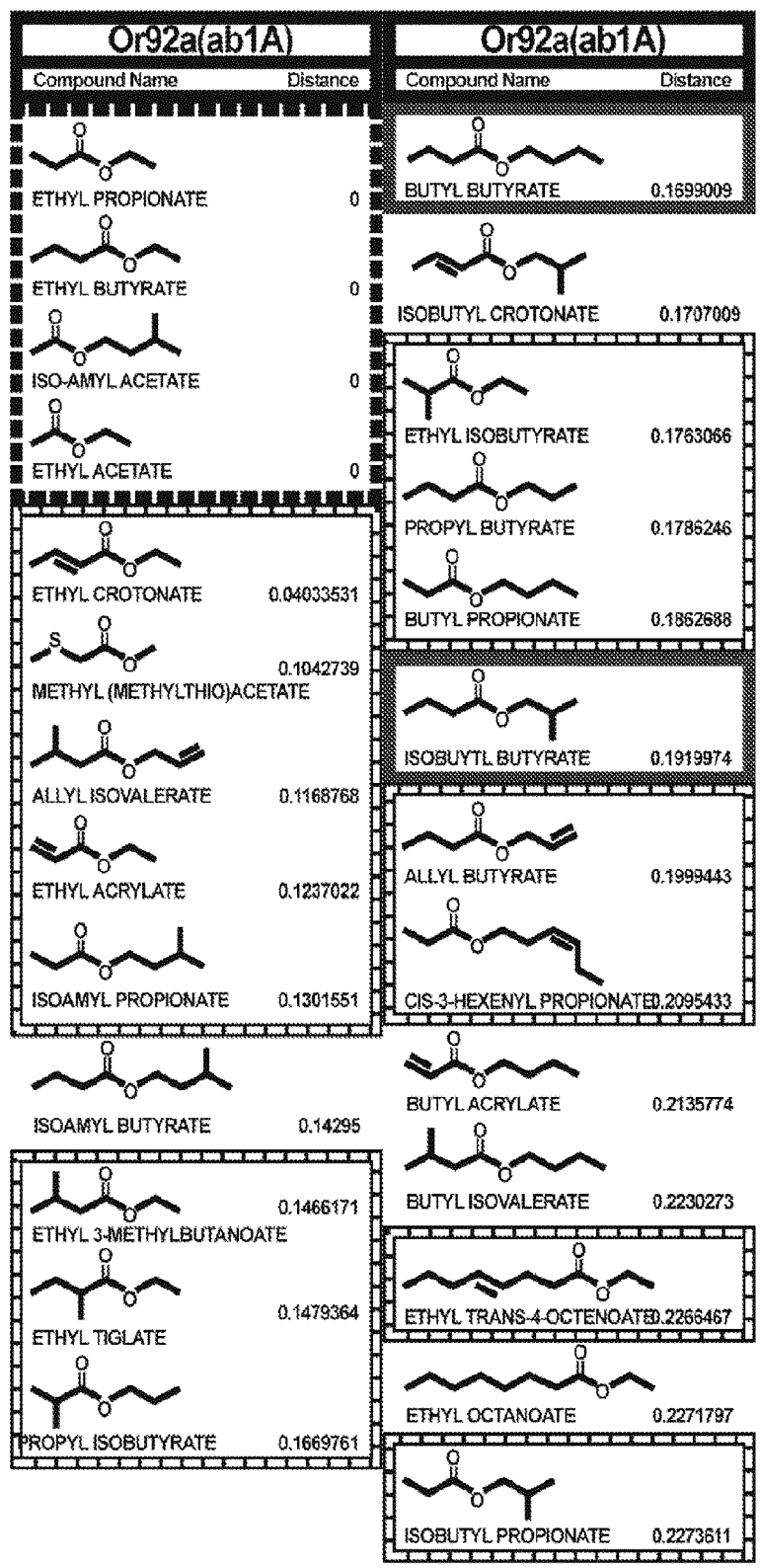
Figure 13F:

Computational validation of *drosophila* optimized descriptor sets. A 5-fold cross-validation was performed by dividing the dataset into 5 equal sized partitions containing roughly 22 compounds each. During each run, one of the partitions is selected for testing, and the remaining 4 sets are used for training. The training process is repeated 5 times with each unique odorant set being used as the test set exactly once. For each training iteration a unique set of descriptors was calculated from the training compound set. These descriptors were then used to calculate minimum distances from the test set compounds to the closest active exactly as used to predict ligands in a ligand discovery pipeline. Once test set compounds have been ranked by distance from closest to furthest to a known active in the training set, a receiver operating characteristics (ROC) analysis is used to analyze the performance of the computational ligand prediction approach. This analysis was performed on 12 Ors that were activated strongly by at least five odors (>100 spikes/sec) and very strongly by at least one odor (>150 spikes/sec) and were considered to have sufficient known ligands for this type of validation (Or7a, Or9a, Or10a, Or22a, Or35a, Or43b, Or47a, Or59b, Or67a, Or67c, Or85b, Or98a). A single average ROC curve for all 12 Ors was calculated and plotted (FIG. 9A).

Computational Validation of mammalian OR Compound Clustering. A 5-fold cross-validation was performed by dividing the dataset into 5 equal sized partitions containing 12 compounds each. During each run, one of the partitions is selected for testing, and the remaining 4 sets are used for training. The training process is repeated 5 times with each unique odorant set being used as the test set exactly once. For each training iteration a unique set of descriptors was calculated from the training compound set. These descriptors were then used to calculate minimum distances from the test set compounds to the closest active exactly as used to predict ligands in the ligand discovery pipeline. Once test set compounds have been ranked by distance from closest to furthest to a known active in the training set, a receiver operating characteristics (ROC) analysis is used to analyze the performance of the computational ligand prediction approach. Using ROC one can determine the predictive ability for 7 of the most broadly tuned receptors (Or2W1, MOr271-1, MOr203-1, Or1A1, MOr272-1, MOr139-1, and MOr41-1). To retain as many active compounds for each test set division as possible, the activity threshold was reduced for each of the Ors to the lowest level. All compounds with a recorded activation in the previous study were considered "active". ROC curve averages for all of the compounds were calculated and plotted (FIGS. 18A-18G).

Or-Ligand Interaction Map. The Or-ligand interaction map was developed using Cytoscape. Each predicted Or-ligand interaction from the top 500 predicted ligands for all of the Ors listed Table 4 were used to calculate the map. All predicted interactions are labelled in grey. In addition all interactions identified in this study, previous study and interactions for ab1A and ab1B from another study were included and labelled in black. All compounds are represented as small black circles and Ors are represented as large coloured circles. Or names are provided on the upper right corner of each Or.

Electrophysiology. Extracellular single-sensillum electrophysiology was performed as before with a few modifications. 50 □l odor at $10^{-2}$ dilution in paraffin oil was applied to cotton wool in odor cartridge. Odor stimulus flow=12 ml/second. Due to variability in temporal kinetics of response across various odors, the counting window was shortened to 250 milliseconds from the start of odor stimulus. A diagnostic panel of odorants to distinguish individual classes of sensilla (ab1-ab7) and therefore unequivocally identified the target ORN.

Since the structure of receptor protein complexes is not known odor-receptor interactions were analyzed by applying the similarity property principle, which reasons that structurally similar molecules (e.g. activating odorants) are more likely to have similar properties. To identify a method that describes common structural features shared by receptor actives in a quantitative fashion tractable for computational analysis four types of vastly differing molecular descriptor systems were tested: Cerius2 (Accelrys Software Inc), Dragon (Talete), Maximum-Common-Substructure, and Atom-Pair, to construct a chemical space for 109 odors that had previously been tested against 24 odor receptors from *Drosophila melanogaster*. These represent virtually all of the Or genes expressed in the *Drosophila* antenna. The four descriptor methods and associated similarity measures varied in their ability to group actives close together in descriptor space as measured for each Or using Accumulative Percentage of Actives (APoA) and value of Area Under the Curve (AUC).

Figure 5:
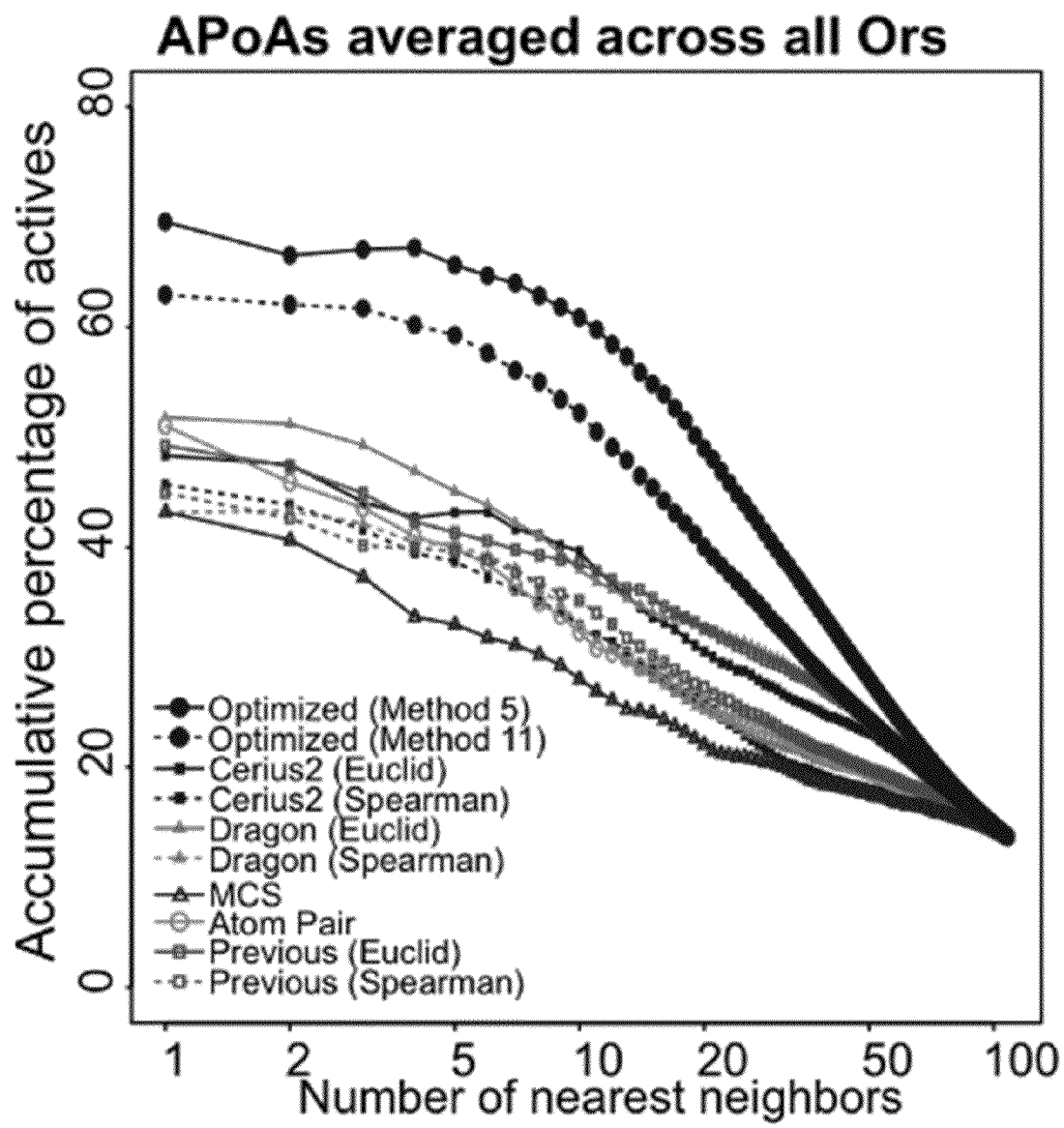
FIG. 5 is a graph comparing APoA values.
Figure 21D:
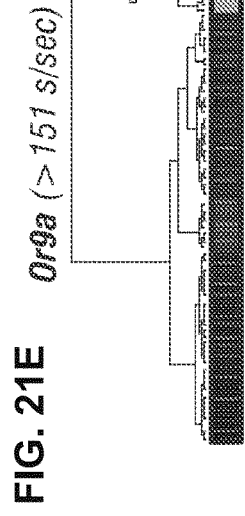
Figure 21E:
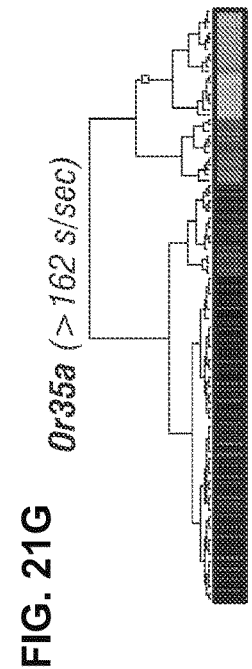
Figure 21F:
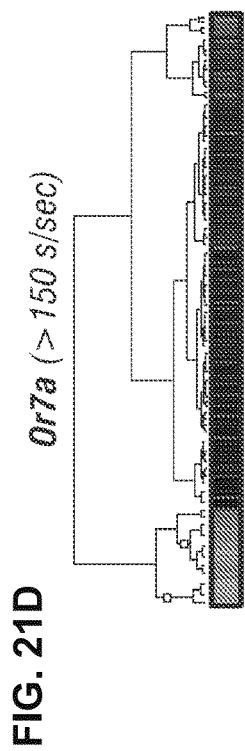
Figure 21G:
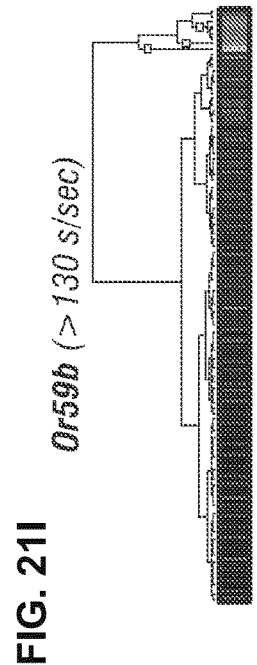
Figure 21H:
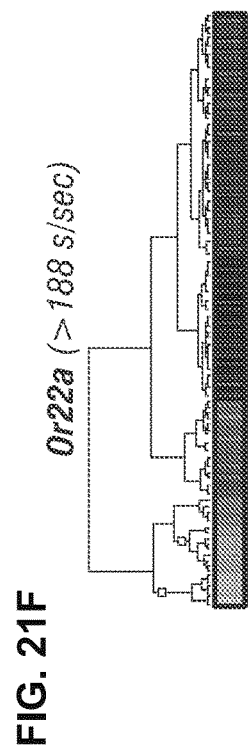
Figure 21I:
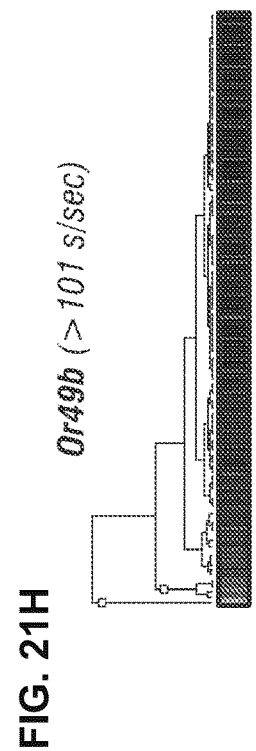
Figure 22:
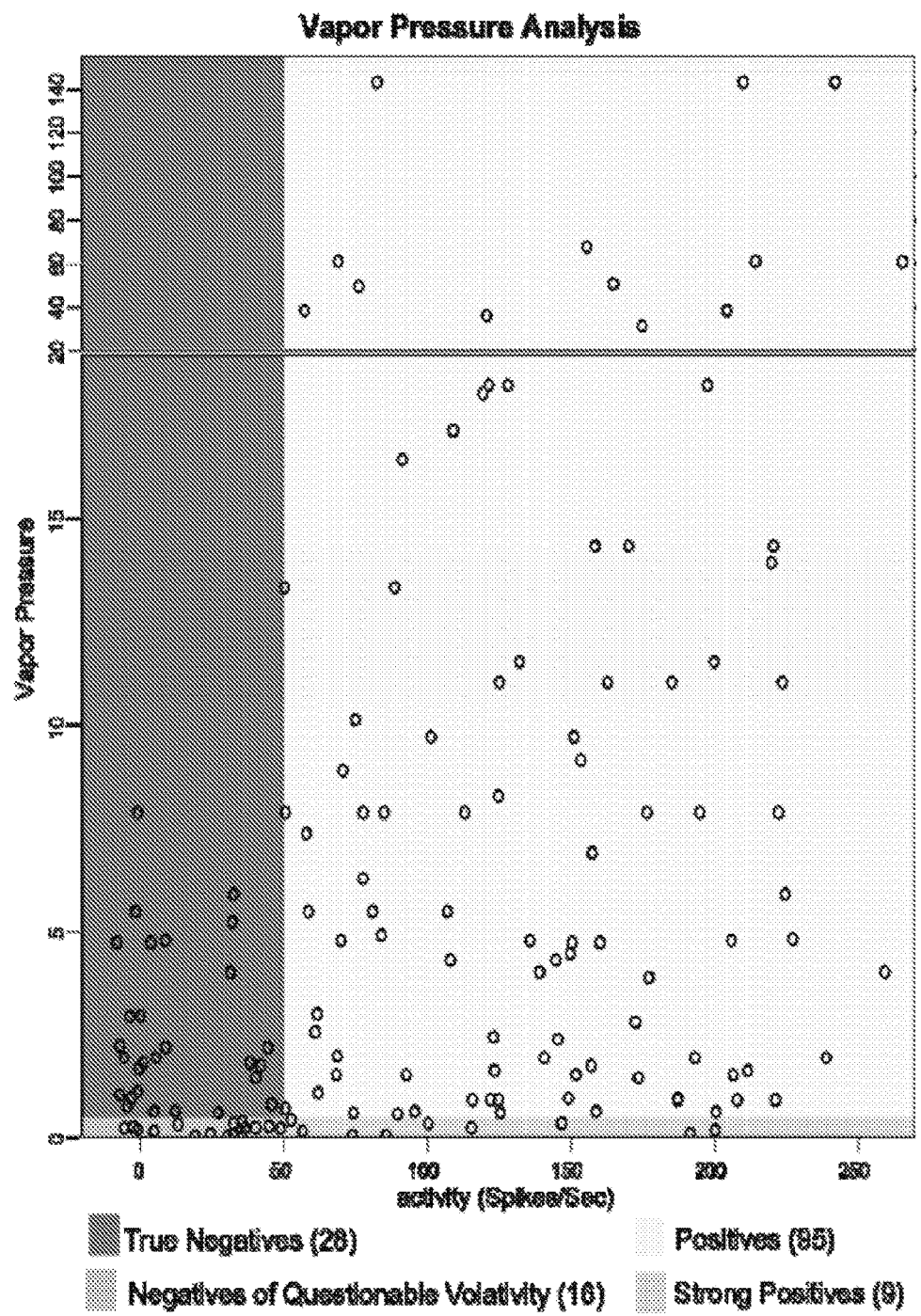
FIG. 22 shows that vapor pressure possibly affects ligand-Odor receptor activation. Vapor pressures and activities (in spikes/sec) were plotted for validated odorant predictions. Compounds are divided into four classes based upon compound activity and vapor pressure values.
Figures 23Q, 23R, 23S:
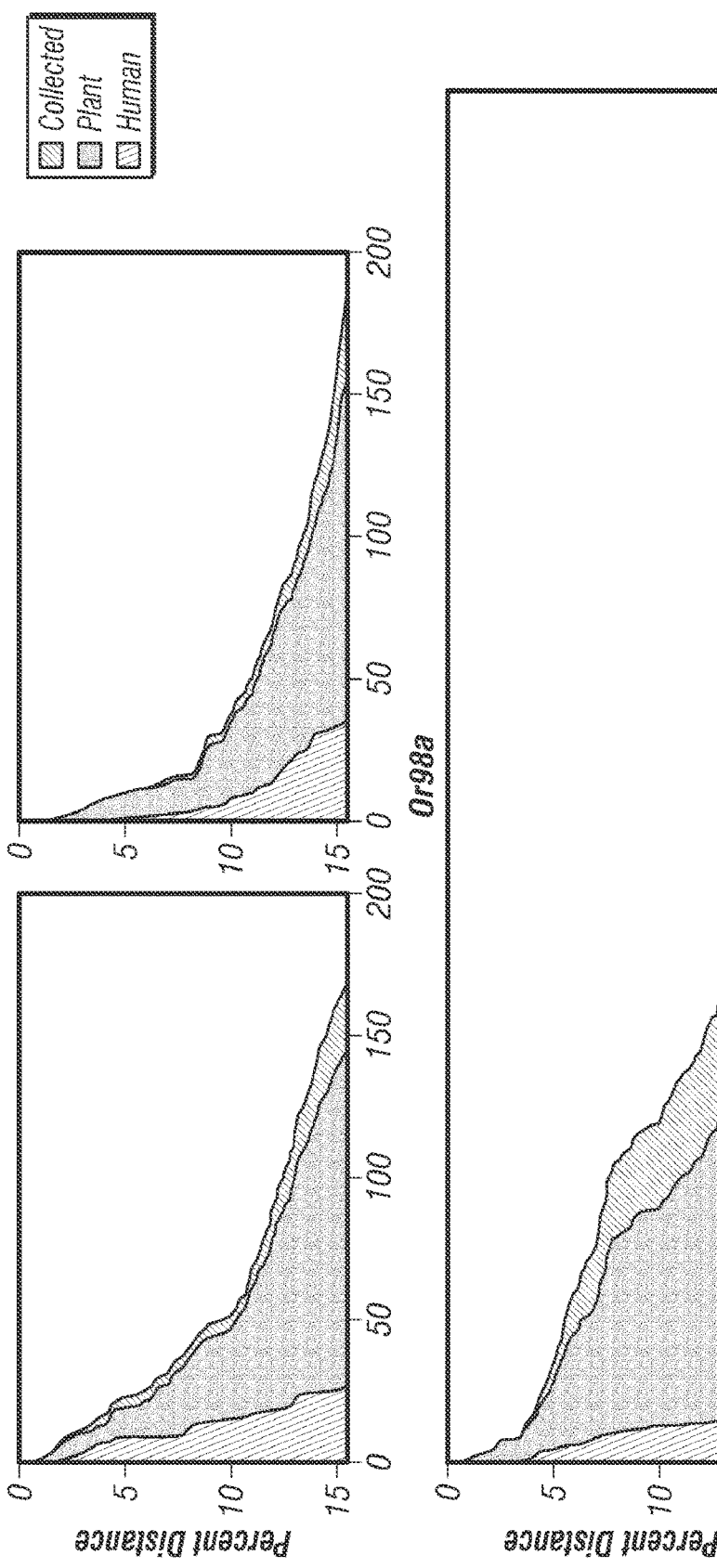
FIGS. 23A-23V show predicted breadth of tuning for collected compounds in Odorant receptors, such as Or23a (FIG. 23A); Or82a (FIG. 23B); Or49b (FIG. 23C); Or92a (FIG. 23D); Or42b (FIG. 23E); Or22a (FIG. 23F); Or59b (FIG. 23G); Or43b (FIG. 23H); Or85a (FIG. 23I); Or85f (FIG. 23J); Or19a (FIG. 23K); Or67c (FIG. 23L); Or85b (FIG. 23M); Or7a (FIG. 23N); Or2a (FIG. 23O); Or67a (FIG. 23P); Or43a (FIG. 23Q); Or35a (FIG. 23R); Or98a (FIG. 23S); Or9a (FIG. 23T); Or47a (FIG. 23U); and Or10a (FIG. 23V). Compounds from the collected compound library that have been catalogued as plant, human and total collected volatiles were ranked according to their relative distance from the compound with highest activity. Frequency distribution of compounds within the top 15% is plotted to generate predicted breadth of tuning curves. X-axes are in logarithmic scale.

Individual Ors are tuned to overlapping but distinct subsets of ligands. It was reasoned that cherry-picked subsets of molecular descriptors that are suited to cluster actives for an individual Or may be more effective at defining Or-specific chemical space, rather than the entire descriptor set that likely includes a number of features irrelevant for that Or. Using a Sequential-Forward-Selection method similar to previously used approaches unique optimized descriptor subsets were incrementally created for each Or from an initial set of 3424 Dragon and Cerius2 descriptors, which had performed better than Atom Pair and MCS (FIG. 1). 18 combinations of distance metrics, descriptor sets, and activity thresholds, were tested to identify the optimal selection method for each Or (FIGS. 2 and 21A-21W). Not surprisingly, the composition of the optimized descriptor sets varied greatly for individual Ors. There is an overwhelming preference for 3-D and 2-D descriptors compared to 1-D and 0-D descriptors, which suggests that structural features rather than the chemical properties of odorants are more important for receptor-odor interactions. The Or-optimized descriptor sets were far superior to non-optimized methods, and to a previous method that did not perform receptor-specific optimization (FIGS. 5 and 21A-21W).

Distances calculated by each Or-optimized descriptor set clustered the highly active compounds (~70%) close together (FIGS. 3A-3T and 8A-8T). In a few cases, such as for Or35a and Or98a, not all the highly active compounds are clustered, suggesting the possibility of multiple or flexible binding sites, or imperfect selection of descriptors. Or2a, Or23a, Or43a and Or85f do not have strong actives, however the few weak actives of each of these 4 receptors do cluster together (FIGS. 3A-3T and 8A-8T). Actives of an Or have similar structures and pharmacophore features (FIGS. 3A-3T and 8A-8T).

Since Or-optimized descriptors can group highly active compounds in chemical space, There were used to rank untested compounds according to their distance from known actives. Approximately 4,500,000 odor-receptors interactions were systematically screened in silico, representing 19 Ors and >240,000 putative volatile compounds, a scale >1500 times that achieved in previous electrophysiology studies of odor-receptor interactions. This represents a significant achievement since high-throughput plate-based assays are not appropriate for screening volatile Or ligands, which are largely absent from the soluble combinatorial chemical libraries available for such methods. The top 500 (0.2%) hits from this vast chemical library for each of the 19 Ors were generated a fraction of which are presented in Table 4.

Figure 17A:
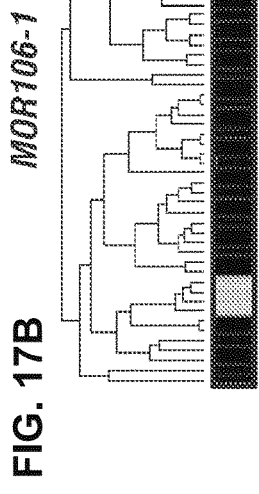
FIGS. 17A-17AK show clustering mammalian odorants by optimized descriptor subsets for MOR1-1 (FIG. 17A); MOR106-1 (FIG. 17B); MOR139-1 (FIG. 17C); MOR162-1 (FIG. 17D); MOF189-1 (FIG. 17E); MOR2-1 (FIG. 17F); MOR107-1 (FIG. 17G); MOR129-1 (FIG. 17H); MOR170-1 (FIG. 17I); MOR184-1 (FIG. 17J); MOR203-1 (FIG. 17K); MOR204-6 (FIG. 17L); MOR136-1 (FIG. 17M); MOR223-1 (FIG. 17N); MOR185-1 (FIG. 17O); MOR260-1 (FIG. 17P); MOR207-1 (FIG. 17Q); MOR273-1 (FIG. 17R); MOR250-1 (FIG. 17S); MOR256-17 (FIG. 17T); MOR261-1 (FIG. 17U); MOR268-1 (FIG. 17V); MOR277-1 (FIG. 17W); MOR30-1 (FIG. 17X); MOR258-1 (FIG. 17Y); MOR259-1 (FIG. 17Z); MOR271-1 (FIG. 17AA); MOR272-1 (FIG. 17AB); MOR33-1 (FIG. 17AC); MOR37-1 (FIG. 17AD); MOR40-1 (FIG. 17AE); MOR41-1 (FIG. 17AF); MOR5-1 (FIG. 17AG); OR1A1 (FIG. 17AH); OR2J2 (FIG. 17AI); OR2W1 (FIG. 17AJ); and OR5P3 (FIG. 17AK).
Figure 17B:
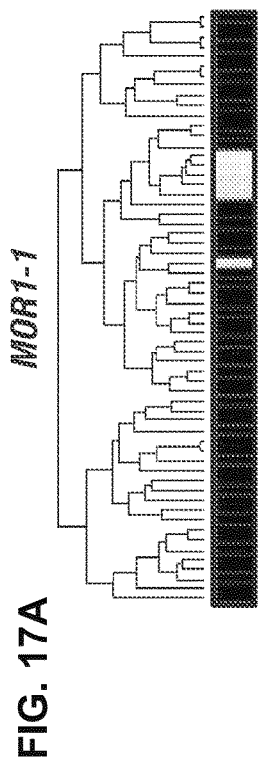
Figure 17C:
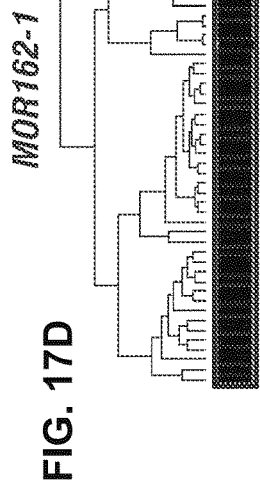
Figure 17D:
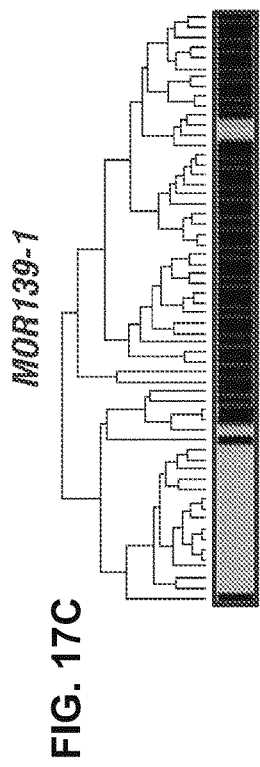
Figure 17E:
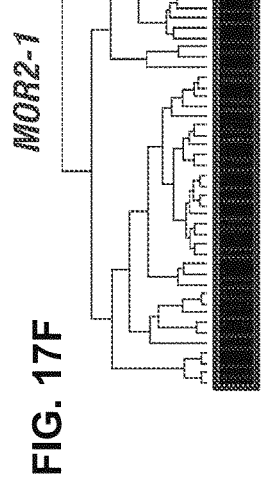
Figure 17F:
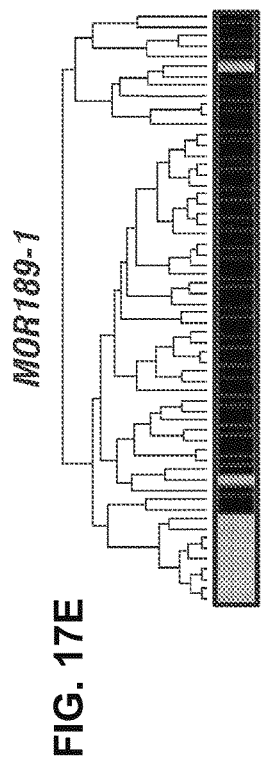
Figure 17G:
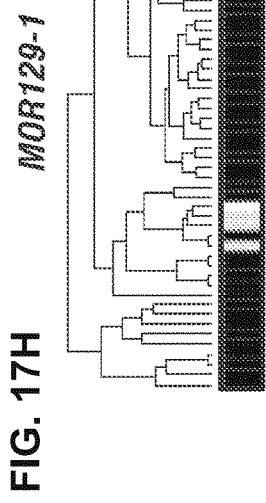
Figure 17H:
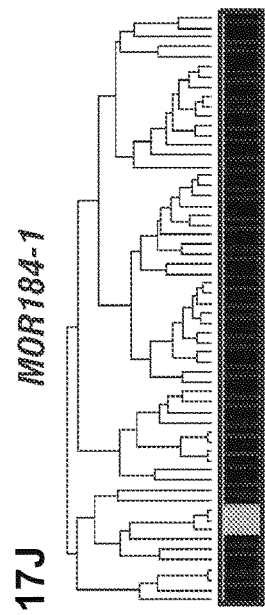
Figure 17I:
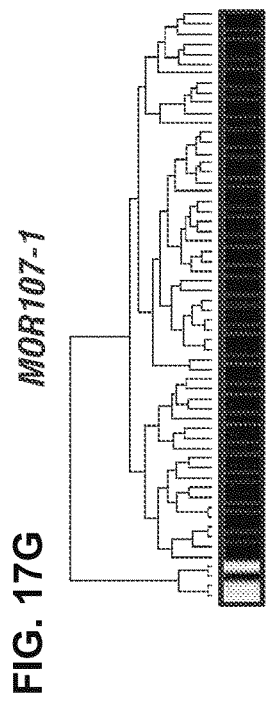
Figure 17J:
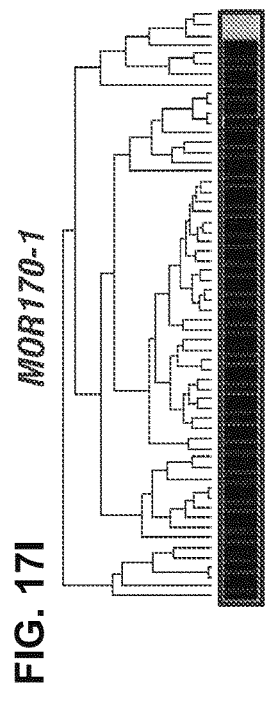
Figure 17K:
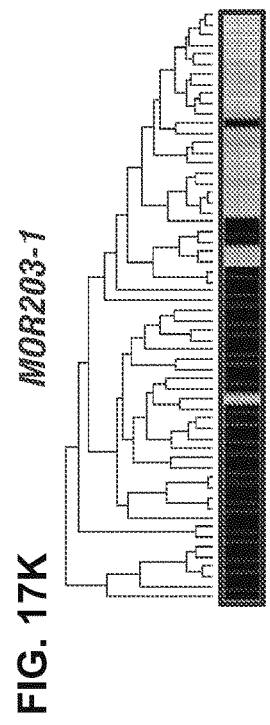
Figure 17L:
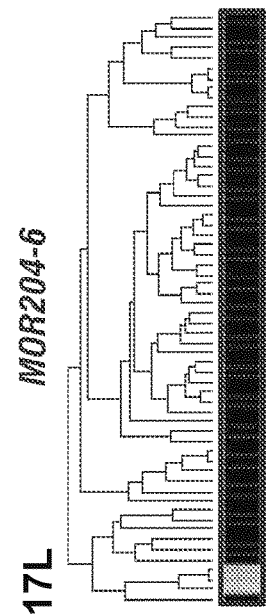

To validate the in silico screen several untested odorants were obtained (192; ~11-25/Or) belonging to the top 500 predicted ligands for 9 different Ors (Tables 3 and 4). They were systematically tested with each predicted receptor-odor combination using single-unit electrophysiology to record from the olfactory receptor neurons (ORNs) to which these 9 Ors have been previously mapped in the *D. melanogaster* antenna (FIGS. 17A-17AK and 18A-18G). A majority of the predicted actives evoked responses from the target ORNs (FIG. 18); ~75% evoked either activation (>50 spikes/sec above the spontaneous activity) or inhibition (>50% reduction in spontaneous activity) (FIG. 14). The success rate varied between Ors (27%-100%). A number of predicted actives that do not evoke a response (16/44) are compounds with very low volatility, raising the possibility that they may not be delivered at adequate levels to the ORNs. Taken together the physiological analysis provides the most important validation of the Or-optimized descriptor-based in silico screen of chemical space to identify volatile ligands for Ors. Previous studies have not performed well (<25% success for >50 spikes/sec) in evaluating novel odorants.

Approximately 10% of the predicted compounds showed a strong inhibitory effect (FIGS. 10A-10I, 14, 15A-15C and 16A-16B). Interestingly, inhibitors for 3 receptors, Or22a, Or47a and Or59b, were identified for which there are no previously reported inhibitors. Compounds that inhibit Ors were identified by virtue of structural similarity to Or activators. Thus the approach may provide a high-throughput method to identify putative competitive inhibitors and provide tools to investigate mechanisms of Or inhibition and their consequences in blocking specific behaviors.

Figure 15B:
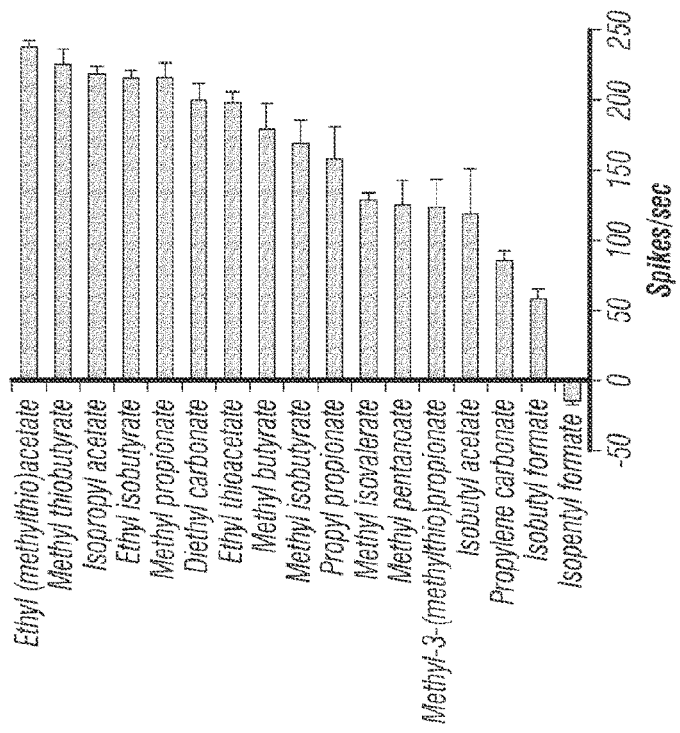
FIGS. 15A-15C show ligand prediction from neuronal activity.
Figure 15A:
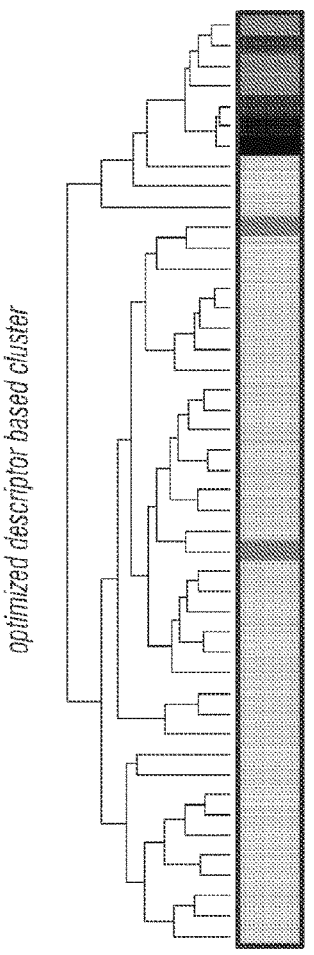
Figure 15C:
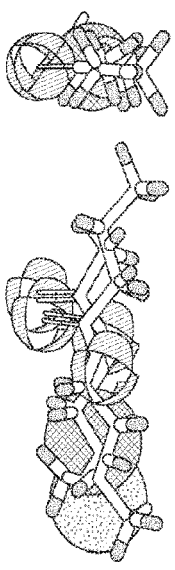

Although an increasing number of insect Ors are being decoded using various methods like the *Drosophila* "empty neuron" system, and heterologous expression in *Xenopus* oocytes or cells, the process is extremely tedious and expensive. However, information on odor response profiles of single ORNs is available for several species of insects and vertebrates and relatively easy to obtain using single cell recording and/or imaging techniques. In most cases, individual ORNs ensure expression of a single Or gene and the response specificity of an ORN is imparted primarily by this associated Or. One can perform descriptor optimization using the odor response profile of the ORN directly. Or92a and Or42b have not been decoded however their corresponding antennal ORNs (ab1A and ab1B) have been tested with a panel of 47 odors. ORN-optimized descriptor sets (FIG. 12A-12F) that were efficient at clustering actives close together in chemical space were used (FIG. 15A-B). The ORN-optimized descriptor sets for ab1A and ab1B were used to screen the >240,000 library and predicted 500 novel ligands as before (Table 3, 4). Approximately 20 novel compounds were tested for each ORN, which revealed a high degree of success: >68% for ab1A and >94% for ab1B (FIGS. 15A and 15B).

Figure 16A:
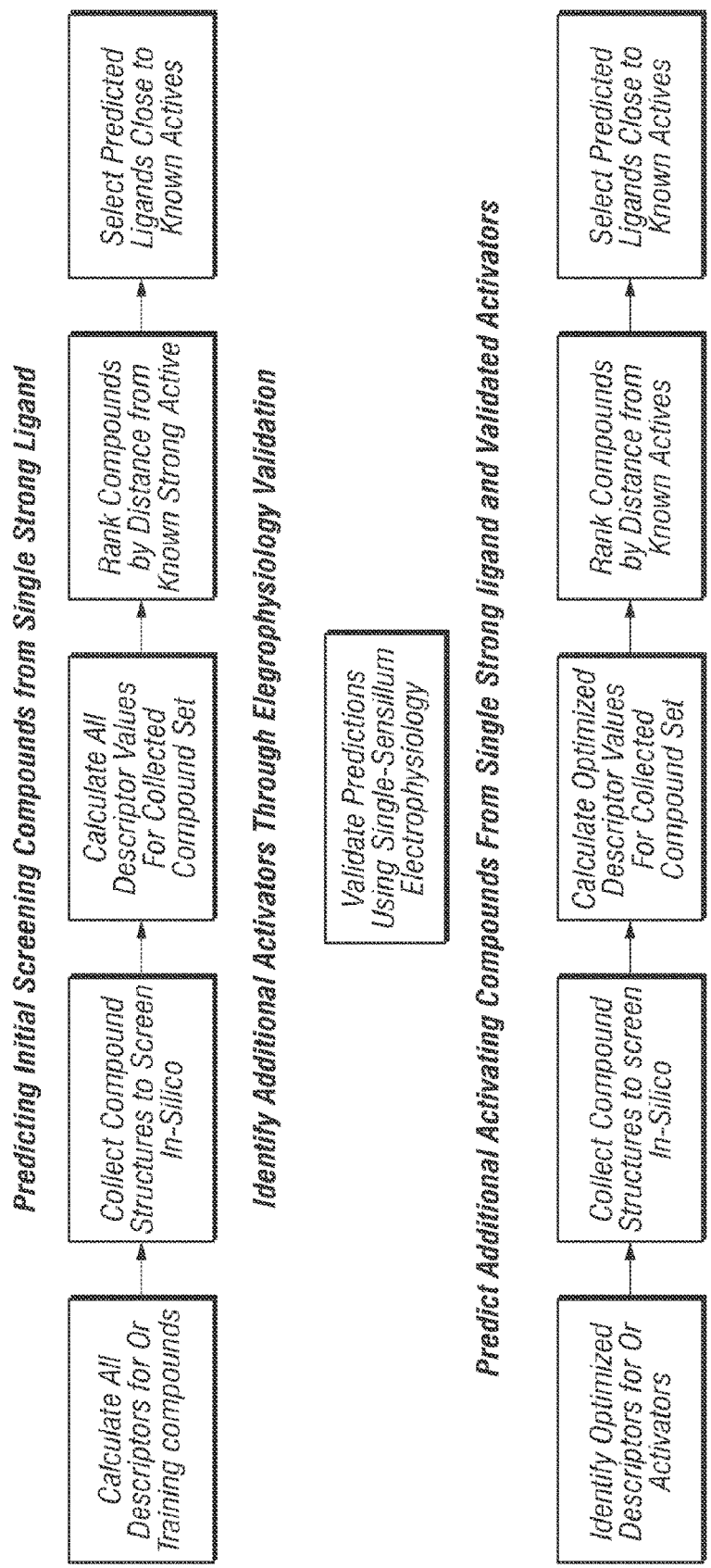
FIGS. 16A and 16B depict ligand prediction from narrowly tuned Ors.
Figure 16B:
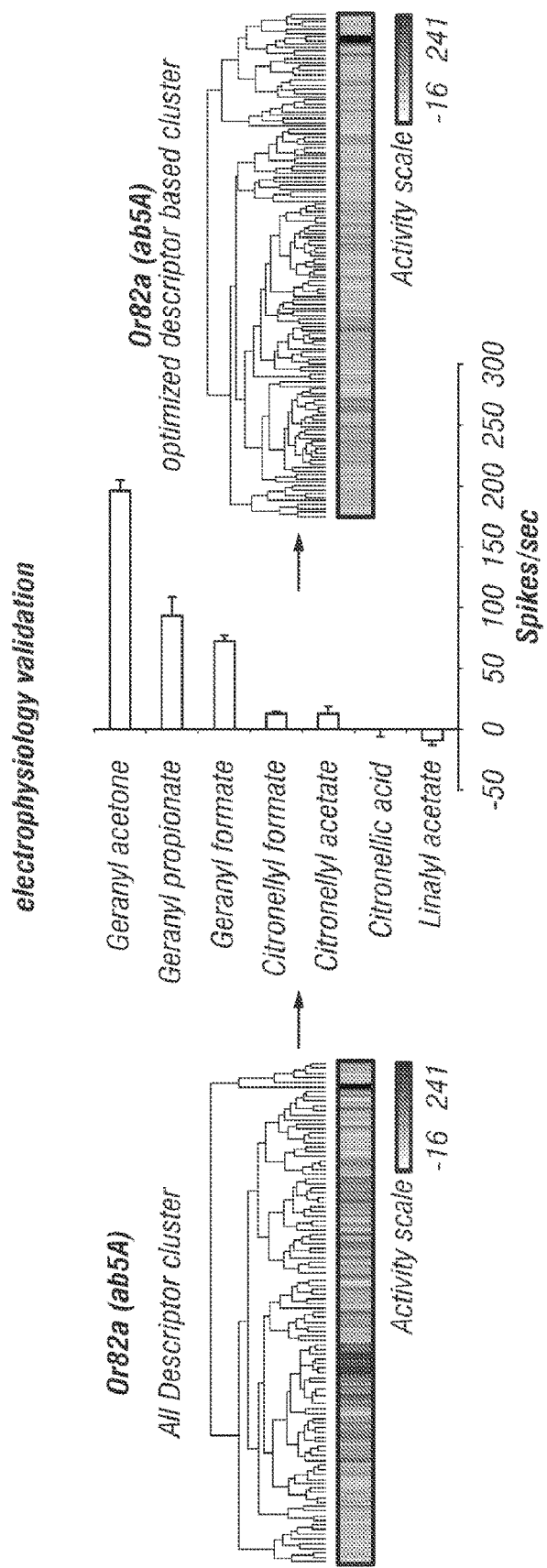

Or82a was intractable to the selection of Or-optimized descriptors because it is activated strongly by a single compound, geranyl acetate, a pheromone-like long-chain hydrocarbon compound. Or82a activity is reminiscent of known insect pheromone receptors, which are often responsive only to single compounds and present an extreme challenge to understanding receptor-odor interactions. To identify novel ligands for the narrowly tuned Or82a, three additional activators of Or82a were identified from approximate predictions made using all 3424 Dragon and Cerius2 descriptors to calculate distances of >240,000 compounds in the library from geranyl acetate (FIGS. 16A-16B). The new set of four activating ligands was used to identify an Or82a-optimized descriptor set, which was successful in clustering the actives close together in chemical space (FIGS. 16A-16B). As described above, ligands were predicted from the library (Table 4), suggesting that this 3-step process can be used to predict novel ligands for narrowly tuned odor receptors, such as pheromone receptors.

The rate of false negative predictions was examined for each Or using electrophysiology to systematically test ligands of each Or against other non-target receptors. Of >640 non-target receptor-odor interactions tested, only 10.8% evoked a response >50 spikes/sec and 4.3% evoked a response >100 spikes/sec. Considering that the Or-optimized descriptor method did not incorporate any additional computational screening to rule out non-target activators, it is quite specific in its predictive ability.

*Drosophila* Or proteins are considered to be 7-transmembrane proteins that have a non-traditional inside-out membrane orientation, active as heteromeric ligand-gated ion channels with an obligate partner Or83b. Mammalian odor receptors on the other hand are G-protein coupled receptors with a traditional outside-in 7-transmembrane orientation. Mammals have far larger families of odor receptors (~1000 in mice, ~350 in humans) and thus pose a greater challenge to examine odor coding. In order to test whether the chemical informatics platform would be as successful with mammalian odor receptors a similar analysis on 33 odor receptors from mouse and 4 odor receptors from humans was performed, for which responses to a panel of 60 odorants have been determined in heterologous cells and >2 actives have been identified.

Optimized descriptor subsets for each OR were selected from an initial set of 3424 Dragon and Cerius2 descriptors as before (Table 5). The ApoA and the AUC values were comparable, if not better, than the *Drosophila* Ors suggesting that the descriptors were able to efficiently cluster actives together (FIGS. 17A-17AK). Since the experimental tests of predictions for mammalian receptors are beyond the scope of the analysis, a well-established computational approach to validate the in silico predictions was used. ORs with >15 known ligands were selected and for each OR 20% of the compounds (12/60) were excluded as a test set, while the remaining were used as a training set to generate the optimized descriptors. Distances of all 60 compounds from each of the known actives were calculated in chemical space and classified as active based on activity threshold. This operation was repeated five times for each receptor, each trial performed by excluding a different subset of 20% of the compounds. Average Receiver Operating Characteristic (ROC) curves were generated and AUC values were calculated, which show that optimized-descriptors generated using the training sets could accurately identify actives from the test sets (FIGS. 18A-18G).

The OR-optimized descriptors were the used to systematically screen ~8,880,000 odor-receptor interactions in silico, representing 33 mouse ORs, 4 human ORs, and >240,000 putative volatile compounds. The top 500 hits for each receptor represent several potential novel ligands for each receptor from various natural plant and animal sources, fragrances and artificial compounds (Table 6).

Since receptor-optimized descriptor sets and the predicted ligand space they define are a function of shared molecular features that a receptor may employ to recognize ligands, it was important to determine how these characteristics correlate with receptor properties, such as their known activity profiles and amino acid sequences. Hierarchical cluster analysis was used to create trees that represent the various receptors based on: shared descriptors selected; known activity-based relationship; degree of overlap of predicted ligands; and amino acid sequence. In *Drosophila*, the known activity and the predicted cross-activity trees overlap to a lesser extent to each other than they do to the descriptor tree (~67% Ors present in common subgroups). In contrast, a similar analysis for the mammalian dataset reveals a greater degree of common relationships across the known activity, predicted cross-activity and descriptor trees (~77% ORs present in common subgroups). Similarly, the *Drosophila* Or-phylogenetic tree has sparser subgroup relationships conserved with each of the other trees (<45%), as opposed to the mammalian ORs where the majority of subgroups in the phylogenetic tree (>56%) are conserved across the various trees. This difference may reflect the much greater amino-acid similarity across the mammalian receptors (47%) as compared to *Drosophila* (23%).

Coding of odors in a large volatile space (>240,000) by a receptor repertoire is virtually impossible to determine experimentally. Based on the Or-optimized descriptor sets tuning curves were computationally derived for the 22 *Drosophila* Ors and 36 mammalian receptors in this large chemical space. Substantial variation in the width of the predicted tuning curves for the different receptors was demonstrated. The predicted response profiles suggest that the olfactory system can potentially detect tens of thousands of volatile chemicals, many of which the organism may never have encountered in its chemical environment.

To analyze breadth of tuning and coding potential of the antennal repertoire of *Drosophila* Ors to natural odors, tuning curves were calculated to an assembled set of 3197 volatile compounds from plants, humans, and a fragrance collection. Plant volatiles constituted an overwhelming majority of compounds that are predicted to be ligands for *Drosophila* Ors, consistent with its chemical ecology. To further analyze odor source representation odors were classified that belong to top 500 prediction lists according to their source, if known and find that Ors are not specialized for odors from a single source.

To study the predicted ensemble activation patterns of odors across all Ors, the across-receptor activation patterns of the collected compounds were analyzed for each receptor listed in Table 4. Surprisingly only a small fraction (<25%) of the collected odors are predicted to activate multiple Ors. Inclusion of all the top 500 predicted actives for each receptor further reduces the proportion of across-receptor activating compounds. Consistent with this prediction it was demonstrated that cross-activation by ligands evaluated in this study (870 receptor-odor interactions for 10 receptor neurons from FIG. 14) is lower than that reported previously using ligands of comparable strength. These data suggest that a significant number of natural odors may in fact be detected by only one or few receptors, particularly at physiologically relevant concentrations. This concept contrasts with the current model of combinatorial coding in which a majority of volatile chemicals, with the exception of pheromones and $CO_2$, are detected by combinations of various odor receptors. One possible explanation for this disparity is that previously tested subsets of odors were typically chosen on the basis of strong responses in electroantennograms and behavior assays, which could bias towards selection of cross activating odors. The observations that complex fruit odors activate fewer Ors than the number activated by single odors at comparable concentrations such as pentyl acetate, hexanol etc. from a typical test panel, and complex stimuli such as apple-cider-vinegar activate no more than 4-6 glomeruli lend support to this notion. The architecture of the olfactory code therefore appears to integrate two different models. On the one hand, most odors are detected by one or few Ors from the repertoire, which may enhance the specificity and efficiency of the olfactory system for detection of a large number of odors. On the other hand, 15-20% of odors are predicted to activate combinations of Ors (up to 50%), which may serve to increase the resolving capacity of the system in discriminating the defining properties of an odor stimulus.

To create a more generalized metric to quantify odorant similarity all *Drosophila* Or-specific molecular descriptors were concantonated and used to compute a 322-dimensional space. By visualizing the space in 2-dimensions using the two principle components, the map of the >240K chemical library overlaps well with the 3197 collected-compound volatile library, except for high molecular weight specialized flavor structures. The new ligands identified (+) overlap with previously tested compounds, and odorants distribute according to size and functional group (colors and shapes).

A network view of peripheral odor coding in the *Drosophila* antenna was created by mapping all predicted and tested odor-receptor combinations as has been done previously for mapping drug-target networks. The ability to decode odor receptors in silico offers a powerful approach to study the chemical ecology of an organism by potentially matching most known odors from a specific environmental source to large repertoires of target receptors or ORNs to engender a systems level view of olfactory system activation. Databases of predicted ligands will provide an invaluable tool for further studies of olfactory systems. The search for novel flavor and fragrance compounds for human beings can also be greatly assisted by a rational prioritization using such a cheminformatics approach. An emerging area of research is the identification of odors that can modify host-seeking behavior in insect disease vectors, either by virtue of their ability to inhibit ORNs that detect host-seeking cues, or by activating ORNs that cause avoidance behavior, or by confounding the pheromone detection pathway and cause mating disruption. In silico screens can provide a rational foundation for identification of novel insect repellents and lures that are environmentally safe and can aid in the fight against insect-borne diseases.

TABLE 1

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

*Drosophila* Descriptor Lists

Descriptor Class Type Counts for all Ors

| | |
|---|---|
| 3D-MoRSE descriptors | 84 |
| GETAWAY descriptors | 84 |
| functional group counts | 51 |
| 2D autocorrelations | 49 |
| edge adjacency indices | 49 |
| 2D binary fingerprints | 48 |
| atom-centred fragments | 41 |
| WHIM descriptors | 40 |
| topological charge indices | 26 |
| atomtypes (Cerius2) | 25 |
| molecular properties | 24 |
| Burden eigenvalues | 23 |
| topological descriptors | 22 |
| geometrical descriptors | 18 |
| 2D frequency fingerprints | 11 |
| RDF descriptors | 8 |
| walk and path counts | 6 |
| information indices | 6 |
| topological (Cerius2) | 5 |
| connectivity indices | 5 |
| constitutional descriptors | 4 |
| structural (Cerius2) | 3 |
| Randic molecular profiles | 2 |
| eigenvalue-based indices | 0 |
| charge descriptors | 0 |

Dimensionality Counts (Weights Included)

| | |
|---|---|
| Num zero dimensional descriptors: | 7 |
| Num one dimensional descriptors: | 140 |
| Num two dimensional descriptors: | 250 |
| Num three dimensional descriptors: | 236 |

Origin (Weights Included)

| | |
|---|---|
| Num Dragon descriptors: | 601 |
| Num Cerius2 descriptors: | 33 |

Dimensionality Counts (Weights Excluded)

| | |
|---|---|
| Num zero dimensional descriptors: | 6 |
| Num one dimensional descriptors: | 50 |
| Num two dimensional descriptors: | 130 |
| Num three dimensional descriptors: | 145 |

Origin (Weights Excluded)

| | |
|---|---|
| Num unique Dragon descriptors: | 315 |
| Num unique Cerius2 descriptors: | 17 |

Number of Descriptors Per Or

| | |
|---|---|
| Mean (Weights Included): | 41.7 |
| Mean (Weights Excluded): | 27 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | Weights | |
|---|---|---|
| | Mean: | 1.5 |
| | SD: | 1.2 |
| | Median: | 1 |
| | Mode: | 1 |

| Descriptor (#Unique) | Weight | Symbol | Description | Class | Dimensionality |
|---|---|---|---|---|---|
| Or2a (18) | 1 | Mor18p | 3D-MoRSE - signal 18/weighted by atomic polarizabilities | 3D-MoRSE descriptors | 3 |
| | 1 | Mor17e | 3D-MoRSE - signal 17/weighted by atomic Sanderson electronegativities | 3D-MoRSE descriptors | 3 |
| | 1 | Mor28u | 3D-MoRSE - signal 28/unweighted | 3D-MoRSE descriptors | 3 |
| | 1 | J3D | 3D-Balaban index | geometrical descriptors | 3 |
| | 2 | O-057 | phenol/enol/carboxyl OH | atom-centred fragments | 1 |
| | 1 | SIC2 | structural information content (neighborhood symmetry of 2-order) | information indices | 2 |
| | 1 | EEig10x | Eigenvalue 10 from edge adj. matrix weighted by edge degrees | edge adjacency indices | 2 |
| | 1 | MATS5e | Moran autocorrelation-lag 5/weighted by atomic Sanderson electronegativities | 2D autocorrelations | 2 |
| | 1 | F05[C—O] | frequency of C—O at topological distance 05 | 2D frequency fingerprints | 2 |
| | 1 | HNar | Narumi harmonic topological index | topological descriptors | 2 |
| | 1 | MATS8m | Moran autocorrelation - lag 8/weighted by atomic masses | 2D autocorrelations | 2 |
| | 1 | G3s | 3st component symmetry directional WHIM index/weighted by atomic electrotopological states | WHIM descriptors | 3 |
| | 1 | Mor27m | 3D-MoRSE - signal 27/weighted by atomic masses | 3D-MoRSE descriptors | 3 |
| | 1 | B04[C—O] | presence/absence of C—O at topological distance 04 | 2D binary fingerprints | 2 |
| | 1 | H8v | H autocorrelation of lag 8/weighted by atomic van der Waals volumes | GETAWAY descriptors | 3 |
| | 1 | Mor10v | 3D-MoRSE - signal 10/weighted by atomic van der Waals volumes | 3D-MoRSE descriptors | 3 |
| | 1 | Mor18v | 3D-MoRSE - signal 18/weighted by atomic van der Waals volumes | 3D-MoRSE descriptors | 3 |
| | 2 | R8p+ | R maximal autocorrelation of lag 8/weighted by atomic polarizabilities | GETAWAY descriptors | 3 |
| Or7a (31) | 1 | MAXDP | maximal electrotopological positive variation | topological descriptors | 2 |
| | 1 | MAXDN | maximal electrotopological negative variation | topological descriptors | 2 |
| | 1 | B06[C—C] | presence/absence of C—C at topological distance 06 | 2D binary fingerprints | 2 |
| | 2 | HATS1v | leverage-weighted autocorrelation of lag 1/weighted by atomic van der Waals volumes | GETAWAY descriptors | 3 |
| | 3 | Hy | hydrophilic factor | molecular properties | 1 |
| | 1 | S_ssO | S_ssO | atomtypes (Cerius2) | 1 |
| | 1 | JGT | global topological charge index | topological charge indices | 2 |
| | 2 | H-051 | H attached to alpha-C | atom-centred fragments | 1 |
| | 2 | EEig10d | Eigenvalue 10 from edge adj. matrix weighted by dipole moments | edge adjacency indices | 2 |
| | 1 | O-057 | phenol/enol/carboxyl OH | atom-centred fragments | 1 |
| | 5 | HATS8u | leverage-weighted autocorrelation of lag 8/unweighted | GETAWAY descriptors | 3 |
| | 1 | G2s | 2st component symmetry directional WHIM index/weighted by atomic electrotopological states | WHIM descriptors | 3 |
| | 2 | Mor16u | 3D-MoRSE - signal 16/unweighted | 3D-MoRSE descriptors | 3 |
| | 4 | B02[O—O] | presence/absence of O—O at topological distance 02 | 2D binary fingerprints | 2 |
| | 1 | R5p+ | R maximal autocorrelation of lag 5/weighted by atomic polarizabilities | GETAWAY descriptors | 3 |
| | 1 | EEig08d | Eigenvalue 08 from edge adj. matrix weighted by dipole moments | edge adjacency indices | 2 |
| | 1 | DISPp | d COMMA2 value/weighted by atomic polarizabilities | geometrical descriptors | 3 |
| | 2 | C-008 | CHR2X | atom-centred fragments | 1 |
| | 1 | R4e+ | R maximal autocorrelation of lag 4/weighted by atomic Sanderson electronegativities | GETAWAY descriptors | 3 |
| | 1 | EEig09d | Eigenvalue 09 from edge adj. matrix weighted by dipole moments | edge adjacency indices | 2 |
| | 1 | nArOH | number of aromatic hydroxyls | functional group counts | 1 |
| | 1 | R2m+ | R maximal autocorrelation of lag 2/weighted by atomic masses | GETAWAY descriptors | 3 |
| | 1 | nRCOOR | number of esters (aliphatic) | functional group counts | 1 |
| | 1 | B02[C—O] | presence/absence of C—O at topological distance 02 | 2D binary fingerprints | 2 |
| | 1 | GATS7m | Geary autocorrelation - lag 7/weighted by atomic masses | 2D autocorrelations | 2 |
| | 1 | E2s | 2nd component accessibility directional WHIM index/weighted by atomic electrotopological states | WHIM descriptors | 3 |
| | 1 | nRCO | number of ketones (aliphatic) | functional group counts | 1 |
| | 1 | Mor03m | 3D-MoRSE - signal 03/weighted by atomic masses | 3D-MoRSE descriptors | 3 |
| | 1 | MATS8m | Moran autocorrelation - lag 8/weighted by atomic masses | 2D autocorrelations | 2 |
| | 1 | CIC5 | complementary information content (neighborhood symmetry of 5-order) | information indices | 2 |
| | 1 | D/Dr06 | distance/detour ring index of order 6 | topological descriptors | 2 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| Or9a (29) | 1 | BEHp8 | highest eigenvalue n. 8 of Burden matrix/weighted by atomic polarizabilities | Burden eigenvalues | 2 |
| | 1 | BELv1 | lowest eigenvalue n. 1 of Burden matrix/weighted by atomic van der Waals volumes | Burden eigenvalues | 2 |
| | 1 | DISPe | d COMMA2 value/weighted by atomic Sanderson electronegativities | geometrical descriptors | 3 |
| | 2 | EEig09d | Eigenvalue 09 from edge adj. matrix weighted by dipole moments | edge adjacency indices | 2 |
| | 2 | BEHp5 | highest eigenvalue n. 5 of Burden matrix/weighted by atomic polarizabilities | Burden eigenvalues | 2 |
| | 1 | E2e | 2nd component accessibility directional WHIM index/weighted by atomic Sanderson electronegativities | WHIM descriptors | 3 |
| | 1 | Mor25m | 3D-MoRSE - signal 25/weighted by atomic masses | 3D-MoRSE descriptors | 3 |
| | 1 | B03[C—C] | presence/absence of C—C at topological distance 03 | 2D binary fingerprints | 2 |
| | 3 | B07[C—C] | presence/absence of C—C at topological distance 07 | 2D binary fingerprints | 2 |
| | 1 | B01[C—O] | presence/absence of C—O at topological distance 01 | 2D binary fingerprints | 2 |
| | 1 | Atype_H_49 | Number of Hydrogen Type 49 | atomtypes (Cerius2) | 1 |
| | 1 | Infective-80 | Ghose-Viswanadhan-Wendoloski antiinfective-like index at 80% | molecular properties | 1 |
| | 3 | O-057 | phenol/enol/carboxyl OH | atom-centred fragments | 1 |
| | 1 | Mor22m | 3D-MoRSE - signal 22/weighted by atomic masses | 3D-MoRSE descriptors | 3 |
| | 1 | EEig10d | Eigenvalue 10 from edge adj. matrix weighted by dipole moments | edge adjacency indices | 2 |
| | 1 | R1u+ | R maximal autocorrelation of lag 1/unweighted | GETAWAY descriptors | 3 |
| | 1 | GATS7m | Geary autocorrelation - lag 7/weighted by atomic masses | 2D autocorrelations | 2 |
| | 1 | MATS4v | Moran autocorrelation - lag 4/weighted by atomic van der Waals volumes | 2D autocorrelations | 2 |
| | 1 | R4e+ | R maximal autocorrelation of lag 4/weighted by atomic Sanderson electronegativities | GETAWAY descriptors | 3 |
| | 1 | G3p | 3st component symmetry directional WHIM index/weighted by atomic polarizabilities | WHIM descriptors | 3 |
| | 1 | Hy | hydrophilic factor | molecular properties | 1 |
| | 1 | S_dssC | S_dssC | atomtypes (Cerius2) | 1 |
| | 1 | nRCHO | number of aldehydes (aliphatic) | functional group counts | 1 |
| | 1 | B08[C—C] | presence/absence of C—C at topological distance 08 | 2D binary fingerprints | 2 |
| | 1 | R2m | R autocorrelation of lag 2/weighted by atomic masses | GETAWAY descriptors | 3 |
| | 1 | HATS5e | leverage-weighted autocorrelation of lag 5/weighted by atomic Sanderson electronegativities | GETAWAY descriptors | 3 |
| | 1 | D/Dr06 | distance/detour ring index of order 6 | topological descriptors | 2 |
| | 1 | RDF030m | Radial Distribution Function - 3.0/weighted by atomic masses | RDF descriptors | 3 |
| | 2 | Jhetv | Balaban-type index from van der Waals weighted distance matrix | topological descriptors | 2 |
| Or10a (11) | 3 | S_dO | S_dO | atomtypes (Cerius2) | 1 |
| | 1 | BEHm7 | highest eigenvalue n. 7 of Burden matrix/weighted by atomic masses | Burden eigenvalues | 2 |
| | 1 | E2u | 2nd component accessibility directional WHIM index/unweighted | WHIM descriptors | 3 |
| | 1 | HATS8m | leverage-weighted autocorrelation of lag 8/weighted by atomic masses | GETAWAY descriptors | 3 |
| | 1 | BELe4 | lowest eigenvalue n. 4 of Burden matrix/weighted by atomic Sanderson electronegativities | Burden eigenvalues | 2 |
| | 1 | Mor25e | 3D-MoRSE - signal 25/weighted by atomic Sanderson electronegativities | 3D-MoRSE descriptors | 3 |
| | 1 | B08[C—C] | presence/absence of C—C at topological distance 08 | 2D binary fingerprints | 2 |
| | 1 | JGI3 | mean topological charge index of order3 | topological charge indices | 2 |
| | 1 | ESpm03u | Spectral moment 03 from edge adj. matrix | edge adjacency indices | 2 |
| | 1 | nR=Ct | number of aliphatic tertiary C(sp2) | functional group counts | 1 |
| | 2 | E2e | 2nd component accessibility directional WHIM index/weighted by atomic Sanderson electronegativities | WHIM descriptors | 3 |
| Or19a (25) | 1 | Mor31p | 3D-MoRSE - signal 31/weighted by atomic polarizabilities | 3D-MoRSE descriptors | 3 |
| | 1 | H2m | H autocorrelation of lag 2/weighted by atomic masses | GETAWAY descriptors | 3 |
| | 1 | L1m | 1st component size directional WHIM index/weighted by atomic masses | WHIM descriptors | 3 |
| | 1 | R1m+ | R maximal autocorrelation of lag 1/weighted by atomic masses | GETAWAY descriptors | 3 |
| | 1 | Mor27u | 3D-MoRSE - signal 27/unweighted | 3D-MoRSE descriptors | 3 |
| | 1 | HATS6u | leverage-weighted autocorrelation of lag 6/unweighted | GETAWAY descriptors | 3 |
| | 3 | GGI7 | topological charge index of order 7 | topological charge indices | 2 |
| | 1 | Gs | G total symmetry index/weighted by atomic electrotopological states | WHIM descriptors | 3 |
| | 1 | O-057 | phenol/enol/carboxyl OH | atom-centred fragments | 1 |
| | 1 | H-049 | H attached to C3(sp3)/C2(sp2)/C3(sp2)/C3(sp) | atom-centred fragments | 1 |
| | 1 | piPC08 | molecular multiple path count of order 08 | walk and path counts | 2 |
| | 2 | R7u+ | R maximal autocorrelation of lag 7/unweighted | GETAWAY descriptors | 3 |
| | 2 | G3s | 3st component symmetry directional WHIM index/weighted by atomic electrotopological states | WHIM descriptors | 3 |
| | 1 | R4m+ | R maximal autocorrelation of lag 4/weighted by atomic masses | GETAWAY descriptors | 3 |
| | 1 | MATS7p | Moran autocorrelation - lag 7/weighted by atomic polarizabilities | 2D autocorrelations | 2 |
| | 1 | R6u+ | R maximal autocorrelation of lag 6/unweighted | GETAWAY descriptors | 3 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| Receptor | Weight | Symbol | Description | Class | Dim |
|---|---|---|---|---|---|
| | 1 | Hy | hydrophilic factor | molecular properties | 1 |
| | 1 | ARR | aromatic ratio | constitutional descriptors | 0 |
| | 1 | BEHp7 | highest eigenvalue n. 7 of Burden matrix/weighted by atomic polarizabilities | Burden eigenvalues | 2 |
| | 1 | RDF050v | Radial Distribution Function-5.0/weighted by atomic van der Waals volumes | RDF descriptors | 3 |
| | 1 | C-005 | CH3X | atom-centred fragments | 1 |
| | 1 | nRCHO | number of aldehydes (aliphatic) | functional group counts | 1 |
| | 1 | nRCOOH | number of carboxylic acids (aliphatic) | functional group counts | 1 |
| | 1 | R5m+ | R maximal autocorrelation of lag 5/weighted by atomic masses | GETAWAY descriptors | 3 |
| | 2 | C-002 | CH2R2 | atom-centred fragments | 1 |
| Or22a (43) | 1 | Mor29v | 3D-MoRSE - signal 29/weighted by atomic van der Waals volumes | 3D-MoRSE descriptors | 3 |
| | 1 | MAXDN | maximal electrotopological negative variation | topological descriptors | 2 |
| | 1 | piPC04 | molecular multiple path count of order 04 | walk and path counts | 2 |
| | 1 | Mor10e | 3D-MoRSE - signal 10/weighted by atomic Sanderson electronegativities | 3D-MoRSE descriptors | 3 |
| | 1 | Mor27m | 3D-MoRSE - signal 27/weighted by atomic masses | 3D-MoRSE descriptors | 3 |
| | 1 | R7p+ | R maximal autocorrelation of lag 7/weighted by atomic polarizabilities | GETAWAY descriptors | 3 |
| | 1 | S__sCH3 | S__sCH3 | atomtypes (Cerius2) | 1 |
| | 2 | EEig12r | Eigenvalue 12 from edge adj. matrix weighted by resonance integrals | edge adjacency indices | 2 |
| | 1 | nRCOOR | number of esters (aliphatic) | functional group counts | 1 |
| | 4 | R6u+ | R maximal autocorrelation of lag 6/unweighted | GETAWAY descriptors | 3 |
| | 1 | Mor32p | 3D-MoRSE - signal 32/weighted by atomic polarizabilities | 3D-MoRSE descriptors | 3 |
| | 1 | AlogP98 | AlogP98 value | structural (Cerius2) | 0 |
| | 4 | O-057 | phenol/enol/carboxyl OH | atom-centred fragments | 1 |
| | 1 | L3s | 3rd component size directional WHIM index/weighted by atomic electrotopological states | WHIM descriptors | 3 |
| | 1 | R1v+ | R maximal autocorrelation of lag 1/weighted by atomic van der Waals volumes | GETAWAY descriptors | 3 |
| | 2 | nHDon | number of donor atoms for H-bonds (N and O) | functional group counts | 1 |
| | 2 | B10[C—C] | presence/absence of C—C at topological distance 10 | 2D binary fingerprints | 2 |
| | 1 | Mor18m | 3D-MoRSE - signal 18/weighted by atomic masses | 3D-MoRSE descriptors | 3 |
| | 1 | B04[C—O] | presence/absence of C—O at topological distance 04 | 2D binary fingerprints | 2 |
| | 2 | Jhetp | Balaban-type index from polarizability weighted distance matrix | topological descriptors | 2 |
| | 1 | STN | spanning tree number (log) | topological descriptors | 2 |
| | 2 | ESpm15u | Spectral moment 15 from edge adj. matrix | edge adjacency indices | 2 |
| | 1 | GATS1v | Geary autocorrelation - lag 1/weighted by atomic van der Waals volumes | 2D autocorrelations | 2 |
| | 1 | F03[O—O] | frequency of O—O at topological distance 03 | 2D frequency fingerprints | 2 |
| | 1 | GATS8m | Geary autocorrelation - lag 8/weighted by atomic masses | 2D autocorrelations | 2 |
| | 2 | HATS5e | leverage-weighted autocorrelation of lag 5/weighted by atomic Sanderson electronegativities | GETAWAY descriptors | 3 |
| | 1 | DISPv | d COMMA2 value/weighted by atomic van der Waals volumes | geometrical descriptors | 3 |
| | 1 | R3v+ | R maximal autocorrelation of lag 3/weighted by atomic van der Waals volumes | GETAWAY descriptors | 3 |
| | 1 | E2e | 2nd component accessibility directional WHIM index/weighted by atomic Sanderson electronegativities | WHIM descriptors | 3 |
| | 1 | Mor32u | 3D-MoRSE - signal 32/unweighted | 3D-MoRSE descriptors | 3 |
| | 2 | B02[O—O] | presence/absence of O—O at topological distance 02 | 2D binary fingerprints | 2 |
| | 1 | G3e | 3st component symmetry directional WHIM index/weighted by atomic Sanderson electronegativities | WHIM descriptors | 3 |
| | 1 | nCrs | number of ring secondary C(sp3) | functional group counts | 1 |
| | 2 | HOMT | HOMA total | geometrical descriptors | 3 |
| | 1 | B05[C-C] | presence/absence of C-C at topological distance 05 | 2D binary fingerprints | 2 |
| | 1 | MATS7m | Moran autocorrelation - lag 7/weighted by atomic masses | 2D autocorrelations | 2 |
| | 1 | RDF030m | Radial Distribution Function-3.0/weighted by atomic masses | RDF descriptors | 3 |
| | 1 | EEig12x | Eigenvalue 12 from edge adj. matrix weighted by edge degrees | edge adjacency indices | 2 |
| | 1 | R1m+ | R maximal autocorrelation of lag 1/weighted by atomic masses | GETAWAY descriptors | 3 |
| | 1 | MATS4p | Moran autocorrelation - lag 4/weighted by atomic polarizabilities | 2D autocorrelations | 2 |
| | 1 | B09[C—O] | presence/absence of C—O at topological distance 09 | 2D binary fingerprints | 2 |
| | 1 | Mor15p | 3D-MoRSE - signal 15/weighted by atomic polarizabilities | 3D-MoRSE descriptors | 3 |
| | 2 | S__sOH | S__sOH | atomtypes (Cerius2) | 1 |
| Or23a (37) | 1 | ATS3p | Broto-Moreau autocorrelation of a topological structure - lag 3/weighted by atomic polarizabilities | 2D autocorrelations | 2 |
| | 2 | O-056 | alcohol | atom-centred fragments | 1 |
| | 1 | J3D | 3D-Balaban index | geometrical descriptors | 3 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

|  |  |  |  |  |  |
|---|---|---|---|---|---|
|  | 1 | BELm5 | lowest eigenvalue n. 5 of Burden matrix/weighted by atomic masses | Burden eigenvalues | 2 |
|  | 1 | TPSA(Tot) | topological polar surface area using N, O, S, P polar contributions | molecular properties | 1 |
|  | 1 | B08[C—O] | presence/absence of C—O at topological distance 08 | 2D binary fingerprints | 2 |
|  | 2 | Mor27v | 3D-MoRSE - signal 27/weighted by atomic van der Waals volumes | 3D-MoRSE descriptors | 3 |
|  | 2 | R6u+ | R maximal autocorrelation of lag 6/unweighted | GETAWAY descriptors | 3 |
|  | 1 | DISPe | d COMMA2 value/weighted by atomic Sanderson electronegativities | geometrical descriptors | 3 |
|  | 1 | ESpm12d | Spectral moment 12 from edge adj. matrix weighted by dipole moments | edge adjacency indices | 2 |
|  | 1 | Mor17m | 3D-MoRSE - signal 17/weighted by atomic masses | 3D-MoRSE descriptors | 3 |
|  | 2 | EEig09d | Eigenvalue 09 from edge adj. matrix weighted by dipole moments | edge adjacency indices | 2 |
|  | 1 | Hy | hydrophilic factor | molecular properties | 1 |
|  | 2 | GATS3e | Geary autocorrelation - lag 3/weighted by atomic Sanderson electronegativities | 2D autocorrelations | 2 |
|  | 1 | GATS8m | Geary autocorrelation - lag 8/weighted by atomic masses | 2D autocorrelations | 2 |
|  | 1 | R4e+ | R maximal autocorrelation of lag 4/weighted by atomic Sanderson electronegativities | GETAWAY descriptors | 3 |
|  | 1 | Mor18m | 3D-MoRSE - signal 18/weighted by atomic masses | 3D-MoRSE descriptors | 3 |
|  | 2 | nRCOOH | number of carboxylic acids (aliphatic) | functional group counts | 1 |
|  | 1 | S_sOH | S_sOH | atomtypes (Cerius2) | 1 |
|  | 1 | E3m | 3rd component accessibility directional WHIM index/weighted by atomic masses | WHIM descriptors | 3 |
|  | 1 | G3s | 3st component symmetry directional WHIM index/weighted by atomic electrotopological states | WHIM descriptors | 3 |
|  | 2 | BELm6 | lowest eigenvalue n. 6 of Burden matrix/weighted by atomic masses | Burden eigenvalues | 2 |
|  | 1 | GATS1m | Geary autocorrelation - lag 1/weighted by atomic masses | 2D autocorrelations | 2 |
|  | 2 | EEig08d | Eigenvalue 08 from edge adj. matrix weighted by dipole moments | edge adjacency indices | 2 |
|  | 1 | F05[C—O] | frequency of C—O at topological distance 05 | 2D frequency fingerprints | 2 |
|  | 2 | nHDon | number of donor atoms for H-bonds (N and O) | functional group counts | 1 |
|  | 1 | EEig10d | Eigenvalue 10 from edge adj. matrix weighted by dipole moments | edge adjacency indices | 2 |
|  | 1 | R5p+ | R maximal autocorrelation of lag 5/weighted by atomic polarizabilities | GETAWAY descriptors | 3 |
|  | 1 | BIC | BIC | topological (Cerius2) | 2 |
|  | 2 | Infective-80 | Ghose-Viswanadhan-Wendoloski antiinfective-like index at 80% | molecular properties | 1 |
|  | 1 | GATS4p | Geary autocorrelation - lag 4/weighted by atomic polarizabilities | 2D autocorrelations | 2 |
|  | 1 | DISPp | d COMMA2 value/weighted by atomic polarizabilities | geometrical descriptors | 3 |
|  | 1 | O-057 | phenol/enol/carboxyl OH | atom-centred fragments | 1 |
|  | 1 | Atype_H_49 | Number of Hydrogen Type 49 | atomtypes (Cerius2) | 1 |
|  | 1 | GATS5m | Geary autocorrelation - lag 5/weighted by atomic masses | 2D autocorrelations | 2 |
|  | 1 | B02[O—O] | presence/absence of O—O at topological distance 02 | 2D binary fingerprints | 2 |
|  | 2 | JGI5 | mean topological charge index of order5 | topological charge indices | 2 |
| Or33b (32) | 6 | O-057 | phenol/enol/carboxyl OH | atom-centred fragments | 1 |
|  | 2 | EEig08x | Eigenvalue 08 from edge adj. matrix weighted by edge degrees | edge adjacency indices | 2 |
|  | 1 | DISPv | d COMMA2 value/weighted by atomic van der Waals volumes | geometrical descriptors | 3 |
|  | 1 | TPSA(NO) | topological polar surface area using N, O polar contributions | molecular properties | 1 |
|  | 5 | B06[C—C] | presence/absence of C—C at topological distance 06 | 2D binary fingerprints | 2 |
|  | 4 | Atype_H_49 | Number of Hydrogen Type 49 | atomtypes (Cerius2) | 1 |
|  | 2 | R3v+ | R maximal autocorrelation of lag 3/weighted by atomic van der Waals volumes | GETAWAY descriptors | 3 |
|  | 1 | G1e | 1st component symmetry directional WHIM index/weighted by atomic Sanderson electronegativities | WHIM descriptors | 3 |
|  | 1 | R2m+ | R maximal autocorrelation of lag 2/weighted by atomic masses | GETAWAY descriptors | 3 |
|  | 4 | B05[C—O] | presence/absence of C—O at topological distance 05 | 2D binary fingerprints | 2 |
|  | 1 | C-006 | CH2RX | atom-centred fragments | 1 |
|  | 2 | TPSA(Tot) | topological polar surface area using N, O, S, P polar contributions | molecular properties | 1 |
|  | 1 | L/Bw | length-to-breadth ratio by WHIM | geometrical descriptors | 3 |
|  | 1 | EEig08d | Eigenvalue 08 from edge adj. matrix weighted by dipole moments | edge adjacency indices | 2 |
|  | 3 | F04[C—O] | frequency of C—O at topological distance 04 | 2D frequency fingerprints | 2 |
|  | 1 | BEHv5 | highest eigenvalue n. 5 of Burden matrix/weighted by atomic van der Waals volumes | Burden eigenvalues | 2 |
|  | 1 | Mor30p | 3D-MoRSE - signal 30/weighted by atomic polarizabilities | 3D-MoRSE descriptors | 3 |
|  | 1 | nArCO | number of ketones (aromatic) | functional group counts | 1 |
|  | 1 | nRCO | number of ketones (aliphatic) | functional group counts | 1 |
|  | 1 | R1p+ | R maximal autocorrelation of lag 1/weighted by atomic polarizabilities | GETAWAY descriptors | 3 |
|  | 1 | MATS4p | Moran autocorrelation - lag 4/weighted by atomic polarizabilities | 2D autocorrelations | 2 |
|  | 1 | nN | number of Nitrogen atoms | constitutional descriptors | 0 |
|  | 1 | B07[C—C] | presence/absence of C—C at topological distance 07 | 2D binary fingerprints | 2 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| | 2 | JGI4 | mean topological charge index of order4 | topological charge indices | 2 |
| | 1 | nRCOOH | number of carboxylic acids (aliphatic) | functional group counts | 1 |
| | 1 | nCconj | number of non-aromatic conjugated C(sp2) | functional group counts | 1 |
| | 1 | C-005 | CH3X | atom-centred fragments | 1 |
| | 1 | JGI3 | mean topological charge index of order3 | topological charge indices | 2 |
| | 1 | HATS3p | leverage-weighted autocorrelation of lag 3/weighted by atomic polarizabilities | GETAWAY descriptors | 3 |
| | 1 | HATS8u | leverage-weighted autocorrelation of lag 8/unweighted | GETAWAY descriptors | 3 |
| | 1 | E2u | 2nd component accessibility directional WHIM index/unweighted | WHIM descriptors | 3 |
| | 2 | H-051 | H attached to alpha-C | atom-centred fragments | 1 |
| Or35a (51) | 1 | ATS4e | Broto-Moreau autocorrelation of a topological structure - lag 4/weighted by atomic Sanderson electronegativities | 2D autocorrelations | 2 |
| | 2 | TPSA(NO) | topological polar surface area using N, O polar contributions | molecular properties | 1 |
| | 1 | Mor27p | 3D-MoRSE - signal 27/weighted by atomic polarizabilities | 3D-MoRSE descriptors | 3 |
| | 8 | R6p+ | R maximal autocorrelation of lag 6/weighted by atomic polarizabilities | GETAWAY descriptors | 3 |
| | 6 | nRCOOH | number of carboxylic acids (aliphatic) | functional group counts | 1 |
| | 3 | EEig10d | Eigenvalue 10 from edge adj. matrix weighted by dipole moments | edge adjacency indices | 2 |
| | 2 | Gs | G total symmetry index/weighted by atomic electrotopological states | WHIM descriptors | 3 |
| | 9 | JGI2 | mean topological charge index of order2 | topological charge indices | 2 |
| | 3 | EEig12r | Eigenvalue 12 from edge adj. matrix weighted by resonance integrals | edge adjacency indices | 2 |
| | 7 | R4e+ | R maximal autocorrelation of lag 4/weighted by atomic Sanderson electronegativities | GETAWAY descriptors | 3 |
| | 7 | Mor28e | 3D-MoRSE - signal 28/weighted by atomic Sanderson electronegativities | 3D-MoRSE descriptors | 3 |
| | 5 | MATS7p | Moran autocorrelation - lag 7/weighted by atomic polarizabilities | 2D autocorrelations | 2 |
| | 2 | L3s | 3rd component size directional WHIM index/weighted by atomic electrotopological states | WHIM descriptors | 3 |
| | 6 | Mor25v | 3D-MoRSE - signal 25/weighted by atomic van der Waals volumes | 3D-MoRSE descriptors | 3 |
| | 4 | Mor30e | 3D-MoRSE - signal 30/weighted by atomic Sanderson electronegativities | 3D-MoRSE descriptors | 3 |
| | 5 | HATS8u | leverage-weighted autocorrelation of lag 8/unweighted | GETAWAY descriptors | 3 |
| | 7 | O-057 | phenol/enol/carboxyl OH | atom-centred fragments | 1 |
| | 3 | HATS5m | leverage-weighted autocorrelation of lag 5/weighted by atomic masses | GETAWAY descriptors | 3 |
| | 3 | Jhetp | Balaban-type index from polarizability weighted distance matrix | topological descriptors | 2 |
| | 4 | JGI8 | mean topological charge index of order8 | topological charge indices | 2 |
| | 3 | Mor04m | 3D-MoRSE - signal 04/weighted by atomic masses | 3D-MoRSE descriptors | 3 |
| | 1 | S_dssC | S_dssC | atomtypes (Cerius2) | 1 |
| | 2 | E1m | 1st component accessibility directional WHIM index/weighted by atomic masses | WHIM descriptors | 3 |
| | 2 | nHDon | number of donor atoms for H-bonds (N and O) | functional group counts | 1 |
| | 2 | RDF135u | Radial Distribution Function-13.5/unweighted | RDF descriptors | 3 |
| | 2 | D/Dr06 | distance/detour ring index of order 6 | topological descriptors | 2 |
| | 3 | E2s | 2nd component accessibility directional WHIM index/weighted by atomic electrotopological states | WHIM descriptors | 3 |
| | 2 | EEig10r | Eigenvalue 10 from edge adj. matrix weighted by resonance integrals | edge adjacency indices | 2 |
| | 1 | G2s | 2st component symmetry directional WHIM index/weighted by atomic electrotopological states | WHIM descriptors | 3 |
| | 3 | GATS3p | Geary autocorrelation - lag 3/weighted by atomic polarizabilities | 2D autocorrelations | 2 |
| | 2 | GGI1 | topological charge index of order 1 | topological charge indices | 2 |
| | 2 | Atype_C_18 | Number of Carbon Type 18 | atomtypes (Cerius2) | 1 |
| | 1 | nRCO | number of ketones (aliphatic) | functional group counts | 1 |
| | 1 | C-005 | CH3X | atom-centred fragments | 1 |
| | 1 | Mor27u | 3D-MoRSE - signal 27/unweighted | 3D-MoRSE descriptors | 3 |
| | 2 | F08[C—O] | frequency of C—O at topological distance 08 | 2D frequency fingerprints | 2 |
| | 3 | G3s | 3st component symmetry directional WHIM index/weighted by atomic electrotopological states | WHIM descriptors | 3 |
| | 3 | SIC5 | structural information content (neighborhood symmetry of 5-order) | information indices | 2 |
| | 1 | G(N...N) | sum of geometrical distances between N...N | geometrical descriptors | 3 |
| | 2 | nR = Ct | number of aliphatic tertiary C(sp2) | functional group counts | 1 |
| | 2 | E3m | 3rd component accessibility directional WHIM index/weighted by atomic masses | WHIM descriptors | 3 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| | 1 | nArCOOR | number of esters (aromatic) | functional group counts | 1 |
| | 1 | HATS6m | leverage-weighted autocorrelation of lag 6/weighted by atomic masses | GETAWAY descriptors | 3 |
| | 1 | nArCO | number of ketones (aromatic) | functional group counts | 1 |
| | 1 | Jhete | Balaban-type index from electronegativity weighted distance matrix | topological descriptors | 2 |
| | 1 | G(O...O) | sum of geometrical distances between O...O | geometrical descriptors | 3 |
| | 1 | nCt | number of total tertiary C(sp3) | functional group counts | 1 |
| | 1 | H-051 | H attached to alpha-C | atom-centred fragments | 1 |
| | 1 | nN | number of Nitrogen atoms | constitutional descriptors | 0 |
| | 1 | P2s | 2nd component shape directional WHIM index/weighted by atomic electrotopological states | WHIM descriptors | 3 |
| | 1 | C-025 | R—CR—R | atom-centred fragments | 1 |
| Or42b (ab1B) (13) | 14 | R3m+ | R autocorrelation of lag 3/weighted by atomic masses | GETAWAY descriptors | 3 |
| | 1 | HATS3m | leverage-weighted autocorrelation of lag 3/weighted by atomic masses | GETAWAY descriptors | 3 |
| | 1 | S_dO | S_dO | atomtypes (Cerius2) | 1 |
| | 4 | Mor15m | 3D-MoRSE - signal 15/weighted by atomic masses | 3D-MoRSE descriptors | 3 |
| | 2 | nDB | number of double bonds | constitutional descriptors | 0 |
| | 4 | nRCO | number of ketones (aliphatic) | functional group counts | 1 |
| | 1 | EEig08d | Eigenvalue 08 from edge adj. matrix weighted by dipole moments | edge adjacency indices | 2 |
| | 3 | nROH | number of hydroxyl groups | functional group counts | 1 |
| | 2 | Ks | K global shape index/weighted by atomic electrotopological states | WHIM descriptors | 3 |
| | 2 | B07[C—C] | presence/absence of C—C at topological distance 07 | 2D binary fingerprints | 2 |
| | 2 | E3v | 3rd component accessibility directional WHIM index/weighted by atomic van der Waals volumes | WHIM descriptors | 3 |
| | 1 | P2s | 2nd component shape directional WHIM index/weighted by atomic electrotopological states | WHIM descriptors | 3 |
| | 1 | R2u+ | R autocorrelation of lag 2/unweighted | GETAWAY descriptors | 3 |
| | 1 | ESpm15u | Spectral moment 15 from edge adj. matrix | edge adjacency indices | 2 |
| | 1 | Mor27e | 3D-MoRSE - signal 27/weighted by atomic Sanderson electronegativities | 3D-MoRSE descriptors | 3 |
| | 1 | nArCO | number of ketones (aromatic) | functional group counts | 1 |
| | 1 | B01[C—N] | presence/absence of C—N at topological distance 01 | 2D binary fingerprints | 2 |
| | 1 | O-057 | phenol/enol/carboxyl OH | atom-centred fragments | 1 |
| | 1 | HATS0p | leverage-weighted autocorrelation of lag 0/weighted by atomic polarizabilities | GETAWAY descriptors | 3 |
| | 1 | EEig08r | Eigenvalue 08 from edge adj. matrix weighted by resonance integrals | edge adjacency indices | 2 |
| | 1 | nR-Cs | number of aliphatic secondary C(sp2) | functional group counts | 1 |
| Or43a (27) | 1 | R4m+ | R autocorrelation of lag 4/weighted by atomic masses | GETAWAY descriptors | 3 |
| | 2 | O-056 | alcohol | atom-centred fragments | 1 |
| | 1 | BELm5 | lowest eigenvalue n. 5 of Burden matrix/weighted by atomic masses | Burden eigenvalues | 2 |
| | 1 | B07[C—O] | presence/absence of C—O at topological distance 07 | 2D binary fingerprints | 2 |
| | 1 | R5e | R autocorrelation of lag 5/weighted by atomic Sanderson electronegativities | GETAWAY descriptors | 3 |
| | 1 | TPSA(Tot) | topological polar surface area using N,O,S,P polar contributions | molecular properties | 1 |
| | 1 | R6e+ | R maximal autocorrelation of lag 6/weighted by atomic Sanderson electronegativities | GETAWAY descriptors | 3 |
| | 2 | JGI7 | mean topological charge index of order7 | topological charge indices | 2 |
| | 3 | B04[C—C] | presence/absence of C—C at topological distance 04 | 2D binary fingerprints | 2 |
| | 1 | EEig10d | Eigenvalue 10 from edge adj. matrix weighted by dipole moments | edge adjacency indices | 2 |
| | 5 | B02[O—O] | presence/absence of O—O at topological distance 02 | 2D binary fingerprints | 2 |
| | 3 | Mor13m | 3D-MoRSE - signal 13/weighted by atomic masses | 3D-MoRSE descriptors | 3 |
| | 3 | nHDon | number of donor atoms for H-bonds (N and O) | functional group counts | 1 |
| | 1 | Mor21m | 3D-MoRSE - signal 21/weighted by atomic masses | 3D-MoRSE descriptors | 3 |
| | 1 | JX | JX | topological (Cerius2) | 2 |
| | 1 | R1m+ | R maximal autocorrelation of lag 1/weighted by atomic masses | GETAWAY descriptors | 3 |
| | 2 | GATS7m | Geary autocorrelation - lag 7/weighted by atomic masses | 2D autocorrelations | 2 |
| | 1 | BELm6 | lowest eigenvalue n. 6 of Burden matrix/weighted by atomic masses | Burden eigenvalues | 2 |
| | 1 | E3m | 3rd component accessibility directional WHIM index/weighted by atomic masses | WHIM descriptors | 3 |
| | 2 | MATS3e | Moran autocorrelation - lag 3/weighted by atomic Sanderson electronegativities | 2D autocorrelations | 2 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| | 1 | F04[C—O] | frequency of C—O at topological distance 04 | 2D frequency fingerprints | 2 |
| | 1 | nRCHO | number of aldehydes (aliphatic) | functional group counts | 1 |
| | 1 | Infective-80 | Ghose-Viswanadhan-Wendoloski antiinfective-like index at 80% | molecular properties | 1 |
| | 1 | EEig09x | Eigenvalue 09 from edge adj. matrix weighted by edge degrees | edge adjacency indices | 2 |
| | 1 | GATS1m | Geary autocorrelation - lag 1/weighted by atomic masses | 2D autocorrelations | 2 |
| | 1 | CIC2 | complementary information content (neighborhood symmetry of 2-order) | information indices | 2 |
| | 1 | EEig01d | Eigenvalue 01 from edge adj. matrix weighted by dipole moments | edge adjacency indices | 2 |
| | 1 | HATS6u | leverage-weighted autocorrelation of lag 6/unweighted | GETAWAY descriptors | 3 |
| Or43b (29) | 1 | EEig04x | Eigenvalue 04 from edge adj. matrix weighted by edge degrees | edge adjacency indices | 2 |
| | 1 | BEHv4 | highest eigenvalue n. 4 of Burden matrix/weighted by atomic van der Waals volumes | Burden eigenvalues | 2 |
| | 1 | Mor25e | 3D-MoRSE - signal 25/weighted by atomic Sanderson electronegativities | 3D-MoRSE descriptors | 3 |
| | 2 | EEig09d | Eigenvalue 09 from edge adj. matrix weighted by dipole moments | edge adjacency indices | 2 |
| | 1 | E1p | 1st component accessibility directional WHIM index/weighted by atomic polarizabilities | WHIM descriptors | 3 |
| | 1 | BEHe8 | highest eigenvalue n. 8 of Burden matrix/weighted by atomic Sanderson electronegativities | Burden eigenvalues | 2 |
| | 1 | R1m+ | R maximal autocorrelation of lag 1/weighted by atomic masses | GETAWAY descriptors | 3 |
| | 2 | B07[C—C] | presence/absence of C—C at topological distance 07 | 2D binary fingerprints | 2 |
| | 1 | MAXDN | maximal electrotopological negative variation | topological descriptors | 2 |
| | 1 | O-057 | phenol/enol/carboxyl OH | atom-centred fragments | 1 |
| | 1 | Infective-80 | Ghose-Viswanadhan-Wendoloski antiinfective-like index at 80% | molecular properties | 1 |
| | 3 | B04[CvC] | presence/absence of C—C at topological distance 04 | 2D binary fingerprints | 2 |
| | 1 | MATS5e | Moran autocorrelation - lag 5/weighted by atomic Sanderson electronegativities | 2D autocorrelations | 2 |
| | 1 | Mor24v | 3D-MoRSE - signal 24/weighted by atomic van der Waals volumes | 3D-MoRSE descriptors | 3 |
| | 1 | Mor25v | 3D-MoRSE - signal 25/weighted by atomic van der Waals volumes | 3D-MoRSE descriptors | 3 |
| | 1 | BEHp4 | highest eigenvalue n. 4 of Burden matrix/weighted by atomic polarizabilities | Burden eigenvalues | 2 |
| | 1 | S_sCH3 | S_sCH3 | atomtypes (Cerius2) | 1 |
| | 1 | HATS3p | leverage-weighted autocorrelation of lag 3/weighted by atomic polarizabilities | GETAWAY descriptors | 3 |
| | 1 | H7m | H autocorrelation of lag 7/weighted by atomic masses | GETAWAY descriptors | 3 |
| | 1 | JGI7 | mean topological charge index of order7 | topological charge indices | 2 |
| | 1 | STN | spanning tree number (log) | topological descriptors | 2 |
| | 1 | nRCOOH | number of carboxylic acids (aliphatic) | functional group counts | 1 |
| | 1 | MATS6m | Moran autocorrelation - lag 6/weighted by atomic masses | 2D autocorrelations | 2 |
| | 1 | HATS1u | leverage-weighted autocorrelation of lag 1/unweighted | GETAWAY descriptors | 3 |
| | 1 | EEig10d | Eigenvalue 10 from edge adj. matrix weighted by dipole moments | edge adjacency indices | 2 |
| | 1 | Atype_H_49 | Number of Hydrogen Type 49 | atomtypes (Cerius2) | 1 |
| | 1 | EEig08d | Eigenvalue 08 from edge adj. matrix weighted by dipole moments | edge adjacency indices | 2 |
| | 1 | nCrs | number of ring secondary C(sp3) | functional group counts | 1 |
| | 2 | H-047 | H attached to C1(sp3)/C0(sp2) | atom-centred fragments | 1 |
| Or47a (21) | 1 | piPC04 | molecular multiple path count of order 04 | walk and path counts | 2 |
| | 2 | DISPm | d COMMA2 value/weighted by atomic masses | geometrical descriptors | 3 |
| | 1 | R7e+ | R maximal autocorrelation of lag 7/weighted by atomic Sanderson electronegativities | GETAWAY descriptors | 3 |
| | 1 | Mor10p | 3D-MoRSE - signal 10/weighted by atomic polarizabilities | 3D-MoRSE descriptors | 3 |
| | 1 | Mor20u | 3D-MoRSE - signal 20/unweighted | 3D-MoRSE descriptors | 3 |
| | 1 | IC1 | information content index (neighborhood symmetry of 1-order) | information indices | 2 |
| | 1 | nRCOOH | number of carboxylic acids (aliphatic) | functional group counts | 1 |
| | 1 | EEig01d | Eigenvalue 01 from edge adj. matrix weighted by dipole moments | edge adjacency indices | 2 |
| | 2 | Infective-80 | Ghose-Viswanadhan-Wendoloski antiinfective-like index at 80% | molecular properties | 1 |
| | 1 | MATS4m | Moran autocorrelation - lag 4/weighted-by atomic masses | 2D autocorrelations | 2 |
| | 1 | GATS5p | Geary autocorrelation - lag 5/weighted by atomic polarizabilities | 2D autocorrelations | 2 |
| | 1 | PW4 | path/walk 4-Randic shape index | topological descriptors | 2 |
| | 1 | Mor32p | 3D-MoRSE - signal 32/weighted by atomic polarizabilities | 3D-MoRSE descriptors | 3 |
| | 1 | Mor09e | 3D-MoRSE - signal 09/weighted by atomic Sanderson electronegativities | 3D-MoRSE descriptors | 3 |
| | 1 | TPSA(NO) | topological polar surface area using N, O polar contributions | molecular properties | 1 |
| | 1 | B04[C—C] | presence/absence of C—C at topological distance 04 | 2D binary fingerprints | 2 |
| | 1 | O-057 | phenol/enol/carboxyl OH | atom-centred fragments | 1 |
| | 1 | Atype_H_49 | Number of Hydrogen Type 49 | atomtypes (Cerius2) | 1 |
| | 1 | ESpm01d | Spectral moment 01 from edge adj. matrix weighted by dipole moments | edge adjacency indices | 2 |
| | 1 | EEig10d | Eigenvalue 10 from edge adj. matrix weighted by dipole moments | edge adjacency indices | 2 |
| | 1 | P2m | 2nd component shape directional WHIM index/weighted by atomic masses | WHIM descriptors | 3 |
| | 2 | Mor06e | 3D-MoRSE - signal 06/weighted by atomic Sanderson electronegativities | 3D-MoRSE descriptors | 3 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| Or47b (14) | 3 | EEig02d | Eigenvalue 02 from edge adj. matrix weighted by dipole moments | edge adjacency indices | 2 |
| | 5 | ESpm03d | Spectral moment 03 from edge adj. matrix weighted by dipole moments | edge adjacency indices | 2 |
| | 1 | nHBonds | number of intramolecular H-bonds (with N, O, F) | functional group counts | 1 |
| | 4 | X5A | average connectivity index chi-5 | connectivity indices | 2 |
| | 1 | EEig08x | Eigenvalue 08 from edge adj. matrix weighted by edge degrees | edge adjacency indices | 2 |
| | 1 | C-006 | CH2RX | atom-centred fragments | 1 |
| | 1 | nRCHO | number of aldehydes (aliphatic) | functional group counts | 1 |
| | 2 | nRCOOR | number of esters (aliphatic) | functional group counts | 1 |
| | 1 | nRCOOH | number of carboxylic acids (aliphatic) | functional group counts | 1 |
| | 1 | EEig08d | Eigenvalue 08 from edge adj. matrix weighted by dipole moments | edge adjacency indices | 2 |
| | 1 | X4Av | average valence connectivity index chi-4 | connectivity indices | 2 |
| | 1 | GATS6m | Geary autocorrelation - lag 6/weighted by atomic masses | 2D autocorrelations | 2 |
| | 1 | EEig07r | Eigenvalue 07 from edge adj. matrix weighted by resonance integrals | edge adjacency indices | 2 |
| | 1 | R2m | R autocorrelation of lag 2/weighted by atomic masses | GETAWAY descriptors | 3 |
| Or49b (37) | 2 | nCb- | number of substituted benzene C(sp2) | functional group counts | 1 |
| | 1 | BEHm6 | highest eigenvalue n. 6 of Burden matrix/weighted by atomic masses | Burden eigenvalues | 2 |
| | 2 | F04[C—O] | frequency of C—O at topological distance 04 | 2D frequency fingerprints | 2 |
| | 1 | D/Dr06 | distance/detour ring index of order 6 | topological descriptors | 2 |
| | 1 | BEHp6 | highest eigenvalue n. 6 of Burden matrix/weighted by atomic polarizabilities | Burden eigenvalues | 2 |
| | 3 | H-047 | H attached to C1(sp3)/C0(sp2) | atom-centred fragments | 1 |
| | 1 | GATS1m | Geary autocorrelation - lag 1/weighted by atomic masses | 2D autocorrelations | 2 |
| | 3 | HATS8p | leverage-weighted autocorrelation of lag 8/weighted by atomic polarizabilities | GETAWAY descriptors | 3 |
| | 2 | ISH | standardized information content on the leverage equality | GETAWAY descriptors | 3 |
| | 1 | Mor16e | 3D-MoRSE - signal 16/weighted by atomic Sanderson electronegativities | 3D-MoRSE descriptors | 3 |
| | 1 | JGI5 | mean topological charge index of order5 | topological charge indices | 2 |
| | 1 | R8e+ | R maximal autocorrelation of lag 8/weighted by atomic Sanderson electronegativities | GETAWAY descriptors | 3 |
| | 1 | Mor25e | 3D-MoRSE - signal 25/weighted by atomic Sanderson electronegativities | 3D-MoRSE descriptors | 3 |
| | 2 | EEig10d | Eigenvalue 10 from edge adj. matrix weighted by dipole moments | edge adjacency indices | 2 |
| | 1 | Mor16p | 3D-MoRSE - signal 16/weighted by atomic polarizabilities | 3D-MoRSE descriptors | 3 |
| | 1 | JGI4 | mean topological charge index of order4 | topological charge indices | 2 |
| | 1 | MATS3p | Moran autocorrelation - lag 3/weighted by atomic polarizabilities | 2D autocorrelations | 2 |
| | 3 | CIC | CIC | topological (Cerius2) | 2 |
| | 1 | P2m | 2nd component shape directional WHIM index/weighted by atomic masses | WHIM descriptors | 3 |
| | 1 | nHDon | number of donor atoms for H-bonds (N and O) | functional group counts | 1 |
| | 1 | Mor03m | 3D-MoRSE - signal 03/weighted by atomic masses | 3D-MoRSE descriptors | 3 |
| | 2 | JGI7 | mean topological charge index of order7 | topological charge indices | 2 |
| | 1 | Mor23v | 3D-MoRSE - signal 23/weighted by atomic van der Waals volumes | 3D-MoRSE descriptors | 3 |
| | 1 | Mor30e | 3D-MoRSE - signal 30/weighted by atomic Sanderson electronegativities | 3D-MoRSE descriptors | 3 |
| | 1 | IC | IC | topological (Cerius2) | 2 |
| | 1 | Mor21m | 3D-MoRSE - signal 21/weighted by atomic masses | 3D-MoRSE descriptors | 3 |
| | 1 | Mor13m | 3D-MoRSE - signal 13/weighted by atomic masses | 3D-MoRSE descriptors | 3 |
| | 1 | R7v+ | R maximal autocorrelation of lag 7/weighted by atomic van der Waals volumes | GETAWAY descriptors | 3 |
| | 1 | piPC07 | molecular multiple path count of order 07 | walk and path counts | 2 |
| | 1 | nArOH | number of aromatic hydroxyls | functional group counts | 1 |
| | 1 | Mor25v | 3D-MoRSE - signal 25/weighted by atomic van der Waals volumes | 3D-MoRSE descriptors | 3 |
| | 1 | Mor08v | 3D-MoRSE - signal 08/weighted by atomic van der Waals volumes | 3D-MoRSE descriptors | 3 |
| | 1 | R6e+ | R maximal autocorrelation of lag 6/weighted by atomic Sanderson electronegativities | GETAWAY descriptors | 3 |
| | 1 | EEig06x | Eigenvalue 06 from edge adj. matrix weighted by edge degrees | edge adjacency indices | 2 |
| | 1 | C-001 | CH3R/CH4 | atom-centred fragments | 1 |
| | 1 | Mor07m | 3D-MoRSE - signal 07/weighted by atomic masses | 3D-MoRSE descriptors | 3 |
| | 1 | DISPe | d COMMA2 value/weighted by atomic Sanderson electronegativities | geometrical descriptors | 3 |
| | 1 | nR05 | number of 5-membered rings | constitutional descriptors | 0 |
| | 1 | Mor07e | 3D-MoRSE - signal 07/weighted by atomic Sanderson electronegativities | 3D-MoRSE descriptors | 3 |
| | 1 | EEig09x | Eigenvalue 09 from edge adj. matrix weighted by edge degrees | edge adjacency indices | 2 |
| | 1 | B05[C—O] | presence/absence of C—O at topological distance 05 | 2D binary fingerprints | 2 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| | 1 | X5Av | average valence connectivity index chi-5 | connectivity indices | 2 |
| | 1 | HATS3p | leverage-weighted autocorrelation of lag 3/weighted by atomic polarizabilities | GETAWAY descriptors | 3 |
| | 1 | R8u+ | R maximal autocorrelation of lag 8/unweighted | GETAWAY descriptors | 3 |
| | 1 | O-060 | Al—O—Ar/Ar—O—Ar/R . . . O . . . R/R—O—C=X | atom-centred fragments | 1 |
| | 2 | B04[C—O] | presence/absence of C—O at topological distance 04 | 2D binary fingerprints | 2 |
| Or59b (23) | 1 | piPC06 | molecular multiple path count of order 06 | walk and path counts | 2 |
| | 1 | R3u | R autocorrelation of lag 3/unweighted | GETAWAY descriptors | 3 |
| | 1 | S__sCH3 | S__sCH3 | atomtypes (Cerius2) | 1 |
| | 4 | B06[C—C] | presence/absence of C—C at topological distance 06 | 2D binary fingerprints | 2 |
| | 1 | R1e+ | R maximal autocorrelation of lag 1/weighted by atomic Sanderson electronegativities | GETAWAY descriptors | 3 |
| | 1 | ESpm03u | Spectral moment 03 from edge adj. matrix | edge adjacency indices | 2 |
| | 1 | EEig10r | Eigenvalue 10 from edge adj. matrix weighted by resonance integrals | edge adjacency indices | 2 |
| | 1 | EEig08d | Eigenvalue 08 from edge adj. matrix weighted by dipole moments | edge adjacency indices | 2 |
| | 1 | E1u | 1st component accessibility directional WHIM index/unweighted | WHIM descriptors | 3 |
| | 1 | nCconj | number of non-aromatic conjugated C(sp2) | functional group counts | 1 |
| | 1 | SP13 | shape profile no. 13 | Randic molecular profiles | 3 |
| | 2 | S_dO | S_dO | atomtypes (Cerius2) | 1 |
| | 2 | Atype__H__49 | Number of Hydrogen Type 49 | atomtypes (Cerius2) | 1 |
| | 1 | EEig10d | Eigenvalue 10 from edge adj. matrix weighted by dipole moments | edge adjacency indices | 2 |
| | 1 | nHDon | number of donor atoms for H-bonds (N and O) | functional group counts | 1 |
| | 1 | R8u+ | R maximal autocorrelation of lag 8/unweighted | GETAWAY descriptors | 3 |
| | 2 | O-057 | phenol/enol/carboxyl OH | atom-centred fragments | 1 |
| | 1 | Mor10v | 3D-MoRSE - signal 10/weighted by atomic van der Waals volumes | 3D-MoRSE descriptors | 3 |
| | 1 | R5m+ | R maximal autocorrelation of lag 5/weighted by atomic masses | GETAWAY descriptors | 3 |
| | 1 | Mor09e | 3D-MoRSE - signal 09/weighted by atomic Sanderson electronegativities | 3D-MoRSE descriptors | 3 |
| | 1 | nOHp | number of primary alcohols | functional group counts | 1 |
| | 1 | EEig09d | Eigenvalue 09 from edge adj. matrix weighted by dipole moments | edge adjacency indices | 2 |
| | 1 | nCrs | number of ring secondary C(sp3) | functional group counts | 1 |
| | 1 | ESpm01d | Spectral moment 01 from edge adj. matrix weighted by dipole moments | edge adjacency indices | 2 |
| Or65a (14) | 1 | F04[O—O] | frequency of O—O at topological distance 04 | 2D frequency fingerprints | 2 |
| | 2 | Mor30m | 3D-MoRSE - signal 30/weighted by atomic masses | 3D-MoRSE descriptors | 3 |
| | 4 | Atype__H__51 | Number of Hydrogen Type 51 | atomtypes (Cerius2) | 1 |
| | 1 | EEig08d | Eigenvalue 08 from edge adj. matrix weighted by dipole moments | edge adjacency indices | 2 |
| | 2 | nArOH | number of aromatic hydroxyls | functional group counts | 1 |
| | 2 | JGI7 | mean topological charge index of order7 | topological charge indices | 2 |
| | 1 | nHBonds | number of intramolecular H-bonds (with N, O, F) | functional group counts | 1 |
| | 1 | Mor13p | 3D-MoRSE - signal 13/weighted by atomic polarizabilities | 3D-MoRSE descriptors | 3 |
| | 1 | EEig07d | Eigenvalue 07 from edge adj. matrix weighted by dipole moments | edge adjacency indices | 2 |
| | 1 | B06[C—O] | presence/absence of C—O at topological distance 06 | 2D binary fingerprints | 2 |
| | 1 | C-008 | CHR2X | atom-centred fragments | 1 |
| | 1 | EEig08r | Eigenvalue 08 from edge adj. matrix weighted by resonance integrals | edge adjacency indices | 2 |
| | 1 | B01[C—O] | presence/absence of C—O at topological distance 01 | 2D binary fingerprints | 2 |
| | 2 | Mor32e | 3D-MoRSE - signal 32/weighted by atomic Sanderson electronegativities | 3D-MoRSE descriptors | 3 |
| Or67a (37) | 2 | AlogP98 | AlogP98 value | structural (Cerius2) | 0 |
| | 8 | B04[C—O] | presence/absence of C—O at topological distance 04 | 2D binary fingerprints | 2 |
| | 6 | F08[C—O] | frequency of C—O at topological distance 08 | 2D frequency fingerprints | 2 |
| | 1 | GGI4 | topological charge index of order 4 | topological charge indices | 2 |
| | 3 | E2u | 2nd component accessibility directional WHIM index/unweighted | WHIM descriptors | 3 |
| | 2 | O-057 | phenol/enol/carboxyl OH | atom-centred fragments | 1 |
| | 1 | Mor03v | 3D-MoRSE - signal 03/weighted by atomic van der Waals volumes | 3D-MoRSE descriptors | 3 |
| | 4 | X5A | average connectivity index chi-5 | connectivity indices | 2 |
| | 3 | Mor10v | 3D-MoRSE - signal 10/weighted by atomic van der Waals volumes | 3D-MoRSE descriptors | 3 |
| | 1 | B03[C—O] | presence/absence of C—O at topological distance 03 | 2D binary fingerprints | 2 |
| | 3 | X4A | average connectivity index chi-4 | connectivity indices | 2 |
| | 3 | nCt | number of total tertiary C(sp3) | functional group counts | 1 |
| | 1 | C-026 | R—CX—R | atom-centred fragments | 1 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| Receptor | Weight | Symbol | Description | Class | Dim |
|---|---|---|---|---|---|
| | 3 | RDF075m | Radial Distribution Function-7.5/weighted by atomic masses | RDF descriptors | 3 |
| | 2 | C-008 | CHR2X | atom-centred fragments | 1 |
| | 2 | B03[C—C] | presence/absence of C—C at topological distance 03 | 2D binary fingerprints | 2 |
| | 1 | B01[C—O] | presence/absence of C—O at topological distance 01 | 2D binary fingerprints | 2 |
| | 1 | nRCHO | number of aldehydes (aliphatic) | functional group counts | 1 |
| | 1 | Jhetv | Balaban-type index from van der Waals weighted distance matrix | topological descriptors | 2 |
| | 1 | L1s | 1st component size directional WHIM index/weighted by atomic electrotopological states | WHIM descriptors | 3 |
| | 1 | Hy | hydrophilic factor | molecular properties | 1 |
| | 2 | C-003 | CHR3 | atom-centred fragments | 1 |
| | 1 | GATS7m | Geary autocorrelation - lag 7/weighted by atomic masses | 2D autocorrelations | 2 |
| | 1 | Mor16e | 3D-MoRSE - signal 16/weighted by atomic Sanderson electronegativities | 3D-MoRSE descriptors | 3 |
| | 1 | Mor06u | 3D-MoRSE - signal 06/unweighted | 3D-MoRSE descriptors | 3 |
| | 1 | RDF030m | Radial Distribution Function-3.0/weighted by atomic masses | RDF descriptors | 3 |
| | 1 | Atype_C_18 | Number of Carbon Type 18 | atomtypes (Cerius2) | 1 |
| | 1 | F03[O—O] | frequency of O—O at topological distance 03 | 2D frequency fingerprints | 2 |
| | 1 | nCrs | number of ring secondary C(sp3) | functional group counts | 1 |
| | 2 | nArOH | number of aromatic hydroxyls | functional group counts | 1 |
| | 1 | GATS8m | Geary autocorrelation - lag 8/weighted by atomic masses | 2D autocorrelations | 2 |
| | 1 | Jhete | Balaban-type index from electronegativity weighted distance matrix | topological descriptors | 2 |
| | 1 | EEig13x | Eigenvalue 13 from edge adj. matrix weighted by edge degrees | edge adjacency indices | 2 |
| | 1 | DISPm | d COMMA2 value/weighted by atomic masses | geometrical descriptors | 3 |
| | 1 | X3A | average connectivity index chi-3 | connectivity indices | 2 |
| | 1 | G(N...N) | sum of geometrical distances between N...N | geometrical descriptors | 3 |
| | 1 | Mor32u | 3D-MoRSE - signal 32/unweighted | 3D-MoRSE descriptors | 3 |
| Or67c (24) | 1 | BEHe8 | highest eigenvalue n. 8 of Burden matrix/weighted by atomic Sanderson electronegativities | Burden eigenvalues | 2 |
| | 1 | O-056 | alcohol | atom-centred fragments | 1 |
| | 1 | Mor25m | 3D-MoRSE - signal 25/weighted by atomic masses | 3D-MoRSE descriptors | 3 |
| | 1 | BELv4 | lowest eigenvalue n. 4 of Burden matrix/weighted by atomic van der Waals volumes | Burden eigenvalues | 2 |
| | 3 | B07[C—C] | presence/absence of C—C at topological distance 07 | 2D binary fingerprints | 2 |
| | 1 | TPSA(Tot) | topological polar surface area using N, O, S, P polar contributions | molecular properties | 1 |
| | 1 | DISPm | d COMMA2 value/weighted by atomic masses | geometrical descriptors | 3 |
| | 4 | HATS6u | leverage-weighted autocorrelation of lag 6/unweighted | GETAWAY descriptors | 3 |
| | 2 | EEig08d | Eigenvalue 08 from edge adj. matrix weighted by dipole moments | edge adjacency indices | 2 |
| | 2 | EEig10d | Eigenvalue 10 from edge adj. matrix weighted by dipole moments | edge adjacency indices | 2 |
| | 1 | Gs | G total symmetry index/weighted by atomic electrotopological states | WHIM descriptors | 3 |
| | 3 | O-057 | phenol/enol/carboxyl OH | atom-centred fragments | 1 |
| | 1 | B08[C—C] | presence/absence of C—C at topological distance 08 | 2D binary fingerprints | 2 |
| | 1 | R1m+ | R maximal autocorrelation of lag 1/weighted by atomic masses | GETAWAY descriptors | 3 |
| | 1 | BELm5 | lowest eigenvalue n. 5 of Burden matrix/weighted by atomic masses | Burden eigenvalues | 2 |
| | 1 | F03[O—O] | frequency of O—O at topological distance 03 | 2D frequency fingerprints | 2 |
| | 1 | STN | spanning tree number (log) | topological descriptors | 2 |
| | 1 | Atype_H_49 | Number of Hydrogen Type 49 | atomtypes (Cerius2) | 1 |
| | 1 | H-051 | H attached to alpha-C | atom-centred fragments | 1 |
| | 1 | B01[C—O] | presence/absence of C—O at topological distance 01 | 2D binary fingerprints | 2 |
| | 1 | Infective-80 | Ghose-Viswanadhan-Wendoloski antiinfective-like index at 80% | molecular properties | 1 |
| | 1 | Hy | hydrophilic factor | molecular properties | 1 |
| | 1 | Mor22m | 3D-MoRSE - signal 22/weighted by atomic masses | 3D-MoRSE descriptors | 3 |
| | 1 | JGI7 | mean topological charge index of order7 | topological charge indices | 2 |
| Or82a (31) | 1 | GGI9 | topological charge index of order 9 | topological charge indices | 2 |
| | 1 | Mor02e | 3D-MoRSE - signal 02/weighted by atomic Sanderson electronegativities | 3D-MoRSE descriptors | 3 |
| | 1 | Mor30v | 3D-MoRSE - signal 30/weighted by atomic van der Waals volumes | 3D-MoRSE descriptors | 3 |
| | 1 | Mor02v | 3D-MoRSE - signal 02/weighted by atomic van der Waals volumes | 3D-MoRSE descriptors | 3 |
| | 1 | Mor30u | 3D-MoRSE - signal 30/unweighted | 3D-MoRSE descriptors | 3 |
| | 2 | BLTD48 | Verhaar model of Daphnia base-line toxicity from MLOGP (mmol/l) | molecular properties | 1 |
| | 2 | Mor10v | 3D-MoRSE - signal 10/weighted by atomic van der Waals volumes | 3D-MoRSE descriptors | 3 |
| | 2 | Atype_H_53 | Number of Hydrogen Type 53 | atomtypes (Cerius2) | 1 |
| | 1 | O-058 | =O | atom-centred fragments | 1 |
| | 1 | B02[C—O] | presence/absence of C—O at topological distance 02 | 2D binary fingerprints | 2 |
| | 2 | R5u+ | R maximal autocorrelation of lag 5/unweighted | GETAWAY descriptors | 3 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| Receptor | Weight | Symbol | Description | Class | Dim |
|---|---|---|---|---|---|
| | 1 | H6e | H autocorrelation of lag 6/weighted by atomic Sanderson electronegativities | GETAWAY descriptors | 3 |
| | 1 | MATS7p | Moran autocorrelation - lag 7/weighted by atomic polarizabilities | 2D autocorrelations | 2 |
| | 1 | GATS3p | Geary autocorrelation - lag 3/weighted by atomic polarizabilities | 2D autocorrelations | 2 |
| | 1 | Mor18m | 3D-MoRSE - signal 18/weighted by atomic masses | 3D-MoRSE descriptors | 3 |
| | 1 | H-051 | H attached to alpha-C | atom-centred fragments | 1 |
| | 2 | Mor13p | 3D-MoRSE - signal 13/weighted by atomic polarizabilities | 3D-MoRSE descriptors | 3 |
| | 1 | SIC2 | structural information content (neighborhood symmetry of 2-order) | information indices | 2 |
| | 1 | Mor32u | 3D-MoRSE - signal 32/unweighted | 3D-MoRSE descriptors | 3 |
| | 1 | Mor10m | 3D-MoRSE - signal 10/weighted by atomic masses | 3D-MoRSE descriptors | 3 |
| | 1 | nR = Cp | number of terminal primary C(sp2) | functional group counts | 1 |
| | 1 | Mor25p | 3D-MoRSE - signal 25/weighted by atomic polarizabilities | 3D-MoRSE descriptors | 3 |
| | 1 | GATS8m | Geary autocorrelation - lag 8/weighted by atomic masses | 2D autocorrelations | 2 |
| | 1 | JGI1 | mean topological charge index of order 1 | topological charge indices | 2 |
| | 1 | E-ADJ-mag | E-ADJ-mag | topological (cerius2) | 2 |
| | 1 | EEig11x | Eigenvalue 11 from edge adj. matrix weighted by edge degrees | edge adjacency indices | 2 |
| | 1 | B03[O—O] | presence/absence of O—O at topological distance 03 | 2D binary fingerprints | 2 |
| | 1 | Mor30e | 3D-MoRSE - signal 30/weighted by atomic Sanderson electronegativities | 3D-MoRSE descriptors | 3 |
| | 1 | Rotlbonds | Number of rotatable bonds | structural (Cerius2) | 0 |
| | 1 | EEig09d | Eigenvalue 09 from edge adj. matrix weighted by dipole moments | edge adjacency indices | 2 |
| | 2 | GATS7m | Geary autocorrelation - lag 7/weighted by atomic masses | 2D autocorrelations | 2 |
| Or85a (15) | 1 | EEig04r | Eigenvalue 04 from edge adj. matrix weighted by resonance integrals | edge adjacency indices | 2 |
| | 2 | C-006 | CH2RX | atom-centred fragments | 1 |
| | 3 | ATS6e | Broto-Moreau autocorrelation of a topological structure - lag 6/weighted by atomic Sanderson electronegativities | 2D autocorrelations | 2 |
| | 3 | JGI5 | mean topological charge index of order5 | topological charge indices | 2 |
| | 2 | B07[C—C] | presence/absence of C—C at topological distance 07 | 2D binary fingerprints | 2 |
| | 1 | nCp | number of terminal primary C(sp3) | functional group counts | 1 |
| | 2 | DISPm | d COMMA2 value/weighted by atomic masses | geometrical descriptors | 3 |
| | 2 | GATS4m | Geary autocorrelation - lag 4/weighted by atomic masses | 2D autocorrelations | 2 |
| | 1 | Mor25p | 3D-MoRSE - signal 25/weighted by atomic polarizabilities | 3D-MoRSE descriptors | 3 |
| | 1 | nHDon | number of donor atoms for H-bonds (N and O) | functional group counts | 1 |
| | 1 | EEig09d | Eigenvalue 09 from edge adj. matrix weighted by dipole moments | edge adjacency indices | 2 |
| | 1 | R2m+ | R maximal autocorrelation of lag 2/weighted by atomic masses | GETAWAY descriptors | 3 |
| | 1 | JGI4 | mean topological charge index of order4 | topological charge indices | 2 |
| | 1 | Mor11e | 3D-MoRSE - signal 11/weighted by atomic Sanderson electronegativities | 3D-MoRSE descriptors | 3 |
| | 2 | HATS7m | leverage-weighted autocorrelation of lag 7/weighted by atomic masses | GETAWAY descriptors | 3 |
| Or85b (26) | 1 | piPC05 | molecular multiple path count of order 05 | walk and path counts | 2 |
| | 1 | BLTF96 | Verhaar model of Fish base-line toxicity from MLOGP (mmol/l) | molecular properties | 1 |
| | 2 | GATS4p | Geary autocorrelation - lag 4/weighted by atomic polarizabilities | 2D autocorrelations | 2 |
| | 1 | GGI7 | topological charge index of order 7 | topological charge indices | 2 |
| | 3 | B05[C—O] | presence/absence of C—O at topological distance 05 | 2D binary fingerprints | 2 |
| | 2 | O-057 | phenol/enol/carboxyl OH | atom-centred fragments | 1 |
| | 1 | Mor27v | 3D-MoRSE - signal 27/weighted by atomic van der Waals volumes | 3D-MoRSE descriptors | 3 |
| | 1 | HATS4v | leverage-weighted autocorrelation of lag 4/weighted by atomic van der Waals volumes | GETAWAY descriptors | 3 |
| | 1 | Gs | G total symmetry index/weighted by atomic electrotopological states | WHIM descriptors | 3 |
| | 2 | Infective-80 | Ghose-Viswanadhan-Wendoloski antiinfective-like index at 80% | molecular properties | 1 |
| | 2 | R7u+ | R maximal autocorrelation of lag 7/unweighted | GETAWAY descriptors | 3 |
| | 2 | nCbH | number of unsubstituted benzene C(sp2) | functional group counts | 1 |
| | 1 | B04[C—O] | presence/absence of C—O at topological distance 04 | 2D binary fingerprints | 2 |
| | 2 | JGI7 | mean topological charge index of order7 | topological charge indices | 2 |
| | 2 | DISPe | d COMMA2 value/weighted by atomic Sanderson electronegativities | geometrical descriptors | 3 |
| | 1 | R4p+ | R maximal autocorrelation of lag 4/weighted by atomic polarizabilities | GETAWAY descriptors | 3 |
| | 1 | EEig12x | Eigenvalue 12 from edge adj. matrix weighted by edge degrees | edge adjacency indices | 2 |
| | 1 | B06[C—O] | presence/absence of C—O at topological distance 06 | 2D binary fingerprints | 2 |
| | 1 | MATS5e | Moran autocorrelation - lag 5/weighted by atomic Sanderson electronegativities | 2D autocorrelations | 2 |
| | 1 | HATS4m | leverage-weighted autocorrelation of lag 4/weighted by atomic masses | GETAWAY descriptors | 3 |
| | 1 | HATS6u | leverage-weighted autocorrelation of lag 6/unweighted | GETAWAY descriptors | 3 |
| | 1 | GATS4m | Geary autocorrelation - lag 4/weighted by atomic masses | 2D autocorrelations | 2 |
| | 1 | F03[O—O] | frequency of O—O at topological distance 03 | 2D frequency fingerprints | 2 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| | 1 | H8v | H autocorrelation of lag 8/weighted by atomic van der Waals volumes | GETAWAY descriptors | 3 |
| | 1 | EEig09d | Eigenvalue 09 from edge adj. matrix weighted by dipole moments | edge adjacency indices | 2 |
| | 2 | Mor16e | 3D-MoRSE - signal 16/weighted by atomic Sanderson electronegativities | 3D-MoRSE descriptors | 3 |
| Or85f (53) | 1 | BEHp8 | highest eigenvalue n. 8 of Burden matrix/weighted by atomic polarizabilities | Burden eigenvalues | 2 |
| | 5 | F05[C—O] | frequency of C—O at topological distance 05 | 2D frequency fingerprints | 2 |
| | 4 | BELm4 | lowest eigenvalue n. 4 of Burden matrix/weighted by atomic masses | Burden eigenvalues | 2 |
| | 1 | HATS8m | leverage-weighted autocorrelation of lag 8/weighted by atomic masses | GETAWAY descriptors | 3 |
| | 2 | B04[C—O] | presence/absence of C—O at topological distance 04 | 2D binary fingerprints | 2 |
| | 6 | O-057 | phenol/enol/carboxyl OH | atom-centred fragments | 1 |
| | 1 | RDF030v | Radial Distribution Function-3.0/weighted by atomic van der Waals volumes | RDF descriptors | 3 |
| | 1 | GGI7 | topological charge index of order 7 | topological charge indices | 2 |
| | 1 | Gs | G total symmetry index/weighted by atomic electrotopological states | WHIM descriptors | 3 |
| | 4 | B07[C—C] | presence/absence of C—C at topological distance 07 | 2D binary fingerprints | 2 |
| | 1 | E2e | 2nd component accessibility directional WHIM index/weighted by atomic Sanderson electronegativities | WHIM descriptors | 3 |
| | 1 | MATS2m | Moran autocorrelation - lag 2/weighted by atomic masses | 2D autocorrelations | 2 |
| | 2 | Mor28u | 3D-MoRSE - signal 28/unweighted | 3D-MoRSE descriptors | 3 |
| | 3 | BEHp5 | highest eigenvalue n. 5 of Burden matrix/weighted by atomic polarizabilities | Burden eigenvalues | 2 |
| | 2 | Infective-80 | Ghose-Viswanadhan-Wendoloski antiinfective-like index at 80% | molecular properties | 1 |
| | 1 | HATS4e | leverage-weighted autocorrelation of lag 4/weighted by atomic Sanderson electronegativities | GETAWAY descriptors | 3 |
| | 3 | JGI6 | mean topological charge index of order6 | topological charge indices | 2 |
| | 6 | B05[C—O] | presence/absence of C—O at topological distance 05 | 2D binary fingerprints | 2 |
| | 2 | JGI7 | mean topological charge index of order7 | topological charge indices | 2 |
| | 2 | DISPm | d COMMA2 value/weighted by atomic masses | geometrical descriptors | 3 |
| | 5 | RDF030m | Radial Distribution Function-3.0/weighted by atomic masses | RDF descriptors | 3 |
| | 1 | R1e+ | R maximal autocorrelation of lag 1/weighted by atomic Sanderson electronegativities | GETAWAY descriptors | 3 |
| | 1 | HATS8p | leverage-weighted autocorrelation of lag 8/weighted by atomic polarizabilities | GETAWAY descriptors | 3 |
| | 1 | Atype_H_49 | Number of Hydrogen Type 49 | atomtypes (Cerius2) | 1 |
| | 2 | Hy | hydrophilic factor | molecular properties | 1 |
| | 1 | Jhetp | Balaban-type index from polarizability weighted distance matrix | topological descriptors | 2 |
| | 1 | H8v | H autocorrelation of lag 8/weighted by atomic van der Waals volumes | GETAWAY descriptors | 3 |
| | 2 | EEig11d | Eigenvalue 11 from edge adj. matrix weighted by dipole moments | edge adjacency indices | 2 |
| | 1 | MATS8m | Moran autocorrelation - lag 8/weighted by atomic masses | 2D autocorrelations | 2 |
| | 1 | MATS2p | Moran autocorrelation - lag 2/weighted by atomic polarizabilities | 2D autocorrelations | 2 |
| | 4 | B08[C—C] | presence/absence of C—C at topological distance 08 | 2D binary fingerprints | 2 |
| | 1 | S_sCH3 | S_sCH3 | atomtypes (Cerius2) | 1 |
| | 2 | HATS1e | leverage-weighted autocorrelation of lag 1/weighted by atomic Sanderson electronegativities | GETAWAY descriptors | 3 |
| | 1 | nCconj | number of non-aromatic conjugated C(sp2) | functional group counts | 1 |
| | 1 | B04[C—C] | presence/absence of C—C at topological distance 04 | 2D binary fingerprints | 2 |
| | 1 | S_aasC | S_aasC | atomtypes (cerius2) | 1 |
| | 1 | R8m+ | R maximal autocorrelation of lag 8/weighted by atomic masses | GETAWAY descriptors | 3 |
| | 1 | nRCOOH | number of carboxylic acids (aliphatic) | fundtional group counts | 1 |
| | 1 | S_sOH | S_sOH | atomtypes (Cerius2) | 1 |
| | 1 | BELe3 | lowest eigenvalue n. 3 of Burden matrix/weighted by atomic Sanderson electronegativities | Burden eigenvalues | 2 |
| | 1 | GATS8m | Geary autocorrelation - lag 8/weighted by atomic masses | 2D autocorrelations | 2 |
| | 1 | BEHp4 | highest eigenvalue n. 4 of Burden matrix/weighted by atomic polarizabilities | Burden eigenvalues | 2 |
| | 2 | MATS5e | Moran autocorrelation - lag 5/weighted by atomic Sanderson electronegativities | 2D autocorrelations | 2 |
| | 1 | E3s | 3rd component accessibility directional WHIM index/weighted by atomic electrotopological states | WHIM descriptors | 3 |
| | 2 | Jhetv | Balaban-type index from van der Waals weighted distance matrix | topological descriptors | 2 |
| | 1 | nR=Ct | number of aliphatic tertiary C(sp2) | functional group counts | 1 |
| | 1 | nRCHO | number of aldehydes (aliphatic) | functional group counts | 1 |
| | 1 | HATS8v | leverage-weighted autocorrelation of lag 8/weighted by atomic van der Waals volumes | GETAWAY descriptors | 3 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| Receptor | Weight | Symbol | Description | Class | Dim |
|---|---|---|---|---|---|
| | 1 | Mor28p | 3D-MoRSE - signal 28/weighted by atomic polarizabilities | 3D-MoRSE descriptors | 3 |
| | 1 | C-003 | CHR3 | atom-centred fragments | 1 |
| | 1 | GATS7m | Geary autocorrelation - lag 7/weighted by atomic masses | 2D autocorrelations | 2 |
| | 1 | JGI9 | mean topological charge index of order9 | topological charge indices | 2 |
| | 1 | B03[C—C] | presence/absence of C—C at topological distance 03 | 2D binary fingerprints | 2 |
| Or88a (19) | 3 | nHBonds | number of intramolecular H-bonds (with N, O, F) | functional group counts | 1 |
| | 2 | nRCO | number of ketones (aliphatic) | functional group counts | 1 |
| | 3 | GATS6m | Geary autocorrelation - lag 6/weighted by atomic masses | 2D autocorrelations | 2 |
| | 2 | EEig08x | Eigenvalue 08 from edge adj. matrix weighted by edge degrees | edge adjacency indices | 2 |
| | 1 | nFuranes | number of Furanes | functional group counts | 1 |
| | 1 | nArCO | number of ketones (aromatic) | functional group counts | 1 |
| | 1 | ESpm15d | Spectral moment 15 from edge adj. matrix weighted by dipole moments | edge adjacency indices | 2 |
| | 1 | C-005 | CH3X | atom-centred fragments | 1 |
| | 1 | O-057 | phenol/enol/carboxyl OH | atom-centred fragments | 1 |
| | 1 | L/Bw | length-to-breadth ratio by WHIM | geometrical descriptors | 3 |
| | 1 | nArCOOR | number of esters (aromatic) | functional group counts | 1 |
| | 1 | ESpm15u | Spectral moment 15 from edge adj. matrix | edge adjacency indices | 2 |
| | 1 | E2u | 2nd component accessibility directional WHIM index/unweighted | WHIM descriptors | 3 |
| | 1 | EEig08d | Eigenvalue 08 from edge adj. matrix weighted by dipole moments | edge adjacency indices | 2 |
| | 1 | H-051 | H attached to alpha-C | atom-centred fragments | 1 |
| | 1 | ESpm14d | Spectral moment 14 from edge adj. matrix weighted by dipole moments | edge adjacency indices | 2 |
| | 1 | GATS7m | Geary autocorrelation - lag 7/weighted by atomic masses | 2D autocorrelations | 2 |
| | 1 | PJI3 | 3D Petitjean shape index | geometrical descriptors | 3 |
| | 2 | X3A | average connectivity index chi-3 | connectivity indices | 2 |
| Or92a (ab1A) (22) | 2 | nRCOOR | number of esters (aliphatic) | functional group counts | 1 |
| | 1 | Mor10u | 3D-MoRSE - signal 10/unweighted | 3D-MoRSE descriptors | 3 |
| | 1 | Mor04m | 3D-MoRSE - signal 04/weighted by atomic masses | 3D-MoRSE descriptors | 3 |
| | 1 | R1e+ | R autocorrelation of lag 1/weighted by atomic Sanderson electronegativities | GETAWAY descriptors | 3 |
| | 1 | Mor27m | 3D-MoRSE - signal 27/weighted by atomic masses | 3D-MoRSE descriptors | 3 |
| | 1 | nHAcc | number of acceptor atoms for H-bonds (N, O, F) | functional group counts | 1 |
| | 1 | E1m | 1st component accessibility directional WHIM index/weighted by atomic masses | WHIM descriptors | 3 |
| | 1 | GATS5m | Geary autocorrelation - lag 5/weighted by atomic masses | 2D autocorrelations | 2 |
| | 1 | nROH | number of hydroxyl groups | functional group counts | 1 |
| | 1 | R5v | R autocorrelation of lag 5/weighted by atomic van der Waals volumes | GETAWAY descriptors | 3 |
| | 1 | Mor10p | 3D-MoRSE - signal 10/weighted by atomic polarizabilities | 3D-MoRSE descriptors | 3 |
| | 1 | C-006 | CH2RX | atom-centred fragments | 1 |
| | 2 | Mor11e | 3D-MoRSE - signal 11/weighted by atomic Sanderson electronegativities | 3D-MoRSE descriptors | 3 |
| Or98a (20) | 1 | Lop | Lopping centric index | topological descriptors | 2 |
| | 4 | O-057 | phenol/enol/carboxyl OH | atom-centred fragments | 1 |
| | 2 | B04[C—O] | presence/absence of C—O at topological distance 04 | 2D binary fingerprints | 2 |
| | 1 | GVWAI-80 | Ghose-Viswanadhan-Wendoloski drug-like index at 80% | molecular properties | 1 |
| | 1 | HATS7p | leverage-weighted autocorrelation of lag 7/weighted by atomic polarizabilities | GETAWAY descriptors | 3 |
| | 1 | HATS5v | leverage-weighted autocorrelation of lag 5/weighted by atomic van der Waals volumes | GETAWAY descriptors | 3 |
| | 1 | MLOGP2 | Squared Moriguchi octanol-water partition coeff. (logP^2) | molecular properties | 1 |
| | 2 | GATS5e | Geary autocorrelation - lag 5/weighted by atomic Sanderson electronegativities | 2D autocorrelations | 2 |
| | 1 | H-049 | H attached to C3(sp3)/C2(sp2)/C3(sp2)/C3(sp) | atom-centred fragments | 1 |
| | 1 | MATS8m | Moran autocorrelation - lag 8/weighted by atomic masses | 2D autocorrelations | 2 |
| | 1 | nCrs | number of ring secondary C(sp3) | functional group counts | 1 |
| | 3 | HATS3p | leverage-weighted autocorrelation of lag 3/weighted by atomic polarizabilities | GETAWAY descriptors | 3 |
| | 1 | G1s | 1st component symmetry directional WHIM index/weighted by atomic electrotopological states | WHIM descriptors | 3 |
| | 1 | S_aasC | S_aasC | atomtypes (Cerius2) | 1 |

TABLE 1-continued

Optimized descriptor sets for each *Drosophila* Or. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | |
|---|---|---|---|---|
| 1 | SP18 | shape profile no. 18 | Randic molecular profiles | 3 |
| 1 | B05[C—C] | presence/absence of C—C at topological distance 05 | 2D binary fingerprints | 2 |
| 1 | JGI2 | mean topological charge index of order2 | topological charge indices | 2 |
| 1 | JGI8 | mean topological charge index of order8 | topological charge indices | 2 |
| 1 | X4A | average connectivity index chi-4 | connectivity indices | 2 |
| 1 | H5e | H autocorrelation of lag 5/weighted by atomic Sanderson electronegativities | GETAWAY descriptors | 3 |

TABLE 4

Top 25 predicted compounds for each *Drosophila* Or. Tables contain SMILES strings, and distances, of the top 25 predicted compounds for each Or. All distances represent the minimum distance based on optimized descriptors to an active compound for that particular Or.

| SMILES | Dist |
|---|---|
| Or2a | |
| CCSC(C)OC(C)O | 0.06547077 |
| CC(C)CCOC(=O)N | 0.07017575 |
| CC(C)CC=CC(=O)C | 0.08148948 |
| C(CCC)OC(=O)C=C | 0.08191658 |
| CCCCSCC(C)O | 0.08378222 |
| CCCCOC(=O)C(=C)C | 0.083826 |
| CC(C)CCOC(=O)C=C | 0.0868181 |
| CC(C)CCOC(=O)CS | 0.09010645 |
| CCCCOC(=O)CS | 0.0962103 |
| CCC(=O)OCCC(C)C | 0.09663025 |
| CCCCCOC(=O)NC | 0.09927085 |
| CC(C)CCOC=O | 0.1000939 |
| CCCCOC(=O)N | 0.1060414 |
| CCCCCOC(=O)CC | 0.1064284 |
| CCCNOC(=O)CC | 0.1068854 |
| CCCC(=O)CCC#CC | 0.1072292 |
| CC(=CC(=C)OC(=O)C)C | 0.1073104 |
| CC(=C)C(=O)OCCCN | 0.1084215 |
| CCCCOC(=O)C(=CC)C | 0.1113651 |
| CCC(C)C(=O)OCC=C | 0.1126422 |
| CCCCC(=O)C=C(C)C | 0.1134776 |
| CCOC(C)OCC#C | 0.1143103 |
| CCCCOC(=O)CN | 0.1163705 |
| CCC#CC(CC(C)C)O | 0.1186069 |
| CCCCOC(=O)C=C(C)C | 0.1191027 |
| Or7a | |
| CCC=CC=O | 0.06287397 |
| CC(=CC)CO | 0.08745256 |
| CC(=CCCO)C | 0.092048 |
| C1=C(ON=C1)C=O | 0.112377 |
| CCC(C)(C)C=NO | 0.1149527 |
| CC=CC=CC=O | 0.1158738 |
| C1CC(=CC=C1)C=O | 0.1165349 |
| C1=COC=C1C=O | 0.1266509 |
| C1=C(OC=N1)C=O | 0.1277235 |
| CCC(C)CC=O | 0.1310643 |
| CCCN=CC=O | 0.1384452 |
| CCC=CCO | 0.1388489 |
| CCC(=C=CCO)C | 0.139234 |
| CCC(=C=CC=O)C | 0.1407318 |
| C=C(CO)CC | 0.1424594 |
| CC(=C)CCCO | 0.1441704 |
| CC(=CCCC=O)C | 0.1441953 |
| C=CC(=C)CCC=O | 0.1466388 |
| CCCC(=C)CCO | 0.1482145 |
| C1CC1CCO | 0.148306 |
| C1CC1CO | 0.1521086 |
| C1=CC=NC(=C1)C=O | 0.153194 |
| CC=CCCCO | 0.1548523 |
| CC=CCO | 0.1553325 |
| CCCC#CCO | 0.1555892 |
| Or9a | |
| CC(CCC=C)O | 0.09391671 |
| CC(CCCO)C | 0.1227934 |
| CC(C)NC(=O)C | 0.1291849 |
| CCC(CCC)O | 0.1337314 |
| CC(C)C(C)O | 0.1449655 |
| CC=CCOC(=O)C | 0.1529503 |
| CCC(=O)NCC#C | 0.165569 |
| COCCC=C=N | 0.1686873 |
| CC(C)NC(=O)C=C | 0.1706617 |
| CC(CCCC)O | 0.1771611 |
| C=CC(CCC)O | 0.1824546 |
| CCC#CCCO | 0.18493 |
| CCC(CC=C)O | 0.1958346 |
| CCC(=O)NCC(=O)C | 0.2001053 |
| CC(CCOC(=O)C)O | 0.2011426 |
| CCC(=O)NCC#N | 0.2057452 |
| CC(CC(C)O)C | 0.2065425 |
| COC(=O)CC(O)C | 0.209219 |
| CC(CC(=O)C)O | 0.2110131 |
| CCC(=O)OC(C)(C)O | 0.2110216 |
| C=CC(C=C)O | 0.2127051 |
| CC(C)C(=O)NC=C | 0.2141241 |
| CC(=O)CNCC(=O)C | 0.2158649 |
| CCC(=O)NCC | 0.2169106 |
| CCC(CC#C)O | 0.2179049 |
| Or10a | |
| C1=CC=C(C=C1)C=S=O | 0 |
| CC1=C(C(=CC=C1)C)N=S=O | 0 |
| CC1=CC(=C(C=C1)OC)C=O | 0 |
| CN(C=O)C1=CC=CC=N1 | 0 |
| CN1C=CC=CC1C=O | 0 |
| C1=CC=C(C=C1)C(C=O)C#N | 0 |
| C1=CC=C(C(=C1)NC=O)O | 0 |
| C1CCC(C1)C(=O)NN | 0 |
| C1=CC=C(C=C1)C=C=O | 0 |
| CNC(=O)C1=CC=NC=C1 | 0 |
| CC(=O)NCN(C)C | 0 |
| CC(C1=CC=CC=C1)N=C=O | 0 |
| CC(=O)C#CC1=CC=CC=C1 | 0 |
| CC(C)CC(C)C=O | 0 |
| C1CCCN(CCC1)N=O | 0 |
| C1CCC(CC1)C=O | 0 |
| C=CC(=O)C1=CC=CC=C1 | 0 |
| C1CCN(CC1)N=O | 0 |
| C1CCC(CC1)NN=O | 0 |

TABLE 4-continued

Top 25 predicted compounds for each *Drosophila* Or.
Tables contain SMILES strings, and distances, of the top
25 predicted compounds for each Or. All distances represent
the minimum distance based on optimized descriptors to
an active compound for that particular Or.

| SMILES | Dist |
|---|---|
| C=CC(=O)C(=O)C1=CC=CC=C1 | 0 |
| C1=CC=C(C=C1)CN(C=O)O | 0 |
| C1=CC=C(C=C1)C(=O)CS | 0 |
| CCN(C=O)C1=CC=CC=N1 | 0 |
| C1=CC=C(C=C1)C(=S=O)C#N | 0 |
| COC(=O)C1=CC=CC=C1N=O | 0 |
| OR19a | |
| CC(CCC(CC)O)CC | 0.1773688 |
| C=CCCCCC | 0.1795821 |
| CCCCCC(=N)C | 0.1837474 |
| CCCCC(=O)CC | 0.1983858 |
| CCCCCC1CO1 | 0.2055113 |
| CCCCOC1CC1 | 0.2097268 |
| CCCCCC1(CO1)C | 0.2192309 |
| CCCCCC(=C)C | 0.2327693 |
| CCCC(CC=C)O | 0.233932 |
| CCCCCC(C)(C#C)O | 0.2437784 |
| CCC(CCCC=C)O | 0.2460947 |
| CCCCCC(=O)C=C | 0.2539876 |
| CCCCCC(C)S | 0.2540855 |
| CCCCC(=O)C(=C)CC | 0.2541479 |
| CC(CC)CCCC | 0.2605213 |
| CCCC(=O)CCC=C | 0.268571 |
| CCCCCC(=O)OC(=O)C | 0.2821946 |
| CCCC(=O)CCC | 0.2839333 |
| CCCCCC(C)(C)O | 0.2848814 |
| OC(C(=O)C)CCCCC | 0.2870452 |
| CCCCC(CC(=C)C)O | 0.2945198 |
| CCCCCC(C)O | 0.3036086 |
| CCCCCOC=C | 0.304017 |
| CCCCCC(C=C)S | 0.3054288 |
| CCCCCC(C)(C=C)O | 0.3074979 |
| Or22a | |
| CCCCOC(=O)CCC | 0.2657116 |
| CCC#CCCOC(=O)C | 0.2798496 |
| CCCCC(=O)OC | 0.2807561 |
| CCC(=O)OCC=CC | 0.3192234 |
| CCCCC(=O)OCC | 0.3386281 |
| C(CC)OC(=O)CCCC | 0.3432405 |
| CCCC=CC(=O)OCC | 0.3470114 |
| COC(=O)C=CC | 0.3564047 |
| CCCOC(=O)CC | 0.3620649 |
| CCCC(=O)OCCC | 0.3642294 |
| CCCCOC(=O)CC | 0.408598 |
| CC(=C)CCCC(=O)OC | 0.4087118 |
| CCCCCC(=O)OCCC | 0.4096699 |
| CCC=CCCOC(=O)C | 0.4280228 |
| CCC=CCC(=O)OCC | 0.4509044 |
| COC(=O)CCC=CCCC | 0.4515538 |
| COC(=O)C=CCC | 0.4606538 |
| CCC#CC(=O)OC | 0.4635536 |
| CCCCCOC(=O)CC | 0.465345 |
| CC(=CCOC(=O)C)C | 0.4677529 |
| COC(=O)CC=CC | 0.4684388 |
| CCC=CC(=O)OCC | 0.4687615 |
| CC(=C)CCCOC(=O)C | 0.4696284 |
| CC(=COC(=O)C)C | 0.4710929 |
| C(C)OC(=O)CCCCCC | 0.4714722 |
| Or23a | |
| CCCCC=CCO | 0.4489215 |
| C(CC=CCC)O | 0.4645003 |
| C=CCCCCCO | 0.4966429 |
| CC=CC=CCO | 0.5369311 |
| CC(CC=C)O | 0.5705127 |
| C#CCCCCO | 0.653074 |
| CCCCCOO | 0.6743714 |
| C(CCCCC)O | 0.679884 |
| C#CCCCCCO | 0.6854802 |
| COC=CCCCO | 0.6878323 |

| SMILES | Dist |
|---|---|
| C(C=CC=CCC)O | 0.730026 |
| CC=CC=CCCO | 0.7327627 |
| CC(CCCC=C)O | 0.7331066 |
| CCCC(C)CCO | 0.7638355 |
| CCCC#CC#CO | 0.7642293 |
| CCCCOO | 0.8340461 |
| CCC#CCCCO | 0.8383432 |
| CCCC=CCCO | 0.8559539 |
| CC(CCC#C)O | 0.8633463 |
| CCCCCCOO | 0.8935004 |
| CCCCCC#CO | 0.895056 |
| CC(CCC=C=C)O | 0.913551 |
| CCC=CCO | 0.9216458 |
| CC#CCCCCO | 0.9630825 |
| CCC#CCCO | 0.9669537 |
| Or35a | |
| CCC#CCCO | 0.150652 |
| CCC=CCCOC(=O)C | 0.153849 |
| C=CCCCCO | 0.1577711 |
| C(CCCCCC=C)O | 0.1896431 |
| CCC=CC=O | 0.1996007 |
| CCC#CCCOC(=O)C | 0.203439 |
| CCCC#CCO | 0.2051737 |
| CC(=O)OCCCCC=C | 0.2169564 |
| CC=CCCCO | 0.2327925 |
| C(CCC=CC)OC(=O)C | 0.2366404 |
| C(CCC=C)O | 0.253342 |
| CC(=O)OCCCC=C | 0.2575001 |
| C#CCCCCO | 0.258166 |
| C(CCCCCCC)O | 0.262205 |
| C(CCO)CCS | 0.2659421 |
| CC=CC=CCOC(=O)C | 0.277348 |
| C(CC=C=O)CS | 0.2857512 |
| CC(=O)OCCCC=C=C | 0.2908757 |
| CCC=CCO | 0.2957919 |
| CC(=O)OCCCCC#C | 0.3021282 |
| C#CCCCCCCO | 0.3034524 |
| CCCC#CC=O | 0.3056329 |
| C=CCCCCCCO | 0.3066109 |
| C(CC=CC)O | 0.3164314 |
| CCC=CCCCCO | 0.3186713 |
| Or43a | |
| CCCCCC(C#C)O | 0.00332052 |
| C1CC1CCCCO | 0.00699056 |
| CCC#CCC(CC)O | 0.01572877 |
| CCCCCC(CC)O | 0.01572877 |
| CCCCCC(CC)O | 0.01642782 |
| CCCCC(C)CO | 0.01782593 |
| CCC#CC(CC)O | 0.0180007 |
| C=CCC(C=C)O | 0.01835023 |
| CCC#CCCO | 0.01887452 |
| CC(=C)CCCO | 0.01904928 |
| C=CC(CCCC)O | 0.02114645 |
| CCCC#CCO | 0.0223698 |
| CCC#CC(C)O | 0.0223698 |
| CCCCC(C)O | 0.0223698 |
| CC=CC=CCO | 0.02341839 |
| CCC=CCO | 0.02376791 |
| CC1(CC1)CCO | 0.02499126 |
| CC#CCCO | 0.02603985 |
| CC=C=CC(C)O | 0.02638937 |
| C=CCCCC(C=C)O | 0.0267389 |
| CC(C)CCCCO | 0.02743796 |
| CCC(CC(C)C)O | 0.02743796 |
| CCC(C#CC)O | 0.02761272 |
| CCCCC(C#C)O | 0.02778749 |
| CCCCC(C=CC)O | 0.02778749 |

TABLE 4-continued

Top 25 predicted compounds for each *Drosophila* Or.
Tables contain SMILES strings, and distances, of the top
25 predicted compounds for each Or. All distances represent
the minimum distance based on optimized descriptors to
an active compound for that particular Or.

| SMILES | Dist |
| --- | --- |
| Or43b | |
| CCCONC(=O)C | 0.0959588 |
| CCN(C(=O)C)O | 0.1130635 |
| CCOC(=O)SCC | 0.1132685 |
| CCNNC(=O)C | 0.1183047 |
| CC#CC(NC)O | 0.1231371 |
| CC=C=CC(C)(C)O | 0.1294547 |
| CCNCNC(=O)C | 0.1317853 |
| CCCC(O)OCC | 0.1391272 |
| CCC(=O)NCC | 0.1435372 |
| CCCC(=O)NCC | 0.1476275 |
| CCC(O)OCC | 0.1478191 |
| CCNC(=O)OCC | 0.1489972 |
| CC#CC(=O)NC | 0.1490445 |
| CC(CN)NC(=O)C | 0.1502223 |
| CCNC(=O)C | 0.1502272 |
| CCCC(=O)NC | 0.1678103 |
| CCOC(C)ON | 0.1752449 |
| CC(C)OC(C)C#N | 0.1764415 |
| CC(=O)C=CCC | 0.1765129 |
| CC(CNC(=O)C)O | 0.1766655 |
| CC(C)C=CC(=O)C | 0.1781594 |
| CC=CC(=O)C | 0.181488 |
| CCOC(C)O | 0.1828469 |
| CCOC(C)OC#N | 0.1867745 |
| CCNC(=O)NCC | 0.1871594 |
| Or47a | |
| CCCCCCC(=O)C | 0.00616096 |
| CCC(CC)CCC(=O)C | 0.00770119 |
| CCCSCO | 0.00847131 |
| CCCOC#N | 0.00924143 |
| CCOCC#N | 0.00924143 |
| CCCCC(=O)COC | 0.01001155 |
| CCCCCCC(=O)C=O | 0.01078167 |
| CCCCC(=O)CC(=O)C | 0.01078167 |
| CCCCC(=O)OC | 0.01078167 |
| CC(C)C(C)COC(=O)C | 0.01155179 |
| CC(C)CCC(=O)OC | 0.01155179 |
| CCCCCOC(=O)C=C | 0.01232191 |
| CCCCCCOC(=O)CC | 0.01232191 |
| CC(C)COC#N | 0.01309203 |
| CCCCCCC(=O)OC | 0.01309203 |
| CCCCCCSSC | 0.01386215 |
| CCCCC(C)CC(=O)C | 0.01386215 |
| CCCCCC(=O)C=C | 0.01386215 |
| CCCCCCC(=O)CO | 0.01386215 |
| CC(C)OCC#N | 0.01386215 |
| CCCCCC(=O)C=C | 0.01386215 |
| CC(=O)OCC(C)(C)C | 0.01463227 |
| CCCCSS(=O)C | 0.01463227 |
| CCCCCSSC | 0.01540239 |
| CCCCCC(=O)OC=C | 0.01540239 |
| Or49b | |
| C1=CC=C(C=C1)N=O | 0.01680465 |
| CC1=CC(=CC=C1)O | 0.02191376 |
| C1=CC=C(C(=C1)O)S | 0.05712351 |
| Cc1ccc(cc1)O | 0.08002216 |
| C1=CC(=CC=C1N)O | 0.08291527 |
| C1=CC=C(C=C1)N=C=O | 0.08630082 |
| C1=CC=C(C(=C1)N)O | 0.08697793 |
| C1=CC(=CC=C1)O)N | 0.08747038 |
| C1=CC=C(C(=C1)O)C1 | 0.08876304 |
| c1(ccccc1)NC=O | 0.09744237 |
| C1=CC=C(C=C1O)S | 0.09756548 |
| C1=CC=C(C=C1)C#CO | 0.1029824 |
| C1=CC=C(C=C1)C=C=O | 0.1066141 |
| CC1=C(C=CC=C1O)N | 0.1069219 |
| CC1=CC=C(C=C1)C)O | 0.1087686 |
| CC1=C(C(=CC=C1)O)C | 0.1101844 |

TABLE 4-continued

Top 25 predicted compounds for each *Drosophila* Or.
Tables contain SMILES strings, and distances, of the top
25 predicted compounds for each Or. All distances represent
the minimum distance based on optimized descriptors to
an active compound for that particular Or.

| SMILES | Dist |
| --- | --- |
| C=C(C1=CC=CC=C1)O | 0.1105537 |
| CC1=C(C=CC=C1S)O | 0.1107999 |
| C1=CC=C(C=C1)NN=O | 0.1138777 |
| CC1=C(C=C(C=C1)N)O | 0.1143086 |
| C1=CC=(CC=C1)O)O | 0.1145548 |
| C1=CC=C(C=C1)C=CO | 0.1148626 |
| CC1=C(C(=CC=C1)O)S | 0.1148626 |
| C1=CC=C(C=C1)NO | 0.1188637 |
| C1=CC(=CC=C1O)O | 0.1207719 |
| Or59b | |
| CCC(=O)OC(C)O | 0.08309379 |
| CCC(=O)OC | 0.08527063 |
| C(C)OC(=O)CC | 0.09857435 |
| CCC(=O)COC | 0.1112024 |
| CCCOC(=O)C | 0.1141674 |
| CCCOC(=O)C | 0.1141674 |
| CCC(O)OC(=O)C | 0.1244704 |
| CC(COC(=O)C)O | 0.1292618 |
| CCC(C(=O)OC)O | 0.1352768 |
| CCC(N=C=O)OC | 0.1459781 |
| COC(=O)CC(O)C | 0.1504875 |
| CCCS(=O)OC | 0.1531444 |
| CCC(=O)C(O)OC | 0.1567203 |
| CCCC(=O)N(C)O | 0.1589646 |
| CC(CC(=O)C)O | 0.1612506 |
| CCC(=O)CC | 0.1613363 |
| CC(N=C=O)OC | 0.1654712 |
| OC(C)C(=O)CC | 0.165828 |
| CC(O)S(=O)C | 0.1659486 |
| COCC(=O)C | 0.1665356 |
| CCN(C)N=O | 0.1718486 |
| CC(=O)CCOC | 0.1721226 |
| CCC#CC(=O)C | 0.1737079 |
| CCS(=O)OC | 0.1760367 |
| CCC(=O)OOC | 0.1770918 |
| Or67a | |
| C=CC(=O)C1=CC=CC=N1 | 0.3008233 |
| C1=CC=C(C(=C1)CC#N)C=O | 0.3080015 |
| CCOC(=N)C1=CC=CC=C1 | 0.312236 |
| COC(=N)C1=CC=CC=C1 | 0.3311703 |
| CCC1=COC(=N1)CC | 0.3703241 |
| CCC(=O)C1=CC=CC=N1 | 0.3768891 |
| C1=CC=C(C(=C1)C=O)C=O | 0.3797241 |
| CCOC(=O)N1C=CC=C1 | 0.3857737 |
| C1=CC=(CC=C1)C=O)C=O | 0.3905579 |
| CC1=CC(=CC=C1)CO | 0.3917814 |
| CCOCC1=CC=CC=C1 | 0.399528 |
| COC(=O)N1C=CC=C1 | 0.4010939 |
| COC(c1ccccc1)O | 0.4035766 |
| C1=CC=C(C=C1)C2=CC=NO2 | 0.4060794 |
| c1(ccccc1)COC | 0.4097667 |
| COC1=NN=CC2=CC=CC=C21 | 0.4106803 |
| COC(=O)C1=CC=CC=C1C#N | 0.4139384 |
| CC1=NOCC2=CC=CC=C12 | 0.4173282 |
| COC1=NC=C(C=C1)C=C | 0.419944 |
| CC(=CCOC)C | 0.4208605 |
| CCC=CCC(=O)C | 0.4243553 |
| CC1=CC2=CC=CC=C2CO1 | 0.4298624 |
| COC1=NN=C2N1C3=CC=CC=C3O2 | 0.4389819 |
| CC1=CC=C(C=C1)C(=O)OC | 0.4404134 |
| C1=CC(=O)C=CC2=C1C=CO2 | 0.4413276 |
| Or67c | |
| CC(CC#C)O | 0.07067509 |
| C=CCC(C=C=C)O | 0.0775118 |
| CC(C)(CC=C)O | 0.0885166 |
| C=CCCCCO | 0.09353587 |
| CC(=C)CCCO | 0.1018462 |
| CC(CCCC)O | 0.1056086 |
| CCC(CC=C)O | 0.1068447 |

TABLE 4-continued

Top 25 predicted compounds for each *Drosophila* Or.
Tables contain SMILES strings, and distances, of the top
25 predicted compounds for each Or. All distances represent
the minimum distance based on optimized descriptors to
an active compound for that particular Or.

| SMILES | Dist |
|---|---|
| CCC#CCCCO | 0.1081803 |
| CCC(CC#C)O | 0.1259778 |
| CC=C(C)C(C)O | 0.1262036 |
| CC=CCCCO | 0.1270505 |
| CC(CC=C)CO | 0.1274556 |
| CCC(CCC)O | 0.1279088 |
| CC(C)(CC#C)O | 0.1294606 |
| CC(CCO)C=C | 0.1341464 |
| CC=C=CCCCO | 0.1372657 |
| CC(C)C(C#C)O | 0.1429075 |
| CCC#CCC(C)O | 0.1430763 |
| CCC(=C)C(C)O | 0.1438052 |
| CCC(C)(CC=C)O | 0.1477914 |
| CCCCC(=C)CO | 0.1527974 |
| CCC(=CC)CO | 0.1538365 |
| CC(CC=C)O | 0.1609561 |
| CCC(C(C)C)O | 0.1618278 |
| CCCC(C)CO | 0.1653694 |
| Or85a | |
| CCC#CCCO | 0.09486577 |
| CC=CCCCO | 0.1241049 |
| CCCC(=N)OCC | 0.1455693 |
| CCCCNC(=C)C | 0.1695939 |
| CCCC#CCO | 0.1791638 |
| CCCC(=O)CCO | 0.1893542 |
| CC=C=CCCCO | 0.1938411 |
| CCN=C(C)CC(=C)O | 0.1971383 |
| CC=CC=CCCO | 0.1971396 |
| CCOC#CC(C)O | 0.2069597 |
| CCC#CCCCO | 0.2311878 |
| CCCC(O)OCC | 0.2512179 |
| CCNC(C)OC=C | 0.255045 |
| CCC(=O)NCC(=O)C | 0.2887675 |
| CC(CCCO)C=C | 0.289174 |
| CC(C)(CCCOC)O | 0.2891912 |
| CCOC(=O)C(C)OC | 0.294917 |
| CCOC(C)OC(=C)O | 0.297801 |
| CCCNC(C)C=O | 0.3026955 |
| CC(C(C)OCC=C)O | 0.3104233 |
| CC=CC=CCO | 0.312425 |
| OCCCCC(=O)C | 0.3180066 |
| CCCCC(=C)CO | 0.3214983 |
| CCC(=O)NCC(=C)C | 0.331915 |
| CCOC(C)C(O)OC | 0.3407239 |
| Or85b | |
| CC(CCCC=C)CO | 0.04010449 |
| CCCCCCC=O | 0.0541304 |
| CCC(=O)C=CCCC | 0.05661388 |
| CCCCC=CC(=O)C | 0.05802127 |
| C(CCCCC=C)O | 0.06257155 |
| CCCCCC(=O)CC | 0.06590403 |
| CC(C(=O)C)CCCC | 0.0741716 |
| CN(CCCC=C)O | 0.08071376 |
| CC(CCC=C=C)C=O | 0.08460999 |
| CCCCC(=C)C=O | 0.08656348 |
| CCC(CCC#CC)O | 0.0872067 |
| CN(CCCCC=C)O | 0.08897917 |
| CCCCC1CCOC1=O | 0.09145651 |
| C=CCCCCO | 0.09536294 |
| CCCCC=CCO | 0.09564121 |
| CCC(CC=C=C)O | 0.0958081 |
| CC(C)CCCCOC | 0.09698922 |
| CCCCCC(CC)O | 0.0993378 |
| CC(=CC)CCC(=O)C | 0.1024115 |
| CCCCC(C)C(C)O | 0.1036823 |
| CCCCC(C)C(C)O | 0.1036823 |
| CCCCC#CC(C)O | 0.1038561 |
| CC(C)CC=CC(=O)C | 0.1081452 |
| CCC(C)CCC(C)O | 0.1082218 |
| CC(CCC=C)N(C)O | 0.1085992 |

| SMILES | Dist |
|---|---|
| Or85f | |
| CC(CCC=C)O | 0.3215251 |
| CCCC#CCO | 0.3977383 |
| CCC#CCCO | 0.4721775 |
| CCCC(=O)OC(C)O | 0.5291351 |
| COC(=O)CC(O)C | 0.5396708 |
| CCCC(COC)O | 0.5401751 |
| CC(CCCC=C)O | 0.574608 |
| CC(CC(=O)OC=C)O | 0.5760439 |
| CC=CCCCO | 0.5830891 |
| CCCC(=O)N(C)O | 0.5926106 |
| CN(CCCCO)N=O | 0.6121783 |
| CC(C)(C1C(O1)C#C)O | 0.6193232 |
| C(CC=CC)O | 0.6211374 |
| CC(CCC=C=C)O | 0.6297574 |
| CCC(C(=O)OCC)O | 0.6342998 |
| CC(=O)OC(COC)O | 0.6391873 |
| CCCC1C(O1)CO | 0.6497865 |
| CCOC(=O)CC(C)O | 0.6566422 |
| CC(C#COC=C)O | 0.663147 |
| CN(CCCC=C)O | 0.6794308 |
| C=CC(CCCC)O | 0.6991725 |
| CCC(COC=C)O | 0.7054714 |
| CCCCCN(C)O | 0.7137121 |
| CC(COCCC#N)O | 0.7174705 |
| CC(CCO)C=C | 0.7219598 |
| Or98a | |
| CC(CCCCO)C=C | 0 |
| CCCC(=O)OCNO | 0 |
| CC(CC=C=C(C)C)O | 0 |
| CNCC(=O)OCCO | 0 |
| CC(C)COCC(C)O | 0.0006135 |
| CC(=O)OC=CC=C | 0.0006135 |
| C=CCCCCC(=C)CO | 0.0006135 |
| C=CCOCC(C=C)O | 0.0006135 |
| C(CN)C(=O)OCCO | 0.0006135 |
| C=CC(COCC#C)O | 0.0006135 |
| CCOCCC(C)O | 0.0006135 |
| CC(CC(=O)OCCO)O | 0.0006135 |
| CCOC(=O)CC(=O)C | 0.0006135 |
| CCOC#CC(C)O | 0.00122699 |
| CC(C)(C#CCN(C)C)O | 0.00122699 |
| CCC(=O)COCC | 0.00122699 |
| CC(=O)CC(=O)OCCO | 0.00122699 |
| CC(C)OC(=O)NCO | 0.00122699 |
| CCOC(=O)CS(=O)C | 0.00122699 |
| CC(CO)OCCC=C | 0.00122699 |
| CCCNOC(=O)CC | 0.00122699 |
| CCCC(=O)OC(=O)C | 0.00122699 |
| CC(=C)COCCOC | 0.00122699 |
| CC(=O)OC(=O)CC=C | 0.00122699 |
| CCOCOC(=O)C | 0.00184049 |
| ab1A | |
| CC(=O)C(=O)C | 0.02090025 |
| CC(OCC(C)C)=O | 0.05702 |
| CC(=O)OCCC#C | 0.07507874 |
| CCC(=O)OOCC | 0.07770847 |
| CCOC(=O)OC | 0.07784295 |
| CCCOC(=O)CC | 0.08788487 |
| CCCOC(=O)OC | 0.09563759 |
| CCOC(=O)CC#C | 0.09593777 |
| CCC(=O)OCC#C | 0.1027616 |
| CC1CC(=O)OC1 | 0.1040388 |
| COCCC(=O)OC | 0.1130966 |
| CCCC(OC)=O | 0.11606 |
| CCSCC(C)C=O | 0.116945 |
| CC1COC(=O)O1 | 0.1170738 |
| CCCOC(=O)C | 0.1177654 |
| C(C)OC(=O)OCC | 0.1181321 |

TABLE 4-continued

Top 25 predicted compounds for each *Drosophila* Or. Tables contain SMILES strings, and distances, of the top 25 predicted compounds for each Or. All distances represent the minimum distance based on optimized descriptors to an active compound for that particular Or.

| SMILES | Dist |
|---|---|
| CC(C)OC=O | 0.1209444 |
| CC(C)CCS(=O)C | 0.1236193 |
| CCC(C)OCC=O | 0.1263356 |
| CCOCS(=O)C | 0.1272632 |
| CCOC(=O)ONN | 0.1288552 |
| CCC(=O)OC | 0.1298152 |
| CC1OCC(=O)O1 | 0.1309472 |
| CC(=O)OCC#C | 0.1313023 |
| COC(=O)CCCS | 0.132371 |

TABLE 5

Optimized descriptor sets for each Mammalian OR. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

Mammalian Descriptor Lists

Descriptor Class Type Counts for all Org

| | |
|---|---|
| GETAWAY descriptors | 109 |
| atom-centred fragments | 49 |
| 2D autocorrelations | 48 |
| RDF descriptors | 48 |
| 3D-MoRSE descriptors | 46 |
| WHIM descriptors | 43 |
| functional group counts | 33 |
| 2D binary fingerprints | 26 |
| Burden eigenvalues | 23 |
| edge adjacency indices | 21 |
| geometrical descriptors | 21 |
| topological descriptors | 14 |
| 2D frequency fingerprints | 13 |
| topological charge indices | 12 |
| atomtypes (Cerius2) | 11 |
| molecular properties | 11 |
| walk and path counts | 7 |
| constitutional descriptors | 6 |
| Randic molecular profiles | 5 |
| topological (Cerius2) | 4 |
| information indices | 4 |
| connectivity indices | 3 |
| structural (Cerius2) | 1 |
| eigenvalue-based indices | 1 |
| charge descriptors | 0 |

Dimensionality Counts (Weights Included)

| | |
|---|---|
| Num zero dimensional descriptors: | 7 |
| Num one dimensional descriptors: | 104 |
| Num two dimensional descriptors: | 176 |
| Num three dimensional descriptors: | 272 |

Origin (Weights Included)

| | |
|---|---|
| Num Dragon descriptors: | 546 |
| Num Cerius2 descriptors: | 13 |

Dimensionality Counts (Weights Excluded)

| | |
|---|---|
| Num zero dimensional descriptors: | 7 |
| Num one dimensional descriptors: | 37 |
| Num two dimensional descriptors: | 93 |
| Num three dimensional descriptors: | 155 |

Origin (Weights Excluded)

| | |
|---|---|
| Num unique Dragon descriptors: | 284 |
| Num unique Cerius2 descriptors: | 8 |

MOR1.1

| | | | | | |
|---|---|---|---|---|---|
| 844 | 2 | Mor17m | 3D-MoRSE - signal 17/weighted by atomic masses | 3D-MoRSE descriptors | 3 |
| 1300 | 8 | H-051 | H attached to alpha-C | atom-centred fragments | 1 |
| 1248 | 2 | R6p+ | R maximal autocorrelation of lag 6/weighted by atomic polarizabilities | GETAWAY descriptors | 3 |

TABLE 5-continued

Optimized descriptor sets for each Mammalian OR. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| 914 | 4 | Mor23e | 3D-MoRSE - signal 23/weighted by atomic Sanderson electronegativities | 3D-MoRSE descriptors | 3 |
| 857 | 5 | Mor30m | 3D-MoRSE - signal 30/weighted by atomic masses | 3D-MoRSE descriptors | 3 |
| 1211 | 4 | R5v+ | R maximal autocorrelation of lag 5/weighted by atomic van der Waals volumes | GETAWAY descriptors | 3 |
| 923 | 1 | Mor32e | 3D-MoRSE - signal 32/weighted by atomic Sanderson electronegativities | 3D-MoRSE descriptors | 3 |
| 519 | 1 | JGI7 | mean topological charge index of order7 | topological charge indices | 2 |
| 1019 | 2 | E1s | 1st component accessibility directional WHIM index/weighted by atomic electrotopological states | WHIM descriptors | 3 |
| 1254 | 1 | nCt | number of total tertiary C(sp3) | functional group counts | 1 |
| 1270 | 1 | nArCO | number of ketones (aromatic) | functional group counts | 1 |
| 1304 | 1 | O-058 | #NAME? | atom-centred fragments | 1 |
| 1344 | 1 | B07[C—O] | presence/absence of C—O at topological distance 07 | 2D binary fingerprints | 2 |
| 302 | 2 | GATS2m | Geary autocorrelation - lag 2/weighted by atomic masses | 2D autocorrelations | 2 |
| 756 | 1 | RDF110e | Radial Distribution Function - 11.0/weighted by atomic Sanderson electronegativities | RDF descriptors | 3 |
| 1262 | 1 | nCconj | number of non-aromatic conjugated C(sp2) | functional group counts | 1 |
| 1282 | 1 | C-006 | CH2RX | atom-centred fragments | 1 |
| 1256 | 1 | nCrs | number of ring secondary C(sp3) | functional group counts | 1 |
| 307 | 1 | GATS7m | Geary autocorrelation - lag 7/weighted by atomic masses | 2D autocorrelations | 2 |
| 1280 | 1 | C-003 | CHR3 | atom-centred fragments | 1 |
| 276 | 1 | MATS8m | Moran autocorrelation - lag 8/weighted by atomic masses | 2D autocorrelations | 2 |
| | | | MOR106.1 | | |
| 948 | 1 | Mor25p | 3D-MoRSE - signal 25/weighted by atomic polarizabilities | 3D-MoRSE descriptors | 3 |
| 476 | 1 | BEHe6 | highest eigenvalue n. 6 of Burden matrix/weighted by atomic Sanderson electronegativities | Burden eigenvalues | 2 |
| 212 | 1 | IC1 | information content index (neighborhood symmetry of 1-order) | information indices | 2 |
| 1282 | 2 | C-006 | CH2RX | atom-centred fragments | 1 |
| 1233 | 2 | RTe+ | R maximal index/weighted by atomic Sanderson electronegativities | GETAWAY descriptors | 3 |
| 147 | 1 | piPC07 | molecular multiple path count of order 07 | walk and path counts | 2 |
| 743 | 1 | RDF045e | Radial Distribution Function - 4.5/weighted by atomic Sanderson electronegativities | RDF descriptors | 3 |
| 1266 | 1 | nRCOOH | number of carboxylic acids (aliphatic) | functional group counts | 1 |
| 1213 | 1 | R7v+ | R maximal autocorrelation of lag 7/weighted by atomic van der Waals volumes | GETAWAY descriptors | 3 |
| 630 | 1 | HOMT | HOMA total | geometrical descriptors | 3 |
| 683 | 1 | RDF035m | Radial Distribution Function - 3.5/weighted by atomic masses | RDF descriptors | 3 |
| 1298 | 1 | H-049 | H attached to C3(sp3)/C2(sp2)/C3(sp2)/C3(sp) | atom-centred fragments | 1 |
| 608 | 1 | SHP2 | average shape profile index of order 2 | Randic molecular profiles | 3 |
| | | | MOR107.1 | | |
| 1255 | 15 | nCq | number of total quaternary C(sp3) | functional group counts | 1 |
| 866 | 1 | Mor07v | 3D-MoRSE - signal 07/weighted by atomic van der Waals volumes | 3D-MoRSE descriptors | 3 |
| 465 | 1 | BELv3 | lowest eigenvalue n. 3 of Burden matrix/weighted by atomic van der Waals volumes | Burden eigenvalues | 2 |
| 1246 | 1 | R4p+ | R maximal autocorrelation of lag 4/weighted by atomic polarizabilities | GETAWAY descriptors | 3 |
| 964 | 1 | E1u | 1st component accessibility directional WHIM index/unweighted | WHIM descriptors | 3 |
| 516 | 1 | JGI4 | mean topological charge index of order4 | topological charge indices | 2 |
| 635 | 1 | DISPv | d COMMA2 value/weighted by atomic van der Waals volumes | geometrical descriptors | 3 |
| 29 | 1 | nR06 | number of 6-membered rings | constitutional descriptors | 0 |
| 684 | 1 | RDF040m | Radial Distribution Function - 4.0/weighted by atomic masses | RDF descriptors | 3 |
| 1232 | 1 | R8e+ | R maximal autocorrelation of lag 8/weighted by atomic Sanderson electronegativities | GETAWAY descriptors | 3 |
| 147 | 1 | piPC07 | molecular multiple path count of order 07 | walk and path counts | 2 |
| 1012 | 1 | L2s | 2nd component size directional WHIM index/weighted by atomic electrotopological states | WHIM descriptors | 3 |
| 148 | 1 | piPC08 | molecular multiple path count of order 08 | walk and path counts | 2 |
| 22 | 1 | nDB | number of double bonds | constitutional descriptors | 0 |
| 1300 | 1 | H-051 | H attached to alpha-C | atom-centred fragments | 1 |
| 975 | 1 | E1m | 1st component accessibility directional WHIM index/weighted by atomic masses | WHIM descriptors | 3 |
| 1338 | 1 | B05[C—O] | presence/absence of C—O at topological distance 05 | 2D binary fingerprints | 2 |
| 497 | 1 | BELp3 | lowest eigenvalue n. 3 of Burden matrix/weighted by atomic polarizabilities | Burden eigenvalues | 2 |

TABLE 5-continued

Optimized descriptor sets for each Mammalian OR. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| | MOR129.1 | | | | |
| 1045 | 1 | Dv | D total accessibility index/weighted by atomic van der Waals volumes | WHIM descriptors | 3 |
| 1136 | 2 | HATS7e | leverage-weighted autocorrelation of lag 7/weighted by atomic Sanderson electronegativities | GETAWAY descriptors | 3 |
| 1355 | 1 | F01[C—C] | frequency of C—C at topological distance 01 | 2D frequency fingerprints | 2 |
| 805 | 1 | Mor10u | 3D-MoRSE - signal 10/unweighted | 3D-MoRSE descriptors | 3 |
| 1094 | 1 | HATS5m | leverage-weighted autocorrelation of lag 5/weighted by atomic masses | GETAWAY descriptors | 3 |
| 1100 | 2 | H1v | H autocorrelation of lag 1/weighted by atomic van der Waals volumes | GETAWAY descriptors | 3 |
| 870 | 1 | Mor11v | 3D-MoRSE - signal 11/weighted by atomic van der Waals volumes | 3D-MoRSE descriptors | 3 |
| 1337 | 1 | B05[C—C] | presence/absence of C—C at topological distance 05 | 2D binary fingerprints | 2 |
| 751 | 1 | RDF085e | Radial Distribution Function - 8.5/weighted by atomic Sanderson electronegativities | RDF descriptors | 3 |
| 1044 | 1 | Dm | D total accessibility index/weighted by atomic masses | WHIM descriptors | 3 |
| 1079 | 1 | H0m | H autocorrelation of lag 0/weighted by atomic masses | GETAWAY descriptors | 3 |
| 901 | 1 | Mor10e | 3D-MoRSE - signal 10/weighted by atomic Sanderson electronegativities | 3D-MoRSE descriptors | 3 |
| 107 | 1 | D/Dr06 | distance/detour ring index of order 6 | topological descriptors | 2 |
| 1095 | 1 | HATS6m | leverage-weighted autocorrelation of lag 6/weighted by atomic masses | GETAWAY descriptors | 3 |
| 297 | 1 | MATS5p | Moran autocorrelation - lag 5/weighted by atomic polarizabilities | 2D autocorrelations | 2 |
| 683 | 1 | RDF035m | Radial Distribution Function - 3.5/weighted by atomic masses | RDF descriptors | 3 |
| 1126 | 1 | H7e | H autocorrelation of lag 7/weighted by atomic Sanderson electronegativities | GETAWAY descriptors | 3 |
| 1099 | 1 | H0v | H autocorrelation of lag 0/weighted by atomic van der Waals volumes | GETAWAY descriptors | 3 |
| 1184 | 1 | R5m | R autocorrelation of lag 5/weighted by atomic masses | GETAWAY descriptors | 3 |
| | MOR136.1 | | | | |
| 682 | 1 | RDF030m | Radial Distribution Function - 3.0/weighted by atomic masses | RDF descriptors | 3 |
| 1466 | 1 | S__dssC | S__dssC | atomtypes (cerius2) | 1 |
| 832 | 1 | Mor05m | 3D-MoRSE - signal 05/weighted by atomic masses | 3D-MoRSE descriptors | 3 |
| 479 | 1 | BELe1 | lowest eigenvalue n. 1 of Burden matrix/weighted by atomic Sanderson electronegativities | Burden eigenvalues | 2 |
| 1175 | 1 | R5u+ | R maximal autocorrelation of lag 5/unweighted | GETAWAY descriptors | 3 |
| 608 | 1 | SHP2 | average shape profile index of order 2 | Randic molecular profiles | 3 |
| | MOR139.1 | | | | |
| 1100 | 2 | H1v | H autocorrelation of lag 1/weighted by atomic van der Waals volumes | GETAWAY descriptors | 3 |
| 1070 | 1 | HATS1u | leverage-weighted autocorrelation of lag 1/unweighted | GETAWAY descriptors | 3 |
| 1310 | 1 | TPSA(NO) | topological polar surface area using N, O polar contributions | molecular properties | 1 |
| 146 | 1 | piPC06 | molecular multiple path count of order 06 | walk and path counts | 2 |
| 1087 | 1 | H8m | H autocorrelation of lag 8/weighted by atomic masses | GETAWAY descriptors | 3 |
| 1316 | 1 | GVWAI-80 | Ghose-Viswanadhan-Wendoloski drug-like index at 80% | molecular properties | 1 |
| 1198 | 1 | R1v | R autocorrelation of lag 1/weighted by atomic van der Waals volumes | GETAWAY descriptors | 3 |
| 302 | 1 | GATS2m | Geary autocorrelation - lag 2/weighted by atomic masses | 2D autocorrelations | 2 |
| 915 | 1 | Mor24e | 3D-MoRSE - signal 24/weighted by atomic Sanderson electronegativities | 3D-MoRSE descriptors | 3 |
| 358 | 1 | EEig09d | Eigenvalue 09 from edge adj. matrix weighted by dipole moments | edge adjacency indices | 2 |
| | MOR162.1 | | | | |
| 627 | 1 | HOMA | Harmonic Oscillator Model of Aromaticity index | geometrical descriptors | 3 |
| 1094 | 1 | HATS5m | leverage-weighted autocorrelation of lag 5/weighted by atomic masses | GETAWAY descriptors | 3 |
| 998 | 1 | E2e | 2nd component accessibility directional WHIM index/weighted by atomic Sanderson electronegativities | WHIM descriptors | 3 |
| 1121 | 1 | H2e | H autocorrelation of lag 2/weighted by atomic Sanderson electronegativities | GETAWAY descriptors | 3 |
| 1212 | 1 | R6v+ | R maximal autocorrelation of lag 6/weighted by atomic van der Waals volumes | GETAWAY descriptors | 3 |
| 993 | 1 | P2e | 2nd component shape directional WHIM index/weighted by atomic Sanderson electronegativities | WHIM descriptors | 3 |
| 297 | 1 | MATS5p | Moran autocorrelation - lag 5/weighted by atomic polarizabilities | 2D autocorrelations | 2 |
| 628 | 1 | RCI | Jug RC index | geometrical descriptors | 3 |
| 1095 | 1 | HATS6m | leverage-weighted autocorrelation of lag 6/weighted by atomic masses | GETAWAY descriptors | 3 |
| 683 | 1 | RDF035m | Radial Distribution Function - 3.5/weighted by atomic masses | RDF descriptors | 3 |
| 1120 | 1 | H1e | H autocorrelation of lag 1/weighted by atomic Sanderson electronegativities | GETAWAY descriptors | 3 |

TABLE 5-continued

Optimized descriptor sets for each Mammalian OR. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

MOR170.1

| | | | | | |
|---|---|---|---|---|---|
| 1290 | 3 | C-025 | R—CR—R | atom-centred fragments | 1 |
| 1371 | 1 | F05[C—O] | frequency of C—O at topological distance 05 | 2D frequency fingerprints | 2 |
| 1212 | 1 | R6v+ | R maximal autocorrelation of lag 6/weighted by atomic van der Waals volumes | GETAWAY descriptors | 3 |
| 998 | 2 | E2e | 2nd component accessibility directional WHIM index/weighted by atomic Sanderson electronegativities | WHIM descriptors | 3 |
| 1464 | 1 | S_aaCH | S_aaCH | atomtypes (cerius2) | 1 |
| 1233 | 2 | RTe+ | R maximal index/weighted by atomic Sanderson electronegativities | GETAWAY descriptors | 3 |
| 1178 | 1 | R8u+ | R maximal autocorrelation of lag 8/unweighted | GETAWAY descriptors | 3 |
| 262 | 1 | ATS2p | Broto-Moreau autocorrelation of a topological structure - lag 2/weighted by atomic polarizabilities | 2D autocorrelations | 2 |
| 297 | 1 | MATS5p | Moran autocorrelation - lag 5/weighted by atomic polarizabilities | 2D autocorrelations | 2 |
| 714 | 1 | RDF045v | Radial Distribution Function - 4.5/weighted by atomic van der Waals volumes | RDF descriptors | 3 |
| 1004 | 1 | P2p | 2nd component shape directional WHIM index/weighted by atomic polarizabilities | WHIM descriptors | 3 |
| 1249 | 1 | R7p+ | R maximal autocorrelation of lag 7/weighted by atomic polarizabilities | GETAWAY descriptors | 3 |
| 1184 | 1 | R5m | R autocorrelation of lag 5/weighted by atomic masses | GETAWAY descriptors | 3 |
| 627 | 1 | HOMA | Harmonic Oscillator Model of Aromaticity index | geometrical descriptors | 3 |

MOR184.1

| | | | | | |
|---|---|---|---|---|---|
| 1461 | 1 | S_dCH2 | S_dCH2 | atomtypes (cerius2) | 1 |
| 301 | 1 | GATS1m | Geary autocorrelation - lag 1/weighted by atomic masses | 2D autocorrelations | 2 |
| 1297 | 1 | H-047 | H attached to C1(sp3)/C0(sp2) | atom-centred fragments | 1 |
| 37 | 1 | Qindex | Quadratic index | topological descriptors | 2 |
| 635 | 1 | DISPv | d COMMA2 value/weighted by atomic van der Waals volumes | geometrical descriptors | 3 |
| 979 | 1 | L2v | 2nd component size directional WHIM index/weighted by atomic van der Waals volumes | WHIM descriptors | 3 |
| 18 | 1 | nCIC | number of rings | constitutional descriptors | 0 |
| 1111 | 1 | HATS2v | leverage-weighted autocorrelation of lag 2/weighted by atomic van der Waals volumes | GETAWAY descriptors | 3 |
| 802 | 1 | Mor07u | 3D-MoRSE - signal 07/unweighted | 3D-MoRSE descriptors | 3 |
| 1222 | 1 | R7e | R autocorrelation of lag 7/weighted by atomic Sanderson electronegativities | GETAWAY descriptors | 3 |
| 136 | 1 | MPC06 | molecular path count of order 06 | walk and path counts | 2 |
| 373 | 1 | EEig09r | Eigenvalue 09 from edge adj. matrix weighted by resonance integrals | edge adjacency indices | 2 |
| 19 | 1 | nCIR | number of circuits | constitutional descriptors | 0 |
| 685 | 1 | RDF045m | Radial Distribution Function - 4.5/weighted by atomic masses | RDF descriptors | 3 |
| 497 | 1 | BELp3 | lowest eigenvalue n. 3 of Burden matrix/weighted by atomic polarizabilities | Burden eigenvalues | 2 |
| 358 | 1 | EEig09d | Eigenvalue 09 from edge adj. matrix weighted by dipole moments | edge adjacency indices | 2 |
| 1001 | 1 | L2p | 2nd component size directional WHIM index/weighted by atomic polarizabilities | WHIM descriptors | 3 |
| 1156 | 1 | HATS7p | leverage-weighted autocorrelation of lag 7/weighted by atomic polarizabilities | GETAWAY descriptors | 3 |
| 1246 | 1 | R4p+ | R maximal autocorrelation of lag 4/weighted by atomic polarizabilities | GETAWAY descriptors | 3 |
| 837 | 1 | Mor10m | 3D-MoRSE - signal 10/weighted by atomic masses | 3D-MoRSE descriptors | 3 |

MOR185.1

| | | | | | |
|---|---|---|---|---|---|
| 103 | 1 | BAC | Balaban centric index | topological descriptors | 2 |
| 1091 | 1 | HATS2m | leverage-weighted autocorrelation of lag 2/weighted by atomic masses | GETAWAY descriptors | 3 |
| 1178 | 1 | R8u+ | R maximal autocorrelation of lag 8/unweighted | GETAWAY descriptors | 3 |
| 168 | 1 | X5A | average connectivity index chi-5 | connectivity indices | 2 |
| 997 | 1 | E1e | 1st component accessibility directional WHIM index/weighted by atomic Sanderson electronegativities | WHIM descriptors | 3 |
| 1233 | 1 | RTe+ | R maximal index/weighted by atomic Sanderson electronegativities | GETAWAY descriptors | 3 |
| 998 | 1 | E2e | 2nd component accessibility directional WHIM index/weighted by atomic Sanderson electronegativities | WHIM descriptors | 3 |
| 302 | 1 | GATS2m | Geary autocorrelation - lag 2/weighted by atomic masses | 2D autocorrelations | 2 |
| 1140 | 1 | H1p | H autocorrelation of lag 1/weighted by atomic polarizabilities | GETAWAY descriptors | 3 |
| 1156 | 1 | HATS7p | leverage-weighted autocorrelation of lag 7/weighted by atomic polarizabilities | GETAWAY descriptors | 3 |
| 683 | 1 | RDF035m | Radial Distribution Function - 3.5/weighted by atomic masses | RDF descriptors | 3 |
| 608 | 1 | SHP2 | average shape profile index of order 2 | Randic molecular profiles | 3 |
| 1244 | 1 | R2p+ | R maximal autocorrelation of lag 2/weighted by atomic polarizabilities | GETAWAY descriptors | 3 |

TABLE 5-continued

Optimized descriptor sets for each Mammalian OR. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | MOR189.1 | | |
|---|---|---|---|---|---|
| 1256 | 1 | nCrs | number of ring secondary C(sp3) | functional group counts | 1 |
| 1457 | 1 | V-DIST-mag | V-DIST-mag | topological (cerius2) | 2 |
| 610 | 1 | J3D | 3D-Balaban index | geometrical descriptors | 3 |
| 1413 | 2 | Atype_C_40 | Number of Carbon Type 40 | atomtypes (Cerius2) | 1 |
| 375 | 1 | EEig11r | Eigenvalue 11 from edge adj. matrix weighted by resonance integrals | edge adjacency indices | 2 |
| 1183 | 1 | R4m | R autocorrelation of lag 4/weighted by atomic masses | GETAWAY descriptors | 3 |
| 930 | 1 | Mor07p | 3D-MoRSE - signal 07/weighted by atomic polarizabilities | 3D-MoRSE descriptors | 3 |
| 1316 | 1 | GVWAI-80 | Ghose-Viswanadhan-Wendoloski drug-like index at 80% | molecular properties | 1 |
| 681 | 1 | RDF025m | Radial Distribution Function - 2.5/weighted by atomic masses | RDF descriptors | 3 |
| 1343 | 1 | B07[C—C] | presence/absence of C—C at topological distance 07 | 2D binary fingerprints | 2 |
| 1174 | 1 | R4u+ | R maximal autocorrelation of lag 4/unweighted | GETAWAY descriptors | 3 |
| 913 | 1 | Mor22e | 3D-MoRSE - signal 22/weighted by atomic Sanderson electronegativities | 3D-MoRSE descriptors | 3 |
| 1304 | 1 | O-058 | #NAME? | atom-centred fragments | 1 |
| 356 | 1 | EEig07d | Eigenvalue 07 from edge adj. matrix weighted by dipole moments | edge adjacency indices | 2 |
| 360 | 1 | EEig11d | Eigenvalue 11 from edge adj. matrix weighted by dipole moments | edge adjacency indices | 2 |
| | | | MOR2.1 | | |
| 685 | 1 | RDF045m | Radial Distribution Function - 4.5/weighted by atomic masses | RDF descriptors | 3 |
| 1316 | 2 | GVWAI-80 | Ghose-Viswanadhan-Wendoloski drug-like index at 80% | molecular properties | 1 |
| 485 | 1 | BELe7 | lowest eigenvalue n. 7 of Burden matrix/weighted by atomic Sanderson electronegativities | Burden eigenvalues | 2 |
| 686 | 1 | RDF050m | Radial Distribution Function - 5.0/weighted by atomic masses | RDF descriptors | 3 |
| 905 | 1 | Mor14e | 3D-MoRSE - signal 14/weighted by atomic Sanderson electronegativities | 3D-MoRSE descriptors | 3 |
| 346 | 1 | EEig12x | Eigenvalue 12 from edge adj. matrix weighted by edge degrees | edge adjacency indices | 2 |
| 843 | 1 | Mor16m | 3D-MoRSE - signal 16/weighted by atomic masses | 3D-MoRSE descriptors | 3 |
| 376 | 2 | EEig12r | Eigenvalue 12 from edge adj. matrix weighted by resonance integrals | edge adjacency indices | 2 |
| 949 | 1 | Mor26p | 3D-MoRSE - signal 26/weighted by atomic polarizabilities | 3D-MoRSE descriptors | 3 |
| 804 | 1 | Mor09u | 3D-MoRSE - signal 09/unweighted | 3D-MoRSE descriptors | 3 |
| 1262 | 1 | nCconj | number of non-aromatic conjugated C(sp2) | functional group counts | 1 |
| 845 | 1 | Mor18m | 3D-MoRSE - signal 18/weighted by atomic masses | 3D-MoRSE descriptors | 3 |
| 1173 | 1 | R3u+ | R maximal autocorrelation of lag 3/unweighted | GETAWAY descriptors | 3 |
| 1344 | 1 | B07[C—O] | presence/absence of C—O at topological distance 07 | 2D binary fingerprints | 2 |
| 1358 | 1 | F02[C—C] | frequency of C—C at topological distance 02 | 2D frequency fingerprints | 2 |
| | | | MOR203.1 | | |
| 1340 | 6 | B06[C—C] | presence/absence of C—C at topological distance 06 | 2D binary fingerprints | 2 |
| 1298 | 1 | H-049 | H attached to C3(sp3)/C2(sp2)/C3(sp2)/C3(sp) | atom-centred fragments | 1 |
| 931 | 1 | Mor08p | 3D-MoRSE - signal 08/weighted by atomic polarizabilities | 3D-MoRSE descriptors | 3 |
| 1390 | 1 | Hbond acceptor | Number of Hydrogen bond acceptors | structural (Cerius2) | 0 |
| 661 | 1 | RDF075u | Radial Distribution Function - 7.5/unweighted | RDF descriptors | 3 |
| 1203 | 1 | R6v | R autocorrelation of lag 6/weighted by atomic van der Waals volumes | GETAWAY descriptors | 3 |
| 1268 | 3 | nRCHO | number of aldehydes (aliphatic) | functional group counts | 1 |
| 1266 | 2 | nRCOOH | number of carboxylic acids (aliphatic) | functional group counts | 1 |
| 272 | 1 | MATS4m | Moran autocorrelation - lag 4/weighted by atomic masses | 2D autocorrelations | 2 |
| 1018 | 1 | G3s | 3st component symmetry directional WHIM index/weighted by atomic electrotopological states | WHIM descriptors | 3 |
| 106 | 1 | D/Dr05 | distance/detour ring index of order 5 | topological descriptors | 2 |
| 1270 | 1 | nArCO | number of ketones (aromatic) | functional group counts | 1 |
| 1352 | 1 | B10[C-C] | presence/absence of C-C at topological distance 10 | 2D binary fingerprints | 2 |
| 274 | 1 | MATS6m | Moran autocorrelation - lag 6/weighted by atomic masses | 2D autocorrelations | 2 |
| 445 | 1 | BEHm7 | highest eigenvalue n. 7 of Burden matrix/weighted by atomic masses | Burden eigenvalues | 2 |
| 80 | 1 | MAXDN | maximal electrotopological negative variation | topological descriptors | 2 |
| 1012 | 1 | L2s | 2nd component size directional WHIM index/weighted by atomic electrotopological states | WHIM descriptors | 3 |
| 481 | 1 | BELe3 | lowest eigenvalue n. 3 of Burden matrix/weighted by atomic Sanderson electronegativities | Burden eigenvalues | 2 |
| 665 | 1 | RDF095u | Radial Distribution Function - 9.5/unweighted | RDF descriptors | 3 |
| | | | MOR204.6 | | |
| 1262 | 1 | nCconj | number of non-aromatic conjugated C(sp2) | functional group counts | 1 |
| 1463 | 1 | S__dsCH | S__dsCH | atomtypes (cerius2) | 1 |
| 1092 | 2 | HATS3m | leverage-weighted autocorrelation of lag 3/weighted by atomic masses | GETAWAY descriptors | 3 |
| 635 | 1 | DISPv | d COMMA2 value/weighted by atomic van der Waals volumes | geometrical descriptors | 3 |
| 1174 | 1 | R4u+ | R maximal autocorrelation of lag 4/unweighted | GETAWAY descriptors | 3 |

TABLE 5-continued

Optimized descriptor sets for each Mammalian OR. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| 107 | 2 | D/Dr06 | distance/detour ring index of order 6 | topological descriptors | 2 |
| 1185 | 1 | R6m | R autocorrelation of lag 6/weighted by atomic masses | GETAWAY descriptors | 3 |
| 837 | 1 | Mor10m | 3D-MoRSE - signal 10/weighted by atomic masses | 3D-MoRSE descriptors | 3 |
| 373 | 1 | EEig09r | Eigenvalue 09 from edge adj. matrix weighted by resonance integrals | edge adjacency indices | 2 |
| 1222 | 1 | R7e | R autocorrelation of lag 7/weighted by atomic Sanderson electronegativities | GETAWAY descriptors | 3 |
| 1173 | 1 | R3u+ | R maximal autocorrelation of lag 3/unweighted | GETAWAY descriptors | 3 |
| 1199 | 1 | R2v | R autocorrelation of lag 2/weighted by atomic van der Waals volumes | GETAWAY descriptors | 3 |
| 1371 | 1 | F05[C—O] | frequency of C—O at topological distance 05 | 2D frequency fingerprints | 2 |
| 1136 | 1 | HATS7e | leverage-weighted autocorrelation of lag 7/weighted by atomic Sanderson electronegativities | GETAWAY descriptors | 3 |

MOR207.1

| | | | | | |
|---|---|---|---|---|---|
| 1290 | 3 | C-025 | R—CR—R | atom-centred fragments | 1 |
| 1371 | 1 | F05[C—O] | frequency of C—O at topological distance 05 | 2D frequency fingerprints | 2 |
| 1212 | 1 | R6v+ | R maximal autocorrelation of lag 6/weighted by atomic van der Waals volumes | GETAWAY descriptors | 3 |
| 998 | 2 | E2e | 2nd component accessibility directional WHIM index/weighted by atomic Sanderson electronegativities | WHIM descriptors | 3 |
| 1464 | 1 | S_aaCH | S_aaCH | atomtypes (cerius2) | 1 |
| 1233 | 2 | RTe+ | R maximal index/weighted by atomic Sanderson electronegativities | GETAWAY descriptors | 3 |
| 1178 | 1 | R8u+ | R maximal autocorrelation of lag 8/unweighted | GETAWAY descriptors | 3 |
| 262 | 1 | ATS2p | Broto-Moreau autocorrelation of a topological structure - lag 2/weighted by atomic polarizabilities | 2D autocorrelations | 2 |
| 297 | 1 | MATS5p | Moran autocorrelation - lag 5/weighted by atomic polarizabilities | 2D autocorrelations | 2 |
| 714 | 1 | RDF045v | Radial Distribution Function - 4.5/weighted by atomic van der Waals volumes | RDF descriptors | 3 |
| 1004 | 1 | P2p | 2nd component shape directional WHIM index/weighted by atomic polarizabilities | WHIM descriptors | 3 |
| 1249 | 1 | R7p+ | R maximal autocorrelation of lag 7/weighted by atomic polarizabilities | GETAWAY descriptors | 3 |
| 1184 | 1 | R5m | R autocorrelation of lag 5/weighted by atomic masses | GETAWAY descriptors | 3 |
| 627 | 1 | HOMA | Harmonic Oscillator Model of Aromaticity index | geometrical descriptors | 3 |
| 1213 | 1 | R7v+ | R maximal autocorrelation of lag 7/weighted by atomic van der Waals volumes | GETAWAY descriptors | 3 |
| 1140 | 1 | H1p | H autocorrelation of lag 1/weighted by atomic polarizabilities | GETAWAY descriptors | 3 |

MOR273.1

| | | | | | |
|---|---|---|---|---|---|
| 1015 | 1 | P2s | 2nd component shape directional WHIM index/weighted by atomic electrotopological states | WHIM descriptors | 3 |
| 77 | 2 | Jhetv | Balaban-type index from van der Waals weighted distance matrix | topological descriptors | 2 |
| 305 | 1 | GATS5m | Geary autocorrelation - lag 5/weighted by atomic masses | 2D autocorrelations | 2 |
| 1070 | 1 | HATS1u | leverage-weighted autocorrelation of lag 1/unweighted | GETAWAY descriptors | 3 |
| 815 | 1 | Mor20u | 3D-MoRSE - signal 20/unweighted | 3D-MoRSE descriptors | 3 |
| 518 | 1 | JGI6 | mean topological charge index of order6 | topological charge indices | 2 |
| 1216 | 1 | R1e | R autocorrelation of lag 1/weighted by atomic Sanderson electronegativities | GETAWAY descriptors | 3 |
| 827 | 1 | Mor32u | 3D-MoRSE - signal 32/unweighted | 3D-MoRSE descriptors | 3 |
| 372 | 1 | EEig08r | Eigenvalue 08 from edge adj. matrix weighted by resonance integrals | edge adjacency indices | 2 |
| 441 | 1 | BEHm3 | highest eigenvalue n. 3 of Burden matrix/weighted by atomic masses | Burden eigenvalues | 2 |

MOR250.1

| | | | | | |
|---|---|---|---|---|---|
| 1045 | 1 | Dv | D total accessibility index/weighted by atomic van der Waals volumes | WHIM descriptors | 3 |
| 1297 | 6 | H-047 | H attached to C1(sp3)/C0(sp2) | atom-centred fragments | 1 |
| 443 | 1 | BEHm5 | highest eigenvalue n. 5 of Burden matrix/weighted by atomic masses | Burden eigenvalues | 2 |
| 1282 | 3 | C-006 | CH2RX | atom-centred fragments | 1 |
| 297 | 2 | MATS5p | Moran autocorrelation - lag 5/weighted by atomic polarizabilities | 2D autocorrelations | 2 |
| 1303 | 1 | O-057 | phenol/enol/carboxyl OH | atom-centred fragments | 1 |
| 107 | 2 | D/Dr06 | distance/detour ring index of order 6 | topological descriptors | 2 |
| 947 | 2 | Mor24p | 3D-MoRSE - signal 24/weighted by atomic polarizabilities | 3D-MoRSE descriptors | 3 |
| 1014 | 3 | P1s | 1st component shape directional WHIM index/weighted by atomic electrotopological states | WHIM descriptors | 3 |
| 356 | 1 | EEig07d | Eigenvalue 07 from edge adj. matrix weighted by dipole moments | edge adjacency indices | 2 |
| 1249 | 1 | R7p+ | R maximal autocorrelation of lag 7/weighted by atomic polarizabilities | GETAWAY descriptors | 3 |
| 986 | 3 | E1v | 1st component accessibility directional WHIM index/weighted by atomic van der Waals volumes | WHIM descriptors | 3 |

TABLE 5-continued

Optimized descriptor sets for each Mammalian OR. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| 1012 | 2 | L2s | 2nd component size directional WHIM index/weighted by atomic electrotopological states | WHIM descriptors | 3 |
| 901 | 2 | Mor10e | 3D-MoRSE - signal 10/weighted by atomic Sanderson electronegativities | 3D-MoRSE descriptors | 3 |
| 1100 | 1 | H1v | H autocorrelation of lag 1/weighted by atomic van der Waals volumes | GETAWAY descriptors | 3 |
| 1183 | 4 | R4m | R autocorrelation of lag 4/weighted by atomic masses | GETAWAY descriptors | 3 |
| 683 | 1 | RDF035m | Radial Distribution Function - 3.5/weighted by atomic masses | RDF descriptors | 3 |
| 447 | 1 | BELm1 | lowest eigenvalue n. 1 of Burden matrix/weighted by atomic masses | Burden eigenvalues | 2 |
| 1096 | 2 | HATS7m | leverage-weighted autocorrelation of lag 7/weighted by atomic masses | GETAWAY descriptors | 3 |
| 1367 | 1 | F04[C—O] | frequency of C—O at topological distance 04 | 2D frequency fingerprints | 2 |
| 1336 | 1 | B04[O—O] | presence/absence of O—O at topological distance 04 | 2D binary fingerprints | 2 |
| 1337 | 1 | B05[C—C] | presence/absence of C—C at topological distance 05 | 2D binary fingerprints | 2 |
| 1280 | 2 | C-003 | CHR3 | atom-centred fragments | 1 |
| 1140 | 3 | H1p | H autocorrelation of lag 1/weighted by atomic polarizabilities | GETAWAY descriptors | 3 |
| 838 | 2 | Mor11m | 3D-MoRSE - signal 11/weighted by atomic masses | 3D-MoRSE descriptors | 3 |
| 341 | 1 | EEig07x | Eigenvalue 07 from edge adj. matrix weighted by edge degrees | edge adjacency indices | 2 |
| 1316 | 3 | GVWAI-80 | Ghose-Viswanadhan-Wendoloski drug-like index at 80% | molecular properties | 1 |
| 519 | 2 | JGI7 | mean topological charge index of order7 | topological charge indices | 2 |
| 147 | 3 | piPC07 | molecular multiple path count of order 07 | walk and path counts | 2 |
| 30 | 1 | nR09 | number of 9-membered rings | constitutional descriptors | 0 |
| 776 | 1 | RDF060p | Radial Distribution Function - 6.0/weighted by atomic polarizabilities | RDF descriptors | 3 |
| 1266 | 1 | nRCOOH | number of carboxylic acids (aliphatic) | functional group counts | 1 |
| 837 | 1 | Mor10m | 3D-MoRSE - signal 10/weighted by atomic masses | 3D-MoRSE descriptors | 3 |
| 302 | 1 | GATS2m | Geary autocorrelation - lag 2/weighted by atomic masses | 2D autocorrelations | 2 |
| 479 | 2 | BELe1 | lowest eigenvalue n. 1 of Burden matrix/weighted by atomic Sanderson electronegativities | Burden eigenvalues | 2 |
| 212 | 1 | IC1 | information content index (neighborhood symmetry of 1-order) | information indices | 2 |
| 272 | 1 | MATS4m | Moran autocorrelation - lag 4/weighted by atomic masses | 2D autocorrelations | 2 |
| 1274 | 1 | nArOR | number of ethers (aromatic) | functional group counts | 1 |
| 106 | 1 | D/Dr05 | distance/detour ring index of order 5 | topological descriptors | 2 |
| 658 | 1 | RDF060u | Radial Distribution Function - 6.0/unweighted | RDF descriptors | 3 |
| | | | MOR256.17 | | |
| 1452 | 7 | BIC | BIC | topological (cerius2) | 2 |
| 335 | 1 | EEig01x | Eigenvalue 01 from edge adj. matrix weighted by edge degrees | edge adjacency indices | 2 |
| 1095 | 6 | HATS6m | leverage-weighted autocorrelation of lag 6/weighted by atomic masses | GETAWAY descriptors | 3 |
| 1272 | 5 | nOHp | number of primary alcohols | functional group counts | 1 |
| 1465 | 3 | S_sssCH | S_sssCH | atomtypes (cerius2) | 1 |
| 1270 | 3 | nArCO | number of ketones (aromatic) | functional group counts | 1 |
| 1298 | 3 | H-049 | H attached to C3(sp3)/C2(sp2)/C3(sp) | atom-centred fragments | 1 |
| 1265 | 3 | nR═Ct | number of aliphatic tertiary C(sp2) | functional group counts | 1 |
| 1088 | 3 | HTm | H total index/weighted by atomic masses | GETAWAY descriptors | 3 |
| 889 | 1 | Mor30v | 3D-MoRSE - signal 30/weighted by atomic van der Waals volumes | 3D-MoRSE descriptors | 3 |
| 306 | 2 | GATS6m | Geary autocorrelation - lag 6/weighted by atomic masses | 2D autocorrelations | 2 |
| 702 | 1 | RDF130m | Radial Distribution Function - 13.0/weighted by atomic masses | RDF descriptors | 3 |
| 742 | 2 | RDF040e | Radial Distribution Function - 4.0/weighted by atomic Sanderson electronegativities | RDF descriptors | 3 |
| 31 | 1 | nR10 | number of 10-membered rings | constitutional descriptors | 0 |
| 1351 | 1 | B09[C—S] | presence/absence of C—S at topological distance 09 | 2D binary fingerprints | 2 |
| 1283 | 1 | C-008 | CHR2X | atom-centred fragments | 1 |
| 168 | 1 | X5A | average connectivity index chi-5 | connectivity indices | 2 |
| 275 | 1 | MATS7m | Moran autocorrelation - lag 7/weighted by atomic masses | 2D autocorrelations | 2 |
| 883 | 1 | Mor24v | 3D-MoRSE - signal 24/weighted by atomic van der Waals volumes | 3D-MoRSE descriptors | 3 |
| 918 | 1 | Mor27e | 3D-MoRSE - signal 27/weighted by atomic Sanderson electronegativities | 3D-MoRSE descriptors | 3 |
| 358 | 1 | EEig09d | Eigenvalue 09 from edge adj. matrix weighted by dipole moments | edge adjacency indices | 2 |
| | | | MOR258.1 | | |
| 1198 | 3 | R1v | R autocorrelation of lag 1/weighted by atomic van der Waals volumes | GETAWAY descriptors | 3 |
| 448 | 1 | BELm2 | lowest eigenvalue n. 2 of Burden matrix/weighted by atomic masses | Burden eigenvalues | 2 |
| 1140 | 2 | H1p | H autocorrelation of lag 1/weighted by atomic polarizabilities | GETAWAY descriptors | 3 |
| 964 | 1 | E1u | 1st component accessibility directional WHIM index/unweighted | WHIM descriptors | 3 |
| 1091 | 1 | HATS2m | leverage-weighted autocorrelation of lag 2/weighted by atomic masses | GETAWAY descriptors | 3 |
| 514 | 1 | JGI2 | mean topological charge index of order2 | topological charge indices | 2 |
| 1234 | 1 | R1p | R autocorrelation of lag 1/weighted by atomic polarizabilities | GETAWAY descriptors | 3 |

TABLE 5-continued

Optimized descriptor sets for each Mammalian OR. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| 1340 | 1 | B06[C—C] | presence/absence of C—C at topological distance 06 | 2D binary fingerprints | 2 |
| 1012 | 1 | L2s | 2nd component size directional WHIM index/weighted by atomic electrotopological states | WHIM descriptors | 3 |
| 631 | 1 | DISPm | d COMMA2 value/weighted by atomic masses | geometrical descriptors | 3 |
| 608 | 1 | SHP2 | average shape profile index of order 2 | Randic molecular profiles | 3 |
| 1060 | 1 | H1u | H autocorrelation of lag 1/unweighted | GETAWAY descriptors | 3 |
| 1015 | 1 | P2s | 2nd component shape directional WHIM index/weighted by atomic electrotopological states | WHIM descriptors | 3 |

MOR259.1

| | | | | | |
|---|---|---|---|---|---|
| 1261 | 1 | nCb– | number of substituted benzene C(sp2) | functional group counts | 1 |
| 1018 | 1 | G3s | 3st component symmetry directional WHIM index/weighted by atomic electrotopological states | WHIM descriptors | 3 |
| 1183 | 1 | R4m | R autocorrelation of lag 4/weighted by atomic masses | GETAWAY descriptors | 3 |
| 136 | 1 | MPC06 | molecular path count of order 06 | walk and path counts | 2 |
| 635 | 1 | DISPv | d COMMA2 value/weighted by atomic van der Waals volumes | geometrical descriptors | 3 |
| 1234 | 1 | R1p | R autocorrelation of lag 1/weighted by atomic polarizabilities | GETAWAY descriptors | 3 |
| 1371 | 1 | F05[C—O] | frequency of C—O at topological distance 05 | 2D frequency fingerprints | 2 |
| 1208 | 1 | R2v+ | R maximal autocorrelation of lag 2/weighted by atomic van der Waals volumes | GETAWAY descriptors | 3 |
| 964 | 1 | E1u | 1st component accessibility directional WHIM index/unweighted | WHIM descriptors | 3 |
| 302 | 1 | GATS2m | Geary autocorrelation - lag 2/weighted by atomic masses | 2D autocorrelations | 2 |
| 998 | 1 | E2e | 2nd component accessibility directional WHIM index/weighted by atomic Sanderson electronegativities | WHIM descriptors | 3 |
| 1060 | 1 | H1u | H autocorrelation of lag 1/unweighted | GETAWAY descriptors | 3 |

MOR260.1

| | | | | | |
|---|---|---|---|---|---|
| 727 | 1 | RDF110v | Radial Distribution Function - 11.0/weighted by atomic van der Waals volumes | RDF descriptors | 3 |
| 1190 | 2 | R2m+ | R maximal autocorrelation of lag 2/weighted by atomic masses | GETAWAY descriptors | 3 |
| 520 | 1 | JGI8 | mean topological charge index of order8 | topological charge indices | 2 |
| 1308 | 1 | Hy | hydrophilic factor | molecular properties | 1 |
| 1302 | 1 | O-056 | alcohol | atom-centred fragments | 1 |
| 1299 | 1 | H-050 | H attached to heteroatom | atom-centred fragments | 1 |
| 276 | 1 | MATS8m | Moran autocorrelation - lag 8/weighted by atomic masses | 2D autocorrelations | 2 |
| 750 | 1 | RDF080e | Radial Distribution Function - 8.0/weighted by atomic Sanderson electronegativities | RDF descriptors | 3 |
| 1095 | 1 | HATS6m | leverage-weighted autocorrelation of lag 6/weighted by atomic masses | GETAWAY descriptors | 3 |

MOR261.1

| | | | | | |
|---|---|---|---|---|---|
| 756 | 1 | RDF110e | Radial Distribution Function - 11.0/weighted by atomic Sanderson electronegativities | RDF descriptors | 3 |
| 1282 | 2 | C-006 | CH2RX | atom-centred fragments | 1 |
| 720 | 1 | RDF075v | Radial Distribution Function - 7.5/weighted by atomic van der Waals volumes | RDF descriptors | 3 |
| 665 | 1 | RDF095u | Radial Distribution Function - 9.5/unweighted | RDF descriptors | 3 |
| 631 | 1 | DISPm | d COMMA2 value/weighted by atomic masses | geometrical descriptors | 3 |
| 1278 | 1 | C-001 | CH3R/CH4 | atom-centred fragments | 1 |
| 446 | 1 | BEHm8 | highest eigenvalue n. 8 of Burden matrix/weighted by atomic masses | Burden eigenvalues | 2 |
| 727 | 1 | RDF110v | Radial Distribution Function - 11.0/weighted by atomic van der Waals volumes | RDF descriptors | 3 |

MOR268.1

| | | | | | |
|---|---|---|---|---|---|
| 260 | 2 | ATS8e | Broto-Moreau autocorrelation of a topological structure - lag 8/weighted by atomic Sanderson electronegativities | 2D autocorrelations | 2 |
| 1282 | 1 | C-006 | CH2RX | atom-centred fragments | 1 |
| 83 | 1 | TIE | E-state topological parameter | topological descriptors | 2 |
| 686 | 1 | RDF050m | Radial Distribution Function - 5.0/weighted by atomic masses | RDF descriptors | 3 |
| 1350 | 3 | B09[C—O] | presence/absence of C—O at topological distance 09 | 2D binary fingerprints | 2 |
| 1343 | 5 | B07[C—C] | presence/absence of C—C at topological distance 07 | 2D binary fingerprints | 2 |
| 1300 | 4 | H-051 | H attached to alpha-C | atom-centred fragments | 1 |
| 1465 | 3 | S_sssCH | S_sssCH | atomtypes (cerius2) | 1 |
| 274 | 1 | MATS6m | Moran autocorrelation - lag 6/weighted by atomic masses | 2D autocorrelations | 2 |
| 1006 | 2 | G2p | 2st component symmetry directional WHIM index/weighted by atomic polarizabilities | WHIM descriptors | 3 |
| 757 | 1 | RDF115e | Radial Distribution Function - 11.5/weighted by atomic Sanderson electronegativities | RDF descriptors | 3 |
| 1298 | 1 | H-049 | H attached to C3(sp3)/C2(sp2)/C3(sp2)/C3(sp) | atom-centred fragments | 1 |
| 1303 | 1 | O-057 | phenol/enol/carboxyl OH | atom-centred fragments | 1 |
| 672 | 1 | RDF130u | Radial Distribution Function - 13.0/unweighted | RDF descriptors | 3 |
| 963 | 1 | G3u | 3st component symmetry directional WHIM index/unweighted | WHIM descriptors | 3 |
| 1268 | 1 | nRCHO | number of aldehydes (aliphatic) | functional group counts | 1 |
| 1270 | 1 | nArCO | number of ketones (aromatic) | functional group counts | 1 |

TABLE 5-continued

Optimized descriptor sets for each Mammalian OR. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| 1266 | 1 | nRCOOH | number of carboxylic acids (aliphatic) | functional group counts | 1 |
| 301 | 1 | GATS1m | Geary autocorrelation - lag 1/weighted by atomic masses | 2D autocorrelations | 2 |
| 1262 | 1 | nCconj | number of non-aromatic conjugated C(sp2) | functional group counts | 1 |
| 297 | 1 | MATS5p | Moran autocorrelation - lag 5/weighted by atomic polarizabilities | 2D autocorrelations | 2 |
| | | | MOR271.1 | | |
| 1299 | 1 | H-050 | H attached to heteroatom | atom-centred fragments | 1 |
| 88 | 1 | PHI | Kier flexibility index | topological descriptors | 2 |
| 518 | 3 | JGI6 | mean topological charge index of order6 | topological charge indices | 2 |
| 691 | 2 | RDF075m | Radial Distribution Function - 7.5/weighted by atomic masses | RDF descriptors | 3 |
| 1298 | 2 | H-049 | H attached to C3(sp3)/C2(sp2)/C3(sp2)/C3(sp) | atom-centred fragments | 1 |
| 621 | 1 | SPH | spherosity | geometrical descriptors | 3 |
| 1308 | 2 | Hy | hydrophilic factor | molecular properties | 1 |
| 343 | 1 | EEig09x | Eigenvalue 09 from edge adj. matrix weighted by edge degrees | edge adjacency indices | 2 |
| 1179 | 1 | RTu+ | R maximal index/unweighted | GETAWAY descriptors | 3 |
| 308 | 1 | GATS8m | Geary autocorrelation - lag 8/weighted by atomic masses | 2D autocorrelations | 2 |
| 1266 | 1 | nRCOOH | number of carboxylic acids (aliphatic) | functional group counts | 1 |
| 786 | 1 | RDF110p | Radial Distribution Function - 11.0/weighted by atomic polarizabilities | RDF descriptors | 3 |
| 304 | 1 | GATS4m | Geary autocorrelation - lag 4/weighted by atomic masses | 2D autocorrelations | 2 |
| 297 | 1 | MATS5p | Moran autocorrelation - lag 5/weighted by atomic polarizabilities | 2D autocorrelations | 2 |
| 1196 | 1 | R8m+ | R maximal autocorrelation of lag 8/weighted by atomic masses | GETAWAY descriptors | 3 |
| | | | MOR272.1 | | |
| 1322 | 1 | BLTF96 | Verhaar model of Fish base-line toxicity from MLOGP (mmol/l) | molecular properties | 1 |
| 639 | 1 | DISPe | d COMMA2 value/weighted by atomic Sanderson electronegativities | geometrical descriptors | 3 |
| 1347 | 1 | B08[C—O] | presence/absence of C—O at topological distance 08 | 2D binary fingerprints | 2 |
| 1155 | 1 | HATS6p | leverage-weighted autocorrelation of lag 6/weighted by atomic polarizabilities | GETAWAY descriptors | 3 |
| 274 | 1 | MATS6m | Moran autocorrelation - lag 6/weighted by atomic masses | 2D autocorrelations | 2 |
| 727 | 1 | RDF110v | Radial Distribution Function - 11.0/weighted by atomic van der Waals volumes | RDF descriptors | 3 |
| 1018 | 1 | G3s | 3st component symmetry directional WHIM index/weighted by atomic electrotopological states | WHIM descriptors | 3 |
| 1298 | 1 | H-049 | H attached to C3(sp3)/C2(sp2)/C3(sp2)/C3(sp) | atom-centred fragments | 1 |
| 1299 | 1 | H-050 | H attached to heteroatom | atom-centred fragments | 1 |
| 1190 | 1 | R2m+ | R maximal autocorrelation of lag 2/weighted by atomic masses | GETAWAY descriptors | 3 |
| 308 | 1 | GATS8m | Geary autocorrelation - lag 8/weighted by atomic masses | 2D autocorrelations | 2 |
| 1134 | 1 | HATS5e | leverage-weighted autocorrelation of lag 5/weighted by atomic Sanderson electronegativities | GETAWAY descriptors | 3 |
| 1082 | 1 | H3m | H autocorrelation of lag 3/weighted by atomic masses | GETAWAY descriptors | 3 |
| 441 | 1 | BEHm3 | highest eigenvalue n. 3 of Burden matrix/weighted by atomic masses | Burden eigenvalues | 2 |
| | | | MOR273.1 | | |
| 1015 | 1 | P2s | 2nd component shape directional WHIM index/weighted by atomic electrotopological states | WHIM descriptors | 3 |
| 77 | 2 | Jhetv | Balaban-type index from van der Waals weighted distance matrix | topological descriptors | 2 |
| 305 | 1 | GATS5m | Geary autocorrelation - lag 5/weighted by atomic masses | 2D autocorrelations | 2 |
| 1070 | 1 | HATS1u | leverage-weighted autocorrelation of lag 1/unweighted | GETAWAY descriptors | 3 |
| 815 | 1 | Mor20u | 3D-MoRSE - signal 20/unweighted | 3D-MoRSE descriptors | 3 |
| 518 | 1 | JGI6 | mean topological charge index of order6 | topological charge indices | 2 |
| 1216 | 1 | R1e | R autocorrelation of lag 1/weighted by atomic Sanderson electronegativities | GETAWAY descriptors | 3 |
| 827 | 1 | Mor32u | 3D-MoRSE - signal 32/unweighted | 3D-MoRSE descriptors | 3 |
| 372 | 1 | EEig08r | Eigenvalue 08 from edge adj. matrix weighted by resonance integrals | edge adjacency indices | 2 |
| 441 | 1 | BEHm3 | highest eigenvalue n. 3 of Burden matrix/weighted by atomic masses | Burden eigenvalues | 2 |
| | | | MOR277.1 | | |
| 1112 | 1 | HATS3v | leverage-weighted autocorrelation of lag 3/weighted by atomic van der Waals volumes | GETAWAY descriptors | 3 |
| 997 | 4 | E1e | 1st component accessibility directional WHIM index/weighted by atomic Sanderson electronegativities | WHIM descriptors | 3 |
| 273 | 1 | MATS5m | Moran autocorrelation - lag 5/weighted by atomic masses | 2D autocorrelations | 2 |
| 1009 | 1 | E2p | 2nd component accessibility directional WHIM index/weighted by atomic polarizabilities | WHIM descriptors | 3 |
| 683 | 2 | RDF035m | Radial Distribution Function - 3.5/weighted by atomic masses | RDF descriptors | 3 |
| 1190 | 2 | R2m+ | R maximal autocorrelation of lag 2/weighted by atomic masses | GETAWAY descriptors | 3 |
| 1232 | 1 | R8e+ | R maximal autocorrelation of lag 8/weighted by atomic Sanderson electronegativities | GETAWAY descriptors | 3 |
| 608 | 3 | SHP2 | average shape profile index of order 2 | Randic molecular profiles | 3 |
| 306 | 1 | GATS6m | Geary autocorrelation - lag 6/weighted by atomic masses | 2D autocorrelations | 2 |

TABLE 5-continued

Optimized descriptor sets for each Mammalian OR. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | | | |
|---|---|---|---|---|---|
| 497 | 1 | BELp3 | lowest eigenvalue n. 3 of Burden matrix/weighted by atomic polarizabilities | Burden eigenvalues | 2 |
| 79 | 1 | Jhetp | Balaban-type index from polarizability weighted distance matrix | topological descriptors | 2 |
| 1300 | 1 | H-051 | H attached to alpha-C | atom-centred fragments | 1 |
| 373 | 1 | EEig09r | Eigenvalue 09 from edge adj. matrix weighted by resonance integrals | edge adjacency indices | 2 |
| 481 | 1 | BELe3 | lowest eigenvalue n. 3 of Burden matrix/weighted by atomic Sanderson electronegativities | Burden eigenvalues | 2 |
| 1267 | 1 | nRCOOR | number of esters (aliphatic) | functional group counts | 1 |
| 965 | 1 | E2u | 2nd component accessibility directional WHIM index/unweighted | WHIM descriptors | 3 |
| 517 | 1 | JGI5 | mean topological charge index of order5 | topological charge indices | 2 |
| 303 | 1 | GATS3m | Geary autocorrelation - lag 3/weighted by atomic masses | 2D autocorrelations | 2 |
| 957 | 1 | L2u | 2nd component size directional WHIM index/unweighted | WHIM descriptors | 3 |
| 1466 | 1 | S__dssC | S__dssC | atomtypes (cerius2) | 1 |
| 996 | 1 | G3e | 3st component symmetry directional WHIM index/weighted by atomic Sanderson electronegativities | WHIM descriptors | 3 |
| 1340 | 1 | B06[C—C] | presence/absence of C—C at topological distance 06 | 2D binary fingerprints | 2 |
| 1001 | 1 | L2p | 2nd component size directional WHIM index/weighted by atomic polarizabilities | WHIM descriptors | 3 |
| | | | MOR30.1 | | |
| 1350 | 1 | B09[C—O] | presence/absence of C—O at topological distance 09 | 2D binary fingerprints | 2 |
| 1302 | 1 | O-056 | alcohol | atom-centred fragments | 1 |
| 1344 | 2 | B07[C—O] | presence/absence of C—O at topological distance 07 | 2D binary fingerprints | 2 |
| 722 | 1 | RDF085v | Radial Distribution Function - 8.5/weighted by atomic van der Waals volumes | RDF descriptors | 3 |
| 1300 | 5 | H-051 | H attached to alpha-C | atom-centred fragments | 1 |
| 691 | 1 | RDF075m | Radial Distribution Function - 7.5/weighted by atomic masses | RDF descriptors | 3 |
| 1282 | 3 | C-006 | CH2RX | atom-centred fragments | 1 |
| 625 | 1 | L/Bw | length-to-breadth ratio by WHIM | geometrical descriptors | 3 |
| 356 | 1 | EEig07d | Eigenvalue 07 from edge adj. matrix weighted by dipole moments | edge adjacency indices | 2 |
| 724 | 1 | RDF095v | Radial Distribution Function - 9.5/weighted by atomic van der Waals volumes | RDF descriptors | 3 |
| 1009 | 1 | E2p | 2nd component accessibility directional WHIM index/weighted by atomic polarizabilities | WHIM descriptors | 3 |
| 307 | 2 | GATS7m | Geary autocorrelation - lag 7/weighted by atomic masses | 2D autocorrelations | 2 |
| 857 | 1 | Mor30m | 3D-MoRSE - signal 30/weighted by atomic masses | 3D-MoRSE descriptors | 3 |
| 804 | 1 | Mor09u | 3D-MoRSE - signal 09/unweighted | 3D-MoRSE descriptors | 3 |
| 355 | 1 | EEig06d | Eigenvalue 06 from edge adj. matrix weighted by dipole moments | edge adjacency indices | 2 |
| 308 | 1 | GATS8m | Geary autocorrelation - lag 8/weighted by atomic masses | 2D autocorrelations | 2 |
| 1321 | 1 | Infective-80 | Ghose-Viswanadhan-Wendoloski antiinfective-like index at 80% | molecular properties | 1 |
| 1230 | 1 | R6e+ | R maximal autocorrelation of lag 6/weighted by atomic Sanderson electronegativities | GETAWAY descriptors | 3 |
| 302 | 1 | GATS2m | Geary autocorrelation - lag 2/weighted by atomic masses | 2D autocorrelations | 2 |
| 743 | 1 | RDF045e | Radial Distribution Function - 4.5/weighted by atomic Sanderson electronegativities | RDF descriptors | 3 |
| | | | MOR33.1 | | |
| 1377 | 1 | F07[C—O] | frequency of C—O at topological distance 07 | 2D frequency fingerprints | 2 |
| 1266 | 1 | nRCOOH | number of carboxylic acids (aliphatic) | functional group counts | 1 |
| 635 | 1 | DISPv | d COMMA2 value/weighted by atomic van der Waals volumes | geometrical descriptors | 3 |
| 1367 | 1 | F04[C—O] | frequency of C—O at topological distance 04 | 2D frequency fingerprints | 2 |
| 908 | 2 | Mor17e | 3D-MoRSE - signal 17/weighted by atomic Sanderson electronegativities | 3D-MoRSE descriptors | 3 |
| 1300 | 1 | H-051 | H attached to alpha-C | atom-centred fragments | 1 |
| 1282 | 1 | C-006 | CH2RX | atom-centred fragments | 1 |
| 307 | 1 | GATS7m | Geary autocorrelation - lag 7/weighted by atomic masses | 2D autocorrelations | 2 |
| 1299 | 1 | H-050 | H attached to heteroatom | atom-centred fragments | 1 |
| | | | MOR37.1 | | |
| 1350 | 1 | B09[C—O] | presence/absence of C—O at topological distance 09 | 2D binary fingerprints | 2 |
| 1302 | 1 | O-056 | alcohol | atom-centred fragments | 1 |
| 1347 | 1 | B08[C—O] | presence/absence of C—O at topological distance 08 | 2D binary fingerprints | 2 |
| | | | MOR40.1 | | |
| 727 | 2 | RDF110v | Radial Distribution Function - 11.0/weighted by atomic van der Waals volumes | RDF descriptors | 3 |
| 1300 | 1 | H-051 | H attached to alpha-C | atom-centred fragments | 1 |
| 908 | 1 | Mor17e | 3D-MoRSE - signal 17/weighted by atomic Sanderson electronegativities | 3D-MoRSE descriptors | 3 |
| 1282 | 1 | C-006 | CH2RX | atom-centred fragments | 1 |
| 307 | 1 | GATS7m | Geary autocorrelation - lag 7/weighted by atomic masses | 2D autocorrelations | 2 |

TABLE 5-continued

Optimized descriptor sets for each Mammalian OR. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | MOR41.1 | | |
|---|---|---|---|---|---|
| 201 | 1 | HVcpx | graph vertex complexity index | information indices | 2 |
| 1443 | 1 | Kappa-3 | Kappa-3 | topological (cerius2) | 2 |
| 303 | 4 | GATS3m | Geary autocorrelation - lag 3/weighted by atomic masses | 2D autocorrelations | 2 |
| 1266 | 8 | nRCOOH | number of carboxylic acids (aliphatic) | functional group counts | 1 |
| 1298 | 3 | H-049 | H attached to C3(sp3)/C2(sp2)/C3(sp2)/C3(sp) | atom-centred fragments | 1 |
| 869 | 2 | Mor10v | 3D-MoRSE - signal 10/weighted by atomic van der Waals volumes | 3D-MoRSE descriptors | 3 |
| 781 | 2 | RDF085p | Radial Distribution Function - 8.5/weighted by atomic polarizabilities | RDF descriptors | 3 |
| 372 | 3 | EEig08r | Eigenvalue 08 from edge adj. matrix weighted by resonance integrals | edge adjacency indices | 2 |
| 1452 | 4 | BIC | BIC | topological (cerius2) | 2 |
| 308 | 5 | GATS8m | Geary autocorrelation - lag 8/weighted by atomic masses | 2D autocorrelations | 2 |
| 1085 | 3 | H6m | H autocorrelation of lag 6/weighted by atomic masses | GETAWAY descriptors | 3 |
| 489 | 1 | BEHp3 | highest eigenvalue n. 3 of Burden matrix/weighted by atomic polarizabilities | Burden eigenvalues | 2 |
| 515 | 1 | JGI3 | mean topological charge index of order3 | topological charge indices | 2 |
| 663 | 4 | RDF085u | Radial Distribution Function - 8.5/unweighted | RDF descriptors | 3 |
| 302 | 1 | GATS2m | Geary autocorrelation - lag 2/weighted by atomic masses | 2D autocorrelations | 2 |
| 913 | 4 | Mor22e | 3D-MoRSE - signal 22/weighted by atomic Sanderson electronegativities | 3D-MoRSE descriptors | 3 |
| 1255 | 3 | nCq | number of total quaternary C(sp3) | functional group counts | 1 |
| 1008 | 1 | E1p | 1st component accessibility directional WHIM index/weighted by atomic polarizabilities | WHIM descriptors | 3 |
| 715 | 1 | RDF050v | Radial Distribution Function - 5.0/weighted by atomic van der Waals volumes | RDF descriptors | 3 |
| 91 | 2 | PW3 | path/walk 3-Randic shape index | topological descriptors | 2 |
| 1316 | 1 | GVWAI-80 | Ghose-Viswanadhan-Wendoloski drug-like index at 80% | molecular properties | 1 |
| 1283 | 1 | C-008 | CHR2X | atom-centred fragments | 1 |
| 1105 | 1 | H6v | H autocorrelation of lag 6/weighted by atomic van der Waals volumes | GETAWAY descriptors | 3 |
| 271 | 1 | MATS3m | Moran autocorrelation - lag 3/weighted by atomic masses | 2D autocorrelations | 2 |
| 1405 | 1 | Atype_C_18 | Number of Carbon Type 18 | atomtypes (Cerius2) | 1 |
| 457 | 1 | BEHv3 | highest eigenvalue n. 3 of Burden matrix/weighted by atomic van der Waals volumes | Burden eigenvalues | 2 |
| 672 | 1 | RDF130u | Radial Distribution Function - 13.0/unweighted | RDF descriptors | 3 |
| 1268 | 1 | nRCHO | number of aldehydes (aliphatic) | functional group counts | 1 |
| 1338 | 1 | B05[C—O] | presence/absence of C—O at topological distance 05 | 2D binary fingerprints | 2 |
| 620 | 1 | MEcc | molecular eccentricity | geometrical descriptors | 3 |
| 165 | 1 | X2A | average connectivity index chi-2 | connectivity indices | 2 |
| | | | MOR5.1 | | |
| 1266 | 1 | nRCOOH | number of carboxylic acids (aliphatic) | functional group counts | 1 |
| 1377 | 1 | F07[C—O] | frequency of C—O at topological distance 07 | 2D frequency fingerprints | 2 |
| 1367 | 1 | F04[C—O] | frequency of C—O at topological distance 04 | 2D frequency fingerprints | 2 |
| 1303 | 1 | O-057 | phenol/enol/carboxyl OH | atom-centred fragments | 1 |
| 908 | 1 | Mor17e | 3D-MoRSE - signal 17/weighted by atomic Sanderson electronegativities | 3D-MoRSE descriptors | 3 |
| | | | OR1A1 | | |
| 1077 | 2 | HATS8u | leverage-weighted autocorrelation of lag 8/unweighted | GETAWAY descriptors | 3 |
| 1019 | 1 | E1s | 1st component accessibility directional WHIM index/weighted by atomic electrotopological states | WHIM descriptors | 3 |
| 1211 | 2 | R5v+ | R maximal autocorrelation of lag 5/weighted by atomic van der Waals volumes | GETAWAY descriptors | 3 |
| 925 | 1 | Mor02p | 3D-MoRSE - signal 02/weighted by atomic polarizabilities | 3D-MoRSE descriptors | 3 |
| 639 | 1 | DISPe | d COMMA2 value/weighted by atomic Sanderson electronegativities | geometrical descriptors | 3 |
| 1340 | 3 | B06[C—C] | presence/absence of C—C at topological distance 06 | 2D binary fingerprints | 2 |
| 1268 | 2 | nRCHO | number of aldehydes (aliphatic) | functional group counts | 1 |
| 944 | 1 | Mor21p | 3D-MoRSE - signal 21/weighted by atomic. polarizabilities | 3D-MoRSE descriptors | 3 |
| 515 | 1 | JGI3 | mean topological charge index of order3 | topological charge indices | 2 |
| 1303 | 1 | O-057 | phenol/enol/carboxyl OH | atom-centred fragments | 1 |
| 696 | 1 | RDF100m | Radial Distribution Function - 10.0/weighted by atomic masses | RDF descriptors | 3 |
| 273 | 1 | MATS5m | Moran autocorrelation - lag 5/weighted by atomic masses | 2D autocorrelations | 2 |
| 1194 | 1 | R6m+ | R maximal autocorrelation of lag 6/weighted by atomic masses | GETAWAY descriptors | 3 |
| 665 | 1 | RDF095u | Radial Distribution Function - 9.5/unweighted | RDF descriptors | 3 |
| 1266 | 1 | nRCOOH | number of carboxylic acids (aliphatic) | functional group counts | 1 |
| 414 | 1 | ESpm06d | Spectral moment 06 from edge adj. matrix weighted by dipole moments | edge adjacency indices | 2 |
| 451 | 1 | BELm5 | lowest eigenvalue n. 5 of Burden matrix/weighted by atomic masses | Burden eigenvalues | 2 |

TABLE 5-continued

Optimized descriptor sets for each Mammalian OR. Optimized descriptors occurrences, symbol, brief description, class, and dimensionality are listed. Descriptors are listed in ascending order of when they were selected into the optimized set. Weights indicate the number of times a descriptor was selected in an optimized descriptor set. A summary of the total number of descriptors selected for the receptor repertoire is provided as the beginning.

| | | | OR2J2 | | |
|---|---|---|---|---|---|
| 1019 | 3 | E1s | 1st component accessibility directional WHIM index/weighted by atomic electrotopological states | WHIM descriptors | 3 |
| 1374 | 1 | F06[C—O] | frequency of C—O at topological distance 06 | 2D frequency fingerprints | 2 |
| 635 | 1 | DISPv | d COMMA2 value/weighted by atomic van der Weals volumes | geometrical descriptors | 3 |
| 517 | 1 | JGI5 | mean topological charge index of order5 | topological charge indices | 2 |
| 1300 | 3 | H-051 | H attached to alpha-C | atom-centred fragments | 1 |
| 1060 | 1 | H1u | H autocorrelation of lag 1/unweighted | GETAWAY descriptors | 3 |
| 631 | 4 | DISPm | d COMMA2 value/weighted by atomic masses | geometrical descriptors | 3 |
| 462 | 1 | BEHv8 | highest eigenvalue n. 8 of Burden matrix/weighted by atomic van der Weals volumes | Burden eigenvalues | 2 |
| 1298 | 2 | H-049 | H attached to C3(sp3)/C2(sp2)/C3(sp2)/C3(sp) | atom-centred fragments | 1 |
| 1341 | 1 | B06[C—O] | presence/absence of C—O at topological distance 06 | 2D binary fingerprints | 2 |
| 1303 | 1 | O-057 | phenol/enol/carboxyl OH | atom-centred fragments | 1 |
| 805 | 1 | Mor10u | 3D-MoRSE - signal 10/unweighted | 3D-MoRSE descriptors | 3 |
| 1087 | 1 | H8m | H autocorrelation of lag 8/weighted by atomic masses | GETAWAY descriptors | 3 |
| 1355 | 2 | F01[C—C] | frequency of C—C at topological distance 01 | 2D frequency fingerprints | 2 |
| 1154 | 2 | HATS5p | leverage-weighted autocorrelation of lag 5/weighted by atomic polarizabilities | GETAWAY descriptors | 3 |
| 297 | 1 | MATS5p | Moran autocorrelation - lag 5/weighted by atomic polarizabilities | 2D autocorrelations | 2 |
| 1085 | 1 | H6m | H autocorrelation of lag 6/weighted by atomic masses | GETAWAY descriptors | 3 |
| 1466 | 1 | S_dssC | S_dssC | atomtypes (cerius2) | 1 |
| 1129 | 1 | HATS0e | leverage-weighted autocorrelation of lag 0/weighted by atomic Sanderson electronegativities | GETAWAY descriptors | 3 |
| 1249 | 1 | R7p+ | R maximal autocorrelation of lag 7/weighted by atomic polarizabilities | GETAWAY descriptors | 3 |
| 541 | 1 | VEA2 | average eigenvector coefficient sum from adjacency matrix | eigenvalue-based indices | 2 |
| | | | OR2W1 | | |
| 1337 | 2 | B05[C—C] | presence/absence of C—C at topological distance 05 | 2D binary fingerprints | 2 |
| 1155 | 2 | HATS6p | leverage-weighted autocorrelation of lag 6/weighted by atomic polarizabilities | GETAWAY descriptors | 3 |
| 698 | 1 | RDF110m | Radial Distribution Function - 11.0/weighted by atomic masses | RDF descriptors | 3 |
| 1190 | 1 | R2m+ | R maximal autocorrelation of lag 2/weighted by atomic masses | GETAWAY descriptors | 3 |
| 297 | 1 | MATS5p | Moran autocorrelation - lag 5/weighted by atomic polarizabilities | 2D autocorrelations | 2 |
| | | | OR5P3 | | |
| 1262 | 2 | nCconj | number of non-aromatic conjugated C(sp2) | functional group counts | 1 |
| 1092 | 1 | HATS3m | leverage-weighted autocorrelation of lag 3/weighted by atomic masses | GETAWAY descriptors | 3 |
| 1222 | 3 | R7e | R autocorrelation of lag 7/weighted by atomic Sanderson electronegativities | GETAWAY descriptors | 3 |
| 206 | 1 | Yindex | Balaban Y index | information indices | 2 |
| 1231 | 1 | R7e+ | R maximal autocorrelation of lag 7/weighted by atomic Sanderson electronegativities | GETAWAY descriptors | 3 |
| 1323 | 2 | BLTD48 | Verhaar model of Daphnia base-line toxicity from MLOGP (mmol/l) | molecular properties | 1 |
| 1185 | 1 | R6m | R autocorrelation of lag 6/weighted by atomic masses | GETAWAY descriptors | 3 |
| 1297 | 1 | H-047 | H attached to C1(sp3)/C0(sp2) | atom-centred fragments | 1 |
| 1183 | 1 | R4m | R autocorrelation of lag 4/weighted by atomic masses | GETAWAY descriptors | 3 |
| 302 | 3 | GATS2m | Geary autocorrelation - lag 2/weighted by atomic masses | 2D autocorrelations | 2 |
| 631 | 1 | DISPm | d COMMA2 value/weighted by atomic masses | geometrical descriptors | 3 |
| 805 | 2 | Mor10u | 3D-MoRSE - signal 10/unweighted | 3D-MoRSE descriptors | 3 |
| 774 | 1 | RDF050p | Radial Distribution Function - 5.0/weighted by atomic polarizabilities | RDF descriptors | 3 |
| 1336 | 1 | B04[O—O] | presence/absence of O—O at topological distance 04 | 2D binary fingerprints | 2 |
| 447 | 1 | BELm1 | lowest eigenvalue n. 1 of Burden matrix/weighted by atomic masses | Burden eigenvalues | 2 |
| 870 | 1 | Mor11v | 3D-MoRSE - signal 11/weighted by atomic van der Waals volumes | 3D-MoRSE descriptors | 3 |
| 1136 | 2 | HATS7e | leverage-weighted autocorrelation of lag 7/weighted by atomic Sanderson electronegativities | GETAWAY descriptors | 3 |
| 1337 | 1 | B05[C—C] | presence/absence of C—C at topological distance 05 | 2D binary fingerprints | 2 |
| 1298 | 1 | H-049 | H attached to C3(sp3)/C2(sp2)/C3(sp2)/C3(sp) | atom-centred fragments | 1 |
| 1343 | 2 | B07[C—C] | presence/absence of C—C at topological distance 07 | 2D binary fingerprints | 2 |
| 1266 | 1 | nRCOOH | number of carboxylic acids (aliphatic) | functional group counts | 1 |
| 941 | 1 | Mor18p | 3D-MoRSE - signal 18/weighted by atomic polarizabilities | 3D-MoRSE descriptors | 3 |
| 1111 | 1 | HATS2v | leverage-weighted autocorrelation of lag 2/weighted by atomic van der Waals volumes | GETAWAY descriptors | 3 |

TABLE 6

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
| --- | --- |
| Mor1-1 | |
| CC1=CC2=C(C=C1)OC(=O)C2 | 0.04917087 |
| CC1=CC2=C(CC(=O)O2)C=C1 | 0.06445035 |
| CC1=CC=CC2=C1OC(=O)C2 | 0.06478577 |
| CC(CCCC(=O)O)N | 0.0766186 |
| CC1=CC(=C2C(=C1)CC(=O)O2)C | 0.09134395 |
| CC1=C(C2=C(CC(=O)O2)C=C1)C | 0.09749545 |
| CC1=CC(=C2CC(=O)OC2=C1)C | 0.1021952 |
| CC(C)(C)C(CCC(=O)O)O | 0.1026351 |
| C1C2=C(C(=CC=C2)N)OC1=O | 0.1122016 |
| C1C2=CC=CC=C2NC1=O | 0.1200522 |
| C1C2=C(C=CC=C2OC1=O)N | 0.1221153 |
| C=CCCCC(=O)O | 0.1245319 |
| CC(C)(C)CCCC(=O)N | 0.1311838 |
| C(CC(N)N)CC(=O)O | 0.1339592 |
| CC(C1=C2CC(=O)NC2=CC=C1)N | 0.1356993 |
| CC1=C2CC(=O)OC2=CC=C1 | 0.136907 |
| CC1=CC=CC2=C1NC(=O)C2 | 0.1403033 |
| C(=O)CCCC | 0.1404621 |
| C1C2=C(C=C(C=C2)O)OC1=O | 0.1431714 |
| CCC(C)(C)CC(=O)N | 0.1436566 |
| CC(CCCC(=O)O)O | 0.1452177 |
| C1C2=C(C=C(C=C2)N)NC1=O | 0.146264 |
| CC(C)(C)C1=CCC(=O)O1 | 0.1538394 |
| CCCCCC(=O)N | 0.1546248 |
| CC(C)(C)CC(CC(=O)O)O | 0.156154 |
| C1=CNC=C1CCC(=O)N | 0.1571392 |
| Mor106-1 | |
| CC=COC1=CC=CC=C1 | 0.08891955 |
| CC(S)SC1=CC=CC=C1 | 0.1534956 |
| C=C(C1=CC=CC=C1)C | 0.1583203 |
| CC(=C)C1=CC=CC=C1 | 0.1583203 |
| CC1=C2C(=CC=C1)N2C | 0.1611889 |
| CC1=CC=CC=C1C=C | 0.1622158 |
| CC1C(N1)C2=CC=CC=C2 | 0.1766318 |
| CSC(=O)C1=CC=CC=C1 | 0.1913783 |
| CSC(C1=CC=CC=C1)S | 0.1981317 |
| C=COC1=CC=CC(=C1)O | 0.1996824 |
| C=CC1=CC=C(C=C1)S)S | 0.2060344 |
| C=CC1=CC=(CC=C1)N=C=S | 0.2098719 |
| C#COC1=CC=CC=C1 | 0.2130395 |
| C1CC1CC2=CC=CC=C2 | 0.2152684 |
| COC=CC1=CC=CC=C1 | 0.2170264 |
| CC1=C(C2=C(O2)C=C1)C | 0.2178679 |
| c1(ccccc1)CC#N | 0.2180725 |
| CC1=CC=CC=C1OC#C | 0.2181859 |
| C=COC1=CC=CC=C1 | 0.2188387 |
| CSC1=CC=CC2=C1C=C2 | 0.219095 |
| C1=CC=C(C=C1)C(=O)NO | 0.2207775 |
| C1=CC=C(C=C1)N(C(=S)S)O | 0.2218528 |
| C1=CC=C2C(=C1)C(=O)SC2=O | 0.2247712 |
| C1=CC=C(C=C1)S(=O)(=O)N=C=S | 0.226246 |
| CCC1=C2C(=CC=C1)N2 | 0.2282767 |
| C1=CC=C(C=C1)C2OS2(=O)=O | 0.2323088 |
| Mor107-1 | |
| CC1(C2(CCC1(CC2=O)N)C)C | 0.2473219 |
| CC1C2(CCC1(C(=O)C2)C)C | 0.2764237 |
| CC1(C2(CCC1(CC2=O)O)C)C | 0.3186515 |
| CC1(C2CC(C1(C(=O)C2)C)O)C | 0.3204451 |
| CC1(C2CC(=O)C1(CC2O)C)C | 0.3482935 |
| CC1(C2CCC1(C(=O)C2)CO)C | 0.366073 |
| CC1(C2CCC1(C(=O)C2)CS)C | 0.4426886 |
| CCC12CCC(C1(C)C)CC2=O | 0.4550365 |
| CC12CCC(C1(C)CO)CC2=O | 0.4566952 |
| CC1(C2CCC1(CC2=O)C)C | 0.4653999 |
| CC1(C2CCC1(C(C2=O)O)C)C | 0.4703974 |
| CC1(C2CC(C1(CC2=O)C)O)C | 0.5505192 |
| CC(C)C12CCC(C1)(CC2=O)C | 0.5732307 |
| CC1(C2CCC1(C(=NC)C2)C)C | 0.5802225 |
| CC1(C(CC2C1(C2)C)CC=O)C | 0.6171489 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
|---|---|
| CC1C2CCC(C1=O)(C2(C)C)C | 0.629438 |
| CC1(C2CCC1(C(=O)C2)C=C)C | 0.6401904 |
| CC1(C2(CCC1(CC2=O)OC)C)C | 0.6463336 |
| CCCC1(CCC(C(=O)C1)(C)C)C | 0.6494132 |
| CC1(CCCC12CC=NC2)C | 0.6903515 |
| CC1(C2CCC1(C(=O)C2)C=O)C | 0.7002376 |
| CC1(C(C1(C)C)C(=O)NC2CC2)C | 0.7104875 |
| CC12CC3C1(C(=O)CC2C3)C | 0.7142688 |
| CCOC(=O)C1C2(C13CC3)CC2 | 0.7263507 |
| CC12CCCC(=O)C1(COC2)C | 0.7281732 |
| CCC12CCC1C(CC2=O)(C)C | 0.7489101 |
| Mor129-1 | |
| C1C(=O)CNC2=CC=CC=C21 | 0.1220788 |
| CC1=CCCC(C1)(C)C(=O)C | 0.131721 |
| C1C2C(=CC=CO2)C=CC1=O | 0.1324226 |
| CC1CC(CC=C1C#N)(C)C | 0.1401867 |
| CC1=CCC(CC1)C(C)C=O | 0.1440427 |
| C1CCC2C(C1)CCC(=O)O2 | 0.1447183 |
| CC(C)(CO)C1=CC=CC=C1 | 0.1488985 |
| C1=CC=C2C(=C1)C=COC2=O | 0.1541709 |
| COC12CCC(CC1)NC(=O)C2 | 0.1556671 |
| C1=CC=C2C(=C1)C=CC(=O)N2 | 0.1562217 |
| CC(=O)C1=CC=CC=C1N | 0.1588058 |
| CC1CC(=CC(C1CO)C)C | 0.1637881 |
| CC1CCC(=CC1=O)C(C)C | 0.1638838 |
| C1=CC=C2C(=C1)C(=O)C=CN2 | 0.1644921 |
| CC1CC(CC=C1C=O)(C)C | 0.1653725 |
| C1=CNC2=CC(=O)C=CC2=C1 | 0.168101 |
| C1=CC=C2C(=C1)C(=O)C=CO2 | 0.1688119 |
| C1C=CC2=C(C1O)N=CC=C2 | 0.1727835 |
| CC1=CCC(CC1O)C(=C)C | 0.1737252 |
| C1C2=CC=CC=C2C(=O)CN1 | 0.1787667 |
| CC1CCC(CC1C)(C)C=O | 0.1795582 |
| C1CC(CC=C1)CC#N | 0.1819388 |
| CC(C)(C)C1=CC=C(CC1)O | 0.1839154 |
| c1(ccccc1)C(C)O | 0.1866107 |
| C1C(=O)C=C2C=CC=CC2=N1 | 0.1886765 |
| C1CC=CC(C1)CC=O | 0.1891273 |
| Mor136-1 | |
| CCC1(CC(OC1=N)(C)C)CC | 0.05816986 |
| C1=CC(=C2C(=C1)S2)C(=S)N | 0.06587855 |
| CC(C)(C)C1CC(=O)C2C1C2 | 0.06816311 |
| CCC1(CCCC1=O)CC | 0.0729801 |
| CCCCCC(CC)C(=O)C1CC1 | 0.07530886 |
| CC(C)C12CCC(C1)(CC2=O)C | 0.07590504 |
| CC(=O)C1CCC2C1CCCC2 | 0.08637492 |
| CC1CCC2(CC1)C=CC(C2=O)C | 0.08638542 |
| CC1(C2CC(=O)C1(CC2=O)C)C | 0.08683412 |
| CCN1C2CCC1CC(=O)C2 | 0.0869081 |
| CC1C=CC2(C1=O)CCCCC2 | 0.08745782 |
| C1CCC(=O)NCCCC(=O)C1 | 0.0884375 |
| CCC1CCCC(=O)CCC1CC | 0.09197357 |
| CC(C)OC1=NC=CC=CN1 | 0.09294477 |
| C1CC2CC(C1)CC(=O)C2 | 0.09388228 |
| C1CC2COCC(C1)C2=O | 0.1089249 |
| CC1(C(=O)CC23C1(CCC2)CCC3)C | 0.1093057 |
| C1CCC(=O)C2CCCC(C1)C2 | 0.1097336 |
| CCCCCC1(CCCC1=O)CC=C | 0.1102119 |
| CN(C)C(=NS(=O)O)N(C)C | 0.1104801 |
| CC(C)(C=C)C1CCCC1=O | 0.1145671 |
| C1=CC=C(OC=C1)NCO | 0.116571 |
| C1C2CC3CC1C(C3=O)C=C2 | 0.1167317 |
| COC1CCC(=O)C12CCCC2 | 0.1170204 |
| CC1C2CCCN1CC2=O | 0.1171827 |
| Mor139-1 | |
| C1CCC2=C(C1)CCCC2=O | 0.04565114 |
| CCC(C)C1CCC(=O)CC1 | 0.04807124 |
| C1CC2CC=CCC2C(=O)C1 | 0.04894259 |
| CC(C)C1=CC(=O)CCC1 | 0.04953565 |
| CCCC(C)C1=CCCC1=O | 0.05030901 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
| --- | --- |
| CC(C)CCC1=CCCC1=O | 0.05046165 |
| CC1CCCC2=C1CCC2=O | 0.05373275 |
| CC(C)CC1=CC(=O)CC1 | 0.05429959 |
| CN(C)CCC1=CC=NC=C1 | 0.0645497 |
| CC1=C2CSCC2CC1=O | 0.0662884 |
| C1CCC2(CCC2)C(=O)C1 | 0.06641502 |
| C1C(=O)COC2=CC=CC=C21 | 0.06771594 |
| CC1CCCC2=C1C(=O)CC2 | 0.06775099 |
| CCCCC1CCC(=O)C1=C | 0.07151075 |
| CC1(C2C1C(=O)C(=C)CC2)C | 0.07206624 |
| CC1=CCCC(=C(C)C)C1=O | 0.07226345 |
| CC1CC(=O)C2=C1CCCC2 | 0.07233297 |
| C1CCC(=C2CCCC2=O)C1 | 0.0727393 |
| C1CC2CCC(=O)C=C2C1 | 0.07644502 |
| CC(=CC1=CC(=O)CCC1)C | 0.07737008 |
| CC1CC2C(C2(C)C)CC1=O | 0.07785543 |
| CCCCCC1=CCCC1=O | 0.07816834 |
| CC1=CC(=O)C(CC1)C(=C)C | 0.07862932 |
| CCC(C)CC1=CCCC1=O | 0.0793086 |
| C1CCC2(CC1)CCC2=O | 0.08011041 |

Mor162-1

| SMILES | Distance |
| --- | --- |
| CC1NC(=O)C2=CC=CC=C2O1 | 0.03923089 |
| C1=CC=C2C(=C1)C=C(NO2)C=O | 0.05289857 |
| CC1=CN=C(C(=N1)C)C=O | 0.06707111 |
| C1C=C(C2=C(O1)N=CC=C2)O | 0.06713544 |
| C1=CC=C2C(=C1)C=C(C(=O)O2)N | 0.06748666 |
| C1CC2=CC3=C(C(=O)N2C1)NC=C3 | 0.06865916 |
| CC1=CC(=C(C=C1)C=O)C | 0.07170324 |
| C1=CC(=CC(=C1)NC(=O)O)C=O | 0.07340692 |
| C1=CC=C(C=C1C(=O)CO)O | 0.07503177 |
| CC1=CC(=C(C(=C1)O)C=O)O | 0.07530568 |
| C1COC(=N1)C2=CN=CC=C2 | 0.07562215 |
| CC(=O)C1=CC2=CC=CC=C2C1 | 0.07665453 |
| CC1=C(NC=C1C(=O)C)C | 0.07707266 |
| C1=C(NC=C1)C2=CN=CO2)C=O | 0.0776176 |
| C1=CC=C2C(=C1)C(=O)C(=CO2)N | 0.07804614 |
| C1=CC2=C(NC(=O)C=C2)N=C1 | 0.07999517 |
| C1=CC2=C(C=CC(=C2O)C=O)C=C1O | 0.08200772 |
| C1=CC=C2C(=C1)C=C(C=N2)O | 0.08304375 |
| CC1=C(NC2=C1C=C(C=C2)C=C)C | 0.08360804 |
| C1=CC(=CC=C1C=O)C2=NN=CO2 | 0.08368816 |
| CC(=O)C1=CC=C(C=C1)N | 0.08371712 |
| CC(=O)C1=CN=CC=C1 | 0.08373728 |
| C1=CC=C2C=C(C=CC2=C1)C=NO | 0.0837472 |
| COC(=O)C1=CC=C(C=C1)O | 0.08383989 |
| C1C=CC2=CC=CC=C2SS1 | 0.08392745 |

Mor170-1

| SMILES | Distance |
| --- | --- |
| C1=CC=C2C(=C1)C=C(NO2)C=O | 0.06619393 |
| CC1=NC(=O)C2=CC=CC=C2N1 | 0.0745505 |
| CN1C=NC2=CC=CC=C2C1=O | 0.08105557 |
| CC1NC(=O)C2=CC=CC=C2O1 | 0.08323528 |
| COC(=N)C1=CC=CC=C1 | 0.09673947 |
| C1=CC=C2C(=C1)C(=O)N=CC=N2 | 0.1024509 |
| C1C2=CC=CC=C2ON=C1C=O | 0.1030488 |
| C1=CC=C(C=C1)C(=O)CCN | 0.1099358 |
| CNCC(=O)C1=CC=CC=C1 | 0.1100806 |
| CC1COC2=CC=CC=C2C1=O | 0.1146739 |
| C=CN1C=NC2=CC=CC=C2C1=O | 0.1150157 |
| C1=CNN(N=C1)C2=CC=C(C=C2)C=O | 0.1202606 |
| CC1=NC2=CC=CC=C2C(=O)N1C | 0.1237537 |
| C=NNC(=O)C1=CC=CC=C1 | 0.1254566 |
| CN1NC(=O)C2=CC=CC=C2O1 | 0.1294035 |
| CC1=NC2=CC=CC=C2C(=O)N1N | 0.1318522 |
| CNNC(=O)C1=CC=CC=C1 | 0.1335452 |
| C1NC(=O)C2=CC=CC=C2S1 | 0.1342063 |
| CC1=CC(=O)C2=CC=CC=C2O1 | 0.134347 |
| CN1C(=O)C2=CC=CC=C2N=N1 | 0.1366252 |
| C1=CC=C2C(=C1)C=C(C(=O)O2)C#N | 0.1383896 |
| C1=CC=C2C(=C1)C(=O)C=NS2 | 0.1389853 |
| CC(=O)NN=CC1=CC=CC=C1 | 0.1393494 |
| C1=CC=C2C(=C1)C=CC(=O)N2 | 0.1397765 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
|---|---|
| CN1C(=O)C2=CC=CC=C2N=C1N | 0.1422149 |

Mor184-1

| SMILES | Distance |
|---|---|
| CC1CCC(C(=C1)O)C(=C)C | 0.2379638 |
| CC(=C)C1CC=C(C(=O)C1)O | 0.3728224 |
| CC1=CCC(CC1=O)C(=C)C=O | 0.3772072 |
| CC1(CCCCC1=O)CC=C | 0.3977689 |
| CC1CC(=O)C(C(=O)C1)CC=C | 0.4097808 |
| CC1=CC(=O)C(CC1)C(=C)C | 0.4227823 |
| CC(=C)CC1(CCCCC1)O | 0.4271719 |
| C=CCC1CCC(=O)NC1=O | 0.4313385 |
| CC(=C)C1CCC(CC1)C=O | 0.4430801 |
| CC1CCC(C(=O)C1)C(=C)C | 0.4515747 |
| CC1C(CCC1C(=O)O)C=C | 0.4557655 |
| CC1=CCC(CC1O)C(=C)C | 0.4625187 |
| CC(=C)C1CCC(=CC1)C(O)O | 0.4628184 |
| CC(=C)C1CCC(=CC1)C(=O)N | 0.472155 |
| C=CCCC1C(=O)CCCC1=O | 0.4769287 |
| CC(CC=C)C1CCCCC1=O | 0.4788082 |
| CC1CCCC1(CC=C)CC=O | 0.48704 |
| C=CCCC(=O)C1(CCCCC1)O | 0.4917173 |
| C=CCCC1(CCCCC1)C=O | 0.4941705 |
| CC(=C)CC1=CCCCC1=O | 0.4981998 |
| C=CC1CCC(CC1)C(=O)OO | 0.5022362 |
| CC(=O)C(=C)C1CCCCC1 | 0.5079129 |
| CC(=C)CC1(CCCCC1=O)C | 0.5103795 |
| CCCCC(=C)C1(CCCCC1)O | 0.5108372 |
| CC1CCC(C(C1)O)C(=C)C | 0.5122089 |

Mor185-1

| SMILES | Distance |
|---|---|
| C1CC2=COC=C2CC1=O | 0.02606647 |
| C1=CC2=C(C=CC(=O)N2)N=C1 | 0.03118136 |
| C1CC(=O)C2=C1C=CC=N2 | 0.0323404 |
| C1CCC2=C(C1)CCC(=O)O2 | 0.03555811 |
| CCC1CCCC(C1)N | 0.0418893 |
| CC(=C)C1=COC=C1 | 0.04258475 |
| CCC1=CCC(CC1)O | 0.04279004 |
| CCC1CCC(CC1)N | 0.04383469 |
| C1CC(=O)C2(C1)CC2 | 0.04396265 |
| C1CC(=O)C2=C1N=CC=C2 | 0.04402903 |
| C1CN2CC(=O)OCC2CN1 | 0.04424295 |
| C1C(CC2C1CNC2)N | 0.046368 |
| C1CCC2C(C1)CC2=O | 0.04657459 |
| C1CN2CCOC(=O)C2CN1 | 0.04905777 |
| C1C2C=CC=C2C(CN1)O | 0.04945669 |
| C1CCC2(CC1)CC2O | 0.04991706 |
| C1CCC2=C(C1)C(=O)CN2 | 0.05012532 |
| CCC1=C(CCCC1)O | 0.0513685 |
| CC(=O)C1=CCCC=C1 | 0.05278158 |
| C1CC(=O)C2=CN=CN=C21 | 0.05282474 |
| C1=CC2=C(NC=CC2=O)N=C1 | 0.05299349 |
| CONCCN1CCCC1 | 0.05360856 |
| CCC1CCCCC(C1)O | 0.0536915 |
| CC1=CC(=CCC1)OC | 0.05373938 |
| CCC1=CC=CC=C1N | 0.05481358 |

Mor189-1

| SMILES | Distance |
|---|---|
| CC1(C2CCC1(CC2=O)C)C | 0.04668916 |
| CC(=C)C1CC=C(C(=O)C1)O | 0.06676451 |
| CC1=CC(=O)C(CC1)C(=C)C | 0.1183577 |
| C=C(C)C(CCC1C)=CC1=O | 0.1347063 |
| CC1CCC(=CC1=O)C(C)C | 0.1680434 |
| CC1=CCCC(C1=O)(C)C#C | 0.1763185 |
| CC1=CC(=O)CC(C1)C(=C)C | 0.1962587 |
| CC1=CC(CC1=O)C(C)C | 0.1976955 |
| CC1C2(CCC1(C(=O)C2)C)C | 0.2061102 |
| CC1CC=C(C(=O)C1)C(C)C | 0.2072536 |
| O=C1C2C(CCC(C2)C1C)=C | 0.2078362 |
| CC1(CC(C(=O)C1)CC=C)C | 0.2092703 |
| CC(C)(C12CCC(=O)C1C2)O | 0.2097237 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
|---|---|
| CCC1=C(C(=O)C(CC1)C)C | 0.2140007 |
| CC1=CCCC(C1=O)(C)C=C | 0.2180427 |
| CCCC1(CCC(=O)C=C1)C | 0.2194855 |
| CC(C1C=CCCN1)C(=O)C | 0.2209319 |
| CC1=CCC(CC1)C(=C)C=O | 0.2250367 |
| CC1(CCC(=O)C=C1C=C)C | 0.2310372 |
| C1CN(CCC1CCN)C=O | 0.2406093 |
| O=C1C=C(C)CCC1C(C)C | 0.241701 |
| C=C1C=CCCC1CCC=O | 0.2420684 |
| CCC1=CC(=O)CCC1(C)C | 0.2445011 |
| CC1C(=C)C2CCC(C2)C1=O | 0.2468526 |
| CCCC1CCC(=O)C(=C1)C | 0.2519408 |

Mor2-1

| | |
|---|---|
| CC1C(=O)N(C1=O)C2=CC=CC=C2 | 0.1582261 |
| CCCOC(=O)CC1=CC=CC=C1 | 0.1927919 |
| C#CCOC(=O)CC1=CC=CC=C1 | 0.2135794 |
| CC1CCC2=C(C1)SC(=N2)CC#N | 0.2261997 |
| C1CC1(C2=CC=CC=C2)OCCS | 0.2307089 |
| C=CCOC(=O)CC1=CC=C(C=C1)O | 0.2685227 |
| COC(=O)Cc1ccc(cc1)OC | 0.2720388 |
| CCC(C1=C(C=NC=C1)CO)OC | 0.2840643 |
| COC(=O)CC1=CC=CC(=C1)C#N | 0.2858069 |
| C1CCS(=O)(=O)C2=CC=CC=C2C1 | 0.2878607 |
| C1CC1(C2=CC=CC=C2CO)O | 0.2910175 |
| CC(C)OC(=O)CC1=CC=CC=C1 | 0.2962586 |
| C1=C(C(=C(N1)CN)CC#N)CCC#N | 0.2973288 |
| CC(CC1=CC=CC=C1)N=C=S | 0.2995831 |
| CCC(COCC1=CC=CC=C1)S | 0.2998371 |
| C1CC2=CC=CC=C2NC(=O)C1 | 0.3024153 |
| C1CC(C2=C(C1)C=CS2)NC(=O)N | 0.3030766 |
| CC1(CN(C2=C1SC=C2)C=O)C | 0.3041082 |
| CCC(C1=CC=CC=C1N)C(=O)O | 0.3045982 |
| C1CC(C2=CC=CC=C2SC1)O | 0.3073687 |
| C1CC(=O)CCC2=C(C1)NC=C2 | 0.3082988 |
| C1CCC(C(=O)CC1)C2=NC=CN2 | 0.3085543 |
| CC(C1=CC=CC=C1N)C(=O)OC | 0.3109102 |
| C1=CC(=CC(=C1)CN)CC(=O)O | 0.3115366 |
| CCOC1=CC=C(C=C1)CC(=O)O | 0.3116775 |

Mor203-1

| | |
|---|---|
| CCCCC(=O)CCC | 0.09870324 |
| CCC(=O)CCCC(C)C | 0.1234426 |
| CCC1CCC(CC1)C(=O)CC | 0.1310437 |
| CC(CCCCCO)C | 0.1429018 |
| CCC1CC(C1)C(=O)C | 0.1522912 |
| CCC(=O)C=CCCC | 0.1569658 |
| CCCCCC(=O)CCC | 0.1636356 |
| CC=CC=CCCO | 0.1710732 |
| CC(=O)CC1CCCC=C1 | 0.1711094 |
| C=CC1=CC=C(C=C1)CCCO | 0.1778983 |
| CCCCCCC(CCC)O | 0.1785371 |
| C#CC1=CCC(CC1)CCO | 0.1786504 |
| CC(CCCC=C)O | 0.1865765 |
| CC(=C)CCCC(=O)C | 0.1901121 |
| CCCCCC1CC(=O)C1 | 0.1926162 |
| CCC(CCC=C=C)O | 0.1948856 |
| CC(C)CCCC(=O)C=C | 0.1949919 |
| CCCC=C=CCO | 0.1959073 |
| CCCCC(=O)NC | 0.196173 |
| C1CC(=CC=C1)CCCO | 0.1965939 |
| C(C=CC=CCC=CCC)O | 0.1966562 |
| CC(C)CCNC(=O)C | 0.1977104 |
| CC(C)C(CCCC=C)O | 0.1995084 |
| C1CC1=CCCCCO | 0.2000587 |
| CC(C)CC=CC(=O)C | 0.2005665 |

Mor204-6

| | |
|---|---|
| CC1(CCCC=C1C(=O)O)C | 0.1592494 |
| CC1CCC(=CC1=O)C(C)C | 0.1767846 |
| CC1CCC(=CC1=O)C(C)C | 0.1767846 |
| C1=CC=C2C(=C1)C=COC2=O | 0.1926777 |
| C1=CC(=O)NC2=C1C=NC=C2 | 0.2034395 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
| --- | --- |
| CC1=CC(=O)C(CC1)CCO | 0.2121746 |
| C=CC1=CC=C(C=C1)C(=O)O | 0.2283565 |
| COC(=O)C1=CCCC(C1)O | 0.2532418 |
| C1=CC2=C(C(=C1)O)C(=O)NC=C2 | 0.2600318 |
| C1=CC2=C(NC(=O)C=C2)N=C1 | 0.2607831 |
| C1=CC(=O)NC2=NC=NC=C21 | 0.2758744 |
| CN1C2C1C(CC(=C2)C(=O)OC)O | 0.2813197 |
| C1=CC2=C3C(=C1)NC=C3C(=O)C=C2 | 0.2828428 |
| C=CC1=CN=C(C=C1)C(=O)O | 0.2854501 |
| CC(=C)CC1=CCCCC1=O | 0.31266 |
| CC1=CCC(CC1=NO)C(=C)C | 0.3135219 |
| C1C(=CC1=O)C2=CC=CC=C2 | 0.3180221 |
| COC(=O)C1=CCC(CC1)SC | 0.3191871 |
| C1CC(=O)C2CC1C(=O)C=C2 | 0.3195927 |
| CCC(=O)C1=CCCC(S1)C | 0.3235687 |
| C1CCC2(C1)CCC=C(C2=O)O | 0.3305075 |
| C1C(=CC(=O)N1)C2=CC=CC=C2 | 0.3309083 |
| C1=CC=C2C(=C1)C=CC(=O)N2 | 0.3342322 |
| CC1CC=C(C(O1)C)C(=O)O | 0.3351069 |
| CC1CCCC=C1C(=O)O | 0.337837 |

Mor207-1

| SMILES | Distance |
| --- | --- |
| C1=CC=C2C(=C1)C=C(NO2)C=O | 0.06933906 |
| CC1=NC(=O)C2=CC=CC=C2N1 | 0.08035855 |
| CC1NC(=O)C2=CC=CC=C2O1 | 0.08366296 |
| CN1C=NC2=CC=CC=C2C1=O | 0.09183173 |
| COC(=N)C1=CC=CC=C1 | 0.1088847 |
| CNCC(=O)C1=CC=CC=C1 | 0.1134785 |
| CC1COC2=CC=CC=C2C1=O | 0.1147292 |
| C1=CC=C(C=C1)C(=O)CCN | 0.1167073 |
| C1C2=CC=CC=C2ON=C1C=O | 0.1201505 |
| C=CN1C=NC2=CC=CC=C2C1=O | 0.124919 |
| CC1=NC2=CC=CC=C2C(=O)N1C | 0.1258814 |
| C1=CC=C2C(=C1)C(=O)N=CC=N2 | 0.1260327 |
| CN1NC(=O)C2=CC=CC=C2O1 | 0.1322961 |
| CNNC(=O)C1=CC=CC=C1 | 0.1338931 |
| CC1=CC(=O)C2=CC=CC=C2O1 | 0.1355292 |
| CC1=NC2=CC=CC=C2C(=O)N1N | 0.1374166 |
| C1=CC=C2C(=C1)C=CC(=O)N2 | 0.1397979 |
| CC(=O)NN=CC1=CC=CC=C1 | 0.1408284 |
| C1=CC=C2C(=C1)C=C(C(=O)O2)C#N | 0.1409447 |
| CCOC(=N)C1=CC=CC=C1 | 0.1460253 |
| CN1C(=O)C2=CC=CC=C2N=N1 | 0.1465203 |
| C=NNC(=O)C1=CC=CC=C1 | 0.1469559 |
| C1NC(=O)C2=CC=CC=C2S1 | 0.1485208 |
| C1=CC=C2C(=C1)C(=O)SN2 | 0.1501398 |
| C1C(C(=O)C2=CC=CC=C2O1)N | 0.1512307 |

Mor223-1

| SMILES | Distance |
| --- | --- |
| C#CCOC(=O)CC1=CC=CC=C1 | 0.09948513 |
| CCOC(=O)CC1=CC=CC=C1 | 0.1235873 |
| CCCOC(=O)CC1=CC=CC=C1 | 0.1371426 |
| C=CC(=O)OCC1=CC=CC=C1 | 0.160449 |
| COC(=O)CC1=CC=CC=C1 | 0.2023979 |
| CCC(=O)OCC1=CC=CC=C1 | 0.2040253 |
| C1=CC=C(C=C1)CCCOC=O | 0.2240541 |
| C=C=CC(=O)OCC1=CC=CC=C1 | 0.228408 |
| CCC(=O)OC1=CC=CC=C1 | 0.2532228 |
| CC=C=CC(=O)OCC1=CC=CC=C1 | 0.2709531 |
| C=CC(=O)OC1=CC=CC=C1 | 0.2744787 |
| CC(=O)OCCCC1=CC=CC=C1 | 0.2756416 |
| C=CCC(=O)OCC1=CC=CC=C1 | 0.2810861 |
| C#CC(=O)OCC1=CC=CC=C1 | 0.2843047 |
| C1=CC=C(C=C1)CCCCOC=O | 0.2902787 |
| CCCC(=O)OC1=CC=CC=C1 | 0.299426 |
| CC#CCOC(=O)CC1=CC=CC=C1 | 0.3071297 |
| CCCCC(=O)OC1=CC=CC=C1 | 0.3087009 |
| COC(=O)CCC1=CC=CC=C1 | 0.3129654 |
| COC(=O)CCCCC1=CC=CC=C1 | 0.3463383 |
| CCCCOC(=O)CC1=CC=CC=C1 | 0.3527429 |
| CC(=O)OC=CC1=CC=CC=C1 | 0.3589161 |
| COC(=O)CCCC1=CC=CC=C1 | 0.3614484 |
| C1=CC=C(C=C1)C=CCOC=O | 0.3668489 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
| --- | --- |
| C=COC(=O)CCC1=CC=CC=C1 | 0.3705043 |

Mor250-1

| SMILES | Distance |
| --- | --- |
| CCC(=O)OC1=CC=CC=C1 | 0.3793798 |
| CCC(=O)OC1=CC=CC=C1 | 0.3793798 |
| C1=CC=C2C(=C1)C=CC(=O)N2 | 0.384888 |
| C1=CC=C(C=C1)OC(=O)N | 0.4700359 |
| CCC(=O)C1=CC=CC=C1 | 0.4719471 |
| C1C(=O)C=CC2=CC=CC=C21 | 0.4828623 |
| CC(=O)NC1=CC=CC=C1 | 0.4926594 |
| C1C=CC2=CC=CC(=O)C2=C1 | 0.5147033 |
| C1=CC=C(C=C1)NOC=O | 0.534839 |
| C1=CC2=CC=CC(=O)N2C=C1 | 0.5353036 |
| C1C=C2C=CC=CC2OC1=O | 0.5594665 |
| C=C1C(=O)OC2=CC=CC=C2N1 | 0.572254 |
| C1=CC=C(C=C1)ON=C=O | 0.5755313 |
| CC(=O)C=C1C=CCC=C1 | 0.5820786 |
| C1=CC=C(C=C1)N(C=O)N | 0.5914498 |
| C1=CC=C(C=C1)NC(=O)O | 0.5925996 |
| CC1=CC=C(C=C1)C(C)O | 0.5991708 |
| C1=CC=C(C=C1)ONC=O | 0.6023895 |
| C1=CC=C(C=C1)OC(=O)NS | 0.6065903 |
| c1(ccccc1)NC=O | 0.6157112 |
| C1=CC=C(C=C1)NC(=O)N | 0.620347 |
| CCC(C1=CC=C(C=C1)N)O | 0.6529591 |
| CC1=CC=CC=C1C(C)O | 0.659726 |
| C1=CC=C(C=C1)OC#N | 0.668126 |
| CC(C1=CC=C(C=C1)N)O | 0.670643 |

Mor256-17

| SMILES | Distance |
| --- | --- |
| CCCCCCCCNC(=O)C | 0.1277119 |
| CCCCCCC(=O)OCCCC | 0.1383745 |
| C(CCCCN)CCCC(=O)O | 0.1551848 |
| CC1(CCCSC1)O | 0.1810965 |
| CCCCCCCCNC(=O)N | 0.201845 |
| CCCCCCOOC(=O)C | 0.2354623 |
| CCCCCCCC(=O)OCCC | 0.2373345 |
| CCCCCC(=O)OOCCCC | 0.2398072 |
| CCCCCCCCCC(=O)N | 0.2537211 |
| C(CCCC(=O)O)CCCN | 0.256625 |
| C(C)OC(=O)CCCCCCCC | 0.2626695 |
| C(CCCCC)OC(=O)CCCC | 0.2654262 |
| C1=CC=C(C=C1)CCCCCCN | 0.2666345 |
| CC(=O)NCCCCCCN | 0.2891708 |
| CCCCCCCOC(=O)CCC | 0.2895618 |
| CC1(NCCCN1)S | 0.2910104 |
| CCCCCCCCOC(=O)N | 0.2941937 |
| CCCCCCCCOC(=C)C | 0.2947368 |
| C1=CC=C2C(=C1)NC(=O)O2 | 0.2981597 |
| CCCCCCNCC(=O)O | 0.2988469 |
| C1CCC(CC1)(O)S | 0.3023335 |
| C1=CC=C(C=C1)CCCCCNO | 0.3041483 |
| CC(=O)CCCCOC(=O)C | 0.3058697 |
| C1=CC=C2C(=C1)NC(=O)N2 | 0.3085566 |
| C1=CC2=CNON2C=C1 | 0.3135061 |

Mor258-1

| SMILES | Distance |
| --- | --- |
| C1=CC=C2C(=C1)NC(=O)C=N2 | 0.04626341 |
| CC1=NC2=CN=CN2C=C1 | 0.06964932 |
| C1=CC2=C(N=CN2C=C1)C=O | 0.07254368 |
| CC1=CC2=C(C=C1)C=C(S2)N | 0.07338813 |
| C1CC(=CC=C1)C=C=O | 0.08079227 |
| CC1CC=NC=N1 | 0.08086793 |
| C1=CSC(=C1)C2=NN(C=C2)O | 0.08123408 |
| C1CNC(C=C1)C=O | 0.08133689 |
| CC1=NC2=C(C=C1)NC=N2 | 0.08243389 |
| CNC1=CC=NC=C1 | 0.08274814 |
| CC1=NC(=NC=C1C#N)C | 0.08415395 |
| CC1=CCC(=O)CC1 | 0.08472221 |
| C1=COC(=C1)C2=NN=NC=C2 | 0.08486507 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
|---|---|
| CC1=CC2=NC=NN2C=C1 | 0.08532597 |
| CC(=O)OCSC | 0.08674062 |
| C1COC2=C1C=C(C=C2)C(=O)O | 0.08754144 |
| C1=CC=C2C(=C1)C=CN2N=O | 0.08813593 |
| C1=C2N=C(N=CN2N=C1)C#N | 0.08876163 |
| C1=CC2=C(N=C1)SC(=C2)C=O | 0.088843 |
| C1CC2=C(C=C1)NNC(=O)C2 | 0.08899985 |
| C1CSN(N1)COC(=O)N | 0.0890455 |
| C1CC(SC1)CO | 0.09011572 |
| CC1=NN(CS1)C | 0.09045361 |
| C1CC2=C(C1)SC(=N2)N | 0.09100104 |
| C1C=CC2=CN=NC2=C1 | 0.09216601 |

Mor259-1

| SMILES | Distance |
|---|---|
| C1=CC=C2C(=C1)NC(=O)C=N2 | 0.04197753 |
| C1=CC=C2C(=C1)NC(=N2)C=O | 0.09240541 |
| C1=CC2=C(NN=C2C=C1)C=O | 0.0990186 |
| C1=CC=C2C(=C1)C(=CC2=O)O | 0.10483 |
| CC(=O)NC1=CC=CC(=C1)C(=N)N | 0.1129747 |
| C1=CC2=COC(=C2C=C1)C=O | 0.1146544 |
| C1=CC=C2C(=C1)NC(=O)O2 | 0.11715 |
| C1C2=CC=CC=C2ON1C=O | 0.1209336 |
| C1=CC=C2C(=C1)NC(=O)NN2 | 0.1401864 |
| C1=COC(=C1)C2=CC=C(C=C2)O | 0.1428006 |
| C=C1C2=CC=CC=C2OC1=O | 0.149781 |
| C1=CC(=CC=C1C(=O)O)NCCC#N | 0.1550444 |
| CN=CC1=CC=C(C=C1)C(=O)OC | 0.1553915 |
| C1=CC=C2C(=C1)C=COC2=O | 0.1566442 |
| C=CC(=O)NC1=CC=C(C=C1)C(=N)N | 0.1586167 |
| C1=CC=C2C(=C1)C=NN2C=O | 0.1601506 |
| CN=NNC1=CC=C(C=C1)C(=O)OC | 0.1621242 |
| C1=CC=C2C(=C1)C(=CO2)N=O | 0.1633878 |
| COC1=CC=C(C=C1)NC(=O)C=C | 0.1651134 |
| CC(=O)NC1=CC=C(C=C1)N(C)C | 0.1651899 |
| CCC(=O)C1=CC=C(C=C1)OC | 0.1667638 |
| C1=CC=C2C(=C1)C=C(C=N2)O | 0.1670003 |
| CCNC1=CC=C(C=C1)N(O)O | 0.1673194 |
| CCC(=O)C1=CC=C(C=C1)NO | 0.1704537 |
| C1=CC=C2C(=C1)OS2(=O)=O | 0.1718171 |

Mor260-1

| SMILES | Distance |
|---|---|
| COC(=O)CCNC1=CC=CC=C1 | 0.04581804 |
| C=CC(=O)CCCCCCCC(=O)O | 0.04753727 |
| C#CCCCCCC=CC(=O)O | 0.04908247 |
| CCOC1=CC=C(C=C1)OC(=O)NC | 0.05223202 |
| CCCCC(CC)COCC(=O)O | 0.06334015 |
| C1CCC(C1)C(=O)CCCCC(=O)O | 0.06629472 |
| CCCCNC1=CC=C(C=C1)OC | 0.06633087 |
| CCCCNC(C)CC(=O)OC | 0.0667401 |
| CNC(=O)COC1=CC=C(C=C1)C#N | 0.07077628 |
| CCCCCCCCC(=O)C(=O)O | 0.07088963 |
| CCCCCCCCCOC(=O)O | 0.07169935 |
| CCCCCC1CCC(CC1)C(=O)O | 0.07283703 |
| CCNCCC1=CC2=C(C=C1)OCO2 | 0.07466881 |
| CC(=O)CCC(=O)NC1=CCCCC1 | 0.07735112 |
| CCCC1CCC(CC1)CCC(=O)O | 0.07825345 |
| COC(=O)C=CCNC1CCCCC1 | 0.0817986 |
| CCOC(=O)CCNC(=O)CC=C | 0.08188413 |
| CNCC1=CC=C(C=C1)N2CCCC2 | 0.0845592 |
| CCCCCCOC(C)CS | 0.08794286 |
| CCCCCC(=O)OC(C)S | 0.08888077 |
| CCCCCCOC(=O)CC(=O)O | 0.08920102 |
| CCNCC1=CC=C(C=C1)C(=O)OC | 0.08954888 |
| CCCCOC1=CN=C(C=C1)C(=O)O | 0.08968592 |
| COC(=O)CNCCC1=CC=CC=C1 | 0.09056786 |
| CCCCCCCC(=O)NCC | 0.09156643 |

Mor261-1

| SMILES | Distance |
|---|---|
| CCCCCC(CCO)O | 0.1725635 |
| CC(=O)SCC1=CC=C(C=C1)C=C | 0.2079287 |
| CCCCC(CCCCO)O | 0.2205779 |
| CCNC1=CN(N=C1)C2=CC=CC=C2 | 0.2643034 |
| CCCCCCCCNN | 0.2799805 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
| --- | --- |
| CC1=CC=C(C=C1)NCC(=O)NN | 0.2822771 |
| CC1=CC=C(C=C1)N2C=C(N=C2)CO | 0.2832535 |
| CCCOC(=O)C1=C(C=C(C=C1)N)O | 0.2852718 |
| CCCCN1N=C2C=CC=CC2=N1 | 0.2984866 |
| CCCCNC(=O)OC1=CC=CC=C1 | 0.3016491 |
| CCCC(=O)CCCCCO | 0.314819 |
| CCCCCOC1=CCCC=C1 | 0.323052 |
| CCCCSC1=CC=C(C=C1)N | 0.3336667 |
| CCOC(=O)CC1=CC(=C(C=C1)N)O | 0.3378758 |
| CC1=CN=C(C=C1)NCCC(=O)O | 0.3419532 |
| CCOC1=CC=C(C=C1)NC(=O)NN | 0.349067 |
| CCCCC=CC=CCO | 0.3594656 |
| CCCCCCC(CCO)O | 0.3622535 |
| CCOC(=N)CCCCC#N | 0.3642063 |
| CCCOC(=O)SC1=CC=CCC1 | 0.3687816 |
| CCCOC1=CC=C(C=C1)CC(=N)N | 0.3695899 |
| CCCCCSC1CCCC1 | 0.3784109 |
| CCOC1=CC(=NO1)C2=CC=CC=C2 | 0.3805914 |
| CC1=CC=C(S1)CNC2CCCC2 | 0.3893983 |
| CC1=CN(N=C1)CCCC(=O)O | 0.3914392 |
| Mor268-1 | |
| C=C(CCO)CC1=CC=CC=C1 | 0.08680266 |
| C1=CC=C(C(=C1)CCCCO)S | 0.09776434 |
| C1=CC=C(C=C1)CC2=C(OC=C2)CO | 0.1173957 |
| CC1=CC=CC=C1C2=CC(=NO2)CO | 0.1177446 |
| C=CCC1=CC=CC=C1C#CCO | 0.12333 |
| CCCC1=CC(=C(C=C1)CN)N | 0.124973 |
| CC1=CC=CC=C1CCCCO | 0.1258311 |
| C1=CC=C(C(=C1)CCCCN)N | 0.132615 |
| CCCCC1=CC=CC=C1CCN | 0.1390437 |
| C1=CC=C(C=C1)N2C=C(C(=N2)N)CO | 0.1412993 |
| CCCCCCN(C)C(=S)N | 0.1478017 |
| C1CCCCCCCCC | 0.1517669 |
| C=C=CCC1=CC=CC=C1CCO | 0.1577928 |
| CN1C(=CC(=N1)C2=CC=CC=C2)CO | 0.1577991 |
| C1=CC=C(C=C1)NNC(=O)CN | 0.1627573 |
| C1=CC=C(C(=C1)CCCCO)N | 0.1671111 |
| CC1N=C(NN1C2=CC=CC=C2)CO | 0.1706577 |
| CCCCCCC1(CNC1=O)C | 0.1736143 |
| C1CCC(=CCCCO)CC1 | 0.1749776 |
| CC(=CCCC(=CCN)C)C | 0.1790916 |
| C1=CC=C(C(=C1)C#CCCO)N | 0.1844991 |
| CC(=C)CCCCCCO | 0.1861627 |
| C1=CC=C(C(=C1)CCCCN)S | 0.192109 |
| C(CCCCCC=C)O | 0.1949365 |
| CC1=C(C=C(C=C1)CCCN)C | 0.1985303 |
| Mor271-1 | |
| CC(=O)CCC(=O)C | 0.00696499 |
| CC=C(C)N=NC)C | 0.02227481 |
| CC=C(C)C(=O)OC | 0.02303129 |
| CCC(=C)C(=O)OC | 0.03826216 |
| CN(C)C(=O)CC=C | 0.03853879 |
| COC(=C)C(=C)OC | 0.05227276 |
| CC(C=C)C(=O)OC | 0.05905649 |
| C1CCC(CC1)C2C=CCOO2 | 0.05928864 |
| CCCC1SCCS1 | 0.059703 |
| CCOCC(=O)C(=C)C | 0.06042718 |
| COC(=C(C#N)C#N)C1=CC=CO1 | 0.06070587 |
| CCCC1(C(O1)(C)C)C(=O)OCC | 0.06170662 |
| CCN1C=C(C(=C(C1=O)C)C)C | 0.06559493 |
| C=CC(=O)OC1CCCCCC1 | 0.06979654 |
| CCN=C1N2CCCC2CCS1 | 0.07527722 |
| CC(C)CC(=O)SC | 0.07652444 |
| CC(C(=O)C=C)OC | 0.07826366 |
| CSC1CCCCO1 | 0.0787251 |
| CC#CC(=O)N(C)C | 0.0789155 |
| C=CCC(CC1CCCCC1)C#N | 0.07892005 |
| COC(=O)C(=C1CCCCC1)C#N | 0.079376 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
|---|---|
| C=C=CCN1C(COC1=O)C#C | 0.08053451 |
| CCC(=O)C1C(=O)CC(CC1=O)(C)C | 0.08254048 |
| CC1C=CN(C=CC1=C)C(=O)C | 0.08378967 |
| CC1=CC=CC(=C1C#N)C(=O)OC | 0.08382356 |
| Mor272-1 | |
| CC1CCC(=O)C1CCC#C | 0.03189391 |
| CC1=C(C/C=C\C)C(CC1)=O | 0.0385644 |
| CC1COC(O1)C(C)(C)C | 0.03930837 |
| CC(C)(C)C1OCCCO1 | 0.04139548 |
| CCCCCC(=O)C=C | 0.04630508 |
| CCC(=C)COC(=O)C | 0.04645563 |
| CC1=NC(OC1)C(C)C | 0.04785742 |
| CCCC(=O)CCC | 0.04868388 |
| CC(=O)CCCCCC | 0.05098426 |
| CCCCCCC(=O)C | 0.05098426 |
| CCC1=NC(CO1)(C)C | 0.05112795 |
| CC1(C(=O)C(S1)(C)C)C | 0.05313001 |
| C(C)OC(=O)C(=C)C | 0.05386116 |
| CCCC1C=C(C(=O)O1)C | 0.05455699 |
| CC(C)(C)C1OCC(=C)O1 | 0.05557511 |
| C=C1CC(CO1)C2=CC=CC=C2 | 0.05582976 |
| CC(C)(C)C(=O)N1C=CC=C1 | 0.05717043 |
| CC1=NCCN1CC2=CC=CC=C2 | 0.05790857 |
| CC(C)C(=O)OC=C | 0.05836228 |
| CC(=C)C(=O)OC(=C)C | 0.05855966 |
| CC(=O)CCCCC=C | 0.05864676 |
| CC(=O)OC1CCCC=C1 | 0.05871441 |
| CCOC(=O)C1(CC1)C | 0.06032142 |
| CC(=CC)COC(=O)C | 0.06154408 |
| CCC(C)COC(=O)C | 0.06223368 |
| Mor273-1 | |
| CC1(C2CCC(C2)(C1=O)N)C | 0.05501643 |
| CCC1(C2CCC(C2)C1=C)CC | 0.0736611 |
| CC1CC2=CC=CC=C2N1 | 0.07383829 |
| CCCCC1=C(OC=C1C)C | 0.07413368 |
| CC1CNC2=CC=CC=C12 | 0.07595554 |
| CC(C)C(=O)OC=C | 0.0776473 |
| CCC(C)NC | 0.08056587 |
| CCSNC(C)C | 0.08292255 |
| CCCCC1=C(CCCC1=O)O | 0.08494866 |
| CCCC(C)OC | 0.08782356 |
| CC12CCCC1=CC=CC2 | 0.08803756 |
| CC1CC1C2=CC=CC=C2 | 0.08885662 |
| CC1CCC(S1)C | 0.08906697 |
| CN(C)C(=O)COC | 0.08911168 |
| CC1C2=CCC(C2)C1(C)C | 0.08918327 |
| CC1CC=C(C1)C(=O)C(C)C | 0.09082242 |
| CC1CC2=C(C(=C(C12)C)C)C | 0.09087068 |
| CC1CC=CC12CCCC2=O | 0.09092754 |
| CC1CCCC=C1C(=O)N(C)C | 0.09201093 |
| CC1=C2C(=NC=NC2=NN1)N | 0.09262628 |
| CC1=CC(C(CC1)C(C)(C)O)O | 0.09308545 |
| CN1C=NC2=C1C(=NC=N2)N | 0.0936681 |
| CC(=NOC(=O)C(C)(C)C)C | 0.09476478 |
| CC(C)C1CCCCC1=O | 0.09521714 |
| CC1=C(C(=O)N(C1=O)NC)C | 0.09626298 |
| Mor277-1 | |
| CC1(C2CC(=O)C1(C=C2)C)C | 0.1480439 |
| CC1C2(CCC1(C(=O)C2)C)C | 0.1501646 |
| C1CC(CC(=O)C1)N | 0.173522 |
| C1C(C2=CC(=O)C(=O)CC2=N1)O | 0.1843483 |
| CC1CCCC(=O)C1 | 0.1871075 |
| C1CC(=O)C2CC=CC1S2 | 0.2020606 |
| CCC12CCC(C1(C)C)CC2=O | 0.2177276 |
| C1CNC2=C(C1=O)C=CC=N2 | 0.2429412 |
| CC1COCC(C1=O)C(C)(C)C | 0.2469828 |
| C1CC(=O)C2=C(NC1)N=CC=C2 | 0.2562849 |
| C1CC(=O)C2=CC=CC=C2OC1 | 0.2580454 |
| CC(C)C12CCC(C1)(CC2=O)C | 0.2605051 |
| CC1(C2(CCC1(C(=O)C2)C)C)C | 0.2605627 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
|---|---|
| C1C2CC3C=CC2CC1C3=O | 0.2618416 |
| CCC1(C(=O)CC12CC2)CC | 0.2665882 |
| C1CC(CC(=O)C1)S | 0.2680335 |
| CC1CCCC12CCC2=O | 0.268307 |
| CC1CCCC(=O)C1(C)C(C)C | 0.2696565 |
| CC1CCCC(=O)C1(C)C | 0.2719524 |
| CC1(CC(=O)CC2(C1O2)C)C | 0.2734493 |
| C1C=CNCC1=O | 0.2802712 |
| CC(C)C1CC(=O)C=CN1 | 0.2822056 |
| C1(=O)C=CCCC1 | 0.2823245 |
| CC(C)(C)C1CC(=O)C=CN1 | 0.2876126 |
| CC1CC(=O)C=CN1 | 0.2899973 |
| Mor30-1 | |
| C(=O)(CCCCCCCCC)O | 0.3122994 |
| C#CCCCCCCC(=O)O | 0.3287775 |
| C=CCCCCCCCC(=O)O | 0.3395462 |
| CC#CCCCCCC(=O)O | 0.3545879 |
| C(=O)CCCCCCCCC | 0.3841893 |
| C=CCCCCCCC(=O)O | 0.4070303 |
| C(=O)CCCCCCCCCC | 0.4113624 |
| CCCC#CCCCC(=O)O | 0.4176973 |
| CCCCCC#CCC(=O)O | 0.4183262 |
| CC#CCCCCCCCC=O | 0.4361534 |
| CCCCCCCCCCCC=O | 0.4486903 |
| C#CC#CCCCCCC(=O)O | 0.4608185 |
| CC(C)CCCCCCC=O | 0.4667896 |
| CCC#CCCCCC(=O)O | 0.4774187 |
| CC(=C)CCCCCCC(=O)O | 0.478635 |
| CCCCCCC1CC(=O)O1 | 0.4816979 |
| C=CCCCCCCC=O | 0.4847203 |
| C#CCCCCCCC=O | 0.4893661 |
| C=CCCCCCCCCC=O | 0.4941443 |
| C1C=C1CCCCCCC(=O)O | 0.4958194 |
| C=CCCCCC1CC(=O)O1 | 0.4999771 |
| C(=O)(CCCCCCCC=C)O | 0.5103754 |
| C1C=C1CCCCCCCC(=O)O | 0.5167787 |
| CC(C)CCCCCCCCC=O | 0.5233348 |
| C(=O)CCC=CCCCC | 0.5329278 |
| Mor33-1 | |
| C1C=C1CCCCCCC(=O)O | 0.03288254 |
| C(=O)(CCC=CCCCCC)O | 0.1022495 |
| C(=O)(CC=CCCCCCC)O | 0.1268822 |
| CCCCCCC=CCCCC(=O)O | 0.1272125 |
| C(C)C(CCC(=O)O)CCCC | 0.143634 |
| CC(C)N1C=C(C=N1)CCC(=O)O | 0.149314 |
| C=C(CCCCC#N)C(=O)O | 0.1541986 |
| CC#CCCCCCCCC(=O)O | 0.1626916 |
| CC(CCC(=O)O)N=NC(C)(C)C#N | 0.1652641 |
| CC(C)CCCCCC(=O)O | 0.181324 |
| CCCC(=C)CCC(=O)O | 0.1901408 |
| CC(C)C1CCC(=CC1)CCC(=O)O | 0.1912924 |
| CCCCC=CCC(=O)O | 0.1939872 |
| CCCCC#CC#CCCCC(=O)O | 0.2014499 |
| C1C=CC=CC1CCC(=O)O | 0.2309548 |
| C1C=C1CCCCCCCC(=O)O | 0.2314075 |
| C(=O)(CCCC=CCCCCCCCC)O | 0.2344658 |
| CC#CCCCCCC(=O)O | 0.2381936 |
| CCC1=CC(=C(C=C1)CCC(=O)O)C | 0.247278 |
| CCC1=CC=C(C=C1)CCC(=O)O | 0.253656 |
| CN(C)C1=CC=C(C=C1)CCC(=O)O | 0.2546323 |
| CC1(CCC(=CC1)CCC(=O)O)C | 0.255894 |
| CCC(C)OC(=O)CC(=O)O | 0.2640391 |
| CCCC(CC(C)C(=O)O)C#N | 0.2650706 |
| C#CCCCCCCC(=O)O | 0.2760099 |
| Mor37-1 | |
| CCCCCCCCCCCCCC(OC(C)C)=O | 0 |
| CCCCCCCCC=O | 0 |
| CCCCCCCCCC=O | 0 |
| O=C(C)CC/C=C(CC/C=C(C)/C)\C | 0 |
| C(=O)(CCCCCCCC)O | 0 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
| --- | --- |
| C(=O)(CCCCCCCCC)O | 0 |
| C(=O)(CCCCCCCCCC)O | 0 |
| C(=O)(CCCCCCCCCCC)O | 0 |
| C(=O)(CCCCCCCCCCCC)O | 0 |
| C(=O)(CCCCCCCCCCCCC)O | 0 |
| CC1=C(C=C(C=C1)[C@H]C)CCC=C(C)C)O | 0 |
| CC(OCCCC/C=C\CCCC)=O | 0 |
| CC/C=C/CCCCCCCCC([H])=O | 0 |
| CCCCCCCCCC[C@H](OC(C)=O)[C@@](O1)([H])CCCC1=O | 0 |
| O=C(CCCCCCC)N1CCC(C2=CC=CC=C2)CC1 | 0 |
| O=C(CCCCCCCC)N1C(CC)CCCC1 | 0 |
| O=C(CCCCCCCCC)N1C(C)CCCC1 | 0 |
| O=C(N1CCC(C)CC1)CCCCCCCCC | 0 |
| O=C(CCCCCCCC=C)N1CCCCC1 | 0 |
| O=C(CCCCCCCC=C)N1C(CC)CCCC1 | 0 |
| O=C(CCCCCCCCC=C)N1CCC(C2=CC=CC=C2)CC1 | 0 |
| O=C(CCCCCCCCC=C)N1CCC(C)CC1 | 0 |
| O=C(CCCCCCCCCC)N1CCCCC1 | 0 |
| O=C(CCCCCCCCCCC)N1C(C)CCCC1 | 0 |
| O=C(CCCCCCCCCCC)N1CC(C)CCC1 | 0 |
| Mor40-1 | |
| C1=CC=C(C=C1)CCC2=NN=C(C=C2)N | 0.02341789 |
| C(=O)(CCCCCCCC=C)O | 0.03694565 |
| COC1=CC=C(C=C1)CCCCC#N | 0.04434623 |
| C=CCCCCCCCC(=O)S | 0.04698026 |
| CNC1=CC=C(C=C1)CCC(=O)OC | 0.04732122 |
| C(CCCC(O)O)CCCC(=O)O | 0.04909072 |
| CCCCC(=O)C1=CC=C(C=C1)OC | 0.05102408 |
| CCCCCC(=O)C1=CC=C(S1)O | 0.05385012 |
| CCCCCCC(CC(=O)O)O | 0.0581458 |
| CCCCCCCC(=O)OS | 0.0582002 |
| CCCCC#CC(=O)CCCC | 0.05901835 |
| CC(=C)CCCCCCC(=O)O | 0.06104174 |
| CCCCCCCC(=O)C#N | 0.06314685 |
| CCCCCCCC(=O)C=C=C | 0.0637365 |
| COC(=O)CCCCCC=CC=C | 0.06446715 |
| CCCCCCC(=O)OC(C)S | 0.06476652 |
| COC(=O)C1=CC=C(C=C1)CCC=O | 0.06633289 |
| CCCCCCCC(=O)NO | 0.06904818 |
| COC(=O)CCC1=CC=C(C=C1)C=C | 0.07307333 |
| CN(C(=O)CCCC1=CC=CC=C1)O | 0.0740539 |
| CCCCCCCC(=O)N(C)N=O | 0.0767582 |
| CCCC(=O)C=C=CC1=CC=CC=C1 | 0.07690233 |
| CCCC(CCCC(=O)C=C)O | 0.07774642 |
| COC(=O)CCCCCCC#C | 0.07783589 |
| COC(=O)CCC1=CC(=CC=C1)NN | 0.07920649 |
| Mor41-1 | |
| C1C(=O)C2=CC=CC=C2ON1 | 0.1690913 |
| C1=CC=C2C(=C1)C=CC(=O)N2 | 0.19021 |
| C1CC2=C(C=C1)OC(=O)C=C2 | 0.195202 |
| CCCCC1=C(NNC1=O)C | 0.1966665 |
| CC=C1CCC(=O)CC1 | 0.2004243 |
| C1C=CC2=C(C1=O)C=CC(=O)O2 | 0.2108212 |
| CCCCC1=C(OCC1=O)O | 0.2185848 |
| C1NC(=O)C2=CC=CC=C2S1 | 0.2228905 |
| C1C(=O)C2=CC=CC=C2OS1 | 0.2251387 |
| C1=CC2=NNN=C2C=C1C(=O)N | 0.2380402 |
| CC1CC1(C2=CC=CC=C2)O | 0.2385417 |
| CC1CCC(=CC1=O)C(C)C | 0.2447182 |
| C1=CC=C(C=C1)S(=O)N | 0.2462735 |
| C1CNC2=CC=CC=C2C1=O | 0.2512114 |
| CC1(C(=O)O1)C2=CC=CC=C2 | 0.252103 |
| C1=CC=C2C(=C1)C(=O)NNN2 | 0.255054 |
| C1CSC2=CC=CC=C2C1=O | 0.2633634 |
| C1=CC2=NSN=C2C=C1C(=O)N | 0.2647783 |
| CS(=O)C1=CC=CC=C1 | 0.2651372 |
| C1C(=O)C2=CC=C(C=C2S1)O)O | 0.2656982 |
| C1C(C(=O)N1)C2=CC=CC=C2 | 0.2658363 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
|---|---|
| C1=CC2=NON=C2C=C1C(=O)N | 0.2685111 |
| CC(=C1CCCCC1)O | 0.2698948 |
| C1=CC(=C(C=C1O)C(=O)NO)O | 0.2742529 |
| CN(C1=CC(=O)CCC1)O | 0.2797649 |

Mor5-1

| SMILES | Distance |
|---|---|
| CCCCC(C)CC(C)C(=O)O | 0.00047992 |
| CCCN1CNC=C1CC(C(=O)O)N | 0.00047992 |
| CCCCC=CCC(=O)O | 0.00047992 |
| CC1=CC=C(C=C1)CC(C(=O)O)N | 0.00047992 |
| C1CCC2=C(C1)CCNC2CC(=O)O | 0.00047992 |
| CCC(C)(C)C(C)C(CC(=O)O)N | 0.00095984 |
| C1CCC(C1)C=C=CCCC(=O)O | 0.00095984 |
| CCSCCCC(=C)C(=O)O | 0.00095984 |
| C1CCC2=C(C1)C=NC2CC(=O)O | 0.00095984 |
| CCCCN=C(C)CC(=O)O | 0.00095984 |
| C(CC(C(=O)O)N)CNCC(=N)N | 0.00143976 |
| C1CC(CC=C1)CCC(=O)O | 0.00143976 |
| C1=CN(C=N1)CCCCCCC(=O)O | 0.00143976 |
| CC(=C=C1CCCCC1)C(=O)O | 0.00143976 |
| CCCCCCC=CC(=O)O | 0.00143976 |
| CC1=C(C=NN1C(C)C)CCC(=O)O | 0.00143976 |
| C1=CC=C(C(=C1)CCC(=O)O)CN | 0.00143976 |
| CCN1C(=C(C(=N1)C)CCC(=O)O)C | 0.00191969 |
| CCC(CCCC(=O)O)S | 0.00191969 |
| CCC1=CN=C(C=C1)CCC(=O)O | 0.00191969 |
| C(CCCC(=O)O)CCS | 0.00191969 |
| CCC1=CC=C(C=C1)N(CC(=O)O)N | 0.00191969 |
| CSCCCC(C(=O)O)N | 0.00191969 |
| C1=CC(=CN=C1)CC(CN)C(=O)O | 0.00191969 |
| CCCCC1NC(CS1)C(=O)O | 0.00191969 |

Or1A1

| SMILES | Distance |
|---|---|
| CCCCC(=O)CCC | 0.06049592 |
| C=CCCC(=NO)C1=CC=CC=C1 | 0.07078234 |
| CCCOCCC(=O)C=C | 0.0717614 |
| C1CCCN(CC1)C(=O)N2CC2 | 0.07369093 |
| C1CCC2=C(C1)C=CC=C2CC(=O)N | 0.07424287 |
| CCC(=NO)C1=CC=C(C=C1)C | 0.07771264 |
| CC1CC=C(NC1=O)C(C)C | 0.07826973 |
| C1CC(=O)N(N=C1)CC2=CC=CC=C2 | 0.07849599 |
| CC1(OCC(CO1)C(=C)O)C | 0.07977273 |
| CCCC(CC1=CC=CC=C1)C(=O)N | 0.08055253 |
| CC1=C2C=(C=CC2=NC=C1)C(=O)N | 0.08126738 |
| C1CC(C2=CC=CC=C2C1)CC(=O)N | 0.08161454 |
| COCC1=CC=CC2=C1CCCC2=O | 0.08240595 |
| CC(CC=C)OC(=O)C1=CC=CC=C1 | 0.08262245 |
| CC(=O)C1=CC2=C(C=C1)OCCNC2 | 0.08372653 |
| C1C=CC=C(C1=C=O)CC2=CC=CC=C2 | 0.0853223 |
| CCOC(=O)CC(C)C1=CC=NC=C1 | 0.08749861 |
| CC1=NC2=CC=CC=C2C1C(=O)N | 0.08760062 |
| CCC(C(=O)C)NC1=CC=CC=C1 | 0.08768825 |
| CCCNC(=O)C1CCCN1C | 0.0881405 |
| C1C(NC(=O)CO1)C2=CC=C(C=C2)N | 0.0887641 |
| CC1=C(N=NC2=CC=CC=C12)C(=O)C | 0.08925951 |
| CCCCC(C1=CC=CC=C1)(O)O | 0.08964993 |
| CC1(OCCO1)CC2=CC=CC=C2 | 0.0898149 |
| CC1(CCCNN1)C2=CC=C(C=C2)N | 0.09071153 |

Or2J2

| SMILES | Distance |
|---|---|
| CCCCC(CCCCO)O | 0.1878163 |
| CC(C)CCCCCCO | 0.2001934 |
| C(CCCCN)CCCCON | 0.2449217 |
| C=CCCCCCC1CO1 | 0.2829139 |
| CCCCCNCC(CC)O | 0.2913393 |
| CCCCCCCCN(C)O | 0.3036347 |
| CC(C)CC1COC(N1)CCO | 0.3482781 |
| CCCCCCCCONC | 0.3506971 |
| CCCCCC(C)NCCO | 0.35406 |
| CCCCCN1CCC(C1)CO | 0.3679643 |
| CCCCCOC(C)CCO | 0.3976565 |
| CCCCCCCC(C)CO | 0.4018389 |
| CCCCCCCCNOC | 0.4019279 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
|---|---|
| C(CCCCNCCO)CCCN | 0.4055974 |
| CC(C)CCCCNCCO | 0.4075006 |
| CCCC1CC(C1O)O | 0.4174384 |
| CCCCC(C)(CC(C)O)O | 0.4285046 |
| CCCC1CCN(CC1)CCO | 0.4289913 |
| CCCCCCCCCNO | 0.4353896 |
| C=CCCCC#CCO | 0.4379203 |
| CCCCCCNC(C)CO | 0.4486621 |
| CCC(C)CCCCCCO | 0.4517683 |
| CCCCCCC1CCNO1 | 0.4523566 |
| CCCCC(CC(C)(C)O)O | 0.459996 |
| C1=CC=C(C=C1)C(=O)NCN=C=O | 0.462984 |
| Or2W1 | |
| CCCC(CCC=C(C)C)O | 0.00049109 |
| CC(C)CC(=O)CC(C)C=C | 0.00069469 |
| C1CCC(CC1)C=NC(=O)CO | 0.00069469 |
| C1C=CNNC2=CC=CC=C21 | 0.00069469 |
| CCCOC1=CC=C(C=C1)C | 0.00085074 |
| CCCCCC1CCC=CO1 | 0.00085074 |
| CC(C)NCCCNCCCN | 0.00098218 |
| CC(=CCCC(C=C)C=O)C | 0.00098218 |
| C=C=CCCCCO | 0.00098218 |
| CCCCCOCC#N | 0.00118032 |
| CC(C)CCCC(C)C1CO1 | 0.00120303 |
| CC(=O)C1CCC(=C)C(=C)C1 | 0.00120303 |
| CC(C)(C)C(=O)OCCCO | 0.00120303 |
| CC(C)C(=C)C(=O)NC1=CC=CC=C1 | 0.00127841 |
| CC(C)NC(=O)CC(CCN)N | 0.00129418 |
| COCCOCCOCC1=CC1 | 0.00129719 |
| CCCCC(=C)N | 0.00138938 |
| CCCCC=C=CC(C)(C)O | 0.00138938 |
| COC(=O)CC1=CC=C(C=C1)C=C | 0.00143135 |
| CC(C)NCC1=CC=C(C=C1)NC | 0.00145282 |
| CN(C)CC#CCCCC#C | 0.00147327 |
| C=CCCCCO | 0.00147361 |
| CC#CC(=O)C1CCCCC1 | 0.00147361 |
| CCCN1C=C(C=N1)C(C)NC | 0.00147361 |
| CC1(CC1C(=O)NC2=CC=CC=C2)C | 0.00153553 |
| Or5P3 | |
| C=CC(=O)C1CCCCC1 | 0.3110759 |
| CC1=CC(=O)C(CC1)C(=C)C | 0.3586025 |
| C1=CC=C2C(=C1)C=CC(=NO)O2 | 0.3721933 |
| C1=CC=C2C(=C1)C=CNC2=S | 0.3723315 |
| C1=CC=C2C(=C1)C=COC2=O | 0.3945556 |
| C=C1C2=CC=CC=C2ONC1=O | 0.3977094 |
| C1=CC=C2C(=C1)C=CC(=O)N2 | 0.4009083 |
| CC1=C(C(=O)CC1)CC=C | 0.4052338 |
| C1=CC(=CC2=C1C=CC(=O)O2)S | 0.4053821 |
| CC1=CCC(CC1=NO)C(=C)C | 0.4125247 |
| CC1(C2C1C(=O)C(=C)CC2)C | 0.4507506 |
| CC1C=CC(=O)C12CCCCC2 | 0.452584 |
| CCC12CCC(=O)C=C1CC(C2)O | 0.4690015 |
| C1=CC=C2C(=C1)C=C(C(=O)O2)O | 0.476153 |
| C1CCC2(CC1)CCC=CC2=O | 0.48111 |
| C=C1CC2CCCCC2C1=O | 0.4838933 |
| C1=CC=C2C(=C1)C(=S)C=CN2O | 0.4840491 |
| C1CCC2(CC1)CC=CC(=O)C2 | 0.4924455 |
| CC(=C)C(=O)CCC#C | 0.4929412 |
| C=C1CC2(C1=O)CCCCC2 | 0.5054476 |
| CC1=CC2CCCC(=O)C2=CC1 | 0.5090888 |
| C1CC=CC2(C1)CC=CC(=O)NC2 | 0.5100904 |
| CC1=C2C(=C)C(=O)NC2=CC=C1 | 0.5151608 |
| C1=CC2=C(C(=C1)O)OC(=O)C=C2 | 0.516556 |
| CC(=O)C1=CCC2(C1)C(=C)CCC2=O | 0.5272902 |
| CCC1=CC2CCCCN2C1=O | 0.5776696 |
| C1=CC=C2C(=C1)NC(=O)C=CS2 | 0.5831019 |
| CC1=C2C=CC(=O)NC2=CC=C1 | 0.5841847 |
| C1CC(=O)C2=C(C=C1)C=CC(=C2)O | 0.5848835 |
| C1=CC2=CN=C(C(=O)N=C2C=C1)N | 0.5849539 |
| C1=CC=C2C(=C1)C=CN3C2=NNC3=O | 0.5850339 |
| C=C1CC2=CC=CC=C2OC1=O | 0.5862692 |

TABLE 6-continued

Top ~25 predicted compounds for each Mammalian OR. Tables contain SMILES strings, and distances, of the top ~25 predicted compounds for each Or. All distances represent the minimum distance based on optimized descriptors to an active compound listed in gray cells for that particular Or.

| SMILES | Distance |
|---|---|
| CCC(=C)CC1=CCCC1=O | 0.5878639 |
| CC1=CC(=O)OC2=C1C(=C(C=C2)O)N | 0.5881438 |
| CC12CC=CCC1CC(=O)C=C2 | 0.5900818 |
| C=CCC1CCC(=O)C=C1 | 0.5902211 |
| C1CC2(CCC=CC2=O)CC=C1 | 0.5931621 |
| CC1=CC(=O)NC2=C1C(=CC=C2)N | 0.5952647 |
| CC1=C(CCC1(C)C)C(=O)OC | 0.5982892 |
| CC1(CC1C(=O)C=C)C | 0.5994571 |
| C1C2=CC=CC=C2C=C(C1=O)O | 0.6030376 |
| CC1=CCC(CC1=O)C2(CO2)C | 0.6032878 |
| CC1C=C(C(=O)O1)C2=CC=CS2 | 0.6051044 |
| CC1=CC(=O)CCCC1CC=C | 0.6074293 |
| CC(C)C1CCC=C1C(=O)C | 0.6076714 |
| CC1=CC(=O)OC1C2=CC=CC=C2 | 0.6080884 |
| CC1=CC(=S)C2=CC=CC=C2O1 | 0.6085333 |
| C1C2=CC=CC=C2C(=O)C1=CN | 0.608787 |
| C1=CC2=C(C=CC(=O)O2)C=C1N | 0.6088277 |
| C1CC2(CC3CC2C=C3)C=CC1=O | 0.6095803 |

The approach described herein was also used to predict activators of neurons that are responsive to $CO_2$. In order to train the platform to predict $CO_2$ neuron activators a large panel of odors was assembled that have previously been tested against $CO_2$ responsive neurons in several species. The panel comprises 108 odors, which have been tested against one or more of the following species: *Anopheles Gambiae, Culex Pipiens, Aedes Aegypti, Drosophila Melanogaster*. The panel consists of a broad collection of functional groups including alcohols, esters, acids, ketones, alkanes, aromatics, terpenes, and heterocycles. The activities of these odors were normalized from 100 to −100 representing the range from the strongest observed activator to the most inhibitory, respectively. Upon normalizing, it was observed that the strongest activators were heterocycles and some moderate activators were non-aromatic cyclic compounds. These distinct structural differences would likely drastically alter the outcome of the predictive platform. Due to this, the dataset was divided odors into two distinct sets. The first set focuses on activating odors with aromatic structures that look very structurally distinct from inhibitors. This set does not include non aromatic activators, activators which share structural characteristics with inhibitory odors, or odors which inhibit the receptor at greater than 30 percent of maximum. The second set is broader in scope and consists of odors both aromatic and non-aromatic structures as well as all inhibitory odors.

| Odor Name | Final Activity | Training Set 1 | Training Set 2 |
|---|---|---|---|
| butanal | −85 | No | Yes |
| pentanal | −51 | No | Yes |
| hexanal | −32 | No | Yes |
| heptanal | −21 | Yes | Yes |
| octanal | −20 | Yes | Yes |
| butanol | −25 | Yes | Yes |
| pentanol | −41 | No | Yes |
| hexanol | −70 | No | Yes |
| heptanol | −38 | No | Yes |
| octanol | −35 | No | Yes |
| butanone | −25 | Yes | Yes |
| pentanone | −28 | Yes | Yes |
| hexanone | −19 | Yes | Yes |
| heptanone | −12 | Yes | Yes |
| octanone | −18 | Yes | Yes |
| butyl acetate | −28 | Yes | Yes |
| pentyl acetate | −15 | Yes | Yes |
| hexyl acetate | −12 | Yes | Yes |
| heptyl acetate | −8 | Yes | Yes |
| octyl acetate | −15 | Yes | Yes |
| butyric acid | −94 | No | Yes |
| pentanoic acid | −26 | Yes | Yes |
| hexanoic acid | −16 | Yes | Yes |
| heptanoic acid | −14 | Yes | Yes |
| octanoic acid | −21 | Yes | Yes |
| pentane | −31 | No | Yes |
| hexane | −25 | Yes | Yes |
| heptane | −29 | Yes | Yes |
| octane | −34 | No | Yes |
| 2,3-butanedione | −99 | No | Yes |
| 1-octen-3-ol | −27 | Yes | Yes |
| Ethanol | −16 | Yes | Yes |
| 3-octanol | −14 | Yes | Yes |
| Methanol | −14 | Yes | Yes |
| Nonanol | −12 | Yes | Yes |
| Eugenol Methyl Ether | −9 | Yes | Yes |
| Acetic Acid | −7 | Yes | Yes |
| gamma-valerolactone | −5 | Yes | Yes |
| Fenchone | −2 | Yes | Yes |
| Isoamyl Acetate | −2 | Yes | Yes |
| Limonene | −2 | Yes | Yes |
| Menthol | −2 | Yes | Yes |
| (E)2-hexenal | 0 | Yes | Yes |
| Geranyl Acetate | 0 | Yes | Yes |
| Methional | 0 | Yes | Yes |
| Eugenol | 1 | Yes | Yes |
| 4-methylphenol | 3 | Yes | Yes |
| Isopropyl Alcohol | 3 | Yes | Yes |
| Carvone | 4 | Yes | Yes |
| Phenylethanone | 5 | Yes | Yes |
| Anisole | 6 | Yes | Yes |
| Benzaldehyde | 6 | Yes | Yes |
| Benzophenone | 8 | Yes | Yes |
| Citronellal | 8 | Yes | Yes |
| Geraniol | 8 | Yes | Yes |
| Ethyl Acetate | 8 | Yes | Yes |
| Methylsalicylate | 13 | No | Yes |
| Thymol | 15 | No | Yes |
| Cyclohexanone | 48 | No | Yes |
| Indole | 21 | Yes | Yes |

-continued

| Odor Name | Final Activity | Training Set 1 | Training Set 2 |
|---|---|---|---|
| 2-methylphenol | 24 | No | Yes |
| methyl pyruvate | −100 | No | Yes |
| propionyl bromide | −88 | No | Yes |
| propionyl chloride | −73 | No | Yes |
| propionaldehyde | −68 | No | Yes |
| 2,3-pentanedione | −55 | No | Yes |
| 2-heptanol | −39 | No | Yes |
| 2-(propylamino)-ethanol | −39 | No | Yes |
| butyryl chloride | −39 | No | Yes |
| propionic acid | −32 | No | Yes |
| 2-methyl-3-heptanone | −26 | Yes | Yes |
| 3-heptanol | −16 | Yes | Yes |
| 4-(methylthio)-1-butanal | −15 | Yes | Yes |
| 4-hydroxy-2-butanone | −11 | Yes | Yes |
| 2,5-dimethylthiophene | −9 | Yes | Yes |
| 6-methyl-5-hepten-2-ol | 0 | Yes | Yes |
| 1,5-pentanediol | 0 | Yes | Yes |
| 1-hepten-3-ol | 0 | Yes | Yes |
| 3-decanone | 1 | Yes | Yes |
| pyruvic acid | 2 | Yes | Yes |
| 3-nonanone | 2 | Yes | Yes |
| 4-heptanone | 2 | Yes | Yes |
| 2-hexanol | 2 | Yes | Yes |
| 1-bromohexane | 3 | Yes | Yes |
| 1-hexanethiol | 3 | Yes | Yes |
| hexylsilane | 3 | Yes | Yes |
| phenylacetaldehyde | 3 | Yes | Yes |
| 1-iodohexane | 3 | Yes | Yes |
| 2,4,5-trimethylthiazole | 5 | Yes | Yes |
| ethyl valerate | 5 | Yes | Yes |
| cis-2-hexene | 5 | Yes | Yes |
| 3-methyl-2-pentene | 5 | Yes | Yes |
| methoxyacetone | 6 | Yes | Yes |
| 1-chlorohexane | 8 | Yes | Yes |
| cis-3-hexen-1-ol | 10 | Yes | Yes |
| fluoroacetone | 10 | Yes | Yes |
| acetophenone | 15 | No | Yes |
| 2-acetylthiophene | 31 | No | Yes |
| pyridine | 99 | Yes | Yes |
| thiazole | 100 | Yes | Yes |
| 2-ethyl-3,5-dimethylpyrazine | 8 | Yes | Yes |
| 2,5-dimethylpyrazine | 26 | Yes | Yes |
| pyrazine | −8 | Yes | Yes |
| naphthalene | −14 | Yes | Yes |

Figure 19:
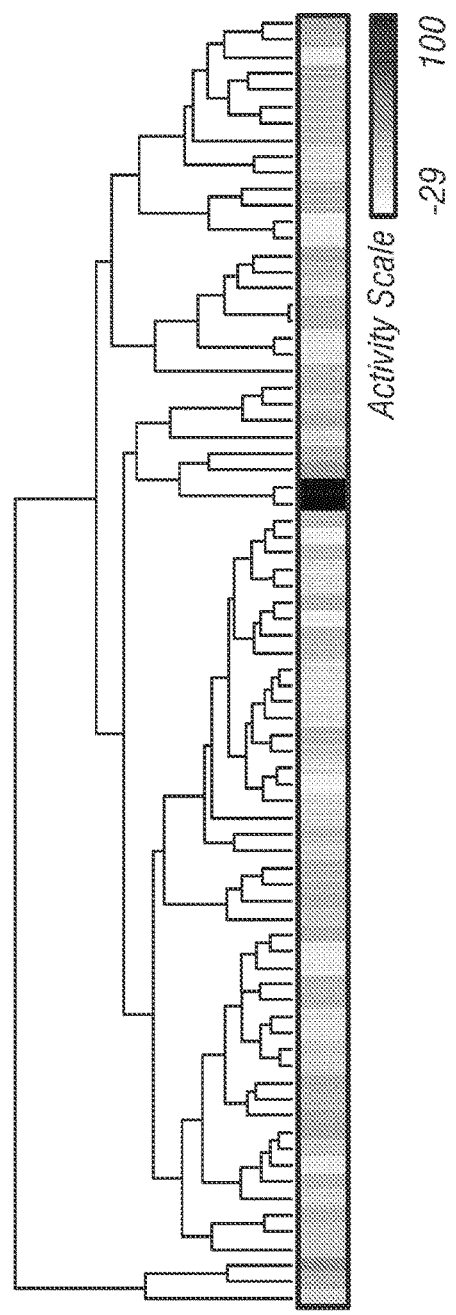
FIG. 19 shows clustering CO2 neuron activating odorants from training set 1 by optimized descriptor subsets.

Optimized descriptors were calculated from the $CO_2$ neuron activity dataset 1. As activities for the odors have been averaged across the top 2 responders of the 4 species, only a single set of descriptors were optimized representing $CO_2$ responsive neuron activity. Molecular descriptors for this class of neuron was optimized using the same method as described above. To better visualize how well each Or-optimized descriptor set grouped $CO_2$ responsive neuron activators, all 78 compounds were clustered by distances calculated using the optimized descriptor sets. As seen in previous examples, highly active ligands clustered tightly for each Or. (See, e.g., FIG. 19).

Figure 20:
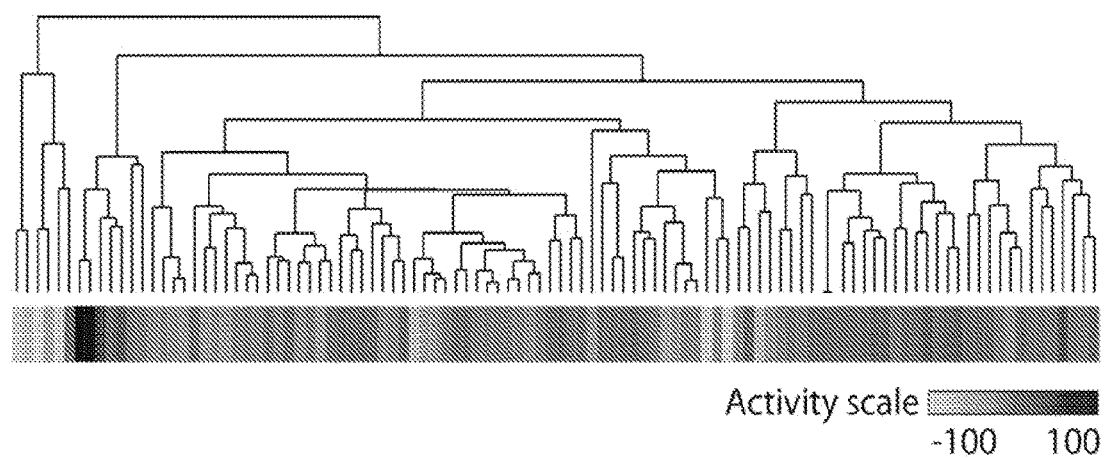
FIG. 20 shows clustering CO2 neuron activating odorants from training set 2 by optimized descriptor subsets.

Optimized descriptors were calculated from the $CO_2$ neuron activity dataset 2. As activities for the odors have been averaged across the top 2 responders of the 4 species, only a single set of descriptors were optimized representing $CO_2$ responsive neuron activity. Molecular descriptors for this class of neuron was optimized using the same method as described in above. To better visualize how well each Or-optimized descriptor set grouped $CO_2$ responsive neuron activators, all 104 compounds were clustered by distances calculated using the optimized descriptor sets. As seen in previous examples, highly active ligands clustered tightly for each Or. (see, e.g., FIG. 20).

Table 7 shows optimized descriptor sets calculated for CO2 activator set 1. The table shows the optimized descriptor subset calculated from activator dataset 1 as described in FIGS. 1-4 and 21. Optimized descriptor occurrences, symbol, brief description, class, and dimensionality are listed. Descriptors are listed in ascending order of when they were selected into the optimized set. Weights indicate the number of times a descriptor was selected in an optimized descriptor set.

| symbol | breif description | class | dimensionality | occurrence |
|---|---|---|---|---|
| HNar | Narumi harmonic topological index | topological descriptors | 2 | 1 |
| R3v+ | R maximal autocorrelation of lag 3/weighted by atomic van der Waals volumes | GETAWAY descriptors | 3 | 4 |
| HATS3m | leverage-weighted autocorrelation of lag 3/weighted by atomic masses | GETAWAY descriptors | 3 | 1 |
| Mor13p | 3D-MoRSE - signal 13/weighted by atomic polarizabilities | 3D-MoRSE descriptors | 3 | 1 |
| ISH | standardized information content on the leverage equality | GETAWAY descriptors | 3 | 2 |
| P1s | 1st component shape directional WHIM index/weighted by atomic electrotopological states | WHIM descriptors | 3 | 1 |
| R4e+ | R maximal autocorrelation of lag 4/weighted by atomic Sanderson electronegativities | GETAWAY descriptors | 3 | 1 |
| nRCHO | number of aldehydes (aliphatic) | functional group counts | 1 | 2 |
| JGI2 | mean topological charge index of order2 | topological charge indices | 2 | 2 |
| E1u | 1st component accessibility directional WHIM index/unweighted | WHIM descriptors | 3 | 2 |
| MATS5m | Moran autocorrelation - lag 5/weighted by atomic masses | 2D autocorrelations | 2 | 1 |
| STN | spanning tree number (log) | topological descriptors | 2 | 2 |
| DISPe | d COMMA2 value/weighted by atomic Sanderson electronegativities | geometrical descriptors | 3 | 1 |
| B06.C.O. | presence/absence of C—O at topological distance 06 | 2D binary fingerprints | 2 | 1 |
| X4A | average connectivity index chi-4 | connectivity indices | 2 | 4 |
| JGI3 | mean topological charge index of order3 | topological charge indices | 2 | 1 |
| De | D total accessibility index/weighted by atomic Sanderson electronegativities | WHIM descriptors | 3 | 2 |
| Mor25u | 3D-MoRSE - signal 25/unweighted | 3D-MoRSE descriptors | 3 | 1 |
| nRCOX | number of acyl halogenides (aliphatic) | functional group counts | 1 | 1 |

| symbol | breif description | class | dimensionality | occurrence |
|---|---|---|---|---|
| B03.O.O. | presence/absence of O—O at topological distance 03 | 2D binary fingerprints | 2 | 1 |
| nHDon | number of donor atoms for H-bonds (N and O) | functional group counts | 1 | 1 |
| MATS3e | Moran autocorrelation-lag 3/weighted by atomic Sanderson electronegativities | 2D autocorrelations | 2 | 1 |
| RBF | rotatable bond fraction | constitutional descriptors | 1 | 1 |
| GATS5m | Geary autocorrelation - lag 5/weighted by atomic masses | 2D autocorrelations | 2 | 1 |
| C.008 | CHR2X | atom-centred fragments | 2 | 1 |
| Mor13v | 3D-MoRSE - signal 13/weighted by atomic van der Waals volumes | 3D-MoRSE descriptors | 3 | 1 |
| R6u. | R maximal autocorrelation of lag 6/unweighted | GETAWAY descriptors | 3 | 1 |

Table 8 shows optimized descriptor sets calculated for $CO_2$ activator set 2. The optimized descriptor subset calculated from activator dataset 2 as described in FIGS. 1-4 and 21. Optimized descriptor occurrences, symbol, brief description, class, and dimensionality are listed. Descriptors are listed in ascending order of when they were selected into the optimized set. Weights indicate the number of times a descriptor was selected in an optimized descriptor set.

| symbol | breif description | class | dimensionality | occurrence |
|---|---|---|---|---|
| N.075 | R—N—R/R—N—X | atom-centred fragments | 2 | 1 |
| R3v. | R maximal autocorrelation of lag 3/weighted by atomic van der Waals volumes | GETAWAY descriptors | 3 | 1 |
| H.049 | H attached to C3(sp3)/C2(sp2)/C3(sp2)/C3(sp) | atom-centred fragments | 2 | 1 |
| nRCHO | number of aldehydes (aliphatic) | functional group counts | 1 | 1 |
| nN | number of Nitrogen atoms | constitutional descriptors | 1 | 1 |
| ISH | standardized information content on the leverage equality | GETAWAY descriptors | 3 | 1 |
| EEig07d | Eigenvalue 07 from edge adj. matrix weighted by dipole moments | edge adjacency indices | 2 | 1 |
| piPC04 | molecular multiple path count of order 04 | walk and path counts | 2 | 1 |
| MATS4e | Moran autocorrelation - lag 4/weighted by atomic Sanderson electronegativities | 2D autocorrelations | 2 | 1 |
| ESpm14d | Spectral moment 14 from edge adj. matrix weighted by dipole moments | edge adjacency indices | 2 | 1 |
| Mor12m | 3D-MoRSE - signal 12/weighted by atomic masses | 3D-MoRSE descriptors | 3 | 1 |

Table 9 shows the top 500 predicted compounds for $CO_2$ activator set 1. The top 500 predicted compounds for predictions made from activator dataset 1.

| SMILES Structures | Distance | SMILES Structures | Distance |
|---|---|---|---|
| c1ccncn1 | 2.033459 | CN(C)CCc1cccnc1 | 3.487232 |
| Cn1cncc1 | 2.170379 | OCCCCCNCc1ccncc1 | 3.491708 |
| C1=NC=CN1 | 2.297704 | OCCC(C)c1ccncc1 | 3.499793 |
| c1ncc[nH]1 | 2.297704 | Cc1cncc(c1)c1ccccc1 | 3.508292 |
| Cc1cnc[nH]1 | 2.409222 | C=COCCNCCc1ccccn1 | 3.512242 |
| OCCCCc1ccncc1 | 2.551873 | CCOCCc1ccccn1 | 3.515488 |
| Cn1cccn1 | 2.646606 | O1CCC(CC1)c1ccncc1 | 3.517108 |
| CCCCCc1ccncc1 | 2.66955 | C#Cc1ccncc1 | 3.522205 |
| Cn1cncn1 | 2.683402 | NNCc1cccn1 | 3.522389 |
| N1N=CC=C1 | 2.768945 | Cc1cncc(C)c1 | 3.522667 |
| c1ccn[nH]1 | 2.768945 | C1CCC(CC1)c1ccncc1 | 3.522853 |
| c1ccnnc1 | 2.785637 | CCCOCCc1ccccn1 | 3.526678 |
| CC(O)/C=C\c1ccccn1 | 2.801027 | CCCn1cncc1 | 3.533624 |
| CC(C)CCCc1ccncc1 | 2.810277 | OCCNCc1ccccn1 | 3.533863 |
| Cc1ncc[nH]1 | 2.819446 | CCCCCC1=NC=CC=C1 | 3.534064 |
| Cc1c[nH]cn1 | 2.821426 | CCCCCc1ccccn1 | 3.534064 |
| CCCCC/C=C/c1ccncc1 | 2.848973 | CCCCC(CC)CCc1ccncc1 | 3.541254 |
| C=COCCNCCc1ccncc1 | 2.856722 | CCCC(C)Nc1ccccn1 | 3.547778 |
| Cc1c[nH]nc1 | 2.864148 | n1ccc(cc1)CNC1CCCC1 | 3.549867 |
| CCCc1ccncc1 | 2.867075 | c1ccc(CNCc2ccc[nH]2)cn1 | 3.555656 |
| CCCCc1ccncc1 | 2.88623 | c1ccc(cc1)\C=C/c1ccncn1 | 3.55859 |
| CCCCCCCCc1ccncc1 | 2.889588 | CN(C)CCc1ccccn1 | 3.561808 |
| c1cnn[nH]1 | 2.890173 | c1ccc(cc1)c1cnc[nH]1 | 3.574979 |
| CC(C)CNCc1ccncc1 | 2.891618 | CC1OCCC(C1)c1ccncc1 | 3.577056 |
| Cc1ccn[nH]1 | 2.894352 | CNCCc1cccnc1 | 3.577696 |
| CNCC/C=C/c1ccncc1 | 2.904657 | N1CCC(CC1)Cc1ccncc1 | 3.581065 |
| NCCc1ccncc1 | 2.919508 | CCOCCCNCc1ccncc1 | 3.582788 |

-continued

| SMILES Structures | Distance | SMILES Structures | Distance |
|---|---|---|---|
| CCCCCCNCc1ccncc1 | 2.930239 | OCCC(N)c1ccncc1 | 3.58383 |
| OCCCc1ccncc1 | 2.963816 | C#CC/N=C\c1ccccc1 | 3.584109 |
| CC(O)CCCc1ccncc1 | 2.972694 | CC(N)Cc1ccccn1 | 3.586069 |
| C/C=C/CCc1ccccn1 | 2.992266 | NNc1ccncc1 | 3.589658 |
| CCCNCc1ccncc1 | 2.995958 | c1ccc(cc1)Cc1ccncc1 | 3.589705 |
| CCCCCCCCn1ncnc1 | 2.997064 | C1CCC(CN1)Cc1ccncc1 | 3.59285 |
| CC1=CSC=N1 | 3.028959 | NCCCc1ccccn1 | 3.592971 |
| Cc1cscn1 | 3.028959 | C=Cn1cncc1 | 3.595285 |
| NCCNCCc1ccncc1 | 3.055465 | OCCCCCNCc1ccccn1 | 3.598167 |
| Cc1n[nH]cn1 | 3.057359 | OC1CCN(CC1)Cc1ccncc1 | 3.599777 |
| C1CCC(CC1)Cc1ccncc1 | 3.067562 | NNc1cccnc1 | 3.608748 |
| OCCNc1ccncc1 | 3.097835 | c1ccc(cn1)c1ccccc1 | 3.609145 |
| N1CCC(CC1)Cc1ccncc1 | 3.125454 | c1ccc(cc1)Cc1ccccn1 | 3.611841 |
| CCCCCCc1ccncc1 | 3.13767 | COc1cncc(OC)n1 | 3.612227 |
| OCCCCCNCc1ccncc1 | 3.138696 | COCCc1nccc(C)c1 | 3.615322 |
| OCCNCCc1ccncc1 | 3.151658 | CCCCCCn1cncc1 | 3.618375 |
| CCCc1ccncc1 | 3.161792 | CCCCCOc1ccncc1 | 3.618896 |
| CCCCCNCc1ccncc1 | 3.163311 | CC(N)CCn1cccn1 | 3.624274 |
| Nc1cncs1 | 3.164302 | C1CCC(CC1)CCCc1ccncc1 | 3.630432 |
| CCCCc1ccncc1 | 3.17431 | c1ccc(cc1)CCCc1ccncc1 | 3.635746 |
| OCCNCc1cccnc1 | 3.190109 | C=CCc1ccccn1 | 3.6393 |
| Cc1csnc1 | 3.190481 | CN(N)c1ccncc1 | 3.642521 |
| Cc1nccs1 | 3.19845 | CCCCCCCCn1ccnc1 | 3.647362 |
| CNCCNCc1ccncc1 | 3.22583 | C1CCC(CC1)NCc1ccncc1 | 3.652448 |
| CNCCc1ccncc1 | 3.232084 | C1CCC(CC1)Nc1ccncc1 | 3.660288 |
| OCCNCCNCc1ccncc1 | 3.2344 | CCCCCOc1ccncc1 | 3.663809 |
| CCC(CO)NCc1ccncc1 | 3.238621 | OCCc1ccnc1 | 3.665454 |
| C=CCNCc1ccncc1 | 3.239061 | n1ccc(cc1)C1CNCC1 | 3.668676 |
| CCC(C)NCc1ccncc1 | 3.249082 | CCCCCc1ccncc1 | 3.669409 |
| CCCCN(C)Cc1ccncc1 | 3.262013 | CC(C)CCNCc1ccncc1 | 3.675901 |
| CC(C)Cc1ccncc1 | 3.276179 | CC(C)NCc1ccncc1 | 3.682412 |
| C=CCNc1ccncc1 | 3.284046 | Oc1cncc(O)c1 | 3.684342 |
| OCCCNCc1ccncc1 | 3.28714 | CCCCNCc1ccccn1 | 3.685337 |
| CC(C)Cc1cccnc1 | 3.290287 | c1ccc(cc1)\C=C/c1nccn1 | 3.688202 |
| CCc1cncc(C)c1 | 3.296279 | C1CNC(C1)Cc1ccncc1 | 3.693127 |
| C1CCC(NC1)Cc1ccncc1 | 3.299132 | CNc1ccccn1 | 3.69627 |
| OCCCc1ccncc1 | 3.300138 | CCn1cncc1 | 3.697594 |
| CCC(CO)NCc1ccncc1 | 3.301803 | CCNc1ccccn1 | 3.69802 |
| n1ccc(cc1)CCn1ccnc1 | 3.309288 | Cc1ccc(cn1)c1ccccc1 | 3.701697 |
| CN(C)/N=C/c1ccccn1 | 3.309846 | CCCCC(CCCC)c1ccccn1 | 3.705387 |
| CCOCCc1ccncc1 | 3.313444 | COc1cc(O)cnc1 | 3.705406 |
| OCCOCCNCc1ccncc1 | 3.324462 | CC(C)OCCCNCc1ccncc1 | 3.706372 |
| CCNCc1ccncc1 | 3.332404 | CNc1nccn1 | 3.706648 |
| OCCNCc1ccncc1 | 3.355513 | NCCc1cccnc1 | 3.710193 |
| CC(N)Cc1ccncc1 | 3.358047 | CCc1ccccn1 | 3.71041 |
| C=Cc1ccncc1 | 3.364881 | CCCCc1cnc(N)nc1 | 3.710859 |
| Nc1nccs1 | 3.369255 | c1ccc(cc1)CCc1ccncc1 | 3.713706 |
| OCCC(CCO)c1ccncc1 | 3.38942 | Cc1ccc(cc1)c1ccncc1 | 3.71477 |
| NCCc1ccncc1 | 3.396504 | C/N=C/c1ccccc1 | 3.716001 |
| C1COC=N1 | 3.400156 | CCO/C=N/c1ccccc1 | 3.717426 |
| CC(C)CCCc1ccccn1 | 3.404779 | CCO/C=N\c1ccccc1 | 3.720444 |
| C=Nc1ccccc1 | 3.40591 | COCCNCc1ccncc1 | 3.721211 |
| CC(O)/C=C/c1ccncc1 | 3.408198 | CN1C=CC=C1 | 3.721854 |
| c1ccns1 | 3.419366 | Cn1cccc1 | 3.721854 |
| CN(C)CCNCc1ccncc1 | 3.422927 | Nn1cccc1 | 3.722507 |
| COCCCNCc1ccncc1 | 3.423191 | CN(C)CCN(C)Cc1ccncc1 | 3.726622 |
| CN(C)CCCc1ccncc1 | 3.429515 | CCCCC(N)c1ccncc1 | 3.728514 |
| CN(C)CCCNCc1ccncc1 | 3.43432 | CC(O)/C=C/c1ccccn1 | 3.728985 |
| Nc1ccn[nH]1 | 3.442882 | n1ccc(cc1)CNC1CC1 | 3.733392 |
| C#CCNCc1ccncc1 | 3.448445 | Nc1cncc(N)c1 | 3.735731 |
| n1ccc(CCNC2CC2)cc1 | 3.449431 | c1ccc(cc1)CNc1ccncc1 | 3.739868 |
| CNCc1ccncc1 | 3.449774 | CC(C)CNc1nccn1 | 3.74062 |
| CC(C)Nc1ccncc1 | 3.450399 | C/C=C/CC(C/C=C/C)c1ccncc1 | 3.743814 |
| N1CCC(CC1)c1ccncc1 | 3.45071 | c1cnc(nc1)c1ccccc1 | 3.749999 |
| OCCNCCNCc1ccncc1 | 3.461336 | CCCCn1cncc1 | 3.751592 |
| OCCOCCNCc1ccncc1 | 3.462592 | COc1nccn1 | 3.752011 |
| CCCCNc1nccn1 | 3.463639 | CCCCC(CCCC)c1ccncc1 | 3.753138 |
| OCCC(=C)c1ccncc1 | 3.464044 | Nc1ccccc1CCc1ccncc1 | 3.75703 |
| C=CCCCCCCCC/C=C/c1ccncc1 | 3.46455 | CCC1=NC(=CN=C1)C | 3.758666 |
| c1ccc(cc1)\C=C/c1ccncc1 | 3.469761 | NCCc1ccncn1 | 3.763006 |
| c1nnn[nH]1 | 3.470708 | CC(N)Cc1ccccn1 | 3.763389 |
| Cc1ccc(\C=C/c2ccncc2)cc1 | 3.478825 | [nH]1nc[nH]nc1 | 3.767631 |
| c1ccc(nc1)CCc1ccccn1 | 3.4792 | OCCCn1cncn1 | 3.770534 |
| Nc1ccccc(\C=C/c2ccncc2)c1 | 3.772142 | Cc1ncc(N)nc1 | 3.921502 |
| Cc1cc[nH]n1 | 3.772838 | c1ccc(cc1)c1ccccn1 | 3.92194 |
| C=C/C=C\CCCCCCCO | 3.778543 | C1CCC(NC1)CCn1cncc1 | 3.922694 |
| CC1CCCCN1Cc1ccncc1 | 3.779824 | Nc1ncc(s1)c1ccccc1 | 3.924187 |

-continued

| SMILES Structures | Distance | SMILES Structures | Distance |
|---|---|---|---|
| C1CCCC(CCC1)NCc1ccncc1 | 3.781268 | CCCCOCCCNCc1ccncc1 | 3.924987 |
| CCCNCc1ccccn1 | 3.781866 | CCCCCCCCOCn1cncn1 | 3.92499 |
| CC(C)CCc1nccnc1 | 3.785656 | CCCCCCCCNCc1ccncc1 | 3.927536 |
| CCOCn1cncn1 | 3.7873 | NCCCC(N)c1ccncc1 | 3.928649 |
| c1ccc(nc1)Cn1cccc1 | 3.788948 | NCCNCCNCCc1ccncc1 | 3.929749 |
| CCN(CC)Cc1ccccn1 | 3.789854 | N1CCC=CC1 | 3.929961 |
| COCCNCc1ccccn1 | 3.792512 | OCCNCCNCc1ccccn1 | 3.930056 |
| n1ccc(nc1)c1cscc1 | 3.804935 | OCCC(CC)c1ccncc1 | 3.933383 |
| NCCCc1cccnc1 | 3.805856 | Oc1cnc(nc1)c1ccccc1 | 3.934528 |
| C=Cn1cncn1 | 3.807139 | Cn1cnnn1 | 3.93691 |
| Nc1cnccc1c1ccccc1 | 3.812096 | Cn1nncn1 | 3.939852 |
| Cc1ccc(CNCc2cccnc2)s1 | 3.812097 | C1CNC(CO1)c1ccncc1 | 3.940647 |
| CCC(N)c1ccncc1 | 3.812101 | CCCCCNCc1ccncc1 | 3.942016 |
| CC1=CN=CC(C)=N1 | 3.815402 | Cc1ncnc(N)c1 | 3.94231 |
| Cc1cncc(C)n1 | 3.815402 | CCCCOc1ccccn1 | 3.94276 |
| CCn1cncn1 | 3.815701 | CCCCC(O)Cc1ccccn1 | 3.943205 |
| CCC1OCCC(C1)c1ccncc1 | 3.816733 | C=CCn1cccn1 | 3.943451 |
| C1=CC=CS1 | 3.817309 | OCCCCCCCCCCCc1ccccn1 | 3.943807 |
| c1cccs1 | 3.817309 | C1CCCC(CCC1)Nc1nccnn1 | 3.947406 |
| CCCCCCCNCc1ccccn1 | 3.821691 | N1CCC(CC1)Cn1cncc1 | 3.948581 |
| Cc1ccc(\C=C/c2ccccn2)cc1 | 3.822084 | NCCCC(N)c1cccnc1 | 3.949274 |
| CCC(CC)c1ccncc1 | 3.824604 | C1NCC(C1)Cc1ccncc1 | 3.952809 |
| Cc1nccnc1CCO | 3.829076 | CC(C)/N=C/c1ccccc1 | 3.953581 |
| n1ccc(cc1)C1CCCN1 | 3.82945 | CCCCCCCCCCCc1ccncc1 | 3.954487 |
| COCCCNCc1ccccn1 | 3.829925 | COCCNCc1cnn(C)c1 | 3.956375 |
| CC1=NC=CN=C1CC | 3.82998 | O=CNc1ccccn1 | 3.95891 |
| CCc1nccnc1C | 3.82998 | c1ccc(cn1)c1ccc[nH]1 | 3.961611 |
| OCCCc1cnn(C)c1 | 3.831839 | c1ccc(cn1)Cn1cccc1 | 3.962207 |
| NNCCc1ccncc1 | 3.836858 | Cc1cc(CC=C)ncc1 | 3.964769 |
| CC1OC(C)CC(C1)c1ccncc1 | 3.837242 | C=Cc1ccccn1 | 3.966734 |
| OCCc1cncc(C)c1 | 3.837984 | c1ccc(cc1)c1cncs1 | 3.967009 |
| Nc1c[nH]cn1 | 3.838209 | C=CCn1cncc1 | 3.967641 |
| N1CCC(CC1)CCn1cncc1 | 3.838228 | C1CCCC(CCC1)NCc1ccncc1 | 3.96989 |
| Cc1ccc(cc1)c1nccs1 | 3.838297 | Nc1ccc(cc1)Cc1ccccc1 | 3.971588 |
| Nc1ncc[nH]1 | 3.838354 | Cc1nccnc1CCCC | 3.972325 |
| Cc1cnc(nc1)c1ccccc1 | 3.839282 | COc1ccccn1 | 3.972372 |
| CCOc1ccncc1N | 3.839786 | CCCCc1ccccn1 | 3.972673 |
| Nc1ccc(CCc2ccncc2)cc1 | 3.840154 | Cc1ccc2cnccc2c1 | 3.974412 |
| CCCCNCc1ccncc1 | 3.840485 | Cc1ccnc(c1)c1ccccc1 | 3.975783 |
| CCc1ccc(C=C)nc1 | 3.844342 | c1csc(c1)\C=N/N=C/c1cccs1 | 3.977461 |
| n1ccc(cc1)C1CC1 | 3.846694 | Cc1ccccnc1 | 3.97977 |
| CC(C)CNCc1ccccn1 | 3.847544 | NCCCCc1ccccn1 | 3.980221 |
| c1ccc(cc1)CCCc1ccncc1 | 3.848581 | OCCNCc1cnn(CC)c1 | 3.98241 |
| NCCC(CCO)c1ccncc1 | 3.849054 | C1CCC(CN1)COc1ccncc1 | 3.982921 |
| C1CCC(CC1)Nc1nccs1 | 3.851878 | c1ccc(cc1)\C=C/c1ccccn1 | 3.983757 |
| CCC1=NC=CN=C1CC | 3.853768 | CN(C)/C=N/c1ccccc1 | 3.984609 |
| CCc1nccnc1CC | 3.853768 | OCC(C)Cn1cccn1 | 3.985181 |
| CCCCn1cncc1 | 3.855689 | C=Cc1ccc(C)nc1 | 3.98793 |
| c1ccc(nc1)c1ccccn1 | 3.857047 | Cc1cncs1 | 3.988318 |
| CCCc1ccccn1 | 3.858559 | COCn1cnccl | 3.989514 |
| n1ccc(cc1)CCNc1ccccc1 | 3.858864 | CCC(C)n1cccn1 | 3.990983 |
| n1ccc(cc1)C1CCC=CC1 | 3.859078 | CCCCOc1ccc(CNCc2cccnc2)cc1 | 3.99149 |
| Oc1cccs1 | 3.861787 | OCn1cncc1 | 3.9916 |
| C1CCNC(CC1)c1ccncc1 | 3.862012 | CCC(C)NCc1cccnc1 | 3.992449 |
| C1CCC(CNCCCn2cncc2)CC1 | 3.862902 | CC(C)NCc1ccccn1 | 3.994445 |
| c1ccc(nc1)Nc1ccccn1 | 3.864257 | c1ccc(cc1)COCc1cncs1 | 3.994736 |
| Nc1nccc(c1)c1ccccc1 | 3.86608 | CCCN(CC1CC1)Cc1ccncc1 | 3.995188 |
| n1ccc(cc1)Cn1cccc1 | 3.867767 | Cc1ccccc1Cc1ccccn1 | 3.996041 |
| NCCCNc1cccnc1 | 3.869999 | CC(C)c1ccccn1 | 4.00194 |
| OCCc1ccncn1 | 3.872425 | CCCCCCNCc1ccncc1 | 4.002367 |
| CCCc1ccc(O)cn1 | 3.873872 | COc1ncc(N)cn1 | 4.00385 |
| Nc1ccc(cn1)c1ccccc1 | 3.87394 | C1CCc2nccnc2C1 | 4.004779 |
| Nc1nncs1 | 3.876929 | c1ccc(cc1)NCc1ccncc1 | 4.005823 |
| c1ccc(cc1)c1c[nH]cn1 | 3.877242 | C=Cc1nccnc1C | 4.006881 |
| c1ccc(cc1)Cc1ccccn1 | 3.881093 | O=Cc1cnc(s1)c1ccccc1 | 4.007171 |
| OCCCc1cnn(CC)c1 | 3.882615 | CC(N)c1ccncc1 | 4.009614 |
| c1ccc(cc1)c1ncc[nH]1 | 3.883167 | CCCC(CCC)c1ccccn1 | 4.012339 |
| c1ccc(cn1)c1n[nH]cc1 | 3.885425 | OCC1CCN(CC1)Cc1ccncc1 | 4.012772 |
| NCCCCn1cncc1 | 3.885956 | Cc1cc(C=O)cnn1 | 4.013137 |
| c1ccc(nc1)\C=C/c1cccnc1 | 3.886201 | CNCCC(O)c1ccccn1 | 4.013331 |
| COCCc1ccccn1 | 3.886334 | NCCCCCc1cnc[nH]1 | 4.014127 |
| C12=CC=CC=C1N=CC=N2 | 3.889099 | COCC(NC)c1ccccn1 | 4.016933 |
| c1ccc2nccnc2c1 | 3.889099 | CCCCc1cnccn1 | 4.017648 |
| c1ccc(cc1)c1ccn[nH]1 | 3.890727 | CCCCCCC(C)Cc1ccncc1 | 4.017949 |
| c1ccc(nc1)NC1CCCC1 | 3.892768 | O1CCN(CC1)c1ccncc1 | 4.018166 |
| OCCNCc1cnn(C)c1 | 3.893737 | C1N=Cc2ccccc2C=C1 | 4.018324 |
| CCOc1ccccn1 | 3.901646 | CCCN1CCC(CC1)NCc1ccncc1 | 4.01907 |

-continued

| SMILES Structures | Distance | SMILES Structures | Distance |
|---|---|---|---|
| Cc1ccnc(C)c1 | 3.902494 | NCCNc1cccnc1 | 4.019396 |
| COCc1ccccn1 | 3.907315 | CCCCCn1ccnc1C | 4.020339 |
| NCCc1cncs1 | 3.909061 | OCCc1ccncc1 | 4.023571 |
| Nc1ccc(c1)c1ccncc1 | 3.90929 | C=CCn1cncn1 | 4.024219 |
| CCCCCCCCCCCn1ccnc1 | 3.910022 | n1ccc(cc1)C1CCCCN1 | 4.024864 |
| CCC1CCC(CC1)NCc1ccncc1 | 3.910398 | OCCNc1ccncc1N | 4.025311 |
| CCCCCCn1cncc1C | 3.911132 | CCCCN(CCCC)c1ccncc1 | 4.025433 |
| n1ccc(cc1)\C=C/c1ccccn1 | 3.91129 | Cc1ncc(C)cn1 | 4.027625 |
| Oc1cnsn1 | 3.912538 | CC(=N)NCCc1ccncc1 | 4.028513 |
| CCC1=NC=CN=C1 | 3.914359 | CC(C)Cn1cccn1 | 4.028995 |
| CCc1cnccn1 | 3.914359 | c1ccc(nc1)NCc1cccs1 | 4.030544 |
| NCCNc1ccccn1 | 3.914758 | C=Cc1ccnc1 | 4.031618 |
| c1cnc(nc1)NC1CCCC1 | 3.915571 | CCC/N=C/c1ccccc1 | 4.032101 |
| CCC(CC)c1ccccn1 | 3.915951 | COc1ncc(O)cn1 | 4.032331 |
| Cc1ccc(CNc2ccnc2)cc1 | 3.917527 | Nc1ccc(cc1)Cc1ccncc1 | 4.032768 |
| OCCC(CCO)c1ccnc(C)c1 | 3.919641 | CC1OC(C)CN(C1)c1ccncc1 | 4.034999 |
| Oc1ccccc1\C=N/c1nccs1 | 3.919723 | CCN(CC)CCc1ccccn1 | 4.035536 |
| COCCNCc1ccncc1 | 3.920298 | n1ccc(cc1)CNCc1cccs1 | 4.037681 |
| OCc1cncn1CC | 3.920528 | CC1=NC=CN=C1OC | 4.038081 |
| O=CNc1nnc(CC(C)C)s1 | 4.075545 | COc1nccnc1C | 4.038081 |
| Cc1cccnc1c1ccccc1 | 4.075705 | CCN(CC)CCc1ccncc1 | 4.038201 |
| C1CCC(CN1)Oc1ccnc1 | 4.075903 | OCC1CCN(CC1)Cc1ccncc1 | 4.038372 |
| N1CCC(CC1)CCc1ccccn1 | 4.077268 | COC1=NC=CN=C1CC | 4.03881 |
| c1ccc(nc1)c1ccncc1 | 4.078491 | COc1nccnc1CC | 4.03881 |
| CCCCc1ccc(C=O)cc1 | 4.07867 | CCn1cccn1 | 4.039322 |
| c1ccc(nc1)C1CCOCC1 | 4.080083 | CCOC(OCC)Cn1cccn1 | 4.039711 |
| c1ccn2nccc2n1 | 4.081331 | N1CCC(CC1)Cc1ccccn1 | 4.0407 |
| CC(CC)n1cncn1 | 4.082857 | N1=CNCCN=CNCC1 | 4.040829 |
| OC1CCN(CC1)Cc1ccncn1 | 4.083942 | NCCCn1cncn1 | 4.041459 |
| Cc1nncc(c1)c1ccccc1 | 4.084906 | Cc1ccc(cc1)c1cncnc1 | 4.043691 |
| CCC/C=N/Nc1ccccc1 | 4.087764 | CCOc1cnccc1OCC | 4.044495 |
| C/C=C/CC(C/C=C/C)c1ccccn1 | 4.089417 | NCC(C)c1ccncc1 | 4.044646 |
| COCC(N)c1ccccn1 | 4.0913 | CN(C)Cc1ccccn1 | 4.045576 |
| CC/C=C\C/C=C\C/C=C\CO | 4.092416 | OCCCNC(C)c1ccncc1 | 4.047575 |
| CCC(N)Cn1cncc1 | 4.092784 | C=CC1=CN=CC(C)=N1 | 4.048223 |
| CC(N)Cn1cncc1 | 4.093284 | NCCCOc1ccnc1 | 4.048408 |
| OCCCNCc1ccccn1 | 4.094216 | Cc1ccc(cc1)c1ccccn1 | 4.048665 |
| C/N=C/c1ccc(cc1)C(C)C | 4.094231 | Cc1ccnc(c1)c1nccc(C)c1 | 4.049527 |
| C[C@H](O)c1ccnc1 | 4.094662 | CCCCC(CCCC)c1ccncc1 | 4.049925 |
| CC(O)c1ccncc1 | 4.094662 | C1CNC(C1)Cn1cccn1 | 4.052425 |
| CC(=C)Cc1ccccn1 | 4.095187 | CC(C)CNc1ccccn1 | 4.053681 |
| CN1CCN(CC1)Cc1ccccn1 | 4.096565 | Nc1cnc(nc1)c1ccccc1 | 4.053727 |
| c1csc(c1)\C=N/N=C\c1cccs1 | 4.097744 | N1CCCN(CC1)Cc1ccncc1 | 4.053805 |
| C=CCNc1nccs1 | 4.098084 | CC(C)Nc1ccncc1N | 4.055925 |
| CC(C)CC(C)c1ccccn1 | 4.098869 | n1ccc(nc1)c1cccs1 | 4.056535 |
| CCCCNc1ccncc1N | 4.100089 | CCOc1ccc(CNc2cccnc2)cc1 | 4.056591 |
| OC1CCCN(C1)Cc1ccncc1 | 4.100969 | NCCCCCC(N)c1ccccn1 | 4.056898 |
| OCc1ccc(CO)cn1 | 4.104339 | CCC(NC)c1ccccn1 | 4.056979 |
| COCCn1ccc1CO | 4.104345 | NCc1ccc(s1)c1ccncc1 | 4.058566 |
| OCc1cnc[nH]1 | 4.104405 | Cc1cccc(c1)c1cncnc1 | 4.058849 |
| OCCC/N=C\c1cccs1 | 4.106196 | CC(C)Oc1nccnc1C | 4.059391 |
| C1CCN(C1)c1nccs1 | 4.109143 | Nc1n[nH]cn1 | 4.059558 |
| C1CCC(NC1)CCc1ccccn1 | 4.11042 | Nc1cncc(O)c1 | 4.061363 |
| CCCn1cc(N)cn1 | 4.111561 | NC1CCCN(C1)Cc1ccncc1 | 4.061742 |
| Cc1c[nH]cc1 | 4.111597 | COCn1cncn1 | 4.062793 |
| Nc1ccc(CCc2cccnc2)cc1 | 4.113066 | Nc1ccc(cc1)c1ncsc1 | 4.064229 |
| C1C=CC=C1 | 4.113191 | CCOc1cnc(C)cn1 | 4.06474 |
| OCC(N)c1ccccn1 | 4.113658 | Cc1nccnc1CCC | 4.066969 |
| c1ccc2ccncc2c1 | 4.113947 | Nc1cc(CO)cnc1 | 4.067234 |
| c1ccc(CNCc2cccs2)cn1 | 4.114262 | OCCCc1ccnc(C)c1 | 4.068903 |
| CC(N)Cn1cncn1 | 4.115272 | c1ccc(cc1)CNc1ccccn1 | 4.069396 |
| CCCn1nccc1C | 4.115424 | CCCCNc1nccs1 | 4.072269 |
| CCC(CO)NCc1ccccn1 | 4.118634 | Cc1ccc[nH]1 | 4.072803 |
| OCCn1nccc1N | 4.119024 | Nc1cnc(C)nc1 | 4.073371 |
| CCCCn1ccnc1C | 4.119754 | CCCCCCCNCc1ccncc1 | 4.073913 |
| Nc1ccccc1c1ccncc1 | 4.121111 | Nc1ccc(nc1)c1ccccc1 | 4.073915 |
| O=Cc1ccnn1CC | 4.121672 | CC1=COC=C1 | 4.074861 |
| OCCCCCCc1ccnc1 | 4.122515 | c1cnc2cccnc2c1 | 4.074967 |
| CC1=NC=C(CC)C=C1 | 4.124326 | C1CNC(C1)Cn1cncn1 | 4.075254 |

TABLE 10

Top 500 predicted compounds for CO₂ activator set 2. The top 500 predicted compounds for predictions made from activator dataset 2.

| SMILES Structures | Distance | SMILES Structures | Distance |
|---|---|---|---|
| O=C1CCNCC1 | 1.66855 | O=C1CNCC1 | 5.644213 |
| O=C1CCCCCN1 | 2.03737 | C1COC=N1 | 5.670562 |
| O=C1CCCCCN1 | 2.03737 | S=C(NCCc1ccccc1)NC(C)(C)C | 5.700199 |
| O=C1NCCCC1 | 2.16724 | N#CC(=C1CCCCCCCCCC1)C#N | 5.701419 |
| O=C1CCCCN1 | 2.16724 | COC1=CC=CCC1 | 5.71922 |
| O=S1CCNCC1 | 2.17659 | CC(C)(C)NCc1ccccc1 | 5.720564 |
| O=C1NCCOCC1 | 2.43129 | CC(C)CC(=O)c1cccnc1 | 5.7212 |
| O=C1CCNCCC1 | 2.50405 | NC1CCCCC1 | 5.72578 |
| O=C1CCC=CCC1 | 2.67564 | CCc1cncc(C)c1 | 5.744045 |
| Oc1ccncn1 | 2.97767 | CNC1CCCC1 | 5.745127 |
| C1=CC=CS1 | 2.99768 | OC1CCNCC1 | 5.749396 |
| c1cccs1 | 2.99768 | CC(C)=C[C@H]1C[C@@H](C)CCO1 | 5.751913 |
| O=C1COCC1 | 3.06572 | COC1CCC=C1 | 5.761583 |
| CC1CCOCO1 | 3.1695 | CC(C)OC(=O)C1CCCCC1 | 5.765544 |
| O=S1CCCCC1 | 3.34159 | CC(=CCOCC1CCCNC1)C | 5.773864 |
| O=C1CCCCCC1 | 3.37411 | C1CCCSC1 | 5.776573 |
| Cc1ccncc1 | 3.44412 | C1CCSCN1 | 5.78245 |
| O=C1CCCNC1 | 3.53322 | O=Cc1c[nH]cn1 | 5.783256 |
| O=C1CCCCO1 | 3.6966 | CCOC(=O)N1CCCCCC1 | 5.783974 |
| NC1CCOCC1 | 3.73016 | C1COC=CC1 | 5.794384 |
| O=CN1CCCC1 | 3.75356 | COC1=CCCCC1 | 5.795498 |
| O=C1CCCCC=C1 | 3.83862 | O=C(OC(C)(C)C)c1cccnc1 | 5.795791 |
| NC1CCSCC1 | 3.88042 | OC1CCCCO1 | 5.807573 |
| CC1=CC=NC(=O)C1 | 3.88476 | OC1CCCCCC1 | 5.823095 |
| O=C1C=CCCC1 | 3.97735 | CCCCCC#Cc1ncccc1C#N | 5.8237 |
| O=C1CCCC=C1 | 3.97735 | CC(=O)CC(=O)N1CCCCCC1 | 5.82382 |
| OC1CCSCC1 | 3.9899 | O=C(CC(C)(C)C)c1ccccc1 | 5.828928 |
| C1CCOCO1 | 4.04859 | CC(C)(C)OCc1ccccc1 | 5.830675 |
| O=C1CCC=CC1 | 4.05289 | CC1(O)CCCCCC1 | 5.846164 |
| N1CCC=CC1 | 4.09099 | O=c1cc[nH]cc1 | 5.850777 |
| C1C=CC=C1 | 4.09349 | C/C=C/C1OCCO1 | 5.852582 |
| O=S1(=O)CCNCC1 | 4.25706 | CS(=O)(=O)N1CCCCCC1 | 5.852941 |
| CC1CCOC(=O)C1 | 4.31492 | Cc1ncc(C)cn1 | 5.872505 |
| O=S1(=O)C=CCCC=C1 | 4.35802 | CC(C)(C)NCC#Cc1ccccc1 | 5.872605 |
| O=c1cccn[nH]1 | 4.38874 | CCCOc1ccc(C)c1 | 5.874069 |
| CC1CCNCC1 | 4.39789 | C1NNC=C1 | 5.876098 |
| CC1CCNCC1 | 4.39789 | CC(=CC(=O)N1CCCCCC1)C | 5.892267 |
| c1ccncn1 | 4.44564 | CC(C)CCOC1CCNCC1 | 5.894852 |
| C1CCC=COC1 | 4.46091 | CCCN1CCCCC1 | 5.899168 |
| c1ccnnc1 | 4.50924 | O=Cc1cccs1 | 5.902546 |
| O=C1CCCC(=O)N1 | 4.53618 | CC(=C)Cc1ncccc1C | 5.90473 |
| O=S1(=O)CCCCC1 | 4.55931 | CC1(C)CCNCC1 | 5.91625 |
| O=C1CNCCN1 | 4.60068 | O=C1CCCCCCCCCC(=O)OCCCCO1 | 5.927301 |
| C1=NC=CN1 | 4.61974 | O=C1CCNC(=O)N1 | 5.933254 |
| c1ncc[nH]1 | 4.61974 | OC1CCNCCC1 | 5.937124 |
| O=C1NCCCN1 | 4.64001 | O=C1COCCN1 | 5.944039 |
| CN1CCOCC1 | 4.6583 | O=C(NC(C)(C)C)c1ccncc1 | 5.947731 |
| O=C1NCCCO1 | 4.721 | CC(O)CC#CCN1CCCCC1 | 5.948158 |
| O=S1(=O)COCC1 | 4.79345 | O=C1CCCC1 | 5.94834 |
| O=C1CCCC(=O)N1 | 4.79537 | O=C1CCCC1 | 5.94834 |
| CN1CCC=CC1 | 4.91248 | C1CC=CC1=O | 5.95686 |
| O=C1C=CC=CO1 | 4.9195 | OCCC#CCN1CCCCC1 | 5.957687 |
| N1N=CC=C1 | 4.94377 | C=CC1OCCO1 | 5.959976 |
| c1ccn[nH]1 | 4.94377 | CN1CCCCCC1 | 5.962768 |
| C1CCCOC1 | 4.97412 | Cc1cc[nH]n1 | 5.96375 |
| O=C1CCCC(=O)C1 | 5.01506 | O=C1NCCNCC1 | 5.967599 |
| Cc1ccncn1 | 5.03254 | CC(C)=CC1C=C(C)CCO1 | 5.971966 |
| c1nnn[nH]1 | 5.0834 | CC(=C=CSc1ccccc1)C | 5.975644 |
| CC1=NNCC1 | 5.12159 | CCOCCCNC(=O)n1cncc1 | 5.979802 |
| N1CCCCCC1 | 5.12723 | OCC1CCCC1 | 5.980761 |
| OCc1cnn[nH]1 | 5.15293 | C1CNCCNC1 | 5.984318 |
| CC(C)CC(=O)N1CCNCCC1 | 5.1552 | CCOC1CCCO1 | 5.986821 |
| CN1CCCCC1 | 5.16702 | CCCCOc1ccc(N)c1 | 5.987676 |
| CN1CCCCC1 | 5.16702 | CC1=CCCN1 | 5.994846 |
| NCc1nnn[nH]1 | 5.23459 | CC(=O)CC(=O)NC1CCCCC1 | 5.995065 |
| c1ccns1 | 5.24232 | O=C1CC(C)(O)CCO1 | 5.996197 |
| C1CNCCOC1 | 5.24713 | O=C1OCCC(C)(O)C1 | 5.996197 |
| C1CCNOC1 | 5.25085 | CCCNC1CCCCCC1 | 5.996813 |
| C1CCCS1 | 5.27768 | OCC1COCC1 | 5.99948 |
| c1cnn[nH]1 | 5.28134 | CCCn1ccc(=N)cc1 | 6.007298 |
| O=c1cn[nH]c(=O)[nH]1 | 5.29523 | OC[C@H]1CNCC1 | 6.00856 |
| O1CCCCCC1 | 5.29737 | CC(=CC(=O)N1CCNCC1)C | 6.009864 |
| O=C1CCCC(=O)O1 | 5.29845 | O=C1OCC[C@@](C)(O)C1 | 6.011353 |
| O=c1ccnc[nH]1 | 5.29899 | O=C1CC2CCC1CC2 | 6.017842 |
| C1OCC=CCO1 | 5.33288 | CC(C)CC(=O)N1CCCCCCC1 | 6.01785 |

TABLE 10-continued

Top 500 predicted compounds for CO₂ activator set 2. The top 500 predicted
compounds for predictions made from activator dataset 2.

| SMILES Structures | Distance | SMILES Structures | Distance |
|---|---|---|---|
| O=S1(=O)CCCCO1 | 5.35017 | CC1CC(C)CC(=O)C1 | 6.018673 |
| C/C=C/C(=O)N1CCCCCC1 | 5.3502 | O=Cc1ccc(OCCC(C)C)cc1 | 6.022296 |
| CC(C)CC(=O)C1CCCCC1 | 5.38026 | CCOC1=CCCCC1 | 6.030238 |
| CNc1nnn[nH]1 | 5.38777 | CC1CNCC(C)C1 | 6.031252 |
| O=C1NCCCN1 | 5.41177 | O=S1(=O)C=CC=CC=C1 | 6.03423 |
| CC/C=C/N1CCCCC1 | 5.41882 | CN(C)NC(=O)c1cccc1 | 6.034587 |
| n1ccnnc1 | 5.42336 | NC1CCNCC1 | 6.039425 |
| C=CCON=C1CCCCC1 | 5.43999 | CC(C)c1nnn[nH]1 | 6.044467 |
| O=C(NC(C)(C)C)c1ccccc1 | 5.44125 | CCCCCCCc1ccc(C#N)cc1 | 6.044688 |
| C[C@H]1CNCC1 | 5.45426 | C1CC=CC1 | 6.044933 |
| CC1CNCC1 | 5.46662 | CN1CCCC1 | 6.046603 |
| NC1=NCCO1 | 5.469 | CC(C)(C)NSc1ccccc1 | 6.046834 |
| C[C@@H]1CNCC1 | 5.48036 | CN(C)CCCNC(=O)n1cncc1 | 6.05255 |
| O=C1CCCCO1 | 5.51226 | N#CC1=CCCCCCCCCCC1 | 6.058942 |
| CCON=C1CCCCC1 | 5.53578 | CN(C)CCC1CCNCC1 | 6.062633 |
| CC(C)NC(=O)n1cncc1 | 5.5454 | O=C1CC=CC1 | 6.06268 |
| CNC1CCCCCC1 | 5.56246 | CCC(=O)NCCCn1cncc1 | 6.068374 |
| CN1CCCN(C)C1 | 5.60836 | CCc1cnc(N)nc1 | 6.07402 |
| CC(C)=CC1CC(C)=CCO1 | 5.60984 | CC(C)=CC1OCCC(C1)C | 6.075926 |
| CC1COCC1 | 5.61068 | CC1CCOC(C1)C=C(C)C | 6.075926 |
| O=Cc1cc[nH]n1 | 5.61618 | CC(C)OC(=O)CCNC(=O)n1ccnc1 | 6.076841 |
| CC(=C)Cc1ccccn1 | 5.61981 | CCCn1cccc1 | 6.081147 |
| CC(C)(C)/N=C/c1ccccc1 | 5.62608 | C1Cc2[nH]ncc2C1 | 6.084577 |
| O=C1CCCS(=O)(=O)CC1 | 5.62707 | CC(C)CCNc1ccccc1 | 6.088477 |
| O=C1OCCOCC1 | 5.62874 | CCCCCCN1CCCCCC1=O | 6.088796 |
| CCCCCCCCn1ccc(=N)cc1 | 6.09256 | CSc1ccc(cc1)C(=O)NC(C)C | 6.328161 |
| CNc1cccc(C)c1 | 6.098 | CCCCCCCCCn1ccc(=N)cc1 | 6.328322 |
| CC(=O)C1CCCCCCCCCC1=O | 6.09886 | CCCNCC1CCCCC1 | 6.33169 |
| CC1=CCCO1 | 6.1036 | S=C(N/N=C/c1ccncc1)NC(C)(C)C | 6.332076 |
| CCCCCn1ccc(=N)cc1 | 6.11175 | N#CC(=CNc1ccncc1)C#N | 6.332338 |
| CCCCc1ccc(N)cc1 | 6.11758 | CCCCNc1ccccc1 | 6.3364 |
| N#CCCOc1cc(C)cc(C)c1 | 6.11793 | CC(C)COC1CCNCC1 | 6.336875 |
| CCNC(=O)C1CCNCC1 | 6.12143 | C1C=CCCC=C1 | 6.337419 |
| Cc1cccc(NN=C(C)C)c1 | 6.12331 | CCOC1CCCCO1 | 6.338426 |
| CN(C)CCCNC(=O)c1cccs1 | 6.12848 | CCOC(=O)C#Cc1cccc(C#CC(=O)OCC)c1 | 6.33956 |
| CCC(=O)NCCC1=CCCCC1 | 6.12936 | COC(=O)\C(=C/C#CC1CCCCC1)/C | 6.340497 |
| CC(=C)Cc1ccc(C)n1 | 6.13039 | CC(=C)COCC1CCCNC1 | 6.341306 |
| C=CCc1ccccn1 | 6.14194 | Cc1ccc(CC=C)n1 | 6.342212 |
| OC1CCCCC1 | 6.14367 | O=C(NCCCn1cccn1)C1CC1 | 6.342747 |
| OC1CCCCC1 | 6.14367 | CCCC(=O)NC1CCN(C)CC1 | 6.345418 |
| CCN(CC)C(=O)Sc1ccccc1 | 6.15327 | OC1CCCCN1 | 6.345647 |
| CCCC(=O)C1CCNCC1 | 6.15506 | CCN(CC)CCCNC(=O)c1cccs1 | 6.347501 |
| CC1CCCS1 | 6.15615 | CC(=O)NCCCNC(=O)c1cccnc1 | 6.348592 |
| C1CCN=CN1 | 6.1566 | CCC1NCC=C1 | 6.348743 |
| CCCCc1ccc(C#N)cc1 | 6.15777 | CCC1CCCCO1 | 6.35009 |
| CC(C)CCNC(=O)c1cccs1 | 6.16447 | CN(C)/C=N/c1ccccc1 | 6.350651 |
| CS(=O)(=O)N1CCNCCC1 | 6.16796 | CSCCC(=O)Nc1nccs1 | 6.353907 |
| CC1CCCN(C)C1 | 6.16806 | CN1CCNCCC1 | 6.355103 |
| O=C1CCCCC(=O)O1 | 6.16947 | O=c1cc[nH]c(=O)[nH]1 | 6.3581 |
| NN1CCCCC1 | 6.16961 | CC(N)CCn1cccn1 | 6.359583 |
| CCOC(=O)C1CCNCC1 | 6.16969 | CCOC(=O)N1CCCCC1 | 6.360332 |
| OCC#CCCOCc1ccc(OC)cc1 | 6.17176 | O=C(Nc1ccncc1)CC(C)(C)C | 6.360498 |
| NCC1COCC1 | 6.17315 | Cc1scc(c1)C(=O)Nc1ccncc1 | 6.361459 |
| O=C(Nc1ccncc1)NC(C)(C)C | 6.17625 | CC(=CCOC1CCCNC1)C | 6.366281 |
| CSc1ccccc1C(=O)NCCCN1CCCCCC1 | 6.17718 | CCCC(=O)NC1CCCCCC1 | 6.370017 |
| CC(C)C1NCC=C1 | 6.18084 | CC(C)CNc1ccc(C)cc1 | 6.372029 |
| OC(=O)C1=CCCCCCCCC1 | 6.18133 | CCCCCOc1ccccc1C | 6.373041 |
| O=C(Nc1ccccc1)CC(C)(C)C | 6.18333 | CCOC1OCCCO1 | 6.373474 |
| CC(=O)CC(=O)NCCCc1ccccc1 | 6.1847 | CCC(CC)C(=O)NCCCN1CCOCC1 | 6.374652 |
| CCCC(=O)N1CCSCC1 | 6.1868 | CC1=NCCC1 | 6.380214 |
| CCc1ccc[nH]1 | 6.18755 | CCC(=O)C1CCCCC1 | 6.380337 |
| O=C(NCCCn1cccn1)C1CCCCC1 | 6.1899 | COC1=NCCCCC1 | 6.382579 |
| Cc1cc(CC=C)ncc1 | 6.19214 | COC(=O)NCCC1=CCCCC1 | 6.382998 |
| O=C1CCCCC(=O)C1 | 6.19215 | CNC(=O)NCc1ccccn1 | 6.383801 |
| O=C1NC=NC(=O)C1 | 6.19497 | CC(C)NC(=O)c1cscc1 | 6.38503 |
| CC(=O)CCC=C1CCCCC1 | 6.1999 | CNCCc1c[nH]cn1 | 6.389962 |
| C=CC(C)CSc1ccccc1 | 6.20114 | CCNC(=O)NC1CCCCC1 | 6.391185 |
| CC(N)c1nnn[nH]1 | 6.20863 | O=C1CC(=CC(=O)O1)C | 6.391193 |
| CC(C)CCNC(=O)n1cncc1 | 6.21052 | C=CCSC(=O)NC(=O)Cc1ccccc1 | 6.393044 |
| CCCC1CCCNC1=O | 6.21079 | CCCC(=O)NCCCc1ccccc1 | 6.39395 |
| CC(=O)NCCCNC(=O)c1cccs1 | 6.21297 | O=S1OCCCCO1 | 6.393961 |
| CC(C)CC(=O)NCCc1ccncc1 | 6.21313 | NCCC(=O)N1CCNCC1 | 6.394319 |
| CC(=O)CC(=O)NC1CCCCCC1 | 6.21501 | CCCCN(C)Cc1ccc(OC)cc1 | 6.394897 |
| CCc1nnn[nH]1 | 6.21826 | Cn1cncc1C=O | 6.395174 |
| S1SCCC1 | 6.22029 | CCCCc1ccc(CN)cc1 | 6.397567 |

TABLE 10-continued

Top 500 predicted compounds for CO$_2$ activator set 2. The top 500 predicted compounds for predictions made from activator dataset 2.

| SMILES Structures | Distance | SMILES Structures | Distance |
| --- | --- | --- | --- |
| C=CC#CCN1CCCC1 | 6.2212 | CC(=CC(=O)CCN1CCCCC1)C | 6.398219 |
| C1NCCS1 | 6.22176 | CCOC(=O)CC1CCCNC1 | 6.399213 |
| CCN(CC)C(=O)N1CCCCC1 | 6.22256 | CC(C)(C)NNc1ccccc1 | 6.40262 |
| ON1CCCCC1 | 6.22438 | CCNC(=O)CCSc1nc(C)cc(C)n1 | 6.403173 |
| CCCCCc1ccc(NC)cc1 | 6.23282 | CC(C)NC(=S)N/N=C/c1cccnc1 | 6.404253 |
| CNCC(=O)N1CCCCC1 | 6.23427 | CC(C)CC(=O)NC1CCCCCC1 | 6.405964 |
| O=C(NCC#Cc1ccccc1)NCCc1cccs1 | 6.23686 | OC1(C)C=CCCC1 | 6.407874 |
| Cc1c[nH]cc1 | 6.24026 | CC1CCCO1 | 6.410532 |
| CC(=O)NCCCNC(=O)c1ccncc1 | 6.24118 | CCCCCCn1ccc(=CC=C(C#N)C#N)cc1 | 6.4135 |
| CC(C)CC1CCCCCN1 | 6.24936 | CCCCC1=CCCOC1 | 6.416425 |
| CCN(CC)C(=S)NCCc1ccccc1 | 6.24969 | CC(C)CCNC(=O)c1cccnc1 | 6.420616 |
| CC(=O)CCCN1CCCCC1 | 6.25029 | CC(C)/N=C(/C)\c1ccccc1 | 6.421906 |
| O=C1C=CCCC=C1 | 6.25035 | Oc1ccncc1 | 6.427433 |
| CC(=CCOC1CCNCC1)C | 6.25104 | CCS/C=C/C#CC1(O)CCCCC1 | 6.428407 |
| CCc1cccc(C)n1 | 6.25801 | CCC(CC)C1CCCCCN1 | 6.428797 |
| N#Cc1ccc(CSC2=NCCCN2)cc1 | 6.25841 | CC1CCCC(O)C1 | 6.429721 |
| O=C(O/N=C/c1ccccc1)N1CCOCC1 | 6.26173 | Cc1c[nH]cn1 | 6.431754 |
| CCCC(C)NC(=O)n1cncc1 | 6.26938 | CCc1ccccc1OCC1CCCNC1 | 6.432372 |
| N#Cc1ccc(\C=N/c2ccccc2)cc1 | 6.27228 | CNC1CCCCC1 | 6.433502 |
| CCCCCC/C=C1\CCCCC/1=O | 6.27628 | CCCCn1cccc1 | 6.434268 |
| CNCCCOc1ccccc1C | 6.28193 | O=C(CCCc1ccccc1)NC(C)(C)C | 6.434314 |
| Oc1cccc(O)n1 | 6.2826 | CC(C)CCCc1cccn1 | 6.435371 |
| OC[C@@H]1CNCC1 | 6.28635 | CC1(C)COCCN1 | 6.435727 |
| OCC1CNCC1 | 6.28726 | S=C(NCCC1=CCCCC1)N(C)C | 6.43606 |
| O=C(NCCCc1ccccc1)C(C)(C)C | 6.2907 | N#CCCNc1ccccc1C | 6.436422 |
| CCc1nnc(N)nn1 | 6.29176 | CN(C)CCCNC(=O)N1CCOCC1 | 6.437192 |
| N#CC1(N)CCCC1 | 6.29315 | CC(=C)Cc1ncc(C)c1 | 6.437725 |
| CC(C)CCSc1ccc(C)cc1 | 6.29428 | NCCOC1CCCCO1 | 6.437952 |
| Cc1ccccc1OCCCCCN1CCCCC1 | 6.2943 | CSc1ccccc1C(=O)NCCCN1CCCC1 | 6.43854 |
| CC(C)CSc1ccccc1 | 6.2943 | NCCCN1CCCCC1 | 6.44011 |
| C/C=C/CCc1ccccn1 | 6.29577 | C=COc1cccc(C)c1 | 6.442179 |
| NC1CCCCCC1 | 6.29817 | Nc1ccncc1 | 6.4422 |
| O=C(NCC#Cc1ccccc1)c1cccs1 | 6.29973 | C[C@H]1CCC[C@@H](O)C1 | 6.442564 |
| CCCCCCCc1ccc(N)cc1 | 6.30274 | CC(C)CCOc1ccc(N)cc1 | 6.445304 |
| O=C(NCCCn1cncc1)C1CCNCC1 | 6.30333 | NCCCN1CCSCC1 | 6.446523 |
| Cc1ccc(C)cn1 | 6.30334 | CN(C)c1ccccc1 | 6.448354 |
| CCCCCCc1ccc(N)cc1 | 6.30632 | CCCCc1ccc(N)n1 | 6.448834 |
| CCCCOCCCNC(=O)N1CCOCC1 | 6.30824 | CCc1ccc(C=C)nc1 | 6.449475 |
| CC(C)(C)COc1cncnn1 | 6.30882 | CC(C)CNCc1cscc1 | 6.450718 |
| COc1ccc(cc1)CN1CCCCCC1 | 6.31102 | CC(C)CCCc1ccncc1 | 6.451931 |
| COc1cccc(C)n1 | 6.31161 | CC(C)NC(=O)N1CCNCC1 | 6.453215 |
| C1C=CCS1 | 6.31378 | Cc1cc(C)nc(Sc2ccc(cc2)C(=O)O)n1 | 6.454888 |
| O=C(NCCCN1CCCC1)C1CCNCC1 | 6.31572 | CC(C)(C)c1ccccn1 | 6.456365 |
| Cc1ncccc1OCC1CCCNC1 | 6.31862 | CCN(CC)C(=O)NC1CCCCC1 | 6.457056 |
| CCCC(=O)NCc1ccccn1 | 6.32015 | CCC1=NCCCN1 | 6.457151 |
| CCCC1OCCS1 | 6.32076 | CN(C)Cc1ccccn1 | 6.457247 |
| CCOC(=O)\C=C\Cc1ccccc1 | 6.32096 | CCCCSC1(C)CCCCC1 | 6.459166 |
| CC(C)(C)COCC1CCCNC1 | 6.32318 | COc1ccc(CNC(=O)CC(C)C)cc1 | 6.459845 |
| NCCCOc1ccc(C)c1 | 6.32451 | N#Cc1ccc(C#Cc2ccccc2)cc1 | 6.463152 |
| O=C(NCCc1ccccc1)OC(C)(C)C | 6.3266 | CC(C)CCNC(=O)Cc1cccs1 | 6.465874 |
| CC1(C)CCCNC1 | 6.46693 | CCNCc1ccccc1 | 6.513302 |
| Cc1n[nH]cn1 | 6.46712 | CCCC1NCC=C1 | 6.514383 |
| CCCC1=NCCO1 | 6.46827 | CCCCCCn1ccc(=N)cc1 | 6.515571 |
| COC1CNCC1 | 6.47129 | CNC(C)Cc1ccccn1 | 6.515612 |
| OC1(C)CCCC1 | 6.47168 | CNCC(=O)N1CCCCCC1 | 6.51581 |
| CC1(O)CCCC1 | 6.47168 | O=C(NCCCN1CCCCC1)c1ccccc1 | 6.516288 |
| O=C(NCCCN1CCSCC1)c1ccccc1 | 6.47174 | CN(C)C1CCCC1 | 6.517077 |
| CCC(CC)C(=O)NCCCc1ccccc1 | 6.47308 | C1CCC(CN1)Oc1nccn1 | 6.52029 |
| CC(C)(C)NCCCc1ccccc1 | 6.47342 | NCc1csnc1 | 6.521403 |
| CCCCN1CCC(C)CC1 | 6.47395 | CCC(=O)NCC#Cc1ccccc1 | 6.521463 |
| O=C(NCCc1ccccc1)C(C)C | 6.47507 | CCCC1CCCS1 | 6.52177 |
| O=C(NCCCn1ccn1)C1CCCC1 | 6.47677 | OC1CCOCC1 | 6.522021 |
| CCc1ccccc1Oc1ncccn1 | 6.4771 | O=S(=O)(NCCCN1CCCCCC1)c1ccccc1 | 6.523599 |
| CC(=O)CC(=O)NCCc1ccccc1 | 6.47888 | CCN(CC)C(=O)NCc1ccccn1 | 6.523717 |
| CCCCc1ccc(C=O)cc1 | 6.48035 | O=C1C/C=C\CCCCCCCO1 | 6.523937 |
| CCCCNC(=O)N1CCOCC1 | 6.48123 | O=C(OCCSC(=S)NC(C)(C)C)Nc1ccccc1 | 6.524631 |
| N#CCCNC(=O)C1CCNCC1 | 6.48516 | CC(C)CNC(=O)c1cscc1 | 6.52518 |
| NCCCOc1ccccc1C | 6.4853 | O=C(NCCC1=CCCCC1)C1CC1 | 6.525225 |
| CCCCNC(=O)Nc1nccs1 | 6.48555 | CC(N)CCN1CCCCCC1 | 6.526511 |
| O=S(=O)(NCCCN1CCCCC1)c1ccccc1 | 6.48645 | CCNC(=O)N(C)Cc1ccccc1 | 6.528375 |
| CCc1ccc(CNCC(C)C)cc1 | 6.48768 | CN(C)C1CCCCC1 | 6.529209 |
| CC(C)(C)NCc1ccncc1 | 6.49017 | CC(C)CNCc1cccnc1C | 6.53036 |
| CCC(C)NC(=O)c1cscc1 | 6.49085 | CC(C)(C)NCc1ccncc1 | 6.5317 |
| CCCc1ccc(N)cc1 | 6.49096 | CCCCNCc1ccc(CC)cc1 | 6.533015 |
| CCCCN1CCCCC1 | 6.49113 | CCCCCn1cccc1 | 6.533323 |

TABLE 10-continued

Top 500 predicted compounds for $CO_2$ activator set 2. The top 500 predicted compounds for predictions made from activator dataset 2.

| SMILES Structures | Distance | SMILES Structures | Distance |
|---|---|---|---|
| CC(C)OC1CCCCO1 | 6.49161 | O=C(OC(C)(C)C)n1cncc1 | 6.533548 |
| CN(C)C(=O)NC1CCCCC1 | 6.49217 | CCNC(=S)Nc1ccc(CC)cc1 | 6.53399 |
| O=C(NCC#Cc1ccccc1)c1cscc1 | 6.49234 | OC[C@@H]1CCCN1 | 6.534219 |
| CN1CCN(CC1)C(=O)CC(C)C | 6.49243 | CC(=C)CN1CCCCCC1=O | 6.53494 |
| CC(C)COc1ccc(N)c1 | 6.49256 | O=C(NCCCc1ccccc1)C(C)C | 6.534992 |
| O=C(NCCCn1cncc1)n1cncc1 | 6.49626 | OCC1CCCN1 | 6.535179 |
| CC(C)C1OCC=CCO1 | 6.49662 | CC(C)(C)N=C=NC(C)(C)C | 6.535355 |
| CCC(=O)N1CCNCC1 | 6.4982 | CN1CCCN(CC1)C(=O)CSc1ccccc1 | 6.535507 |
| CC(C)NC(=O)C1CCNCC1 | 6.49827 | COc1ccc(cc1)C(=O)NC(C)(C)C | 6.536675 |
| CCCCN1CCC(N)CC1 | 6.49841 | CCCS(=O)c1ccccc1 | 6.539592 |
| O=C1NCCN(CC1)C(=O)OC(C)(C)C | 6.49861 | CC(O)CC#CCN1CCOCC1 | 6.539593 |
| CC(C)(C)NCCCOc1ccccc1 | 6.49939 | CC(=CCCC(=CCCC1=COC=C1)C)C | 6.54101 |
| O=C(Nc1cccnc1)N1CCCCC1 | 6.50169 | N#CCCCCCC1CCCC(=O)C1 | 6.541903 |
| NN1CCOCC1 | 6.50235 | Cc1ccsc1CNCc1ccnc c1 | 6.542274 |
| CC(C)(C)N=C=NCc1ccccc1 | 6.5031 | CC(=CCCC#CCCOC1CCCCO1)C | 6.546339 |
| CCCC1OCCCO1 | 6.5042 | CCCCn1cncc1 | 6.547629 |
| O=S1(=O)CCOCCS(=O)(=O)NCCOCCN1 | 6.50421 | OC1CCCC1 | 6.550298 |
| CNC1CCCCNC1 | 6.50462 | CCC(=O)Nc1nccs1 | 6.552381 |
| CC(C)C1CCCCCN1 | 6.50482 | O=CNc1nnn[nH]1 | 6.552698 |
| O=Cc1cnc(nc1)NC(C)C | 6.50527 | CC1(C)CCOCO1 | 6.554363 |
| CN1CCCN(CC1)C(=O)CC(C)C | 6.50672 | CCNC(=S)NCCN1CCCCC1 | 6.555586 |
| Cc1ccc(OCC2CNCC2)cc1 | 6.50714 | CCOc1ccc(N)c1 | 6.555999 |
| COC(=O)NCCCn1cncc1 | 6.50724 | CN(C)CCCNCc1ccncc1 | 6.556703 |
| Cc1ccsc1CNCc1cccnc1 | 6.51228 | CC(=O)NCC1CCNCC1 | 6.556707 |
| C1CCSCS1 | 6.55782 | O=C(NCCCN1CCCC1=O)Cc1cccs1 | 6.556977 |

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A method of attracting one or more insect species comprising the use of a composition comprising 2-ethylpyrazine.

2. The method of claim 1, wherein said method is effected by activating odor receptors or odor receptor neurons.

3. The method of claim 1, wherein 2-ethylpyrazine is present in said composition at a concentration of from about 10% to about 99% by weight.

4. The method of claim 3, wherein 2-ethylpyrazine is present in said composition at a concentration of from about 50% to about 99% by weight.

5. The method of claim 1, wherein said composition further comprises a carrier.

6. The method of claim 1, wherein said composition further comprises a suitable solvent.

7. The method of claim 6, wherein said solvent is an organic solvent.

8. The method of claim 1, wherein said composition is present in a wicked apparatus.

9. The method of claim 2, wherein said odor receptors comprise one or more members of the Gustatory receptor (Gr) family.

10. The method of claim 9, wherein said one or more members of the Gr family comprise $CO_2$ receptors.

11. The method of claim 10, wherein said $CO_2$ receptors comprise Gr21a, Gr63a, AgGr22, AgGr23 and/or AgGr24 proteins.

12. The method of claim 1, wherein said insect species is selected from the group consisting of mosquitoes, sandflies and Testse flies.

13. The method of claim 12, wherein said insect species comprises mosquitoes selected from the group consisting of *Anopheles gambiae*, *Culex pipiens* and *Aedes aegypti* mosquitoes.

14. A method of luring one or more insect species to a trap comprising the use of a composition comprising 2-ethylpyrazine.

15. The method of claim 14, wherein said method of luring is carried out by virtue of activating odor receptors or odor receptor neurons in said one or more insect species.

16. The method of claim 14, wherein 2-ethylpyrazine is present in said composition at a concentration of from about 50% to about 99% by weight.

17. The method of claim 14, wherein said composition further comprises a carrier.

18. The method of claim 14, wherein said composition further comprises a suitable solvent.

19. The method of claim 18, wherein said solvent is an organic solvent.

20. The method of claim 14, wherein said composition is present in a wicked apparatus.

21. The method of claim 15, wherein said odor receptors comprise one or more members of the Gustatory receptor (Gr) family.

22. The method of claim 21, wherein said one or more members of the Gr family comprise $CO_2$ receptors.

23. The method of claim 22, wherein said $CO_2$ receptors comprise Gr21a, Gr63a, AgGr22, AgGr23 and/or AgGr24 proteins.

24. The method of claim 14, wherein said insect species is selected from the group consisting of mosquitoes, sandflies and Testse flies.

25. The method of claim 24, wherein said insect species comprises mosquitoes selected from the group consisting of *Anopheles gambiae*, *Culex pipiens* and *Aedes aegypti* mosquitoes.

26. The method of claim 14, wherein said trap is selected from the group consisting of a tape and a mechanical trap.

27. The method of claim 26, wherein said mechanical trap is selected from the group consisting of a suction-based trap, a light-based trap and an electric current-based trap.

28. A method of inhibiting, preventing or reducing the incidence of insect-borne disease in a subject, said method comprising luring one or more insect species to a trap comprising the use of a composition comprising 2-ethylpyrazine, thereby reducing or eliminating said one or more insect species and thereby inhibiting, preventing or reducing the incidence of insect-born disease in said subject.

29. The method of claim 28, wherein said luring is carried out by virtue of activating odor receptors or odor receptor neurons in said one or more insect species.

30. The method of claim 28, wherein 2-ethylpyrazine is present in said composition at a concentration of from about 50% to about 99% by weight.

31. The method of claim 28, wherein said composition further comprises a carrier.

32. The method of claim 28, wherein said composition further comprises a suitable solvent.

33. The method of claim 32, wherein said solvent is an organic solvent.

34. The method of claim 28, wherein said composition is present in a wicked apparatus.

35. The method of claim 28, wherein said insect-borne disease is selected from the group consisting of malaria, dengue, yellow fever, river blindness, lymphatic filariasis, sleeping sickness, leishmaniasis, epidemic polyarthritis, West Nile virus disease and Australian encephalitis.

\* \* \* \* \*